(12) United States Patent
Catacchio et al.

(10) Patent No.: US 10,369,069 B2
(45) Date of Patent: Aug. 6, 2019

(54) SURGICAL ARM POSITIONING SYSTEMS AND METHODS

(71) Applicant: Allen Medical Systems, Inc., Batesville, IN (US)

(72) Inventors: Anthony V. Catacchio, Arlington, MA (US); Andrew D. Clark, Allston, MA (US); Zachary B. Konsin, Brighton, MA (US)

(73) Assignee: Allen Medical Systems, Inc., Batesville, IN (US)

( * ) Notice: Subject to any disclaimer, the term of this patent is extended or adjusted under 35 U.S.C. 154(b) by 703 days.

(21) Appl. No.: 14/876,066

(22) Filed: Oct. 6, 2015

(65) Prior Publication Data

US 2016/0095785 A1 Apr. 7, 2016

Related U.S. Application Data

(60) Provisional application No. 62/060,645, filed on Oct. 7, 2014, provisional application No. 62/060,674, filed
(Continued)

(51) Int. Cl.
*A61F 5/37* (2006.01)
*A61H 1/02* (2006.01)
(Continued)

(52) U.S. Cl.
CPC ......... *A61H 1/0218* (2013.01); *A61F 5/3761* (2013.01); *A61G 13/0072* (2016.11);
(Continued)

(58) Field of Classification Search
CPC .. A61H 1/0218; A61H 1/0222; A61H 1/0229; A61H 1/0237; A61H 1/0274;
(Continued)

(56) References Cited

U.S. PATENT DOCUMENTS 2,053,753 A * 9/1936 Wellington ............... A61F 5/04
248/231.61
2,590,739 A 3/1952 Wagner et al.
(Continued)

FOREIGN PATENT DOCUMENTS

DE 10028881 A1 9/2001
WO 99/00100 A1 1/1999
(Continued)

OTHER PUBLICATIONS

EP Search Report for Application No. 17178477.0 dated Oct. 18, 2017 (8 pages).
(Continued)

*Primary Examiner* — Alireza Nia
*Assistant Examiner* — Rachel A Berezik
(74) *Attorney, Agent, or Firm* — Barnes & Thornburg LLP

(57) ABSTRACT

A surgical arm positioning system has a cable including two end portions coupled to a connection member of a hand grip. The cable and connection member form a continuous loop. The surgical arm positioning system further includes a frame that supports a number of pulleys. The continuous loop is trained around the pulleys. The surgical arm positioning system also includes a tensile resistance member engaged with the cable. The tensile resistance member provides tensile force to the cable to resist movement of the continuous loop relative to the frame, thereby to hold the patient's arm relatively still during surgery.

27 Claims, 97 Drawing Sheets

Related U.S. Application Data on Oct. 7, 2014, provisional application No. 62/060,793, filed on Oct. 7, 2014, provisional application No. 62/131,500, filed on Mar. 11, 2015, provisional application No. 62/236,721, filed on Oct. 2, 2015.

(51) Int. Cl.
*A61G 13/00* (2006.01)
*A61G 13/12* (2006.01)

(52) U.S. Cl.
CPC ....... *A61G 13/124* (2013.01); *A61G 13/1235* (2013.01); *A61H 2001/0203* (2013.01)

(58) Field of Classification Search
CPC .. A61H 1/0277; A61H 1/0281; A61H 1/0285;
A61H 1/0288; A61H 1/02; A61H 1/005;
A61H 1/008; A61H 2001/0203; A61H
3/00; A61H 3/008; A61H 2201/0142;
A61H 2201/0146; A61H 2201/0149;
A61H 2201/0157; A61H 2201/0161;
A61H 2201/1445; A61H 2201/1614;
A61H 2201/1616; A61H 2201/1635;
A61H 2201/1638; A61H 2201/165; A61H
2201/1652; A61H 2201/1657; A61H
2201/1659; A61H 2201/1664; A61H
2201/1666; A61H 2201/1671; A61H
2201/1676; A61H 2201/168; A61H
2203/0481; A61H 2203/0487; A61H
2203/0493; A61H 2205/06; A61H
2205/062; A61H 2205/065; A61H
2205/067; A61F 5/01; A61F 5/0102;
A61F 5/0118; A61F 5/013; A61F 5/04;
A61F 5/048; A61F 5/05; A61F 5/05858;
A61F 5/05866; A61F 5/05875; A61F
5/37; A61F 5/3715; A61F 5/3723; A61F
5/373; A61F 5/3761; A61F 5/3769; A61F
5/3753; A61F 5/3776; A61G 7/00; A61G
7/0005; A61G 7/10; A61G 7/1001; A61G
7/1013; A61G 7/1015; A61G 7/1017;
A61G 7/1019; A61G 7/1038; A61G
7/1044; A61G 7/1049; A61G 7/1051;
A61G 7/1053; A61G 7/1055; A61G
7/1057; A61G 7/1078; A61G 7/108;
A61G 7/1032; A61G 7/1042; A61G
13/0036; A61G 13/0045; A61G 13/0072;
A61G 13/009; A61G 13/101; A61G
13/1235; A61G 13/124; A61G 13/1255;
A61B 6/04; A61B 6/0407; A61B 6/0414;
A61B 6/0421; A61B 6/0428; A61B
6/0457; A61B 6/0471; A61B 6/0478;
A61B 6/0485; A63B 21/152; A63B
21/153; A63B 21/154; A63B 21/156
See application file for complete search history.

(56) References Cited

U.S. PATENT DOCUMENTS

| | | | |
|---|---|---|---|
| 2,875,753 A * | 3/1959 | Sulmonetti | A61F 5/04 602/34 |
| 4,042,232 A | 8/1977 | Lile et al. | |
| 4,492,224 A * | 1/1985 | Singleton | A61H 1/0218 602/33 |
| 4,616,637 A | 10/1986 | Caspari et al. | |
| 4,679,552 A | 7/1987 | Caspari | |
| 4,698,837 A | 10/1987 | Van Steenburg | |
| 4,807,618 A | 2/1989 | Auchinleck et al. | |
| 4,930,523 A * | 6/1990 | Laico | A61F 5/04 5/87.1 |
| D309,184 S | 7/1990 | Sanderson et al. | |
| 4,941,464 A * | 7/1990 | Scott | A61F 5/04 128/856 |
| 5,003,967 A | 4/1991 | McDonnell | |
| 5,104,103 A | 4/1992 | Auchinleck et al. | |
| 5,306,232 A * | 4/1994 | Whitmyer | A61F 5/3707 482/10 |
| 5,360,019 A | 11/1994 | Witzel et al. | |
| 5,419,756 A | 5/1995 | McConnell | |
| 5,632,726 A | 5/1997 | Repice et al. | |
| 5,775,334 A | 7/1998 | Lamb et al. | |
| 5,788,659 A | 8/1998 | Haas | |
| 5,961,512 A | 10/1999 | Purnell | |
| 6,190,345 B1 * | 2/2001 | Henderson | A61H 1/0218 602/32 |
| 6,394,972 B1 | 5/2002 | Slishman | |
| 6,467,487 B1 | 10/2002 | Rios | |
| 6,488,030 B1 | 12/2002 | Wardle et al. | |
| 6,599,263 B1 | 7/2003 | Bonutti et al. | |
| 6,786,882 B2 | 9/2004 | Slishman | |
| 6,811,541 B2 | 11/2004 | Lambert | |
| 6,824,498 B2 | 11/2004 | Hassler | |
| 6,860,668 B2 | 3/2005 | Ibrahim et al. | |
| 6,895,969 B2 | 5/2005 | Malcolm et al. | |
| 6,971,997 B1 | 12/2005 | Ryan et al. | |
| 7,093,313 B2 | 8/2006 | DeBraal et al. | |
| 7,094,240 B2 | 8/2006 | Molz, IV et al. | |
| 7,131,955 B2 | 11/2006 | Price et al. | |
| 7,143,458 B2 | 12/2006 | Slater, Jr. | |
| 7,144,380 B2 | 12/2006 | Gilliam | |
| 7,223,213 B2 | 5/2007 | Golesh | |
| 7,297,128 B2 | 11/2007 | Binder et al. | |
| 7,316,040 B2 | 1/2008 | Siccardi et al. | |
| 7,364,555 B1 * | 4/2008 | Davidson | A61H 1/0274 482/131 |
| 7,544,175 B1 | 6/2009 | D'Amico | |
| 7,604,583 B2 | 10/2009 | Denisco | |
| 7,621,857 B2 | 11/2009 | Pompile | |
| 7,686,775 B2 | 3/2010 | Branch | |
| 7,771,378 B2 | 8/2010 | Price et al. | |
| 7,857,778 B2 | 12/2010 | De Muinck | |
| 7,857,779 B2 | 12/2010 | Gondringer | |
| 7,857,780 B2 | 12/2010 | Sommers et al. | |
| 8,028,702 B2 | 10/2011 | DaSilva | |
| 8,051,515 B1 | 11/2011 | Kring | |
| 8,088,089 B2 | 1/2012 | Ciamillo et al. | |
| 8,109,273 B2 | 2/2012 | Golden et al. | |
| 8,182,417 B2 | 5/2012 | Danitz | |
| 8,273,047 B1 | 9/2012 | McKeon et al. | |
| 8,287,439 B2 | 10/2012 | Evans et al. | |
| 8,540,656 B1 | 9/2013 | Powlan | |
| 8,591,441 B2 | 11/2013 | Bonutti et al. | |
| 2005/0027225 A1 | 2/2005 | Bohn | |
| 2006/0161086 A1 | 7/2006 | Lambert | |
| 2006/0200061 A1 | 9/2006 | Warkentine | |
| 2010/0069809 A1 | 3/2010 | Sommers et al. | |
| 2010/0106067 A1 | 4/2010 | Horvath | |
| 2011/0178449 A1 | 7/2011 | Foote | |
| 2011/0237991 A1 | 9/2011 | Bonutti et al. | |
| 2012/0101419 A1 | 4/2012 | Bonutti et al. | |
| 2012/0103344 A1 | 5/2012 | Hunter, Jr. | |
| 2015/0068534 A1 | 3/2015 | Lubbers et al. | |

FOREIGN PATENT DOCUMENTS

| | | |
|---|---|---|
| WO | 2012109981 A1 | 8/2012 |
| WO | WO2012/109981 A1 | 8/2012 |

OTHER PUBLICATIONS

Extended EP Search Report for Application No. 15188738.7, dated Jun. 3, 2016 (10 pages).
EP Search Report for Application No. 15188738.7, dated Jan. 29, 2016 (6 pages).

(56) References Cited

OTHER PUBLICATIONS

Extended European Search Report for EP 18169981.0 dated Jul. 25, 2018; 6 pages.

* cited by examiner

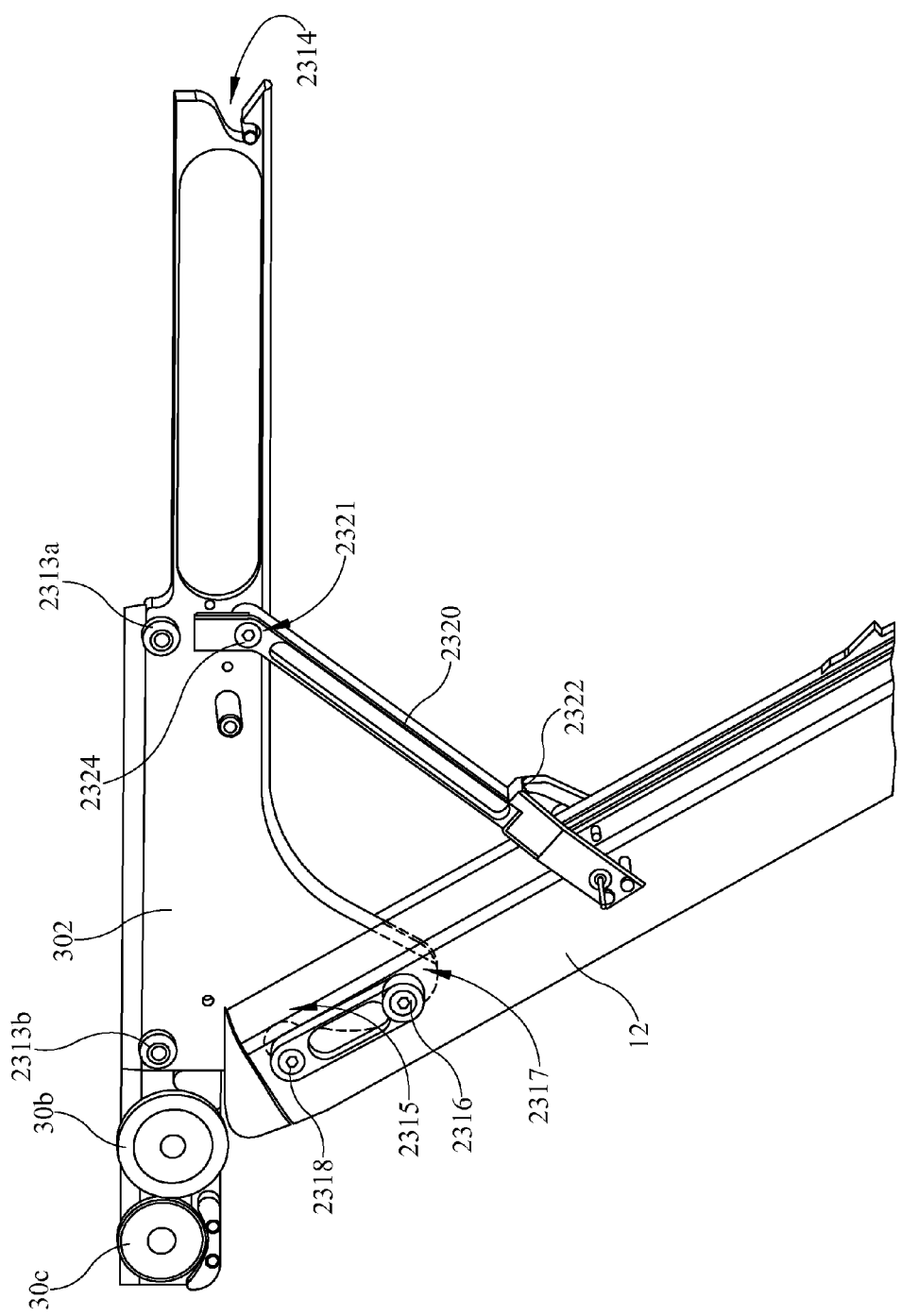

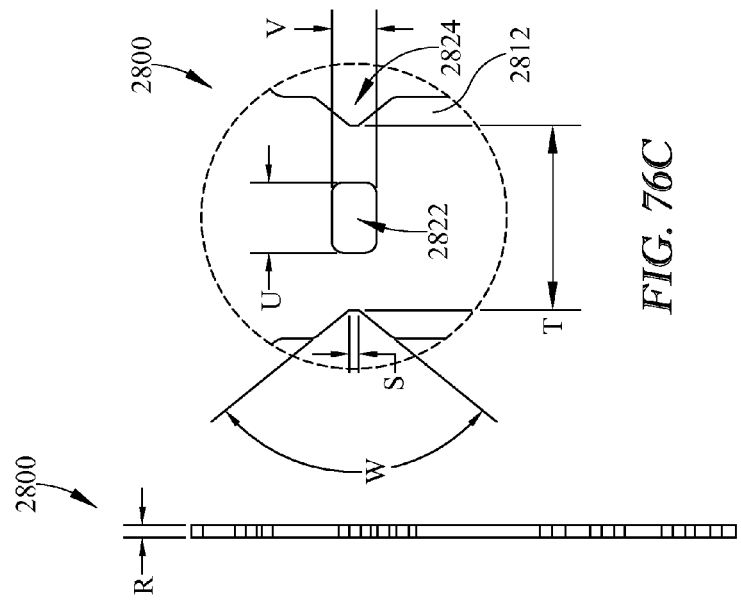
FIG. 76C
FIG. 76B
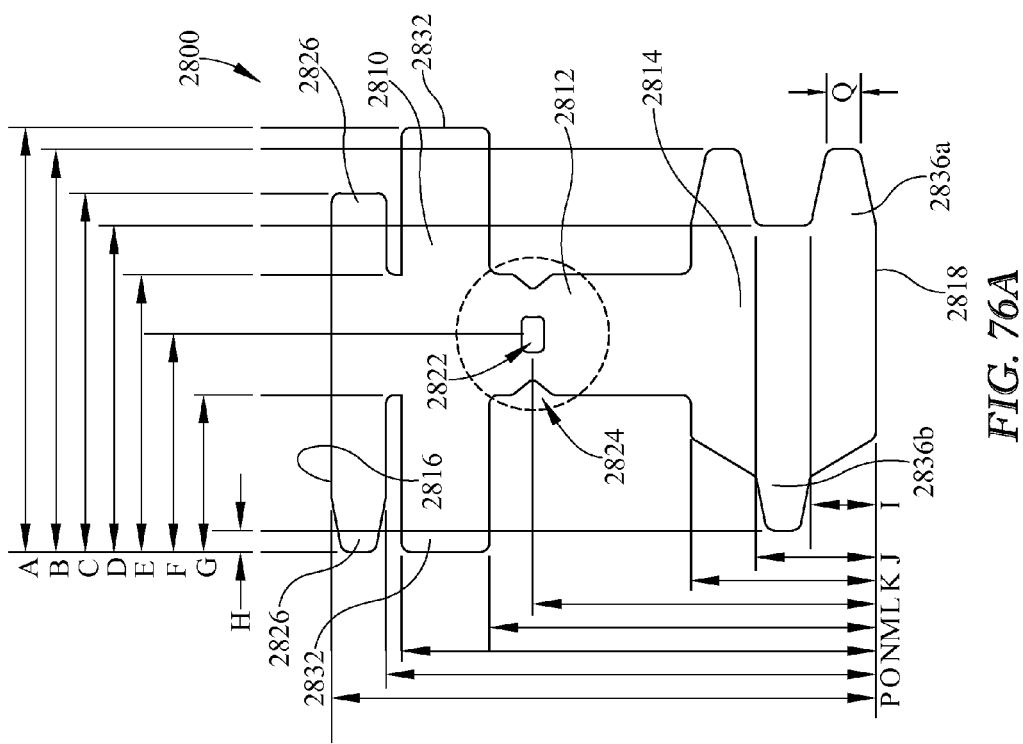
FIG. 76A

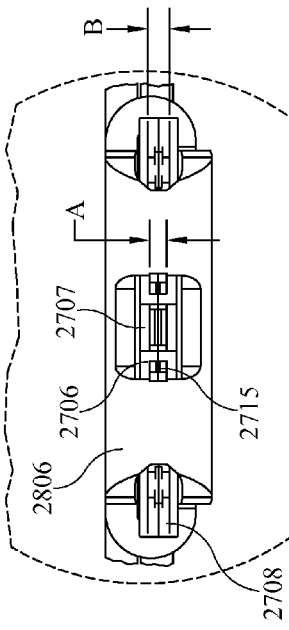
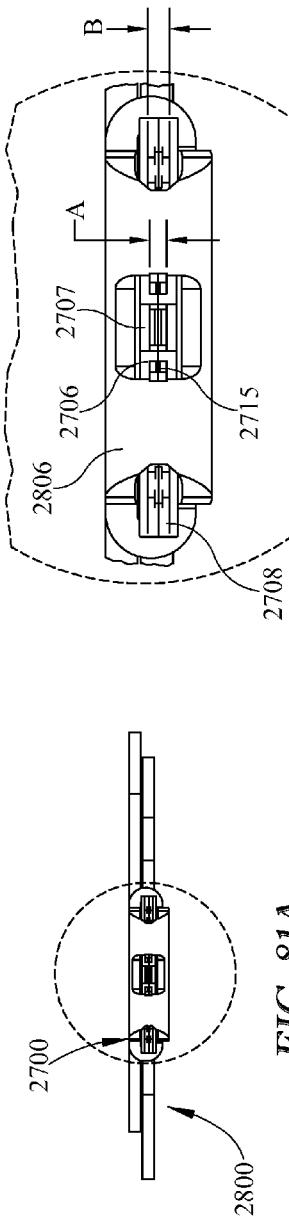
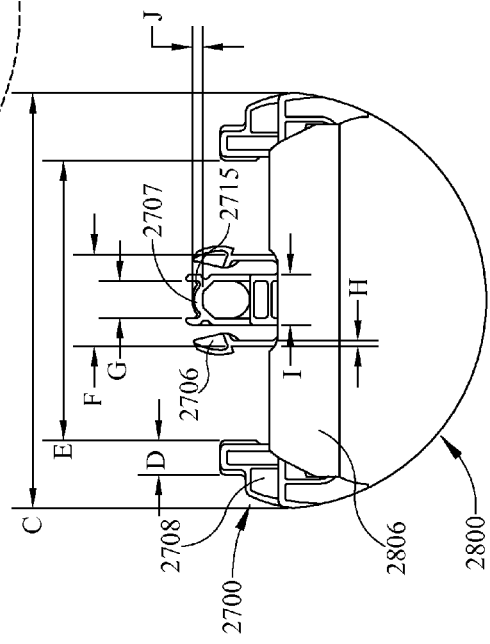

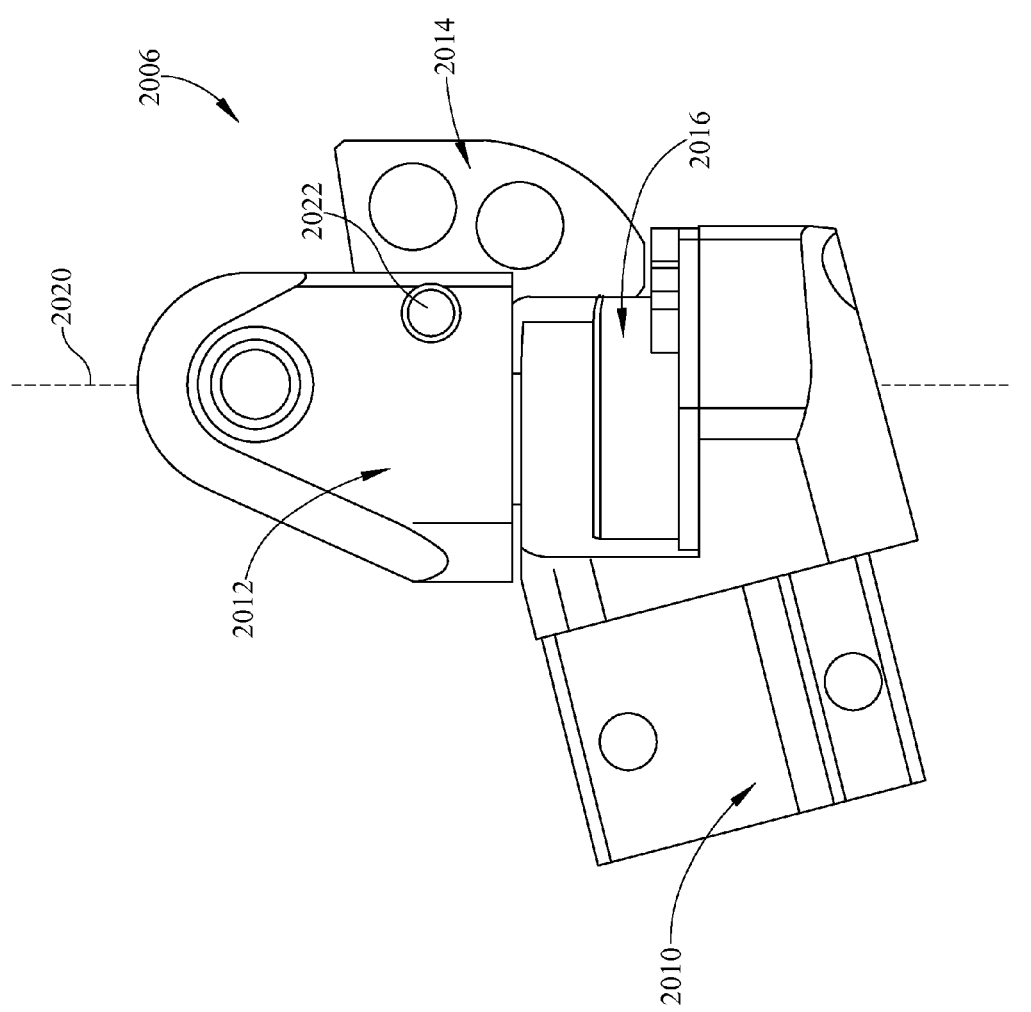

SURGICAL ARM POSITIONING SYSTEMS AND METHODS

The present application claims the benefit, under 35 U.S.C. § 119(e), of U.S. Provisional Application Nos. 62/060,645, 62/060,674, and 62/060,793, which were filed Oct. 7, 2014, U.S. Provisional Application No. 62/131,500, which was filed Mar. 11, 2015, and U.S. Provisional Application No. 62/236,721, which was filed Oct. 2, 2015, each of the foregoing applications being hereby expressly incorporated by reference herein in their entireties.

BACKGROUND

The present disclosure relates to a sterile connection for attaching to a patient's limb during surgery. More particularly, the present disclosure relates to an apparatus that applies lateral traction to a patient's arm.

Shoulder arthroscopy includes several procedures including rotator cuff repair, bone spur removal, labrum repair, ligament repair, removal of inflamed tissue or loose cartilage, and repair for recurrent shoulder dislocation. During such procedures, a patient's arm may be connected to an arm positioning system. Internal or external rotation of the humeral head may be beneficial for some types of shoulder arthroscopy.

Arm positioning systems known in the art often require multiple staff members or extra draping to attach a patient's limbs to a support device. Such systems may require sterile and non-sterile staff to work together to attach the limb or require the entire non-sterile device to be covered with a sterile drape. Furthermore, such systems often require adjustment of non-sterile components in order to move a patient's arm to a desired location.

Shoulder arthroscopy towers known in the art may have a connection point for lateral traction with little adjustability. The connection point may only move in a single direction. The tower may have a non-sterile locking mechanism positioned high above the sterile field, making adjustments difficult. The locking mechanisms may require users to pull levers, push buttons, or turn knobs that are difficult to reach in some instances. Therefore, such shoulder arthroscopy towers are cumbersome to use.

SUMMARY

A surgical arm positioning system, sterile connection, lateral distraction apparatus, and lateral distraction strap have one or more of the features recited in the appended claims and/or the following features, which, alone or in any combination, may comprise patentable subject matter:

A surgical arm positioning system that may have a cable is disclosed. The cable may have two end portions coupled to a connection member of a hand grip. The cable and connection member may form a continuous loop. The surgical arm positioning system may further include a frame. Pulleys may be attached to the frame. The continuous loop may be trained around the pulleys. The surgical arm positioning system may also include a tensile resistance member engaged with the cable. Such a tensile resistance member may provide tensile force to the cable to resist movement of the continuous loop.

In some embodiments, the tensile resistance member may be a clutch. The clutch may provide a resistive torque to one of the pulleys. The tensile resistance member may also be a weight.

It is contemplated that the two end portions of the cable may form an angle from about 120 to about 180 degrees at the connection member.

According to this disclosure, a patient's arm may be attached to the connection member. When a patient's arm is attached to the connection member, the cable may resist movement along the pulleys. The cable resisting movement may allow the surgical arm positioning system to keep the patient's arm stationary over about 30 degrees of arm abduction.

In some embodiments, at least one of the pulleys may be adjustable along the frame. The pulley(s) adjustable along the frame may resist(s) movement along the frame.

It is contemplated that the surgical arm positioning system may also include a semi-locked clamp capable of pivoting the frame. The semi-locked clamp may provide resistance to rotation of the frame.

The present disclosure also teaches a surgical arm positioning system that may have two cable portions. An end of each cable portion may be coupled to a connection member of a hand grip. Additionally, the surgical arm positioning system may also have a lower assembly and an upper assembly. Further, the assemblies may be coupled to the cable portions. When a patient's arm is attached to the connection member, the lower and upper assemblies may resist movement to keep the arm stationary. The assemblies may move relative to the frame in response to moving a patient's arm.

In some embodiments, movement of the lower assembly may influence movement of the upper assembly. Additionally, movement of the upper assembly may influence movement of the lower assembly. The distance between the assemblies is fixed. The surgical arm positioning system may have a connecting rod that fixes the distance between the lower and upper assemblies.

It is contemplated that the cable portions and connection member may form a continuous loop. Additionally, the lower assembly and upper assembly may each comprise a pulley. The continuous loop may be trained around the pulleys. A tensile resistance member may be engaged with the cable portions. The tensile resistance member may provide tensile force to the cable portions. The tensile force provided to the cable portions may resist movement of the continuous loop.

According to this disclosure, the tensile resistance member may comprise a clutch. The clutch may provide a resistive torque to one of the pulleys. In some embodiments, the tensile resistance member may comprise a weight.

It is contemplated that a patient's arm may be attached to the connection member. When a patient's arm is attached to the connection member, the cable may resist movement along the pulleys. Additionally, the assemblies may resist movement along the frame. The cable and the assemblies resisting movement may allow the surgical arm positioning system to keep the patient's arm stationary over about 70 degrees of arm abduction.

In some embodiments, the surgical arm positioning system may also include a semi-locked clamp that permits pivoting of the frame. The semi-locked clamp may provide resistance to rotation of the frame.

This disclosure also teaches a surgical arm positioning system that may have a cable. The cable may have two end portions. The end portions may be coupled to a connection member of a hand grip. The cable and connection member may form a continuous loop. The continuous loop may be trained around the pulleys. Additionally, the surgical arm positioning system may have a tensile resistance member.

The tensile resistance member may be engaged with the cable. Such a tensile resistance member may provide tensile force to the cable to resist movement of the continuous loop. The surgical arm positioning system may further include a frame. The surgical arm positioning system may have pulleys. Also, the surgical arm positioning system may have a lower assembly and an upper assembly. The assemblies each may have one of the pulleys. The lower and upper assemblies may be adjustable along the frame. A connecting rod may fix the distance between the lower and upper assemblies.

In some embodiments, the tensile resistance member may be a clutch. The clutch may provide a resistive torque to one of the pulleys. The tensile resistance member may also be a weight.

It is contemplated that the two end portions of the cable may form an angle from about 120 to about 180 degrees at the connection member.

According to this disclosure, the surgical arm positioning system may also have a connecting rod. The connecting rod may fix the distance between the lower and upper pulley assemblies.

It is contemplated that a patient's arm may be attached to the connection member. When a patient's arm is attached to the connection member, the cable may resist movement along the pulleys. Additionally, the assemblies may resist movement along the frame. The cable and the assemblies resisting movement may allow the surgical arm positioning system to keep the patient's arm stationary over about 70 degrees of arm abduction.

In some embodiments, the surgical arm positioning system may also include a semi-locked clamp that permits pivoting of the frame. The semi-locked clamp may provide resistance to rotation of the frame.

A distraction apparatus for use with a lateral distractor strap is disclosed. The distraction apparatus may have a beam. The distraction apparatus may also have a wheel bracket coupled to a first end region of the beam. The distraction apparatus may also have a brake coupled to the wheel bracket. At least one wheel may be coupled to the wheel bracket. The distraction apparatus may also have an extension bar that extends and retracts relative to the beam. The extension bar may be positioned over the brake. At least one wheel may guide movement of the extension bar relative to the beam during extension and retraction. The lateral distractor strap may hang downwardly from a first end of the extension bar. Application of a downward force to the lateral distractor strap may force the extension bar against the brake to prevent the extension bar from extending or retracting relative to the beam until the downward force is removed.

According to this disclosure, the downward force may include the weight of a patient's arm. In some embodiments, the extension bar may have an I-shaped cross section to provide wheel-receiving tracks on opposite sides of the extension bar. Two wheels may be provided and each wheel may be coupled to a respective side of the wheel bracket and may be engaged by a respective side of the wheel-receiving tracks of the extension bar.

It is contemplated that the wheel bracket may have a body and two arms extending from opposite sides of the body. The body and the arms may define a gap and the two wheels may be coupled to the arms. Both wheels may extend into the gap. The gap may also receive the extension bar. The wheels may be engaged by the wheel-receiving tracks of the extension bar.

According to this disclosure, opposite ends of the extension bar may have stop surfaces. The stop surfaces may limit the range of extension and retraction of the extension bar relative to the beam.

In some embodiments, the distraction apparatus may also have a platform that couples the wheel bracket to the first end region of the beam. The wheel bracket may be rotatable relative to the platform about a first rotation axis. The distraction apparatus may further have a second brake coupled to the wheel bracket. The second brake may be positioned over a side of the platform. The side of the platform may extend circumferentially around the platform and may be centered at the first rotation axis.

It is contemplated that the distraction apparatus may also have a brake foot coupled to the wheel bracket. The brake foot may be pivotable relative to the wheel bracket. The brake may be coupled to the brake foot. The distraction apparatus may further have a second brake coupled to the brake foot. The second brake may be oriented perpendicular to the first brake and positioned over a side of the platform.

According to this disclosure, application of the downward force to the lateral distractor strap may force the second brake against the side of the platform to prevent the extension bar from rotating relative to the platform until after the downward force is removed.

In some embodiments, the distraction apparatus may also have a magnetic catch coupled to a second end of the extension bar opposite the first end of the extension bar. When the extension bar is fully retracted in a storage position, the magnetic catch may hold the extension bar alongside the beam.

It is contemplated that the distraction apparatus may also have a hanger that couples the lateral distractor strap to the first end of the extension bar and a flange positioned between the first end of the extension bar and the lateral distractor strap. The distraction apparatus may further have a tension meter between the hanger and the lateral distractor strap.

The present disclosure also contemplates a distraction apparatus for use with a lateral distractor strap. The distraction apparatus may have a beam. The distraction apparatus may also include a platform coupled to a first end region of the beam. The distraction apparatus may further have an extension bar that rotates relative to the platform. The distraction apparatus may still further have a brake coupled to the extension bar. The brake may be positioned over a side of the platform. The lateral distractor strap may hang downwardly from a first end of the extension bar. Application of a downward force to the lateral distractor strap may force the brake against the platform to prevent the extension bar from rotating relative to the platform until the downward force is removed.

According to this disclosure, the downward force may include the weight of a patient's arm. In some embodiments, the extension bar may rotate relative to the platform about a first rotation axis. The side of the platform may extend circumferentially around the platform and may be centered at the first rotation axis. The side of the platform may extend about 180° around the platform.

It is contemplated that the distraction apparatus may also include a bracket that couples the platform to the beam. There may be a stud in the platform. There may also be a hole in the bracket. The hole may engage the stud such that the bracket is rotatable relative to the platform.

According to this disclosure, the distraction apparatus may also have a wheel bracket that couples the platform to the beam. The distraction apparatus may further include at least one wheel coupled to the wheel bracket. The extension bar may extend and retract relative to the beam. The at least one wheel may guide movement of the extension bar relative to the beam during extension and retraction. The distraction apparatus may also have a second brake coupled to the wheel bracket. The extension bar may be positioned over the second brake.

In some embodiments, the distraction apparatus may also have a brake foot coupled to the wheel bracket. The brake foot may be pivotable relative to the wheel bracket. The brake may be coupled to the brake foot. The distraction apparatus may further have a second brake coupled to the brake foot. The second brake may be oriented perpendicular to the first brake. The extension bar may be positioned over the second brake.

According to this disclosure, application of the downward force to the lateral distractor strap may force the second brake against the extension bar against the brake to prevent the extension bar from extending or retracting relative to the beam until the downward force is removed.

According to another aspect of the present disclosure, a distraction apparatus for use with a lateral distractor strap is provided. The distraction apparatus may include a beam, a wheel bracket coupled to a first end region of the beam, and a platform coupled to the wheel bracket. A brake foot may be coupled to the wheel bracket and the brake foot may be pivotable relative to the wheel bracket. A first brake and a second brake may be coupled to the brake foot. At least one wheel may be coupled to the wheel bracket. The distraction apparatus may further have an extension bar that extends and retracts relative to the beam and rotates relative to the platform. The extension bar may be positioned over the first brake. The second brake may be positioned over a side of the platform. The at least one wheel may guide movement of the extension bar relative to the beam during extension and retraction. The lateral distractor strap may hang downwardly from an end of the extension bar. Application of a downward force to the lateral distractor strap may force the extension bar against the first brake to prevent the extension bar from extending or retracting relative to the beam and may force the second brake against the side of the platform to prevent the wheel bracket from rotating relative to the platform until the downward force is removed.

A sterile hand connection device is disclosed. The sterile hand connection device may attach a patient's arm to a cable adaptor. The cable adaptor may have a pin and may be connected to two cable ends. The cable ends may be of a surgical arm positioning system.

The sterile hand connection device may have a buckle that may have a snap feature receiving hole and two wide feature receiving gaps. The sterile hand connection device also may have a connector that may be operably attached to the buckle such that the buckle and the connector are rotationally coupled. The connector may have a distal end and a proximal end. The connector also may have a hook its distal end for attaching to the cable adaptor. The sterile hand connection device further may have a flange separating the cable adaptor from the proximal end of the connector.

According to this disclosure, the sterile hand connection device may have a nut engaged with the connector for adjusting the buckle. The connector may have a distal end and a proximal end. The connector may have a threaded portion adjacent to its distal end. The threaded portion of the connector may be cooperatively engaged with the nut. The connector also may have a body adjacent to its proximal end.

In some embodiments, the sterile hand connection device also may have a clip adaptor. The clip adaptor may have a proximal end and a distal end. The distal end of the clip adaptor may have a rim that may define an opening in the distal end of the clip adaptor. The clip adaptor may surround the body of the connector and may be attached and rotationally coupled to the buckle. The connector may have a cap at its proximal end. The nut may have a distal end and a proximal end. The proximal end of the nut may be in contact with the distal end of the clip adaptor. When the nut is moved proximally by rotation, friction between the rim of the clip adaptor and the cap of the connector may increase. The friction may rotationally couple the buckle and the connector.

It is contemplated that the sterile hand connection device may also have a knob engaged with the connector for locking the sterile hand connection device to the cable adaptor. The connector may have a distal end and a proximal end. The connector may have a threaded portion adjacent to the distal end of the connector. The threaded portion may be cooperatively engaged with the knob. The connector also may have a body adjacent to the proximal end of the connector. The sterile hand connection device may have a hook at the distal end of the connector. The knob may be in contact with the cable adaptor such that when the knob is moved distally by rotation the force between the cable adaptor and the hook may increase. This increase in force may lock the connector to the cable adaptor.

According to the present disclosure, therefore, a sterile hand wrap for attaching a patient's arm to a sterile clip is disclosed. The sterile clip may have a snap feature for connection to a sterile hand connection device. The sterile clip may be for attaching to a sterile hand connection device of a surgical arm positioning system. The sterile hand wrap may have a foldable sheet that may have an interior side and an exterior side. The interior side may have a foam material.

The foldable sheet may have a wrist portion that may have at least one wrist strap for wrapping around a patient's wrist. The wrist strap may have a wrist strap fastener. The foldable sheet may also have a snap feature receiving opening for receiving the snap feature. The wrist strap fastener may have a hook material and the exterior of the foldable sheet may have a loop material.

It is contemplated that the sterile hand wrap may have a forearm portion that may at least one forearm strap for wrapping around a patient's forearm. The at least one forearm strap may have a forearm strap fastener. The forearm strap fastener may have a hook material and the exterior of the foldable sheet may have a loop material.

In some embodiments, the sterile hand wrap may have two wide feature receiving indentations. The sterile clip may have two wide features for engaging a sterile hand connection device. The wide feature receiving indentations may be for receiving the wide features.

It is contemplated that the sterile hand wrap may be sterilized by ultraviolet irradiation.

The present disclosure also teaches a sterile hand wrap for attaching a patient's arm to a sterile clip. The sterile clip may have a snap feature for connection to a sterile hand connection device and two wide features for engaging a sterile hand connection device. The sterile clip may be for attaching to a sterile hand connection device of a surgical arm positioning system. The sterile hand wrap may have a foldable sheet that may have an interior side and an exterior side. The interior side may have a foam material.

The foldable sheet may have a wrist portion that may have at least one wrist strap for wrapping around a patient's wrist. The wrist strap may have a wrist strap fastener. The foldable sheet may also have a forearm portion that may have at least one forearm strap for wrapping around a patient's forearm. The forearm strap may have a forearm strap fastener.

In some embodiments, the foldable sheet may include a snap feature receiving opening for receiving the snap feature and two wide feature receiving indentations or notches for receiving the wide features.

According to this disclosure, therefore, a sterile clip for attaching a patient's arm to a sterile hand connection device of a surgical arm positioning system is disclosed. The sterile clip may have a body having a distal end and a proximal end. The sterile clip may also have two clip arms extending from the distal end to the proximal end. The sterile clip may further have a distal cross portion that may be substantially perpendicular to the clip arms and that connects the clip arms. The distal cross portion and clip arms may form a hand receiving gap. The sterile clip may still further have a snap feature for connection to a sterile hand connection device. The snap feature may be attached to the distal cross portion.

It is contemplated that the sterile clip may further have two wide features for engaging a sterile hand connection device. The wide features may be attached to the distal cross portion. The wide features may be adjacent to the clip arms.

The present disclosure also teaches a sterile clip for attaching a patient's arm to a sterile hand connection device of a surgical arm positioning system. The sterile clip may have a body that may have a distal end and a proximal end. The sterile clip may also have two clip arms extending from the distal end to the proximal end. The sterile clip may further have a distal cross portion substantially perpendicular to the clip arms. The distal cross portion may connect the clip arms. The distal cross portion and clip arms may form a hand receiving gap. The sterile clip may still further have a snap feature for connection to a sterile hand connection device. The snap feature may be attached to the distal cross portion.

The sterile clip for attaching a patient's arm to a sterile hand connection device of a surgical arm positioning system may further have a sterile hand wrap for attaching the patient's arm to a sterile clip. The sterile hand wrap may have a foldable sheet that may have an interior side and an exterior side. The interior side may have a foam material. The foldable sheet may have a wrist portion that may have at least one wrist strap for wrapping around a patient's wrist. The wrist strap may have a wrist strap fastener. The foldable sheet may also have a snap feature receiving opening for receiving the snap feature.

In some embodiments, the sterile clip has two wide features for engaging a sterile hand connection device. The wide features may be to the distal cross portion. The wide features may be adjacent to the clip arms. The foldable sheet may have two wide feature receiving indentations for receiving the wide features.

It is contemplated that the sterile hand wrap may have a forearm portion that may have least one forearm strap for wrapping around a patient's forearm. The forearm strap may have a forearm strap fastener.

In some embodiments, the sterile hand wrap may be sterilized by ultraviolet irradiation.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which:

FIG. 67B is a perspective view of the surgical arm positioning system of FIG. 61 from a different angle showing the latching mechanism of an internal pivot with a cover omitted;

FIG. 76A is a front elevation view of another embodiment of the sterile wrap of FIG. 28 showing labels for measurements of the sterile wrap;

FIG. 76B is a side elevation view of the sterile wrap of FIG. 76A showing labels for measurements of the sterile wrap;

FIG. 76C is a sectional view of the sterile wrap of FIG. 76A showing labels for measurements of the sterile wrap;

FIG. 81A is a top plan view of the sterile wrap and clip of FIG. 77 showing labels for measurements of the clip;

FIG. 81B is a sectional view of the sterile wrap and clip of FIG. 81;

FIG. 81C is a side elevation view of the sterile wrap and clip of FIG. 77 showing labels for measurements of the clip;

FIG. 88 is a side elevation view showing components of another embodiment of the shoulder distraction apparatus of FIG. 38 including a wheel bracket, a platform beneath the wheel bracket, and a brake foot to the right of both the wheel bracket and the platform;

DETAILED DESCRIPTION

Figure 1:
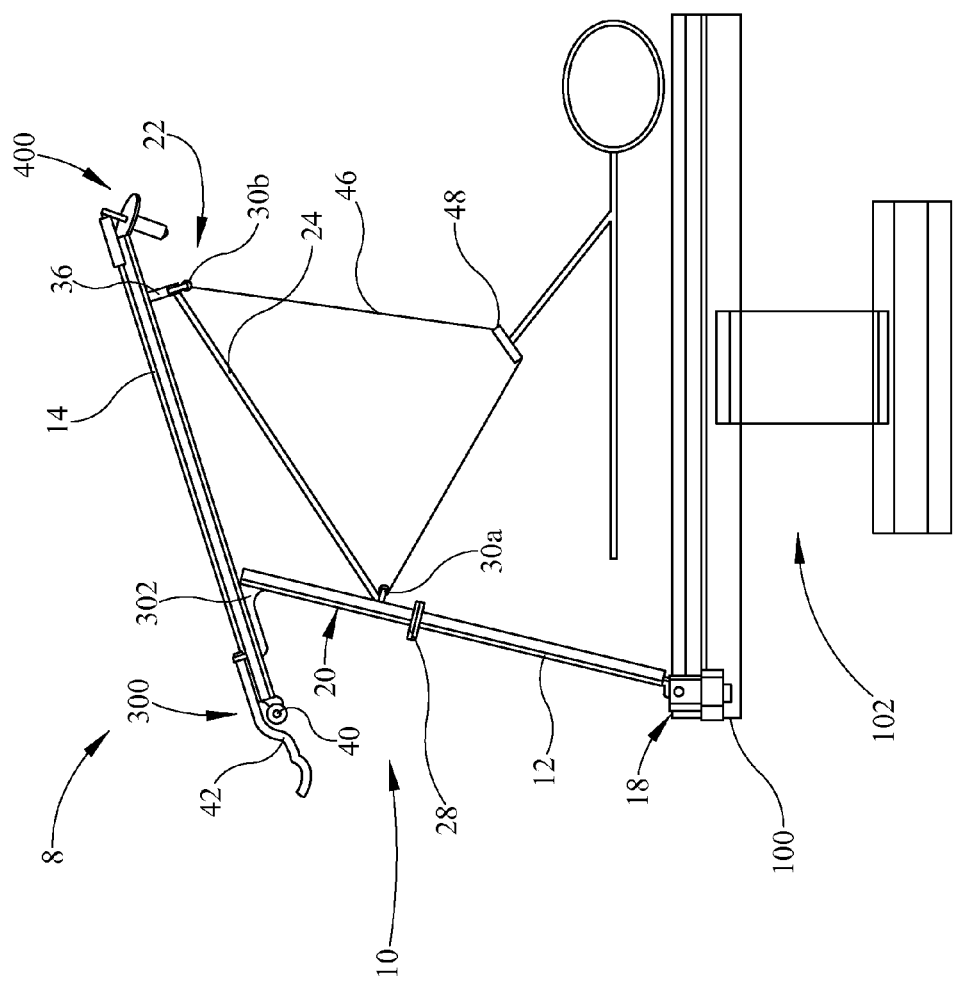
FIG. 1 is a side elevation view of a surgical arm positioning system showing a frame secured to an accessory rail of a surgical table by a semi-locked clamp assembly with a patient's arm supported by the surgical arm positioning system.

A surgical arm positioning system 8 mounted to a surgical table 102 is shown in FIG. 1. The surgical arm positioning system 8 is adapted to receive and position a patient's arm during surgery and includes a frame 10 (also referred to as a tower) with a lower pulley assembly 20, an upper pulley assembly 22, and a clutch assembly 300 coupled to the frame 10. A cable 46 is routed through the pulley assemblies 20 and 22 and the clutch assembly 300 and attached to a connection member 48 for attaching to the patient's arm.

The surgical arm positioning system 8 is configured to resist motion of the cable 46, thereby holding the arm in position across a range of abduction angles. However, by moving the patient's arm, an operator can overcome this resistance to motion. For example, the operator can grasp the patient's arm and move it from a first position having a first abduction angle 25, shown in FIG. 2A, to a second position having a second abduction angle 25', shown in FIG. 2B, and the cable 46 will move along a plurality of pulleys 30 in response to the movement. Upon releasing the arm in the second position, the system 8 sufficiently resists motion to once again stabilize the position of the arm. By adjusting the patient's arm by only making contact with the arm, the operator avoids touching non-sterile components of the system 8, thus maintaining sterility.

Figure 2A:
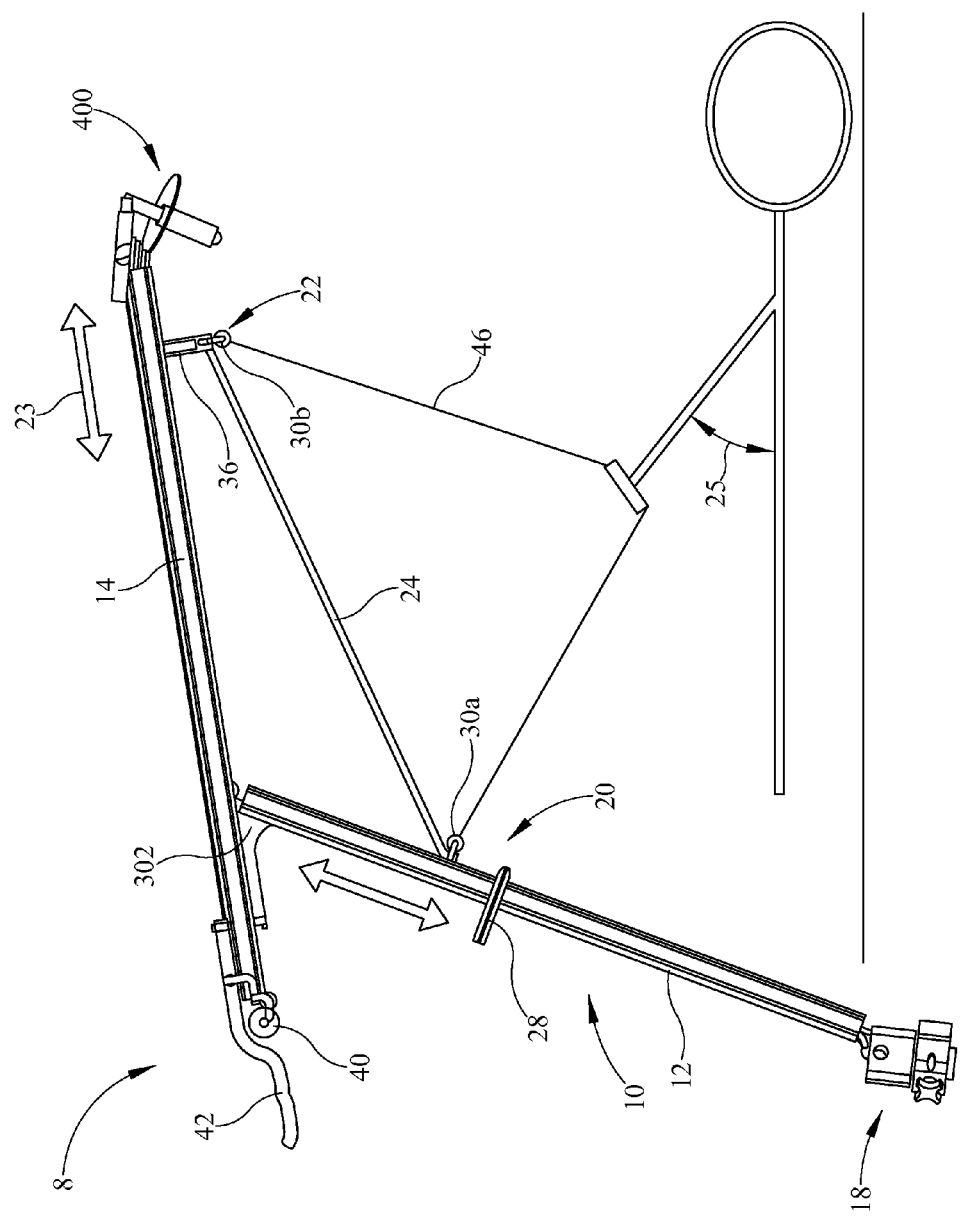
FIG. 2A is a side elevation view of the surgical arm positioning system of FIG. 1 including lower and upper pulley assemblies and a cable in a first position.
Figure 2B:
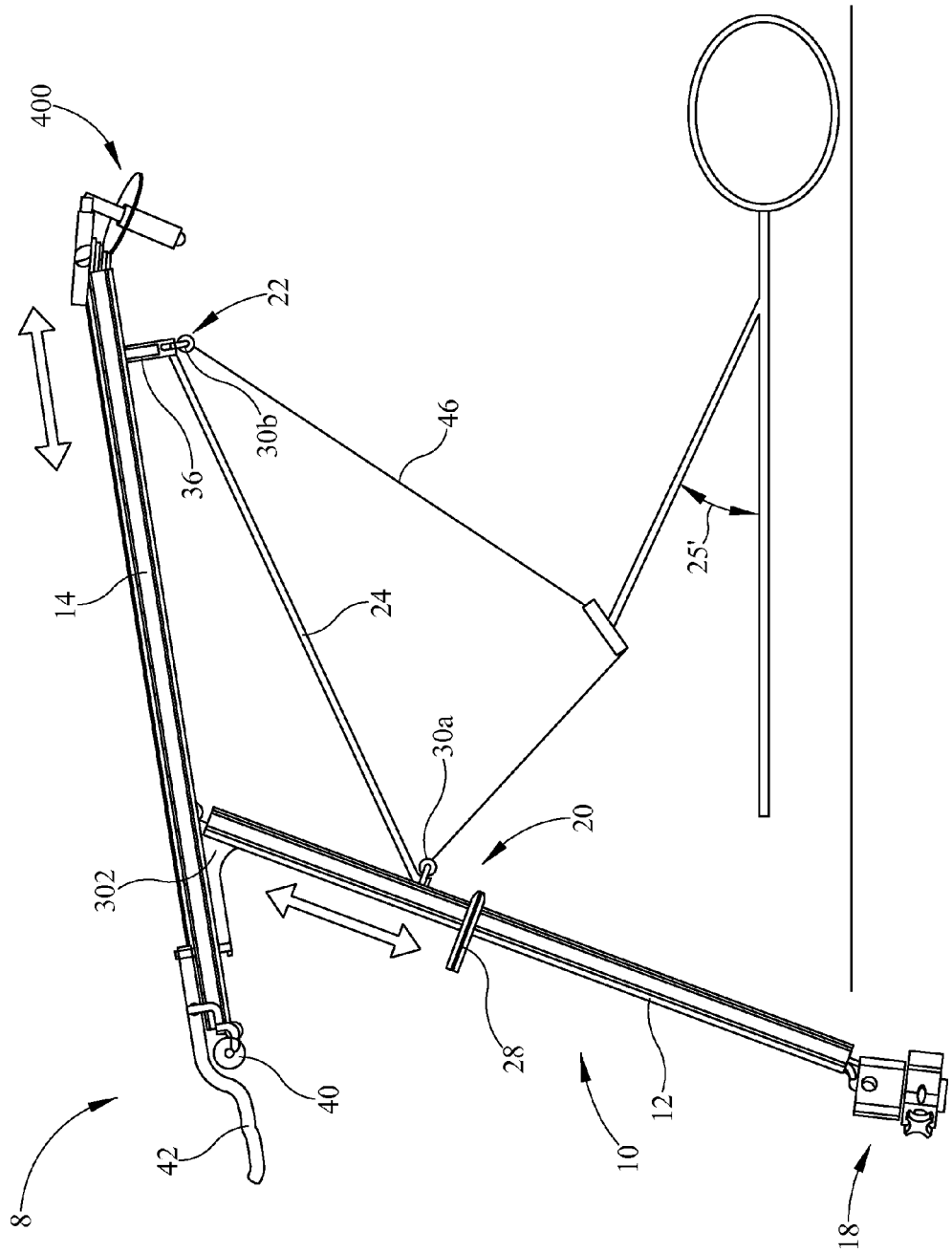
FIG. 2B is a side elevation view of the surgical arm positioning system of FIG. 1 including lower and upper pulley assemblies and a cable in a second position.
Figure 3:
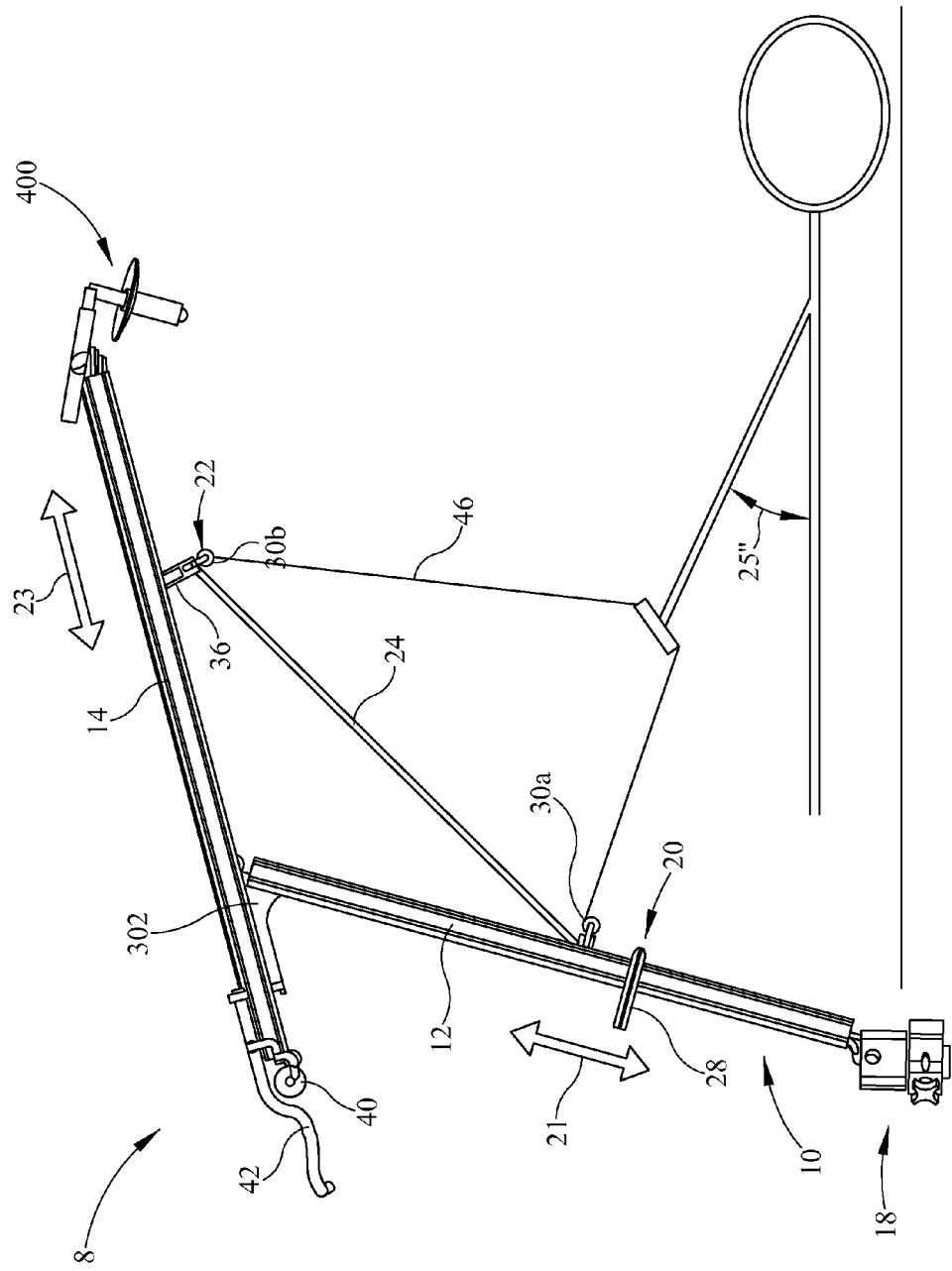
FIG. 3 is a side elevation view of the surgical arm positioning system of FIG. 2 showing the lower and upper pulley assemblies in a third position.

Additionally, referring to FIGS. 2A and 3, the lower and upper pulley assemblies 20 and 22 are adjustable along the frame 10 for access to further positions of the arm. For example, a patient's arm can be moved from the first position having the first abduction angle 25, shown in FIG. 2A to a third position having a third abduction angle 25", shown in FIG. 3, corresponding to movement of the pulley assemblies 20 and 22 along the directions of arrows 21 and 23, respectively. In some embodiments, the lower and upper pulley assemblies 20 and 22 may move in response to the operator moving the patient's arm and may hold the patient's arm in place due to friction between the pulley assemblies 20 and 22 and the frame 10. It is also contemplated that the lower and upper pulley assemblies may be moved by adjusting a handle 28. By combining the adjustability of the cable 46 and the pulley assemblies 22, the system 8 allows for a wide range of abduction angles. To allow for additional arm positions, the frame 10 is attached to the surgical table 100 by a rotatable clamp 18 that allows the frame 10 to pivot relative to the surgical table 102.

Figure 8:
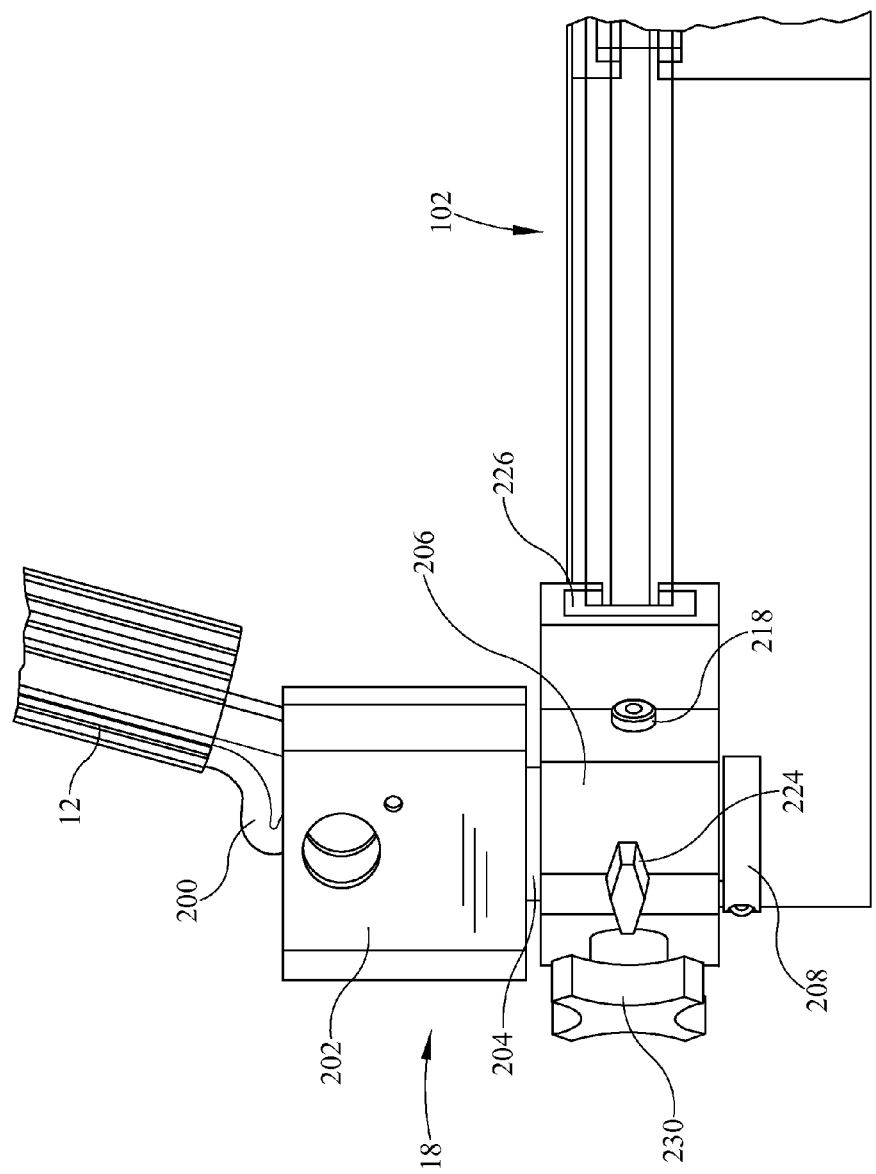
FIG. 8 is a perspective view of the semi-locked clamp assembly attached to the accessory rail of the surgical table and to a lower rod of the surgical arm positioning system of FIG. 1.
Figure 70:
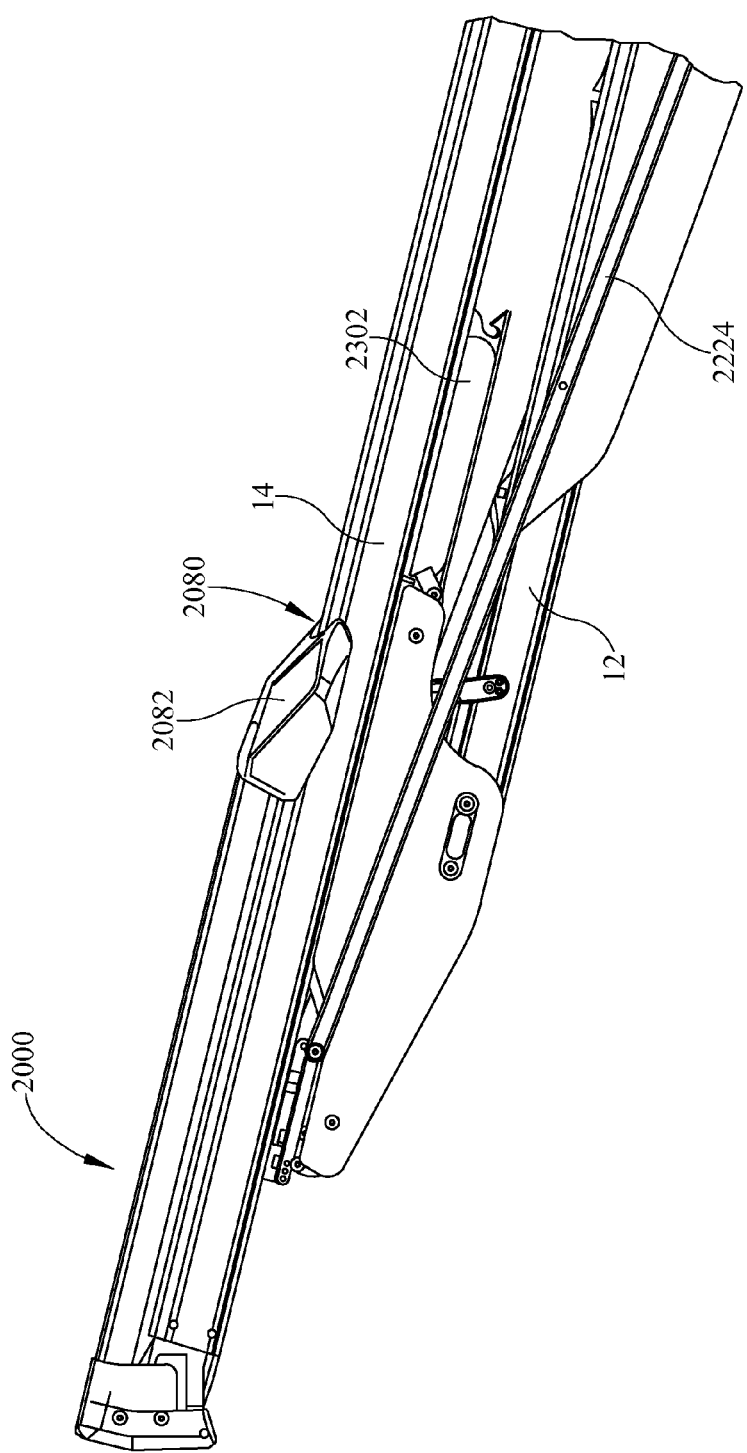
FIG. 70 is a partial perspective view of the surgical arm positioning system of FIG. 61 in a folded position.

As shown in FIG. 2A, the frame 10 includes a lower beam 12, an upper beam 14, an internal pivot 302 connecting the lower and upper beams 12 and 14, and a release handle 42. As will be described in further detail below, when the operator pulls the release handle 42, a locking mechanism in the internal pivot 302 releases, allowing the upper beam 14 to fold toward the lower beam 12. As shown in FIG. 70, the frame 10 may be folded for storage when the system 8 is not in use. Referring to FIG. 8, the lower rod 12 engages with a semi-locked clamp assembly 18 that clamps the frame 10 to the distal end 100 of a surgical table 102. In particular, semi-locked clamp assembly 18 attaches to an accessory rail 101 of the surgical table 102.

Figure 20:
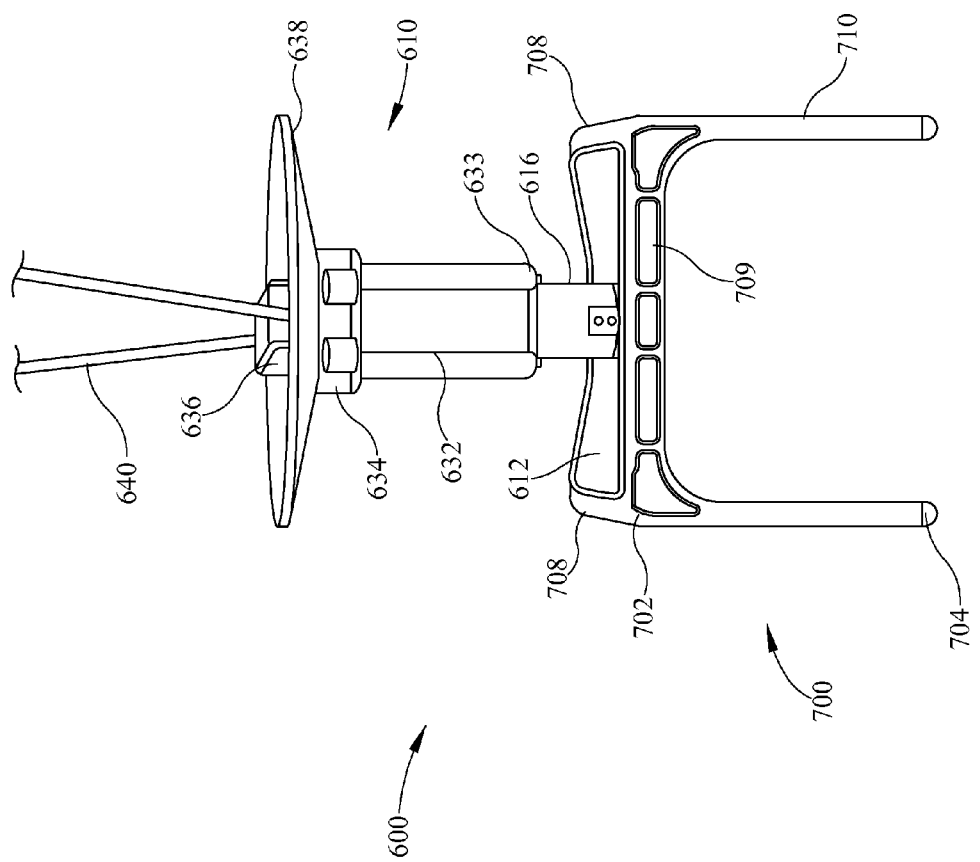
FIG. 20 is a perspective view of a sterile connection attached to a clip.
Figure 75:
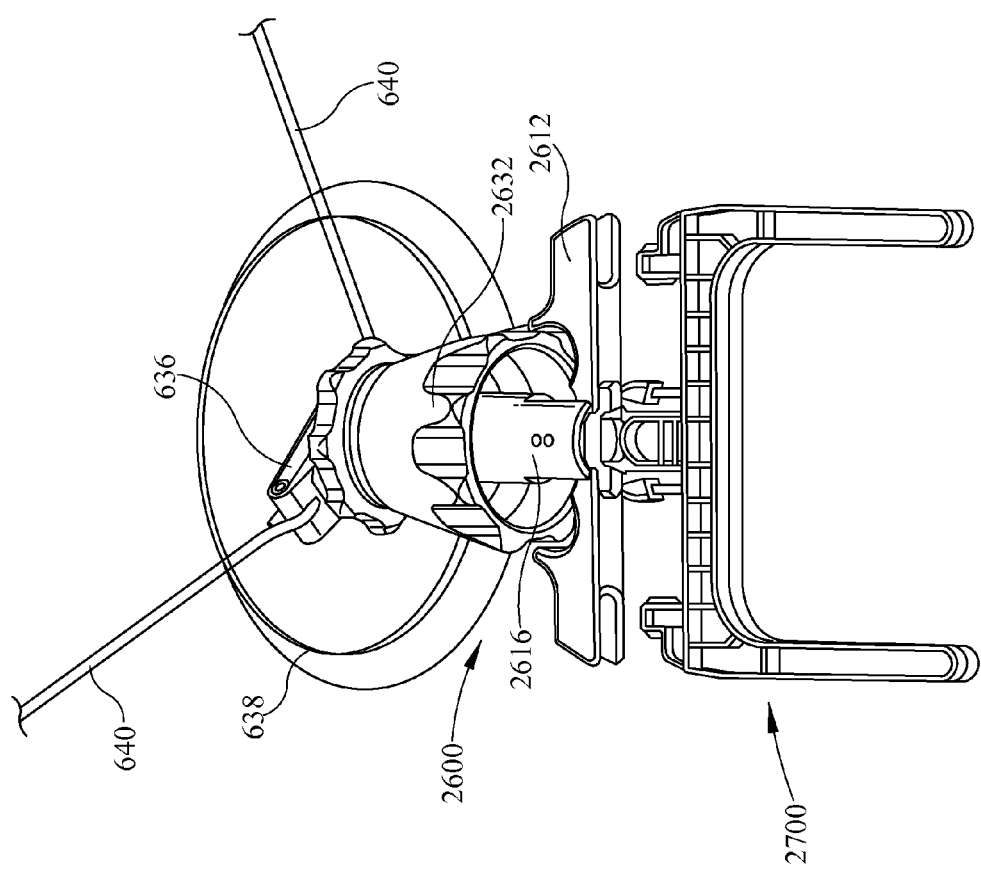
FIG. 75 is a perspective view of another embodiment of the sterile connection of FIG. 20 with a detached clip.

Referring now to FIG. 20, the connection member 48 is part of a sterile connection 600 configured to allow the operator to attach the patient's arm to the rest of the system 8 while maintaining sterility. The sterile connection 600 includes a receiving assembly 610 and a clip 700. The receiving assembly 610 attaches to the sterile connection member 48 and can be detached after use for sterilization, as shown in FIG. 75. In some embodiments, the clip receiving assembly 610 may be resistant to high temperatures so that it can be sterilized in an autoclave. A hand wrap 800, which is adapted to receive the patient's hand, is coupled to the clip 700, such as by sewing the hand wrap 800 onto the clip 700, as shown, for example, in FIG. 32. When the patient's hand is secured to the clip 700 by the hand wrap 800, the operator can attach the clip 700 to the clip receiving assembly 610 and, by extension, the rest of the surgical arm positioning system 8. Illustratively, the clip 700, hand wrap 800, or both may be made of inexpensive plastic materials and may be discarded after use.

Figure 14:
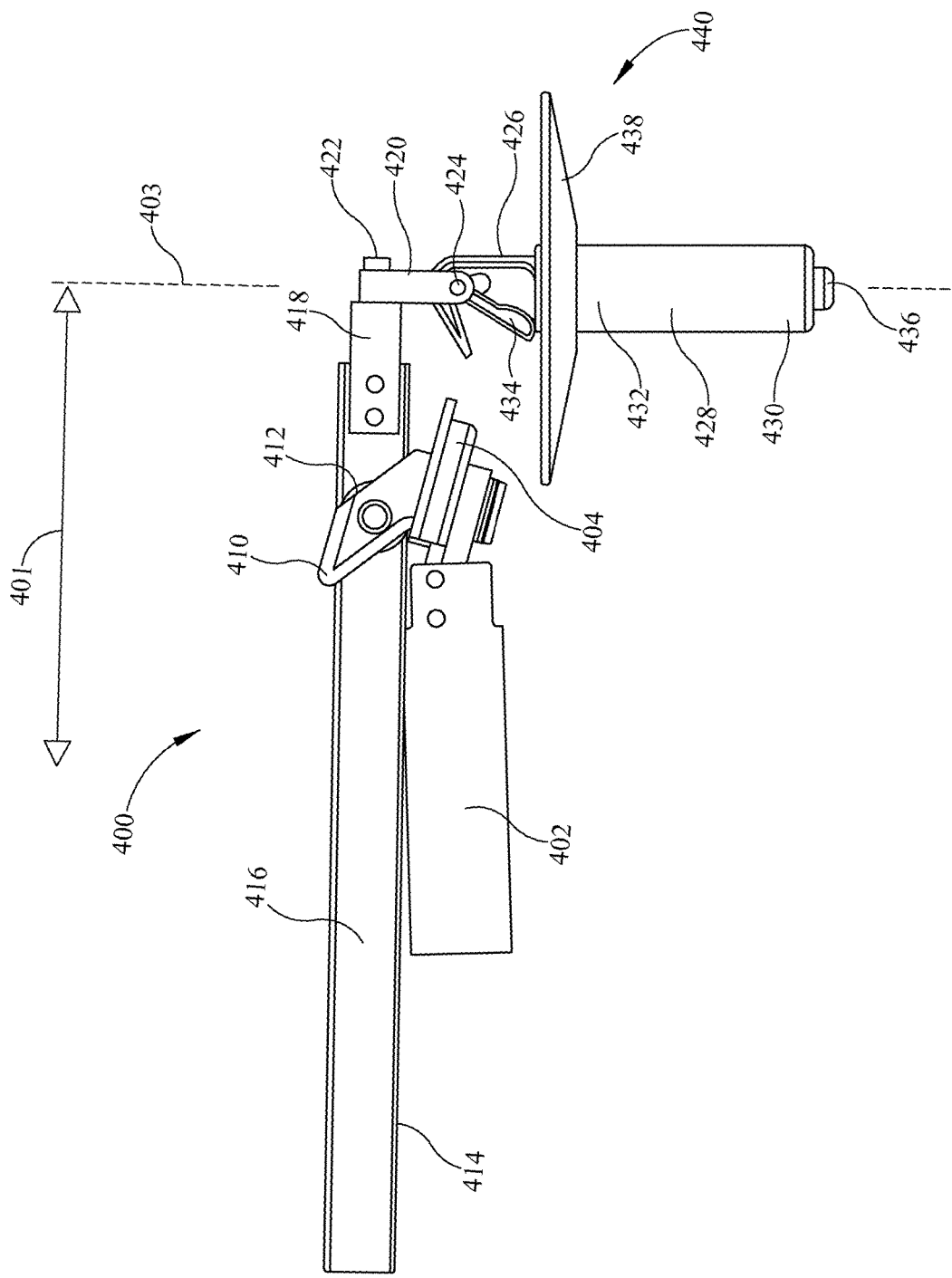
FIG. 14 is a side elevation view of a distraction apparatus for use with a lateral distractor strap.

Referring again to FIG. 1, the surgical arm positioning system 8 further includes a lateral traction system 400 coupled to the frame 10. As shown in FIG. 14, the lateral traction system 400 includes a hanger 436 and a lateral traction strap 500 (shown in FIG. 18) hanging from the hanger 436. The lateral traction strap 500 can form a loop around the patient's arm, for providing a lateral traction force to the arm during a surgical operation. Illustratively, the lateral traction strap 500 may be made of inexpensive plastic materials and may be discarded after use.

The surgical arm positioning system 8 described herein allows for non-discrete positioning of the patient's arm in the lateral decubitus position. Specifically, the surgical arm positioning system 8 allows for an expanded abduction range compared to previous towers while keeping traction forces relatively consistent throughout. The surgical arm positioning system 8 may be used in shoulder arthroscopy.

Additionally, the surgical arm positioning system 8 allows a sterile doctor to adjust a patient's arm directly within a range of motion without requiring non-sterile personnel to adjust non-sterile parts of the surgical arm positioning system 8. Specifically, the interaction between the operator and the surgical arm positioning system 8 does not require direct contact with the surgical arm positioning system 8.

Although several illustrative embodiments of the surgical arm positioning system 8 are described herein, it contemplated that various components of the various embodiments can be substituted for each other when, for example, the components have similar functions.

Figure 11:
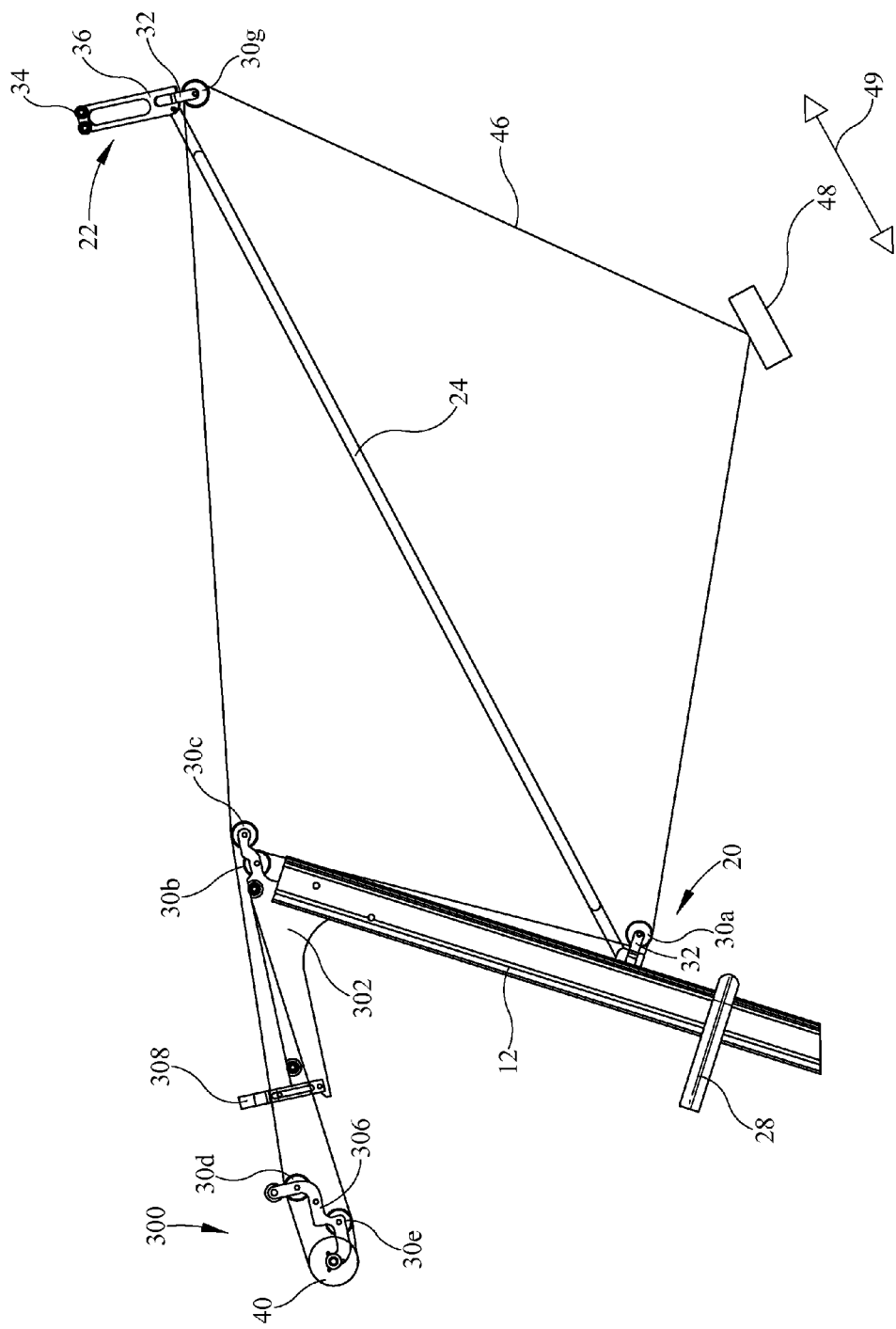
FIG. 11 is a side elevation view of the surgical arm positioning system of FIG. 1 showing a cable trained around the pulleys of the surgical arm positioning system with an upper rod of the frame being omitted and a handle and a handle pin lever of the internal pulley assembly of FIG. 7 being omitted.
Figure 12:
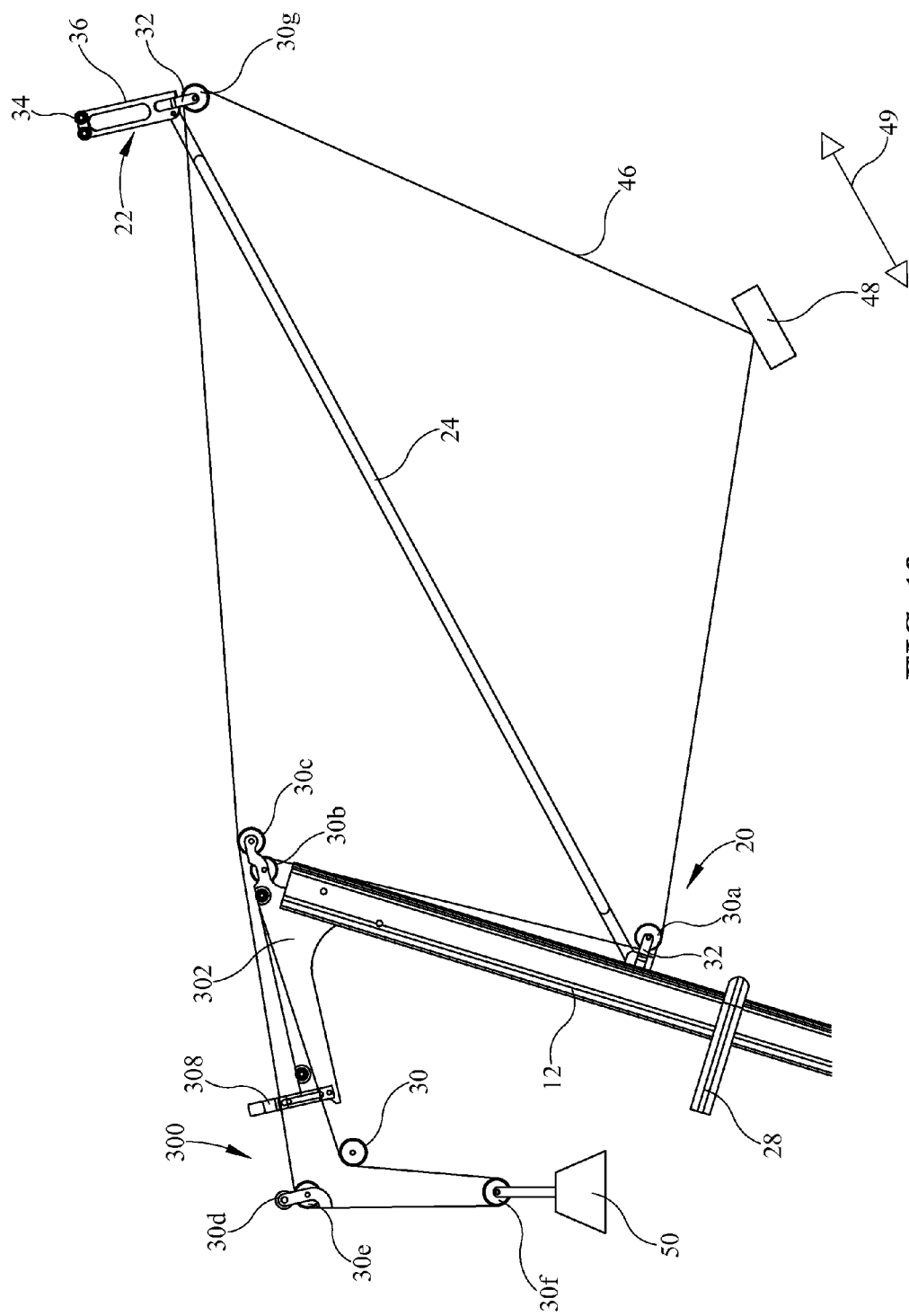
FIG. 12 is a side elevation view of a surgical arm positioning system, similar to FIG. 11, showing the surgical arm positioning system having a weight attached to the cable.

Referring now to FIGS. 11 and 12, two ends of the cable 46 are attached to the connection member 48. When the connection member 48 is moved along the direction of arrow 49, corresponding to changes in the abduction angle 25 of the patient's arm (shown in FIGS. 2A, 2B, and 3), the cable 46 moves along a plurality of pulleys 30 and one or more clutch pulleys 40. The cable 46 and connection member 48 define a continuous loop around the free pulleys 30 and the internal clutch pulley 40. The pulleys 30 and 40 route the cable 46 and allow for both motion control and force transfer. Starting at the connection member 48, the cable 46 is routed through the lower pulley assembly 20, the internal pivot 302, the clutch assembly 300, optionally a weight 50 having a pulley 30 (shown in FIG. 12), the internal pivot 302 again, and the upper pulley assembly 22, before returning back to the connection member 48 to form a loop.

Figure 5:
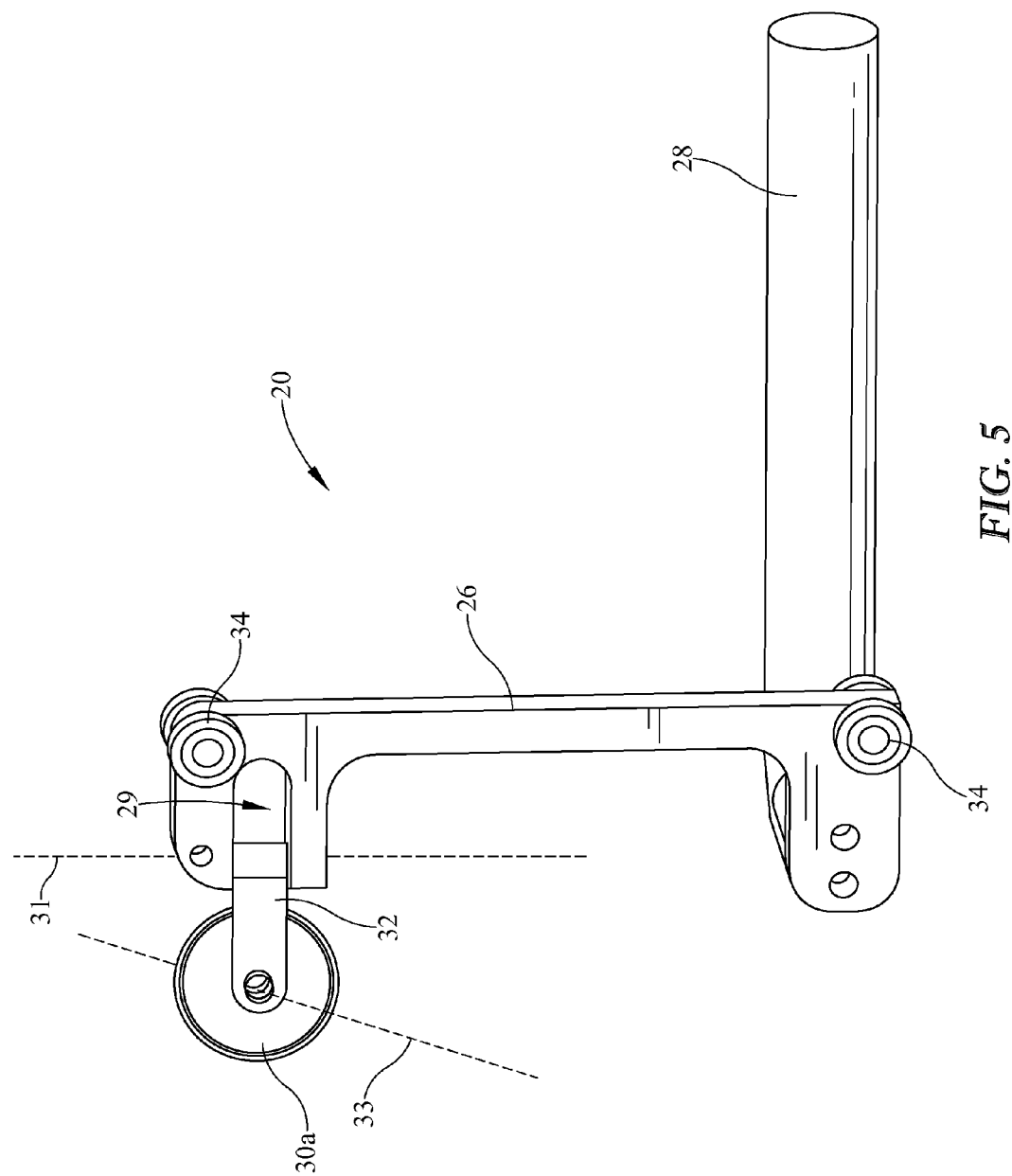
FIG. 5 is a perspective view of the lower pulley assembly.

The lower pulley assembly 20 includes a sled body 26, a pulley swinger 32, a pulley 30a attached to the pulley swinger 32, and four wheels 34 attached to the sled body 26, as shown in FIG. 5. The sled body 26 includes a gap 29 sized to receive the pulley swinger 32. Opposite the pulley 30a, the pulley swinger 32 includes an aperture (not shown). A pivot pin (not shown) extends across the gap 29 of the sled body 26, through the aperture of the pulley swinger 32, so that the pulley swinger 32 is free to pivot about a first axis 31. The pulley 30a rotates about a second axis 33 that is perpendicular to the first axis 31. As shown in FIG. 11, the cable 46 passes along the pulley 30a proximal to the sled body 26. Referring to FIG. 1, when the patient's arm 6 moves into or out of the plane of the surgical arm positioning system 8, such flexion or extension when the patient is on his or her side, the pulley swinger 32 pivots about the first axis 31 in response.

Figure 7:
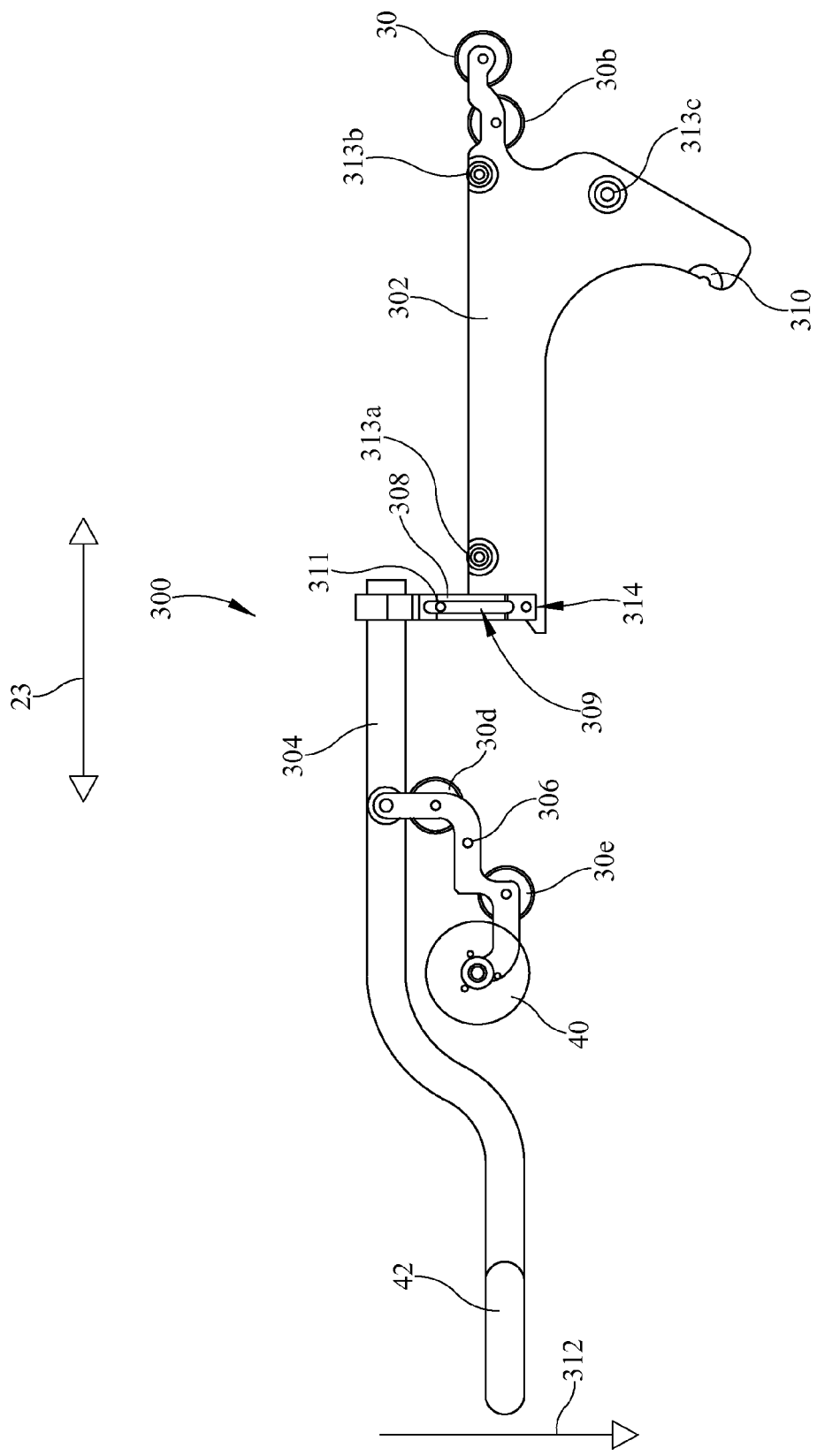
FIG. 7 is a side elevation view of an internal pulley assembly.

Referring now to FIG. 7, two pulleys 30b and 30c are attached to the internal pivot 302. After passing through the lower pulley assembly 20, the cable 46 passes along pulley 30b, distal to the internal pivot 302, before reaching the clutch assembly 300. The clutch assembly 300 includes a rear pulley mount 306 having two pulleys 30d and 30e and a clutch pulley 40 attached thereto. The internal clutch pulley 40 is commercially available from Dynatect Manufacturing, Inc. of New Berlin, Wis. as Part No. EFO16-4. As shown in FIG. 11, the cable 46 passes along pulley 30e, distal to pulley 30d, followed by the clutch pulley 40. In some embodiments, the cable 46 may wrap around the clutch pulley 40 one time or multiples times, such as two, three, or four times. Embodiments having cable 46 only partially wrapped (e.g., less than) 360° around one or more of pulleys 30, 40 are also within the scope of this disclosure. After passing along, and possibly wrapping around the clutch pulley 40, the cable 46 passes along pulley 30d, distal to 30e and continues past pulley 30c, distal to pulley 30b, to the upper pulley bracket 22.

Movement of the cable 46 is restricted by the application of a resistive torque created by the internal clutch pulley 40. This tensile resistance is sufficient to resist motion of the cable 46, thereby holding the arm in position across a range of abduction angles. However, by moving the patient's arm, an operator can overcome this resistance to motion. After adjusting the position of the patient's arm, the resistance of cable 46 is sufficient that the cable 46 and pulleys 30, 40 reach a state of equilibrium and the patient's arm is held in place. The resistive torque of the internal clutch pulley 40 and other resistance to movement of the cable 46 allows the system to achieve equilibrium in a consistent manner across a wider range of abduction angles, within a given envelope of movement, as compared to prior art systems. Illustratively, due to inclusion of internal clutch pulley 40 in the surgical arm positioning system 8, about 30 degrees of adjustability of arm abduction is possible. This is an improvement over systems that have no internal clutch pulley 40 or other resistance member in which only about 10 degrees of adjustability of arm abduction may be possible. This range of adjustability is independent of the movement of other components of the surgical arm positioning system, which may further extend the range of adjustability.

In some embodiments, the internal clutch pulley 40 may be replaced by a weight with one or more pulleys 30f attached thereto, as shown in FIG. 12. It is contemplated that the weight may be an adjustable weight system 1500, as discussed in further detail below. Embodiments having one or more internal clutch pulleys 40 and the weight 50 are also within the scope of the present disclosure.

One skilled in the art will appreciate that the surgical arm positioning system may include any number of internal clutch pulleys 40 and free pulleys 30 capable of restricting movement of cable 46 to a desired extent. Thus, in some embodiments, more than one internal clutch pulley 40 is used. In other embodiments, free pulleys 30 may be used without the use of an internal clutch pulley 40.

Figure 6:
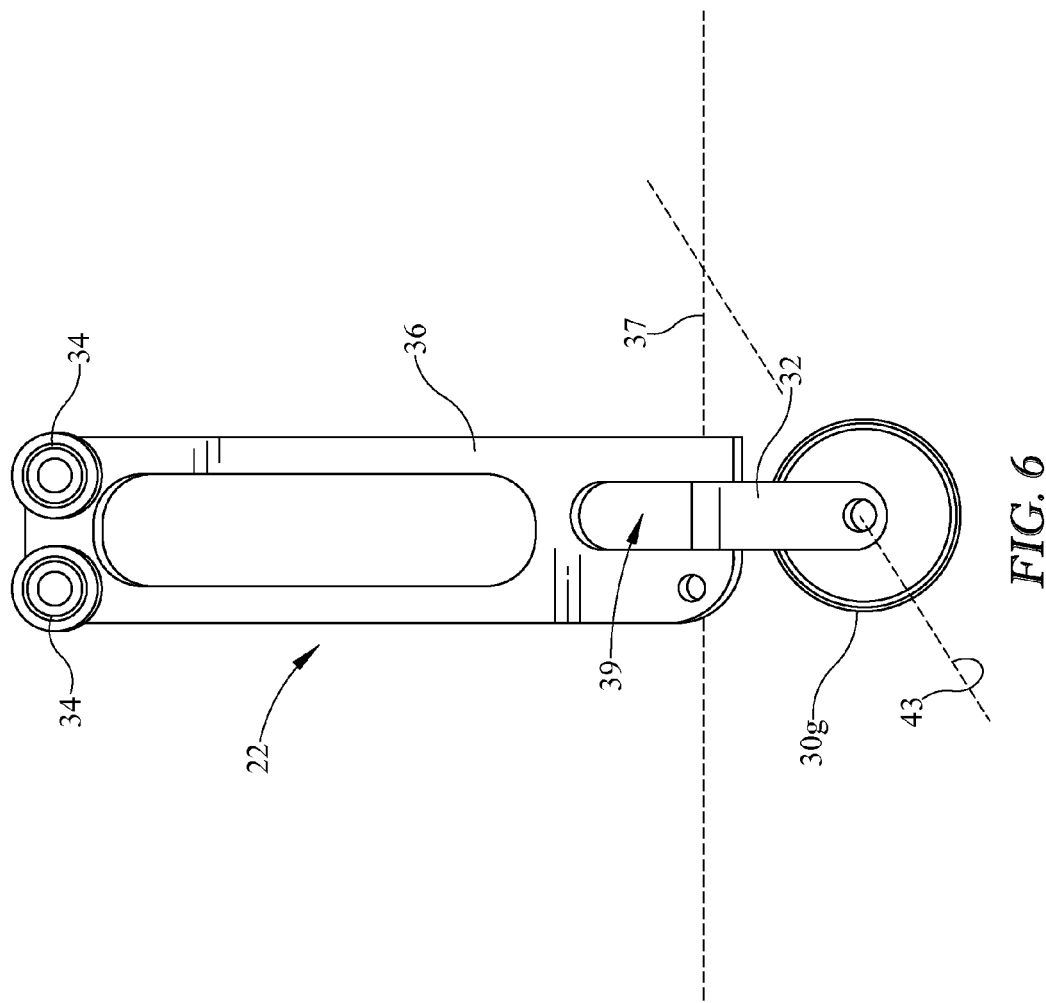
FIG. 6 is a side elevation view of the upper pulley assembly.

Referring now to FIG. 6, the upper pulley assembly 22 includes a sled body 36, a pulley swinger 32, a pulley 30f attached to the pulley swinger 32, and four wheels 34 attached to the sled body 36. The sled body 26 includes a gap 39 sized to receive the pulley swinger 32. Opposite the pulley 30a, the pulley swinger 32 includes an aperture (not shown). A pivot pin (not shown) extends across the gap 39 of the sled body 36, through the aperture of the pulley swinger 32, so that the pulley swinger 32 is free to pivot about a first axis 37. The pulley 30g rotates about a second axis 43 that is perpendicular to the axis 37. As shown in FIG. 11, the cable 46 passes along the pulley 30g proximal to the sled body 36. Referring to FIG. 1, when the patient's arm 6 is moves into or out of the plane of the surgical arm positioning system 8, such flexion or extension when the patient is on his or her side, the pulley swinger 32 pivots about the first axis 37 in response. After passing along pulley 30g, the cable 46 reaches the connection member 48.

The surgical arm positioning system 8 is configured such that the cable 46 forms an angle between 120 and 180 degrees at connection member 48. In some embodiments, the angle is between about 120 and about 180 degrees. In further embodiments, the angle is about 110, about 115, about 120, about 125, about 130, about 135, about 140, about 145, about 150, about 155, or about 160 degrees. One skilled in the art will appreciate that the surgical arm positioning system 8 may be configured such that the cable forms a variety of angles and is not limited to the angles recited herein. Accordingly, any angle that creates a force vector such that the tensile force in the cable 46 is transferred to the arm of a patient is within the scope of the present disclosure.

The connection member 48 may be attached directly or indirectly to a patient's arm. In some embodiments, the connection member 48 includes, or is configured to receive, a hand grip. When the patient's arm is attached to connection member 48, the cable 46 is under constant tension due to at least the weight of the patient's arm, the system reaches a state of equilibrium, and the patient's arm is held in place. Accordingly, the cable 46 is configured in a manner to apply a traction force to the patient's arm. Details of connection member 48 and the associated hand grip can be found below.

Referring again to FIGS. 2A, 2B, and 3, the lower pulley assembly 20 is connected to the lower rod 12 and an upper pulley assembly 22 is connected to the upper rod 14 such that the lower and upper pulley assemblies 20 and 22 can move about the lower and upper rods 12 and 14, respectively. The lower pulley assembly 20 and upper pulley assembly 22 are linked by a connecting rod 24 such that movement of the lower pulley assembly 20 or the upper pulley assembly 22 results in movement of the other. The connecting rod 24 maintains a consistent distance between assemblies 20 and 22 as they move along respective rods 12 and 14. As the lower and upper pulley assemblies 20 and 22 are moved along the frame 10, the connecting rod 24 pivots at its points of attachment to the lower and upper pulley assemblies 20 and 22. It is to be appreciated that in some embodiments two or more connecting rods may extend between assemblies 20 and 22.

Figure 4:
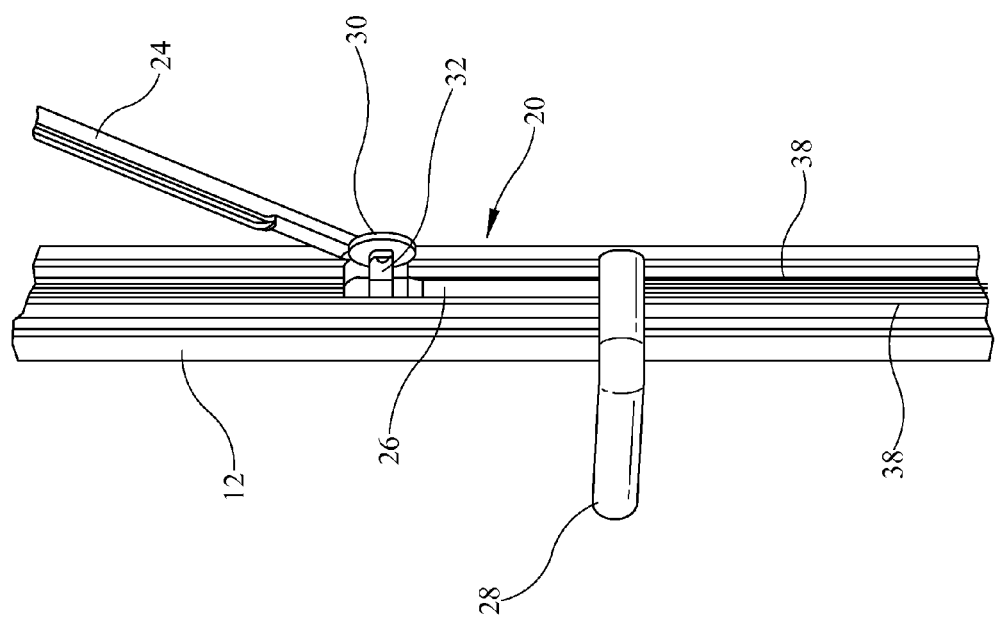
FIG. 4 is a perspective view of the surgical arm positioning system of FIG. 1 showing a lower rod with the lower pulley assembly attached to the lower rod.

The lower rod 12 and the upper rod 14 include rails 38 as shown in FIG. 4 with regard to lower rod 12. In some embodiments, the lower and upper rods 12 and 14 are extrusions having cutout portions resulting in the rails 38. The rails 38 of lower rod 12 interact with the lower pulley assembly 20 such that the wheels 34 are held within lower rod 12 by the rails 38 and the lower pulley assembly 20 can move along the length of lower rod 12. Similarly, the rails 38 of upper rod 14 interact with the upper pulley assembly 22 such that the wheels 34 are held within upper rod 14 by the rails 38 and the upper pulley assembly 22 can move along the length of upper rod 14.

Still referring to FIG. 4, the lower pulley assembly 20 and the upper pulley assembly 22 can be adjusted by a handle 28. For example, the caregiver or clinician can grip the handle 28 when making the adjustments in the positions of lower and upper pulley assemblies 20 and 22.

In further embodiments, the lower pulley assembly 20 and the upper pulley assembly 22 may be adjusted by moving the patient's arm directly. The surgical arm positioning system 8 responds to movement of the patient's arm without the operator contacting the system 8. Illustratively, movement of the lower pulley assembly 20 and the upper pulley assembly 22, may be resisted to an extent such that when the patient's arm is attached, the resistance is sufficiently weak to be overcome by a clinician to change the position of the lower pulley assembly 20 and the upper pulley assembly 22 as shown in FIGS. 2A and 3 and thus adjust the patient's arm. After adjusting the arm, the resistance is sufficient that the lower pulley assembly 20 and the upper pulley assembly 22 reach a state of equilibrium and the patient's arm is held in place. The adjustment is made in one motion, with both the lower pulley assembly 20 and the upper pulley assembly 22 moving together.

By linking the movement of the lower pulley assembly 20 and the upper pulley assembly 22, along lower rod 12 and upper rod 14, respectively, the surgical arm positioning system allows for a broader range of arm abduction angles compared to allowing the pulley assemblies 20 and 22 to move independent of each other. As shown in FIGS. 2A and 3, when pulley assemblies 20, 22 are attached and move along the lower rod 12 and the upper rod 14, respectively, the angle formed at the connection member 48 by the ends of the cable 46 is constant compared to the assemblies moving independent of each other, allowing the system 8 to maintain a relatively consistent force vector over a broader range of motion.

The broad range of adjustability of arm abduction angles 25 (shown in FIG. 2A) associated with linking the movement of the lower pulley assembly 20 and the upper pulley assembly 22 expands upon the broader range of adjustability of arm abduction angles associated with resistive motion of the continuous loop defined by the cable 46 and connection member 48. The combination of both adjustment mechanisms allows the overall arm abduction range of the surgical arm positioning system to be expanded while keeping traction forces to the patient's arm relatively consistent. Similarly, allowing the lower pulley assembly 20 and the upper pulley assembly 22 to move along lower and upper rods 12 and 14, respectively, results in the surgical arm positioning system 8 maintaining a relatively consistent force vector over this expanded abduction range. The force vector decreases at the center of an expanded range created by the loop defined by the cable 46 and connection member 48 when the lower pulley assembly 20 and the upper pulley assembly 22 are fixed. For example, an abduction range of about 60 degrees can split into at least two ranges of about 30 degrees by movement of the lower pulley assembly 20 and the upper pulley assembly 22.

Referring now to FIG. 8, the lower beam 12 is attached to the surgical table 102 by the locked clamp assembly 18. In particular, semi-locked clamp assembly 18 is attached to an accessory rail 101 of the surgical table 102. The semi-locked clamp assembly 18 allows for adjustments to arm flexion angle during lateral decubitus shoulder procedures. When adjustments are desired, the lower rod 12 may pivot to rotate the frame 10 to allow for changes in arm flexion. When the frame 10 rotates, the pulley swingers 32 of the lower and upper pulley assemblies 20 and 22 allow the pulleys 30a and 30g to swing in response. This swinging prevents strain on the pulleys 30a and 30g and keeps traction forces on a patient's arm relatively consistent throughout rotation of frame 10.

Figure 9:
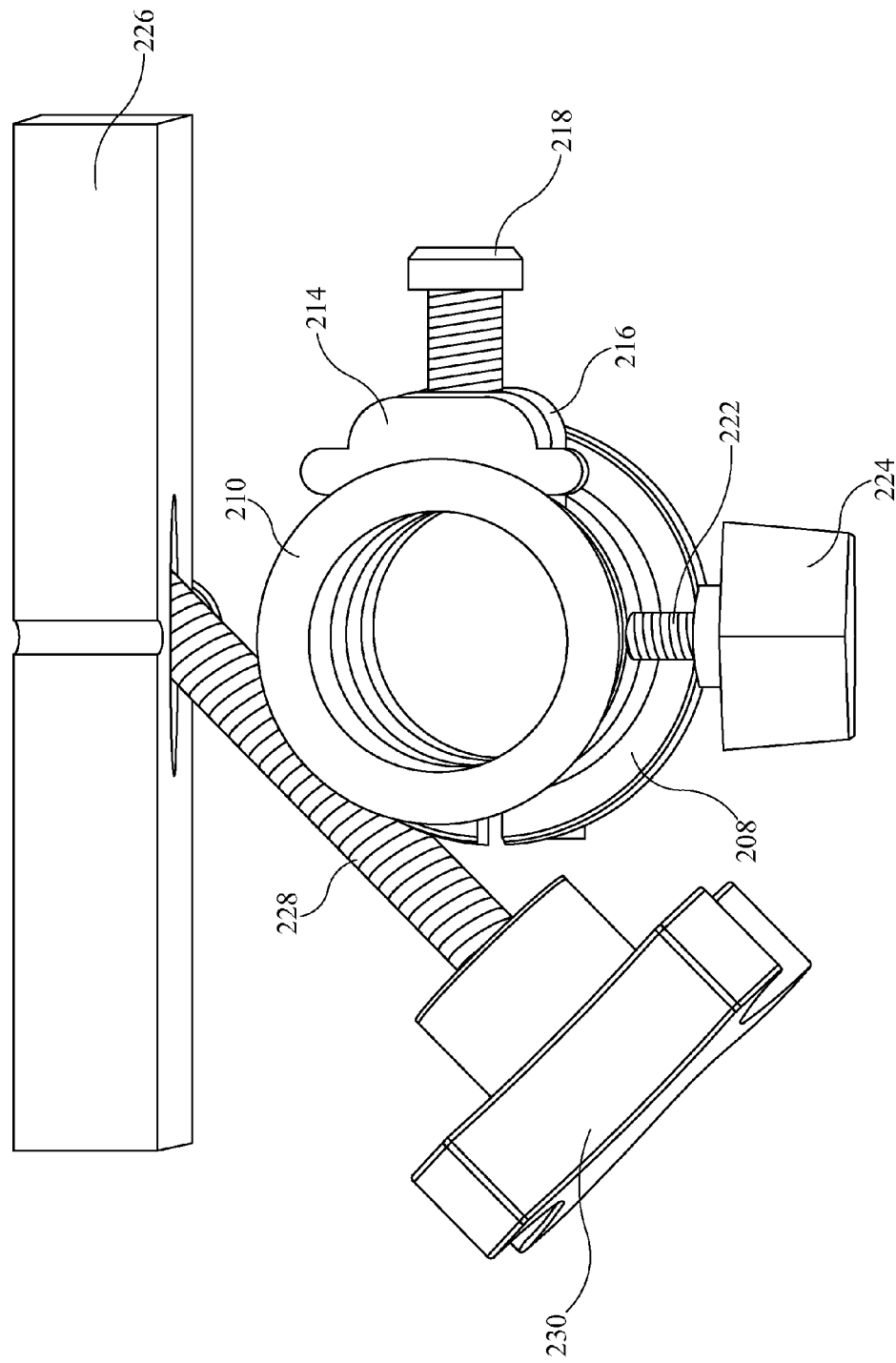
FIG. 9 is a perspective view of internal components of the semi-locked clamp assembly of FIG. 8 with a clamp body of the semi-locked clamp assembly omitted.
Figure 10:
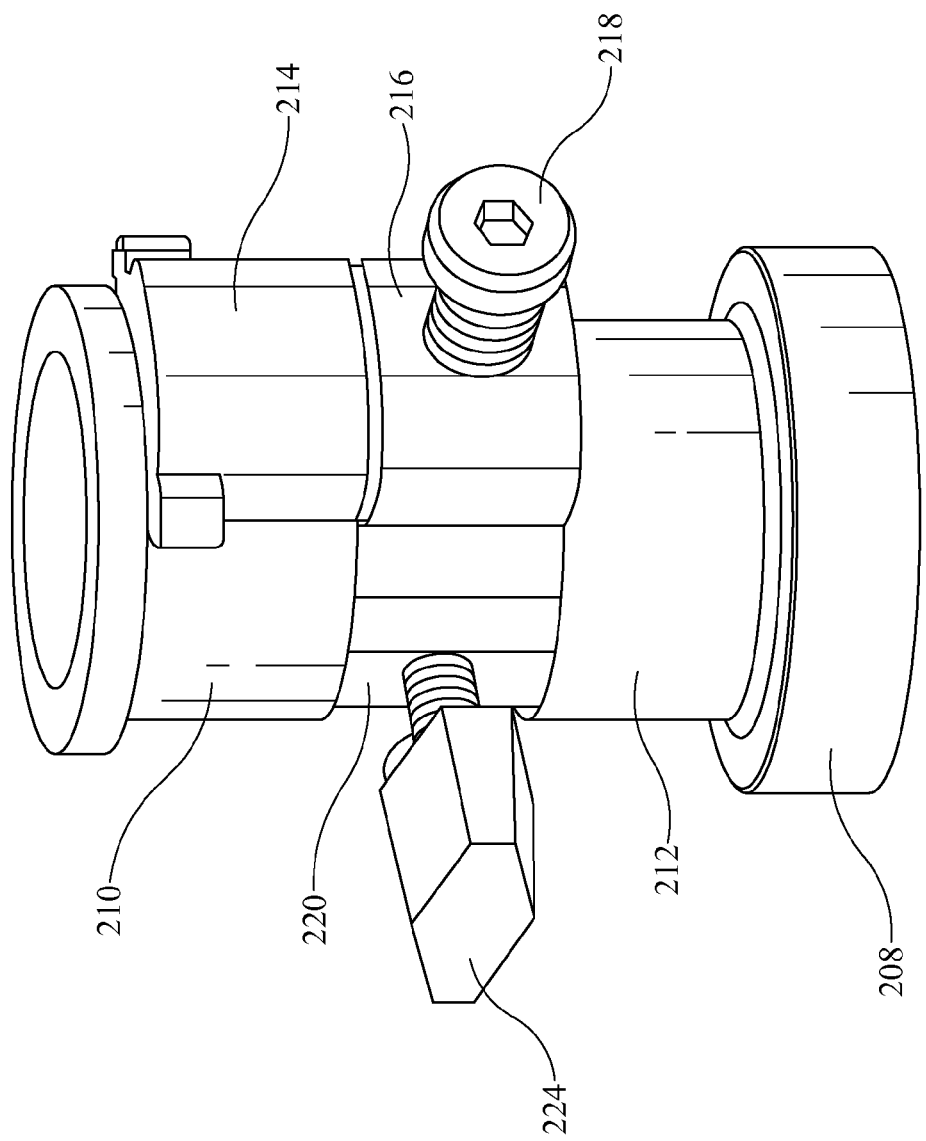
FIG. 10 is a perspective view of the internal components of FIG. 9 as viewed from another angle.

The semi-locked clamp assembly 18 shown in FIGS. 8-10 includes a hook 200 extending downwardly from an interior of lower rod 12. The hook 200 is inserted into a base sleeve 202 having a tube 204 protruding therefrom. The tube 204 is positioned in the interior of a clamp body 206. An end of the tube 204 is engaged by a bottom collar 208 to retain the tube 204 in the clamp body 206.

The tube 204 is engaged by a flange bearing 210 and a sleeve bearing 212 which are both shown in FIGS. 9 and 10. The bottom collar 208 is of sufficient diameter to prevent the sleeve bearing 212 from sliding off of the tube 204. Flange bearing 210 is in contact with a top block 214 that is in contact with a press 216. The press 216 is in contact with a side bolt 218 that is threaded through clamp body 206 such that rotation of the side bolt 218 applies pressure to the press 216. Rotation of tube 204 and, by extension, upper rod 14 relative to the clamp body 206 may be semi-locked due to friction between the press 216 and the tube 204. "Semi-locked" as used herein, including in the claims, means capable of moving when adjusted by an operator but resisting movement such that the frame 10 does not rotate when the system 8 is in use with a patient. The side bolt 218 is tuned to create a desired resistance to rotation of tube 204. In some embodiments, side bolt 218 is adjusted to create a predetermined resistance to rotation.

A brake 220 is located between the flange bearing 210 and the sleeve bearing 212 and is in contact with a lock bolt 222 attached to a lock knob 224 as shown in FIG. 12. The lock bolt 222 is threaded through clamp body 206 such that rotation of the lock knob 224 and thus, the lock bolt 222, applies pressure to the brake 220. Rotation of tube 204 and, by extension, upper rod 14, relative to the clamp body 206 may be locked due to friction between the brake 220 and the tube 204.

The clamp body 206 is adapted to receive the flange bearing 210, the sleeve bearing 212, the top block 214, the press 216, the brake 220, and the tube 204 such that movement of the tube 204 relative to the clamp body 206 is restricted to rotational movement. Clamp body 206 is fixed to a rail attachment 226. A rail bolt 228 attached to a rail knob 230 is threaded within the clamp body 206 such that the rail bolt 228 penetrates the rail attachment 226 and contacts the accessory rail 101 of surgical table 102. Rotation of the rail knob 230 secures the surgical arm positioning system 8 to the accessory rail 101 of surgical table 102.

Illustratively, movement of the tube 204 may be resisted by press 216 to an extent such that when a patient's arm is attached, the resistance is sufficiently weak to be overcome by a clinician to change the position of the tube 204 and by extension lower rod 12 and upper rod 14 relative to the clamp body 206 and thus, adjust the patient's arm. After adjusting the arm, the resistance due to press 216 is sufficient that the tube 204 reaches a state of equilibrium and the patient's arm is held in place.

In some embodiments, the frame 10 may be rotated by the handle 52 as shown in FIG. 1. In further embodiments, the frame 10 may be rotated by moving the patient's arm directly. The surgical arm positioning system 8 responds to movement of the patient's arm without direct contact from its operator. Thus, a surgeon or surgeon's assistant does not need to touch the mechanical components of frame 10 that would result in a break in the sterile field in order to reposition the patient's arm.

The combination of the rotation mechanism with the other adjustment mechanisms described herein allows the overall arm abduction range of the surgical arm positioning system 8 to be expanded while keeping traction forces relatively consistent throughout. This combination allows the surgical arm positioning system 8 to respond to movement of the patient's arm without direct contact from its operator.

Figure 13:
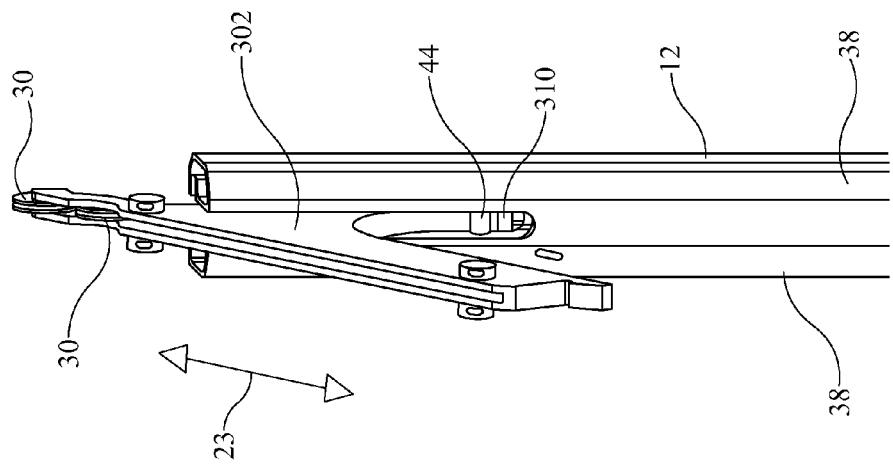
FIG. 13 is a perspective view of the surgical arm positioning system of FIG. 1 showing a latching mechanism that is releasable for folding the surgical arm positioning system.

When not in use, the surgical arm positioning system 8 folds into a more compact form. The internal pulley assembly 300, shown in FIG. 7, is positioned in the interior of upper rod 14 and is configured to prevent the upper rod 14 from collapsing toward the lower rod 12, until the operator pulls the handle 42. The internal pulley assembly 300 includes an internal pivot 302, a handle pin lever 304 connected to the handle 42, a slot lifter 308, and the rear pulley mount 306. The internal pivot 302 has three pairs of wheels 313a, 313b, and 313c. Referring to FIGS. 7 and 13, wheels 313a and 313b are engaged by the rails 38 of the upper rod 14 and wheel 313c is engaged by the rails 38 of the lower rod 12, similar to the way that the lower and upper pulley assemblies 20 and 22 are engaged by the rails 38. Still referring to FIG. 13, the internal pivot 302 has a first latch 310 that engages a pin 44 of the lower rod 12 to prevent the internal pivot 302 from falling toward the lower rod 12. Additionally, the internal pivot 302 has a second latch 314 engaged by the slot lifter 308 to prevent the upper rod 14 from moving along wheels 313a and 313b relative to the internal pivot 302. As such, the internal pivot 302 holds the lower and upper rods 12 and 14 at a fixed angle.

When the operator pulls the release handle 42 in the direction indicated by arrow 312, the resulting motion moves the handle pin lever 304 and slot lifter 308 in a direction opposite arrow 312. The slot lifter 308 has a guide slot 309 that receives a guide pin 311. As the slot lifter 308 moves opposite arrow 312, it disengages from the second latch 314 of the internal pivot 302, freeing the upper rod 14 to move in the direction of arrow 23, distal to the patient. Referring again to FIGS. 7 and 13, as the upper rod 14 retracts, it eventually causes the internal pivot 302 to pivot about wheel 313c, thus disengaging the first latch 310 from the pin 44. The upper rod 14 can continue to retract and rotate into a position substantially parallel to the lower rod 12. When the lower and upper rods 12 and 14 are substantially parallel, the system 8 is in a folded position for transport and storage.

Referring again to FIG. 1, in a second embodiment of the instant disclosure of the surgical arm positioning system 8, several components attached to frame 10 are substituted by functionally similar components. Starting at the connection member 48, the cable 46 is routed through a pulley carriage 1220 (shown in FIGS. 45-47), an internal pivot 1302 (shown in FIGS. 48 and 54), a clutch assembly 1300 (shown in FIGS. 48 and 54), a weight assembly 1500 (shown in FIGS. 52 and 53), the internal pivot 1302 again, and another pulley carriage 1220, before returning back to the connection member 48 to form a loop.

Figure 45:
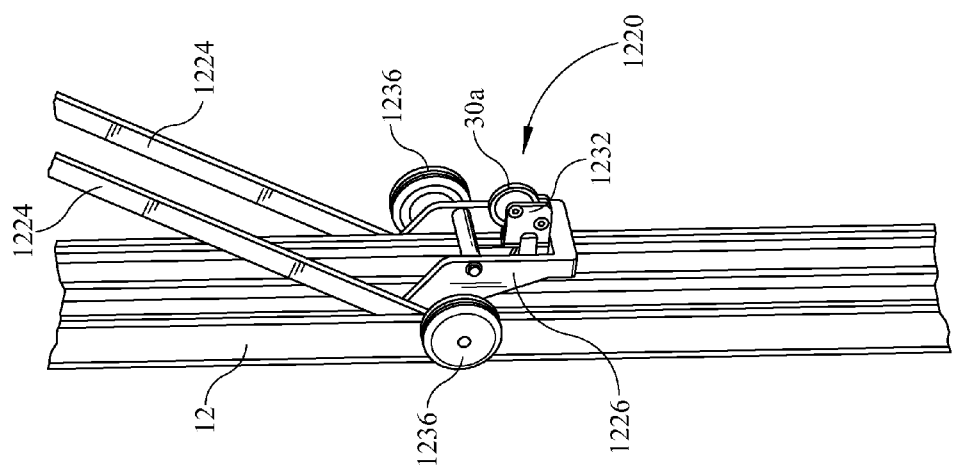
FIG. 45 is a perspective view of the surgical arm positioning system of FIG. 1 showing a lower rod with a pulley carriage having lock knobs instead of the lower pulley assembly attached to the lower rod.
Figure 46:
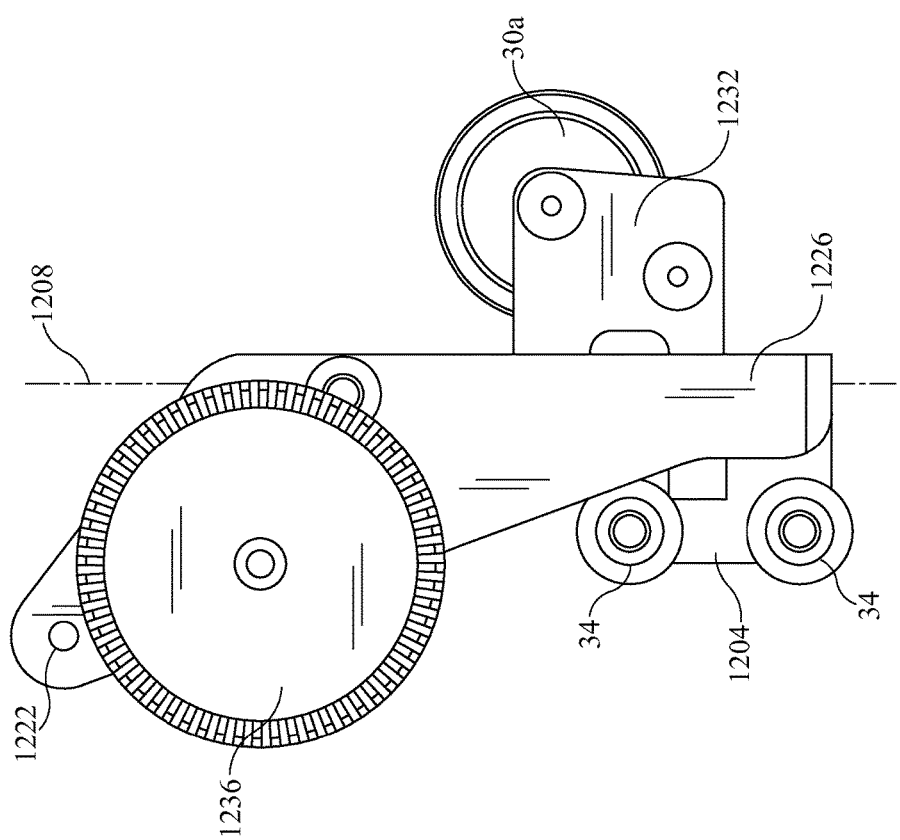
FIG. 46 is a side elevation view of the pulley carriage of FIG. 45.
Figure 47:
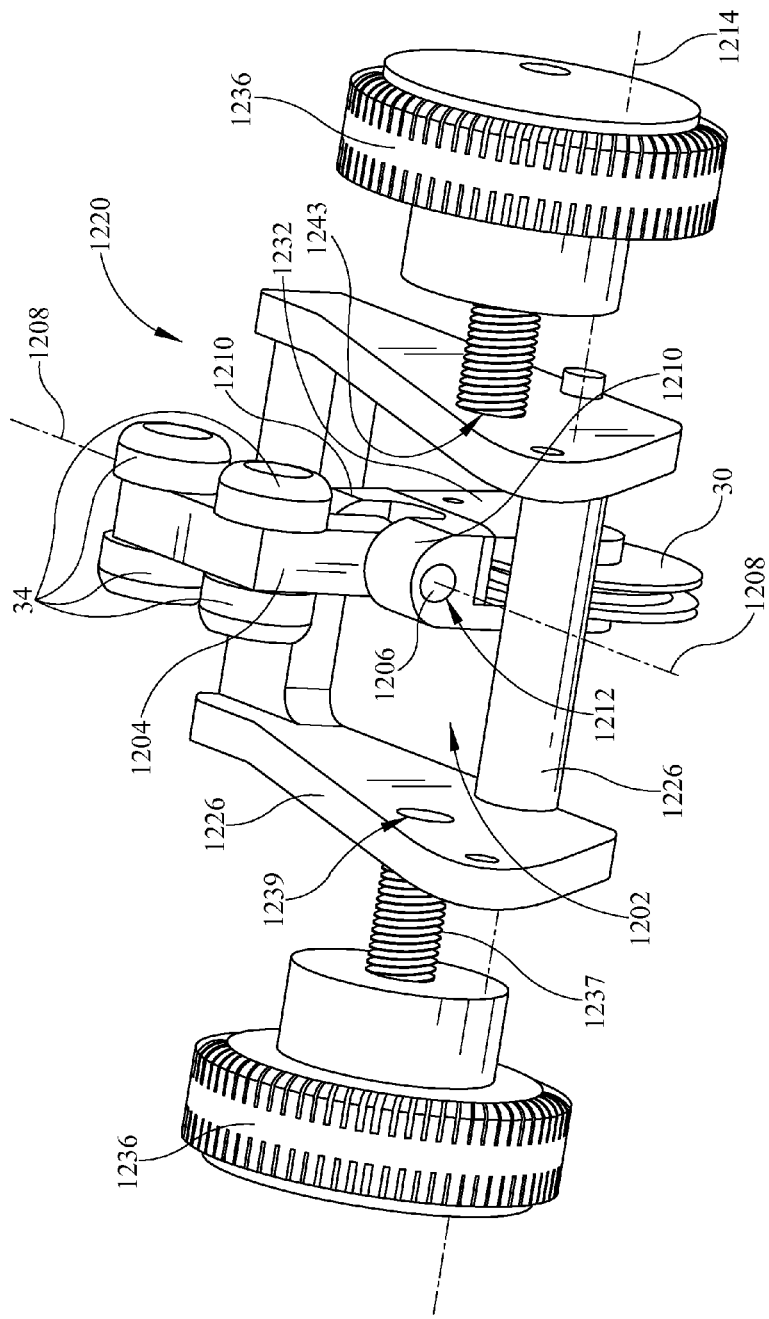
FIG. 47 is a perspective view of the pulley carriage of FIGS. 45 and 46.

In the second embodiment, the lower and upper pulley assemblies 20 and 22 are each substituted by a pulley carriage 1220, as shown in FIGS. 45-47. The pulley carriage 1220 includes a sled body 1226, lock knobs 1236, a pulley 30a, a pulley swinger 1232, and a plurality of wheels 34. As shown in FIG. 47, the roller sled 1226 has an opening 1202, and a bracket 1204 protrudes from the roller sled 1226 into the opening 1202. Four wheels 34 are attached to the bracket 1204 opposite two pins 1206, which define a first axis 1208. The pulley swinger 1232 has two arms 1210, each having an aperture 1212. Each of the pins 1206 extends through the aperture 1212 of one of the arms 1210 such that the pulley swinger 1232 can pivot about the first axis 1208. The pulley 30a rotates about a second axis 1214 that is perpendicular to the axis 1208. When pulley swinger 1220 is used with the system 8, the cable 46 passes along the pulley 30 a proximal to the sled body 1226. Referring to FIG. 1, when the patient's arm is moved into or out of the plane of the plane of the surgical arm positioning system 8, such flexion or extension when the patient is on his or her side, the pulley swinger 1232 pivots about the first axis 1208 in response.

Figure 48:
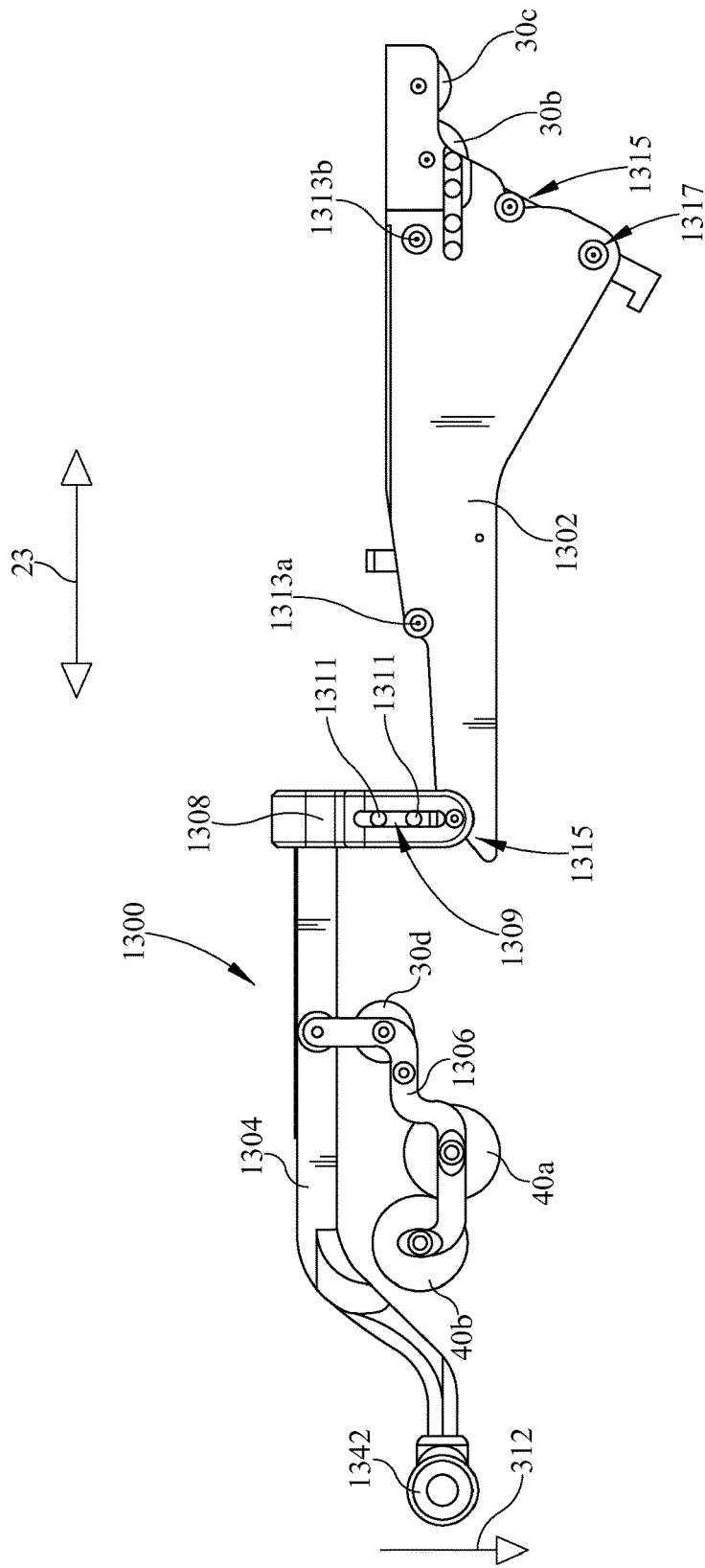
FIG. 48 is a side elevation view of a second embodiment of the internal pulley assembly of FIG. 7 having a reshaped internal pivot.

Referring now to FIG. 48, two pulleys 30b and 30c are attached to the internal pivot 1302. After passing through the pulley carriage 1220, the cable 46 passes along pulley 30b, distal to the internal pivot 1302, before reaching the clutch assembly 1300. The clutch assembly 1300 includes a rear pulley mount 1306 having a pulley 30d and two clutch pulleys 40a and 40b attached thereto. The cable 46 passes along clutch pulley 40a, proximal to pulley 30d, and continues to the weight assembly 1500.

Figure 52:
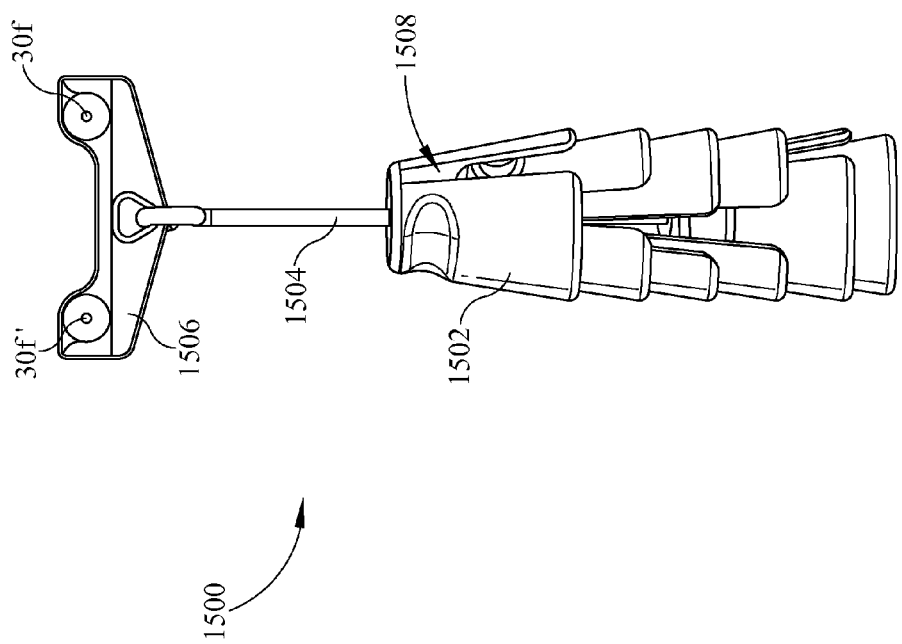
FIG. 52 is a weight assembly for attaching to the surgical arm positioning system.
Figure 53:
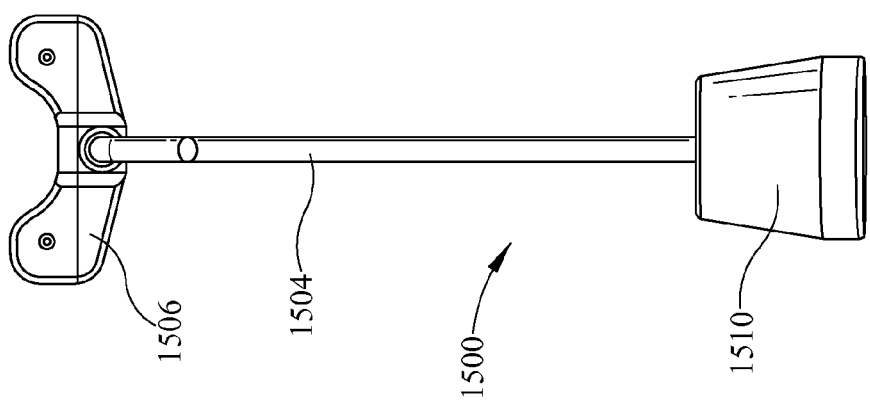
FIG. 53 is a weight assembly for attaching to the surgical arm positioning system with weights omitted.

Referring now to FIGS. 52 and 53, the weight assembly 1500 includes a plurality of detachable weights 1502, a tether 1504, and a pulley housing 1506. The pulley housing 1506 houses two pulleys 30f and 30f (shown in FIG. 53 with part of pulley housing 1506 omitted). The pulleys 30f and 30f are sufficiently separated from each other that cable 46 does not twist when the system 8 is in use with a patient. Referring to FIG. 53, the pulley housing 1506 surrounds the pulleys 30f and 30f to avoid displacement of the cable 46 wrapped around the pulleys 30f and 30f. The pulley housing 1506 is coupled to the tether 1504, which is adapted to receive detachable weights 1502 thereon. The detachable weights 1502 each have a substantially frustoconical shape to facilitate stacking several weights on a base 1510 of the tether 1504. Referring again to FIG. 52, the detachable weights 1502 also each have a gap 1508 therein. The gap 1508 is wider than the width of the tether 1504 such that an operator can elevate the detachable weights 1502 toward the pulley housing 1506 and pull the detachable weights 1502 off of the weight assembly 1500 by passing the tether 1504 through the gap 1508. The operator can add or removing detachable weights 1502 depending on the amount of force to be applied to the cable 46.

The cable 46 passes along pulleys 30f and 30f, proximal to the detachable weights 1502, before returning to the rear pulley mount 1306 to pass along clutch pulley 40b, distal to clutch pulley 40a, as shown in FIG. 48. In some embodiments, the cable 46 may wrap around one or both of the clutch pulleys 40a and 40b one time or multiple times, such as two, three, or four times. Embodiments having cable 46 only partially wrapped (e.g., less than) 360° around one or more of pulleys 30, 40 is also within the scope of this disclosure. After passing along, and possibly wrapping around, the clutch pulleys 40a and 40b, the cable 46 passes along pulley 30d, proximal to 40a and continues to the pulley carriage 1220 on the upper rod 14. After passing along pulley 30a of the pulley carriage 1220 on the upper rod 12, proximal to the sled body 1226, the cable 46 reaches the connection member 48.

One skilled in the art will appreciate that the surgical arm positioning system may include any number of internal clutch pulleys 40 and free pulleys 30 capable of restricting movement of cable 46 to a desired extent. Thus, in some embodiments, more than one internal clutch pulley 40 is used. In other embodiments, free pulleys 30 may be used without the use of an internal clutch pulley 40.

Referring again to FIG. 46, one pulley carriage 1220 is connected to the lower rod 12 and another pulley carriage 1220 is connected to the upper rod 14. The pulley carriages are linked by a two connecting rods 1224 such that movement of one of the pulley carriages 1220 results in movement of the other. The connecting rods 1224 maintain a consistent distance between pulley carriages 1220 as they move along respective rods 12 and 14. The connecting rods 1224 are connected to the pulley carriages 1220 by pins (not shown) that extend through apertures 1222 in the sled bodies 1226 of the pulley carriages 1220, as shown in FIG. 46. As the pulley carriages 1220 are moved along the frame 10, the connecting rods 1224 pivot about the apertures 1222 of pulley carriages 1220. The rails 38 of lower rod 12 interact with one of the pulley carriages 1220 such that the wheels 34 are held within lower rod 12 by the rails 38 and the pulley carriage 1220 can move along the length of lower rod 12. Similarly, the rails 38 of upper rod 14 interact with the other pulley carriage 1220 such that the wheels 34 are held within upper rod 14 by the rails 38 and the pulley carriage 1220 can move along the length of upper rod 14.

As shown in FIGS. 45-47, the pulley carriages 1220 have lock knobs 1236 that have a threaded portion 1237 extending through holes 1239 and 1243 of the sled body 1226. The lock knobs 1236 can be rotated by the operator in one direction to lock one or both of the pulley carriages 1220 in place relative to the lower and upper rods 12 and 14 and can be rotated in an opposite direction to release the pulley carriages 1220. When pulley carriages 1220 are used instead of lower and upper pulley assemblies 20, 22, the pulley carriages 1220 can be locked in place by adjusting lock knobs 1236 after the patient's arm has been positioned.

Figure 49:
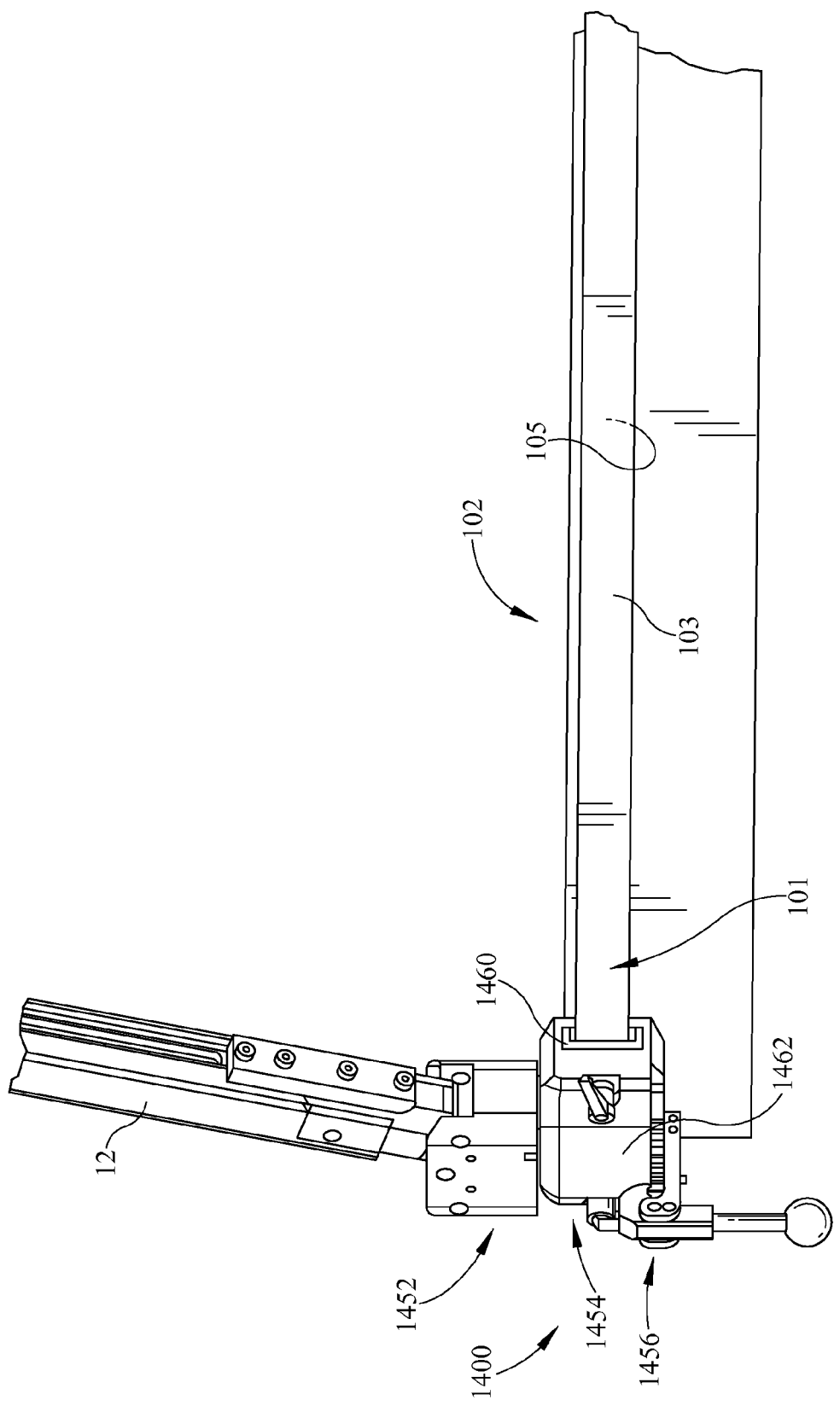
FIG. 49 is a perspective view of a modified clamp assembly attached to the accessory rail of the surgical table and to the lower rod of the surgical arm positioning system of FIG. 1.

In the second embodiment, the semi-locked clamp assembly 18 is substituted by a modified clamp assembly 1400. As shown in FIG. 49, the modified clamp assembly 1400 includes a rod bracket 1452, a clamp body assembly 1454, and a lever assembly 1456. The rod bracket 1452 is fixed to the lower rod 12 and the lever assembly 1456 is coupled to the rod bracket 1452 for transmitting rotational motion thereto. The clamp body assembly 1554 is configured to clamp to the rail 101 of a surgical table 102 and thus mount the system 8 top the surgical table 102.

Figure 50:
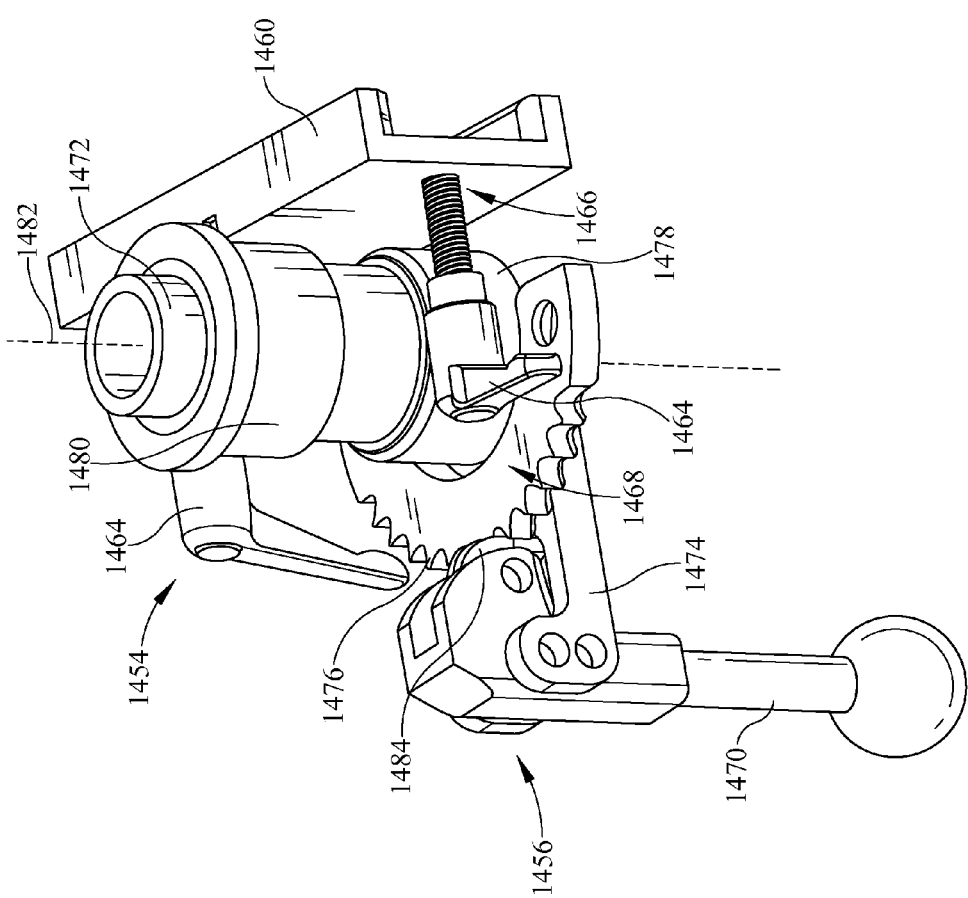
FIG. 50 is a perspective view of internal components of the modified clamp assembly of FIG. 49 with a clamp body of the modified clamp assembly omitted.
Figure 51:
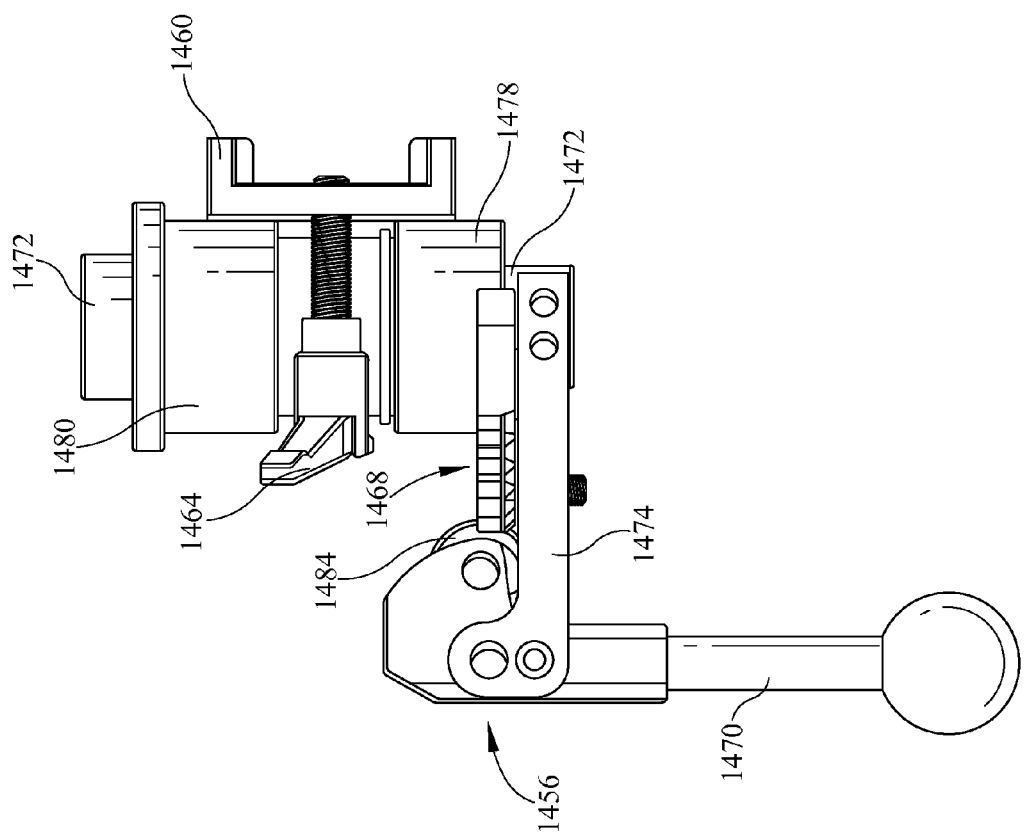
FIG. 51 is another perspective view of internal components of the modified clamp assembly of FIG. 49 with a clamp body of the modified clamp assembly omitted.

Referring to FIGS. 49-51, the clamp body assembly 1454 includes a mounting plate 1460, a housing 1462, and two bolts 1464. As best seen in FIG. 49, when the clamp body assembly 1454 is clamped to the rail 101 of surgical table 102, the mounting plate 1460 interfaces the rail 101 and the housing 1462 surrounds the mounting plate 1460 and the rail 101 to hold the mounting plate 1460 to the rail 101. The bolts 1464 extend through apertures 1466 in the mounting plate 1460 and push against a front surface 103 of the rail 101. As the bolts 1464 further push against front the surface 103 of the rail 101, the housing 1462 experiences a corresponding force against a back surface 105 of the rail 101, thus securing the clamp body assembly 1454 to the rail 101.

Referring again to FIGS. 50 and 51, the lever assembly 1456 includes a lever 1470 coupled to a longitudinal tube 1472 by an arm 1474. A cogwheel 1468 has a plurality of cogs 1476 and is fixed to the housing 1462 (shown in FIG. 49). The tube 1472 is surrounded by a lower bearing 1478 and a flange bearing 1480, which reside in a cylindrical cavity (not shown) of the housing 1462. The arm 1474 and lever 1470 are coupled to the tube 1472 such that movement of the lever 1470 along the cogwheel 1468 causes the longitudinal tube 1474 to rotate about an axis 1482 within the housing 1462. The lever 1470 pivots relative to the arm 1474 and includes a pin 1484 for engaging the cogwheel 1468 to block rotation of the tube 1472. The rod bracket 1452 is attached to the tube 1472 opposite the lower bearing 1478.

The modified clamp assembly 1400 can be used by the operator to rotate the frame 10 of the surgical arm positioning system 8. Still referring to FIGS. 49-51, the lever 1470 is shown in an engaged position for blocking rotation of the frame 10. When the lever 1470 is pulled away from the surgical table 102, the pin 1484 disengages from the cogwheel 1468 and no longer blocks the tube 1472 from rotating. By moving the disengaged lever 1470 about axis 1482, the tube 1472, and by extension the rod bracket 1452 and the frame 10, are rotated about axis 1482. Rotation of the frame 10 about the axis 1482 causes changes in flexion angle when the system 8 is in use with a patient. Once the frame 10 reaches a desired position, the lever 1470 can be pushed toward the surgical table 102 to engage the pin 1484 in the cogwheel 1468 and lock rotation of the frame 10.

Figure 54:
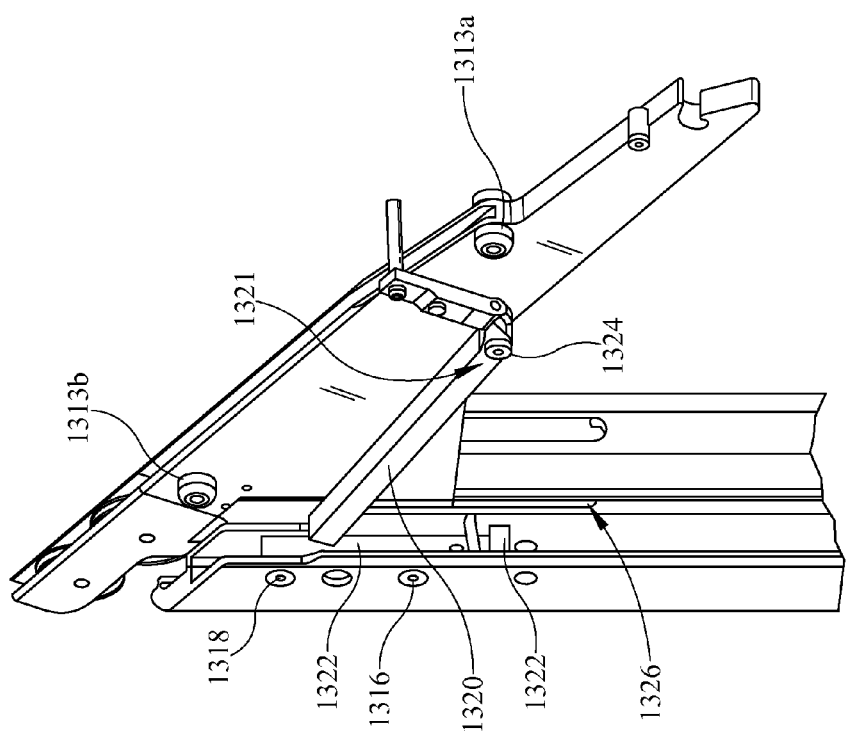
FIG. 54 is a perspective view of the surgical arm positioning system of FIG. 13 showing the latching mechanism with the reshaped internal pivot of FIG. 48.

In the second embodiment, the internal pulley assembly 300 is substituted by a modified internal pulley assembly 1300, as shown in FIG. 48. The internal pulley assembly 1300, as shown in FIG. 48, is positioned in the interior of upper rod 14 and is configured to prevent the upper rod 14 from collapsing toward the lower rod 12, until the operator pulls the handle 1342. The internal pulley assembly 1300 includes an internal pivot 1302, a handle pin lever 1304 connected to the handle 1342, a slot lifter 1308, and the rear pulley mount 1306. The internal pivot 1302 has two pairs of wheels 1313a and 1313b, a notch 1315, an aperture 1317, and a stud 1320 (shown in FIG. 54). The wheels 1313a and 1313b are engaged by the rails 38 of the upper rod 14 similar to the way that the lower and upper pulley assemblies 20 and 22 are engaged by the rails 38. As shown in FIG. 54, a first pin 1316 extends through lower rod 12 and aperture 1317 to couple the internal pivot 1302 to the lower rod 12. A second pin 1318 extends through the lower rod 12 above pin 1316 and is engaged by notch 1315 to prevent the upper rod 14 from falling toward the patient. Additionally, the stud 1320 has an aperture 1321 therein and is attached to the internal pivot 1302 by a pin 1324. The stud 1320 can rotate and rest against a bracket 1322 that is attached to the lower rod 12 to prevent the upper rod 14 from falling away from the patient. As such, the internal pivot 1302 holds the lower and upper rods 12 and 14 at a fixed angle.

Referring again to FIG. 48, when the operator pulls the release handle 1342 in the direction indicated by arrow 312, the resulting motion moves the handle pin lever 1304 and slot lifter 1308 in a direction opposite arrow 312. The handle pin lever 1304 has a guide slot 1309 that receives two guide pins 1311. As the slot lifter 1308 moves, it disengages from the notch 1315 of the internal pivot 1302, freeing the upper rod 14 to move in the direction of arrow 23, distal to the patient. Referring again to FIG. 54, as the upper rod 14 retracts, it eventually causes the stud 1320 to disengage from the bracket 1322, thus allowing the internal pivot 1302 to pivot about the pin 1316. In the second embodiment, the lower rod 14 has a gap 1326 therein, which the internal pivot 1302 partly passes through while pivoting. The upper rod 14 can continue to retract and rotate into a position substantially parallel to the lower rod 12. When the lower and upper rods 12 and 14 are substantially parallel, the system 8 is in a folded position for transport and storage.

Figure 61:
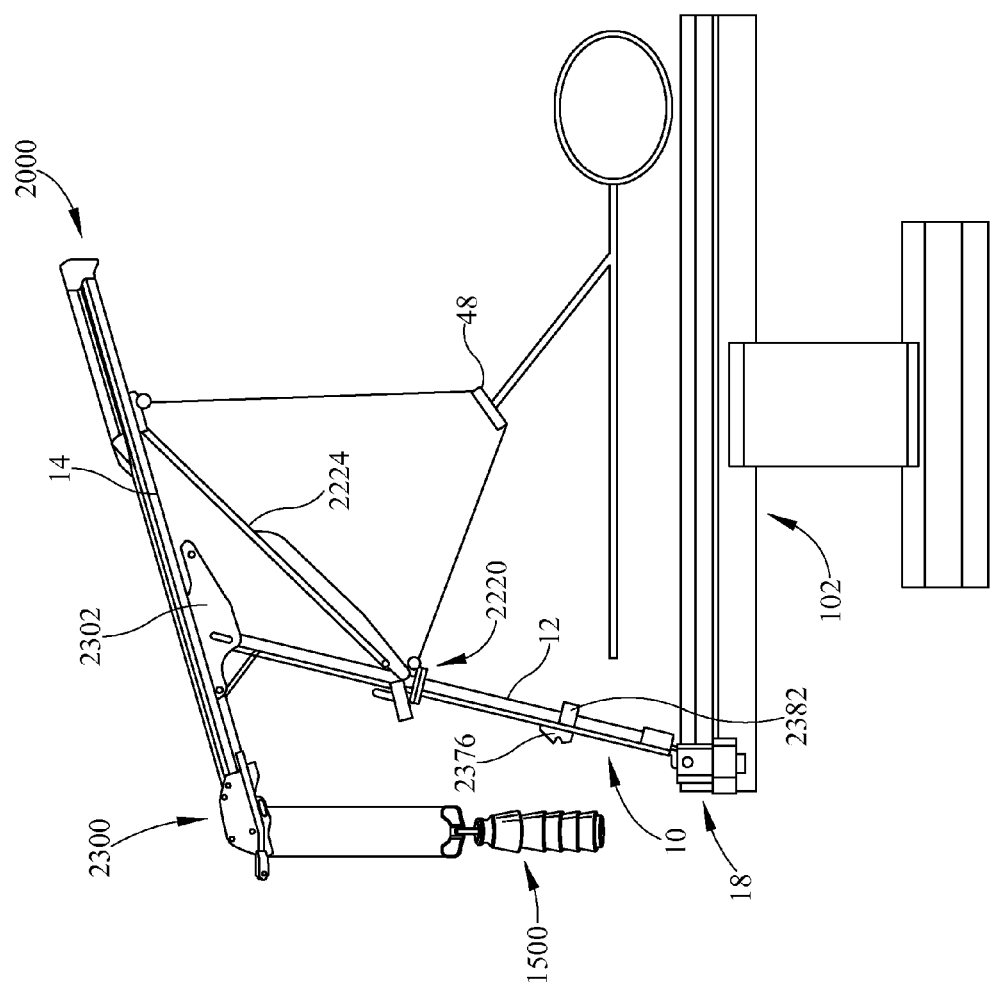
FIG. 61 is a side elevation view of another embodiment of the surgical arm positioning system of FIG. 1.

Referring now to FIG. 61, in a third embodiment of the instant disclosure of the surgical arm positioning system 8, several components attached to frame 10 are substituted by functionally similar components. In a third embodiment of the instant disclosure of the surgical arm positioning system 8, starting at the connection member 48, the cable 46 is routed through a pulley carriage 2220, an internal pivot 2302, a clutch assembly 2300, a weight assembly 1500, the internal pivot 2302 again, and another pulley carriage 2220, before returning back to the connection member 48 to form a loop.

Figure 62:
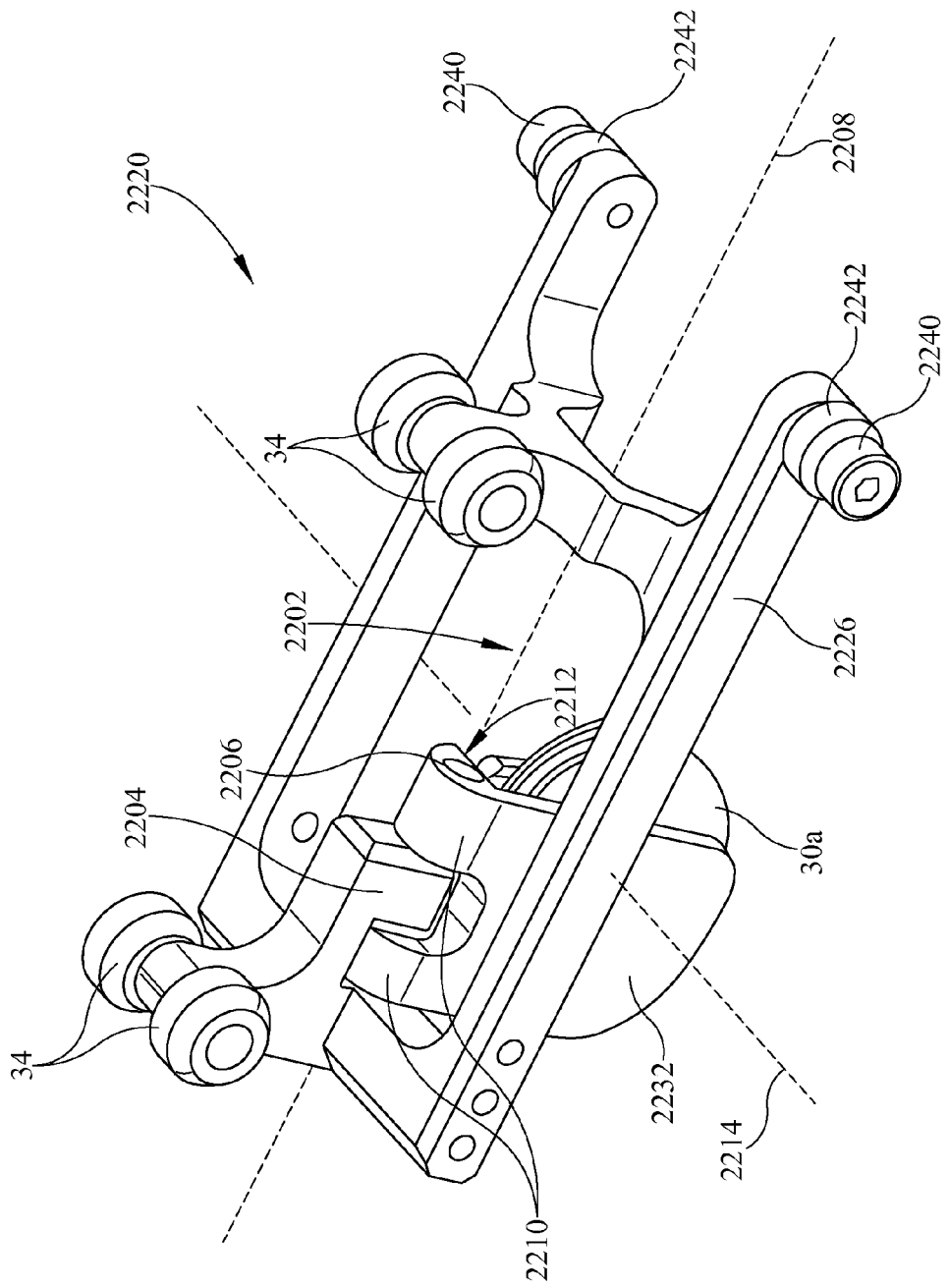
FIG. 62 is a perspective view of another embodiment of the pulley carriage of FIGS. 46 and 47.
Figure 63:
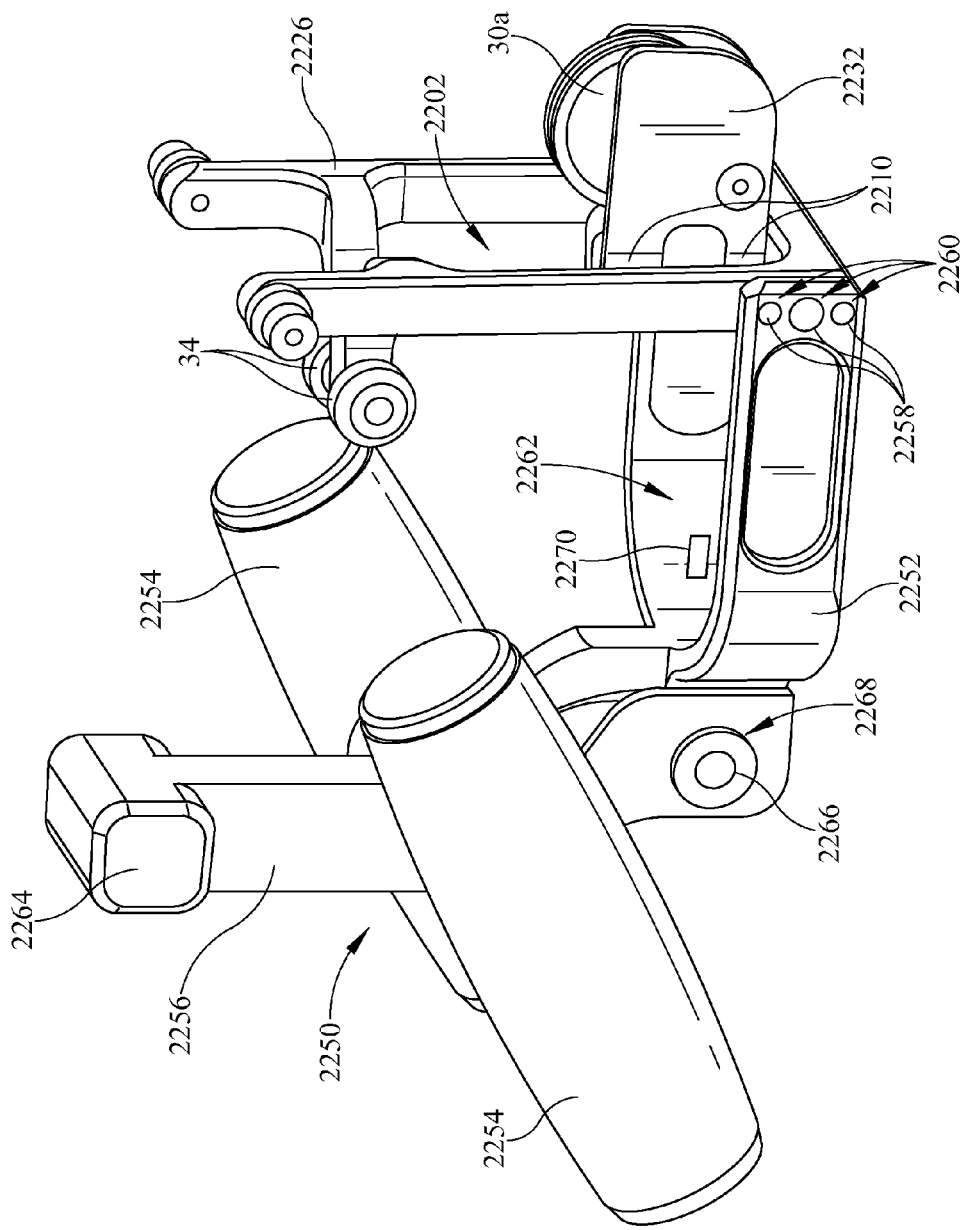
FIG. 63 is a perspective view of the pulley carriage of FIG. 62 including a handle assembly.

In the third embodiment, the lower and upper pulley assemblies 20 and 22 are each substituted by a pulley carriage 2220, as shown in FIGS. 62 and 63. The pulley carriage 2220 includes a sled body 2226, a pulley 30a, a pulley swinger 2232, and a plurality of wheels 34. The roller sled 2226 has an opening 2202, and a bracket 2204 protrudes from the roller sled 2226 into the opening 2202. Two of the wheels 34 are attached to the bracket 2204 opposite two pins 2206, which define a first axis 2208. The pulley swinger 2232 has two arms 2210, each having an aperture 2212. Each of the pins 2206 extends through the aperture 2212 of one of the arms 2210 such that the pulley swinger 2232 can pivot about the first axis 2208. The pulley 30a rotates about a second axis 2214 that is perpendicular to the first axis 2208. Referring to FIG. 61, when pulley carriage 2220 is used with the system 8, the cable 46 passes along the pulley 30a proximal to the sled body 2226. When the patient's arm is moved into or out of the plane of the surgical arm positioning system 8, such flexion or extension when the patient is on his or her side, the pulley swinger 2232 pivots about the first axis 2208 in response.

Figure 67A:
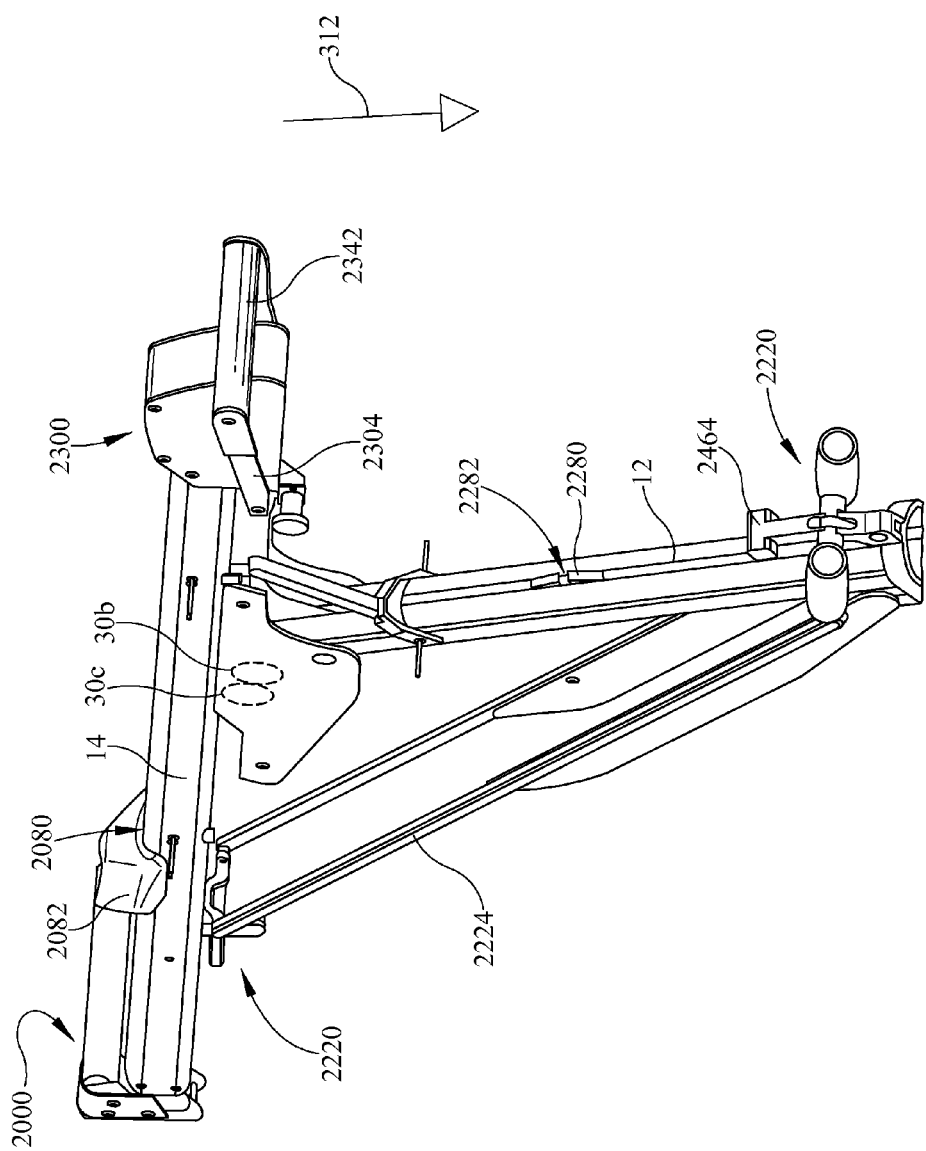
FIG. 67A is a perspective view of the surgical arm positioning system of FIG. 61 showing the latching mechanism of an internal pivot.
Figure 68:
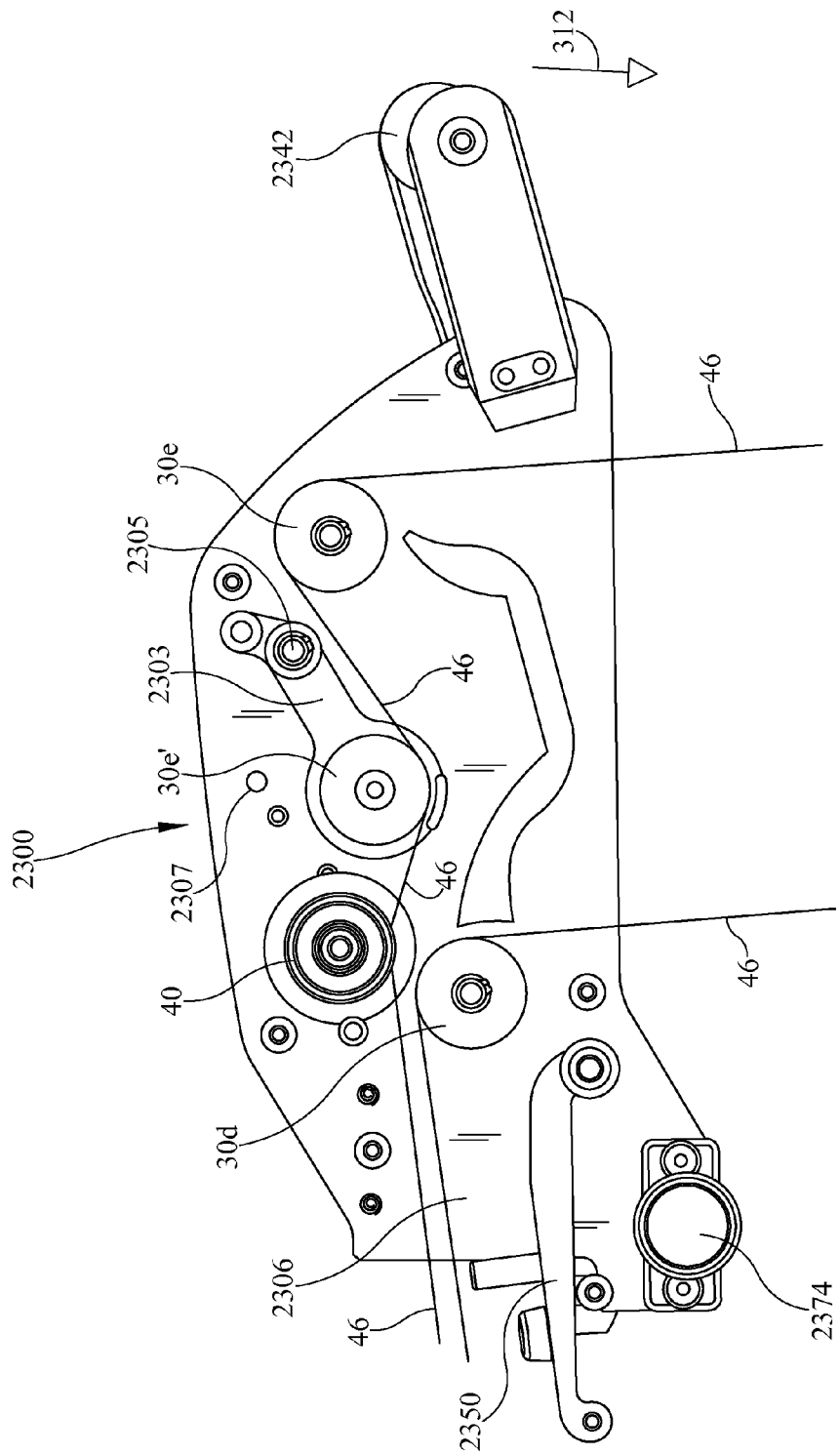
FIG. 68 is a perspective view of an internal pulley assembly of the surgical arm positioning system of FIG. 61.

Referring now to FIGS. 67A and 67B two pulleys 30b and 30c are attached to the internal pivot 2302. After passing through the pulley carriage 2220, the cable 46 passes along pulley 30b, proximal to pulley 30b, before reaching the clutch assembly 2300. Referring now to FIG. 68, the clutch assembly 2300 includes a rear pulley plate 2306 having three pulleys 30d, 30e, and 30e' and a clutch pulley 40 attached thereto. Pulley 30e' is mounted to a spring loaded pivot 2303 that is mounted to the rear pulley plate 2306 by a pin 2305. The spring loaded pivot 2303 is biased to resist rotating about the pin 2303 toward a block pin 2307. The block pin 2307 limits the range of rotation of the spring loaded pivot 2303. The cable 46 passes along pulley 30d, distal to the clutch pulley 40, and continues to the weight assembly 1500. Referring again to FIGS. 52 and 53, the cable 46 passes along pulleys 30f and 30f', proximal to the detachable weights 1502, before returning to the rear pulley plate 2306. The cable 46 next passes along pulley 30e distal to pulley 30e', before passing along pulley 30e' distal to the pin 2305. Next, the cable passes along clutch pulley 40, wrapping around clutch pulley 40 one time. In some embodiments, the cable 46 may wrap around the clutch pulley 40 multiples times, such as two, three, or four times. Embodiments having cable 46 only partially wrapped (e.g., less than 360°) around one or more of pulleys 30 and 40 is also within the scope of this disclosure. Referring now to FIG. 67, after wrapping around the clutch pulley 40, the cable 46 continues to pulley 30c, above pulley 30b, and continues to the pulley carriage 2220 on the upper rod 14. After passing along pulley 30a, proximal to the sled body 1226, the cable 46 reaches the connection member 48.

One skilled in the art will appreciate that the surgical arm positioning system may include any number of internal clutch pulleys 40 and free pulleys 30 capable of restricting movement of cable 46 to a desired extent. Thus, in some embodiments, more than one internal clutch pulley 40 is used. In other embodiments, free pulleys 30 may be used without the use of an internal clutch pulley 40.

Figure 64:
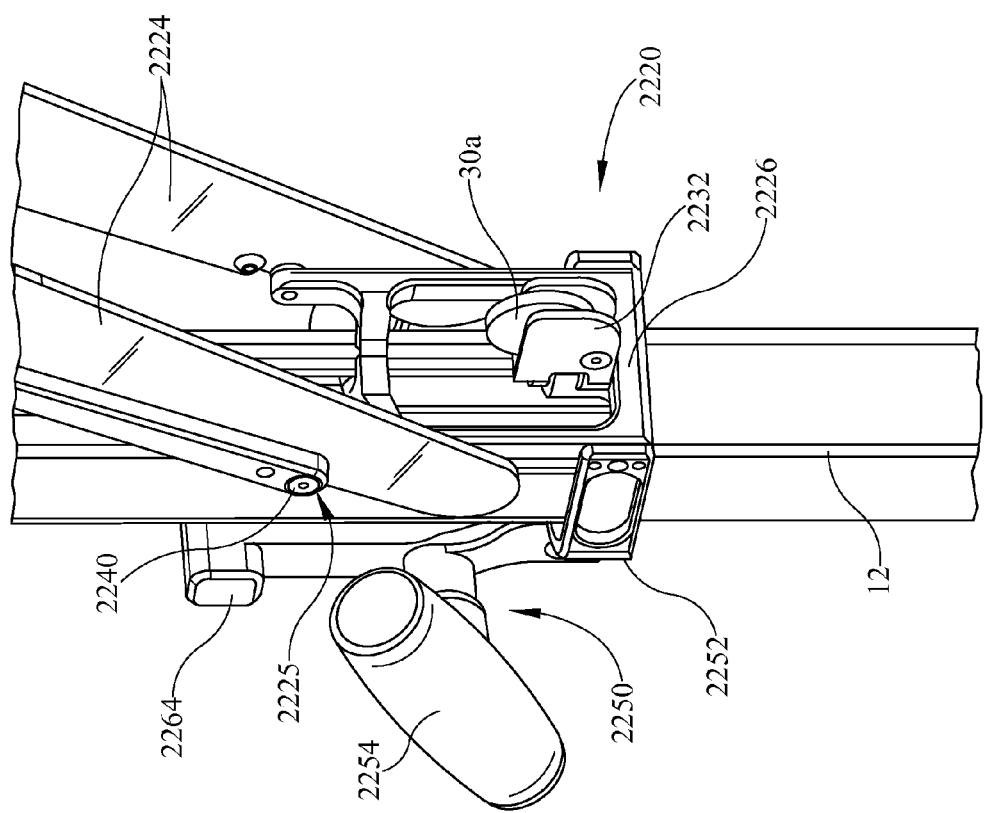
FIG. 64 is a perspective view of the surgical arm positioning system of FIG. 61 showing a lower rod with the pulley carriage and handle assembly of FIG. 63.

Referring now to FIGS. 62 and 64, one pulley carriage 2220 is connected to the lower rod 12 and another pulley carriage 2220 is connected to the upper rod 14. The pulley carriages are linked by a two connecting rods 2224 such that movement of one of the pulley carriages 2220 results in movement of the other. The connecting rods 2224 maintain a consistent distance between pulley carriages 2220 as they move along respective rods 12 and 14. The connecting rods 2224 are connected to the pulley carriages 2220 by pins 2240 that extend through a bearing 2242 and an aperture 2225 in each connecting rod 2224 to attach the connecting rod 2224 to the pulley carriages 2220. As the pulley carriages 2220 are moved along the frame 10, the connecting rods 2224 pivot about the apertures 2225 of pulley carriages 2220. The rails 38 of lower rod 12 interact with one of the pulley carriages 2220 such that the wheels 34 are held within lower rod 12 by the rails 38 and the pulley carriage 2220 can move along the length of lower rod 12. Similarly, the rails 38 of upper rod 14 interact with the other pulley carriage 2220 such that the wheels 34 are held within upper rod 14 by the rails 38 and the pulley carriage 2220 can move along the length of upper rod 14.

As shown in FIGS. 63 and 64, the pulley carriage 2220 coupled to the lower rod 12 includes a handle assembly 2250. The handle assembly 2250 includes a U-shaped handle bracket 2252, two handles 2254, and a block arm 2256. The handle bracket 2252 is mounted to the sled body 2226 of the pulley carriage 2220 by bolts 2258 that extend through apertures 2260 of the handle bracket 2252 into the sled body 2226. The handle bracket 2252 and the sled body 2226 define an opening 2262 sized to surround that lower rod 12, as shown in FIG. 64. The block arm 2256 is attached to the handle bracket 2252 opposite the pulley carriage 2220 and extends parallel to the sled body 2226 into a block head 2264. The block arm 2256 is mounted to the handle bracket 2252 by a bolt 2266 that extends through an aperture 2268 in the block arm 2256. The handles 2254 are attached to the block arm 2256.

The handle assembly 2250 is configured for an operator to grasp one of the handles 2254 to move the pulley carriages 2220 along the frame 10. Referring again to FIG. 63, the handle assembly 2250 includes a pin 2270 that extends into the opening 2262. A plurality of clips 2280 are attached to the lower rod 12, as shown in FIG. 67A. The clips 2280 each have a wedge 2282 that can engage the pin 2270 to hold the handle assembly 2250 and pulley carriage 2220 stationary relative to the lower rod 12 when the system 8 is in use for surgery. Depending on the desired position of the pulley carriages 2220, the operator can apply sufficient force to the handle 2254 to disengage the pin 2270 from one of the clips 2280 and use the handle 2254 to move the handle assembly 2250 and pulley carriage 2220 along the lower rod 12 until the pin 2270 engages another one of the clips 2280.

Figure 65:
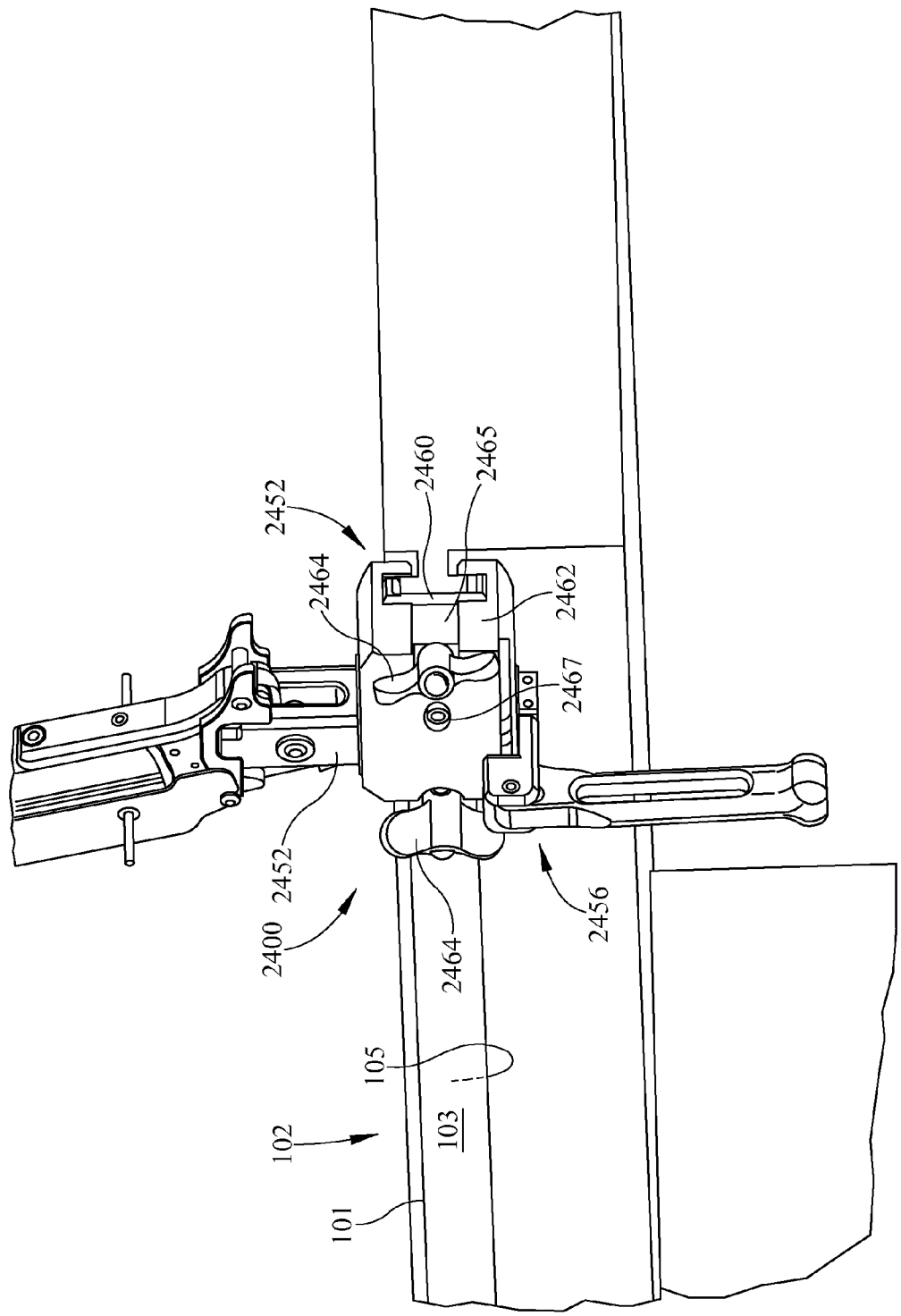
FIG. 65 is a perspective view of a modified clamp assembly attached to the accessory rail of the surgical table and to the lower rod of the surgical arm positioning system of FIG. 61.
Figure 66:
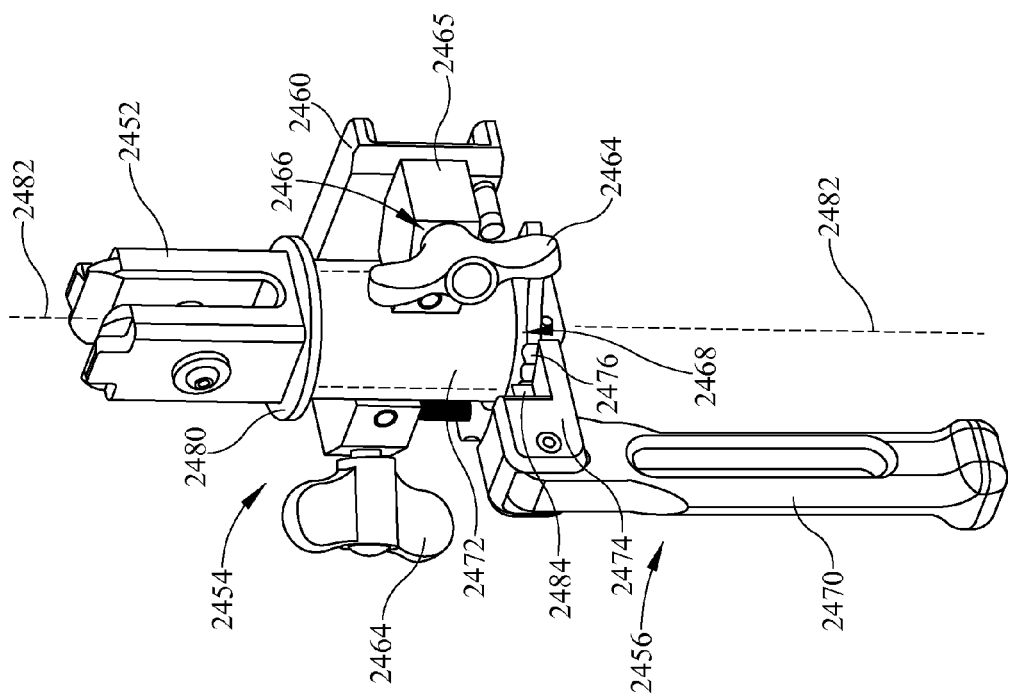
FIG. 66 is a perspective view of internal components of the modified clamp assembly of FIG. 65 with a mounting plate of the modified clamp assembly omitted.

In the third embodiment, the semi-locked clamp assembly 18 is substituted by a modified clamp assembly 2400. As shown in FIGS. 65 and 66, the modified clamp assembly 2400 includes a rod bracket 2452, a clamp body assembly 2454, and a lever assembly 2456. The rod bracket 2452 is secured to the lower rod 12 and the lever assembly 2456 is coupled to the rod bracket 2452 for transmitting rotational motion thereto. The clamp body assembly 2554 is configured to clamp to the rail 101 of surgical table 102 and thus mount the system 8 top surgical table 102.

Still referring to FIGS. 65 and 66, the clamp body assembly 2454 includes a mounting plate 2460, a housing 2462, two bolts 2464, and two press blocks 2465. When the clamp body assembly 2454 is clamped to the rail 101 of surgical table 102, the mounting plate 2460 interfaces the rail 101 and the housing 2462 surrounds the mounting plate 2460 and the rail 101 to hold the mounting plate 2460 to the rail 101. The bolts 2464 extend through apertures 2466 in the press blocks 2465, which are secured to the housing 2462 by two screws 2467. The press blocks 2465 are disposed against a front surface 103 of the rail 101. As the bolts 2460 further push the press blocks 2465 against front the surface 103 of the rail 101, the housing 2462 experiences a corresponding force against a back surface 105 of the rail 101, thus securing the clamp body assembly 2454 to the rail.

Referring to FIG. 66, the lever assembly 2456 includes a cogwheel 2468 and a lever 2470 coupled to a longitudinal tube 2472 by an arm 2474. The cogwheel 2468 has a plurality of cogs 2476 and is fixed to the housing 2462. The tube 2472 is surrounded by a flange bearing 2480, which resides in a cylindrical cavity (not shown) of the housing 2462. The arm 2474 and lever 2470 are coupled to the tube 2472 such that movement of the lever 2470 along the cogwheel 2468 causes the longitudinal tube 2472 to rotate about an axis 2482 within the housing 2462. The lever 2470 pivots relative to the arm 2474 and includes a pin 2484 for engaging the cogwheel 2468 to block rotation of the tube 2472. The rod bracket 2452 attaches the lower rod 12 to the tube 1472 opposite the lower bearing 2478.

The modified clamp assembly 2400 can be used by the operator to rotate the frame 10 of the surgical arm positioning system 8. Referring again to FIGS. 65 and 66, the lever 2470 is shown in an engaged position for blocking rotation of the frame 10. When the lever 2470 is pulled away from the surgical table 102, the pin 2484 disengages from the cogwheel 2468 and no longer blocks the tube 2472 from rotating. By moving the disengaged lever 2470 about axis 2482, the tube 2472, and by extension the rod bracket 2452 and the frame 10, are rotated about axis 2482. Rotation of the frame 10 about the axis 2482 causes changes in flexion angle when the system 8 is in use with a patient. Once the frame 10 reaches a desired position, the lever 2470 can be pushed toward the surgical table 102 to engage the pin 2484 in the cogwheel 2468 to lock rotation of the frame 10.

Figure 69:
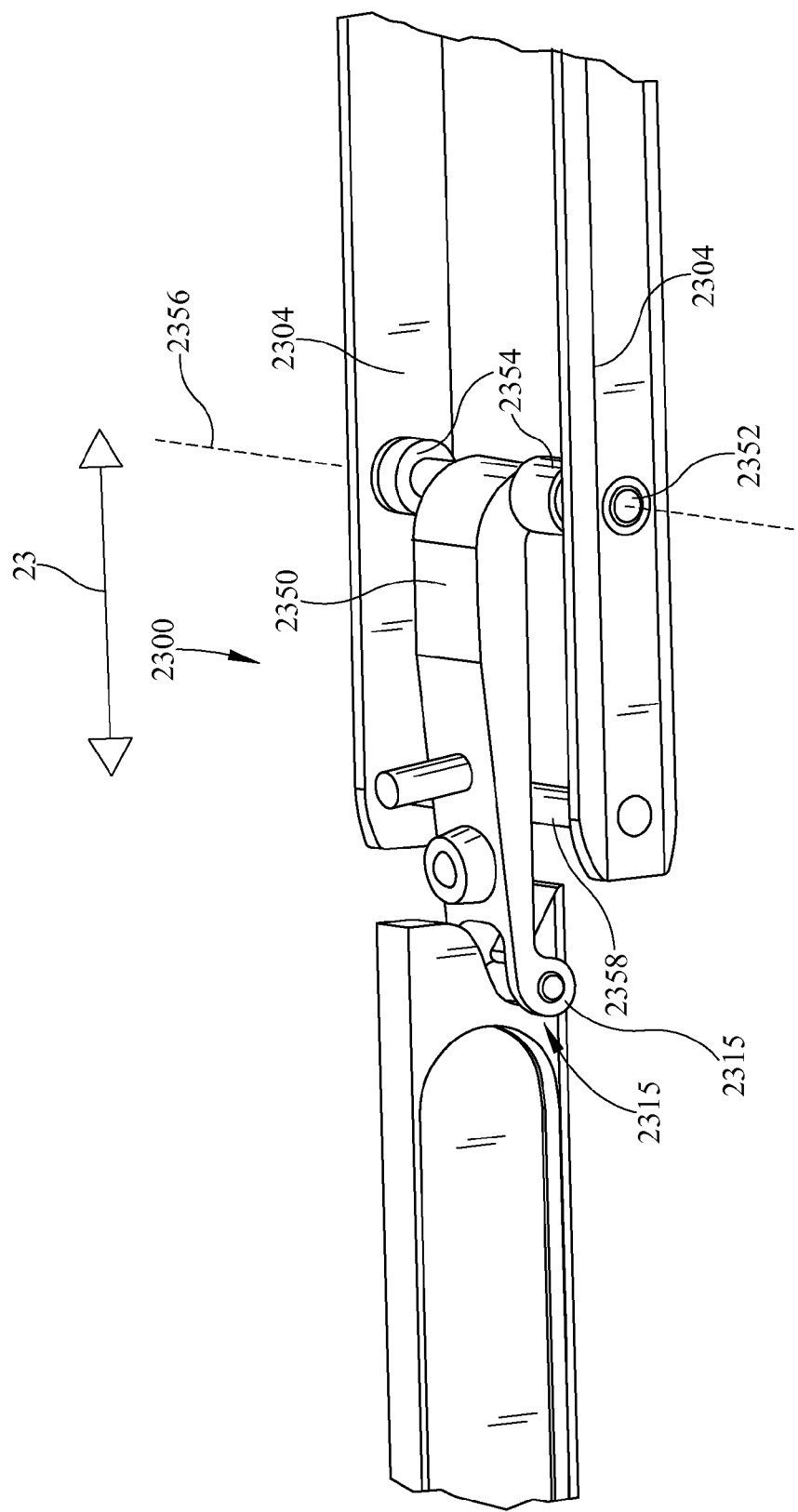
FIG. 69 is a perspective view of the latching mechanism of the internal pivot of FIGS. 67A and 67B.

In the third embodiment, the internal pulley assembly 300 is substituted by a modified internal pulley assembly 2300, as shown in FIGS. 68 and 69. The internal pulley assembly 2300 is attached to the end of upper rod 14 and is configured to prevent the upper rod 14 from collapsing toward the lower rod 12, until the operator pulls the handle 2342. The internal pulley assembly 2300 includes an internal pivot 2302 (shown in FIGS. 67A and 67B), two handle levers 2304 connected to the handle 2342, an arm 2350, and the rear pulley plate 2306. Referring to FIG. 67B, the internal pivot 2302 has two pairs of wheels 2313a and 1313b, a wedge 2315, an aperture 2317, and a stud 2320. The wheels 2313a and 2313b are engaged by the rails 38 of the upper rod 14 similar to the way that the lower and upper pulley assemblies 20 and 22 are engaged by the rails 38. A first pin 2316 extends through lower rod 12 and aperture 2317 to couple the internal pivot 1302 to the lower rod 12. A second pin 2318 extends through the lower rod 12 above pin 2316 and is engaged by wedge 2315 to prevent the upper rod 14 from falling toward the patient. Additionally, the stud 2320 has an aperture 2321 therein and is attached to the internal pivot 3302 by a pin 2324. The stud 2320 can rotate and rest against a bracket 2322 attached to the lower rod 12 to prevent the upper rod 14 from falling away from the patient. As such, the internal pivot 2302 holds the lower and upper rods 12 and 14 at a fixed angle.

Referring again to FIGS. 67A and 69, when the operator pulls the release handle 2342 in the direction indicated by arrow 312, the resulting motion moves the handle levers 2304, including a crossbar 2358 that extends between the handle levers 2304, in a direction opposite arrow 312. The arm 2350 is attached between the handle levers 2304 by two pins 2352 and two bearings 2354 such that the arm 2350 can rotate about an axis 2356. The arm 2350 has a wedge 2315 positioned opposed the handle 2342 that engages a notch 2314 of the internal pivot 2302. As the crossbar 2358 moves opposite arrow 312, it pushes the wedge 2315 out of the notch 2314, freeing the upper rod 14 to move in the direction of arrow 23, distal to the patient. As the upper rod 14 retracts, it eventually causes the stud 2320 to disengage from the bracket 2322, thus allowing the internal pivot 2302 to pivot about pin 2316, as shown in FIG. 67B. In the third embodiment, the lower rod 14 has a gap 2326 therein, which the internal pivot 2302 partly passes through while pivoting.

Figure 71:
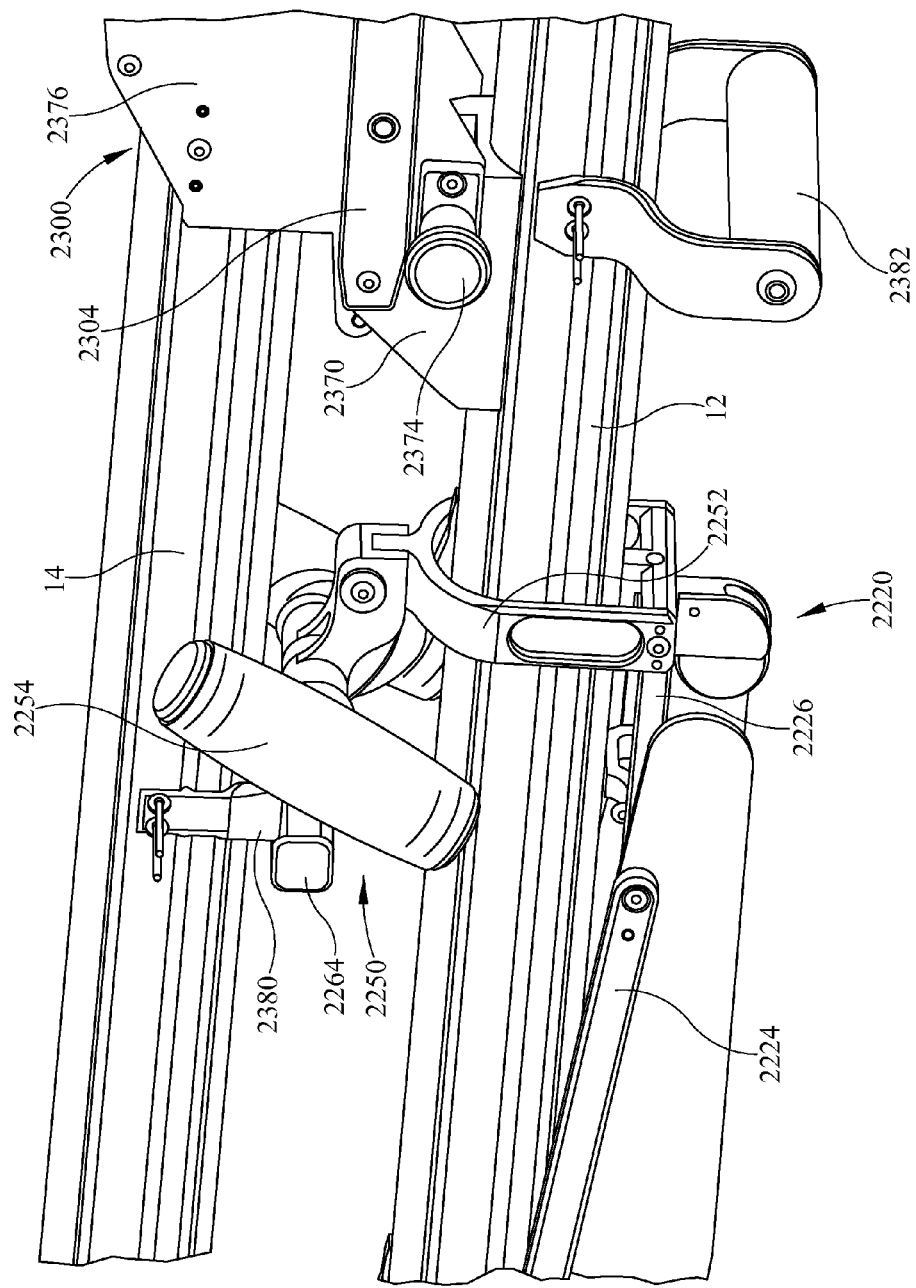
FIG. 71 is a partial perspective view of the surgical arm positioning system of FIG. 61 in a folded position showing the pulley carriage of FIG. 63.

Referring now to FIGS. 70 and 71, the upper rod 14 can continue to retract into a position substantially parallel to the lower rod 12. When the lower and upper rods 12 and 14 are substantially parallel, the system 8 is in a folded position for transport and storage. In the folded position, the upper rod 14 is held within a mount 2370 attached to the lower rod. The mount 2370 has an opening (not shown) that receives a spring-loaded pin 2374 attached to a housing 2376 that covers the internal pulley assembly 2300 to hold the frame 10 in the folded position. Additionally, an upper block 2380 is attached to the upper rod 14. In the folded position, the upper block 2380 rests against the block head 2264 of the handle assembly 2250 to prevent the housing 2376 from contacting the lower rod 12. A handle 2382 is attached to the lower rod 12 to facilitate transport of the folded system 8. The operator may pull the spring-loaded pin 2374 to release the frame 10 from the folded position and reposition upper rod 14 to prepare the system 8 for use with a patient.

Referring now to FIG. 1, in some embodiments, the upper rod 14 of the surgical arm positioning system 8 receives shoulder distraction apparatus 400 for applying a lateral distraction force to the patient's arm. The shoulder distraction apparatus 400 and the lateral traction strap 500, which is attached to the shoulder distraction apparatus, allow a physician to apply lateral traction force to a patient's arm throughout a range of positions during shoulder arthroscopy while maintaining sterility. When a physician or other sterile staff adjust a patient's sterile arm, the shoulder distraction apparatus 400 responds to such adjustments without requiring the operator to touch non-sterile components. As such, the shoulder distraction apparatus 400 does not require assistance from a non-sterile staff member.

Figure 18:
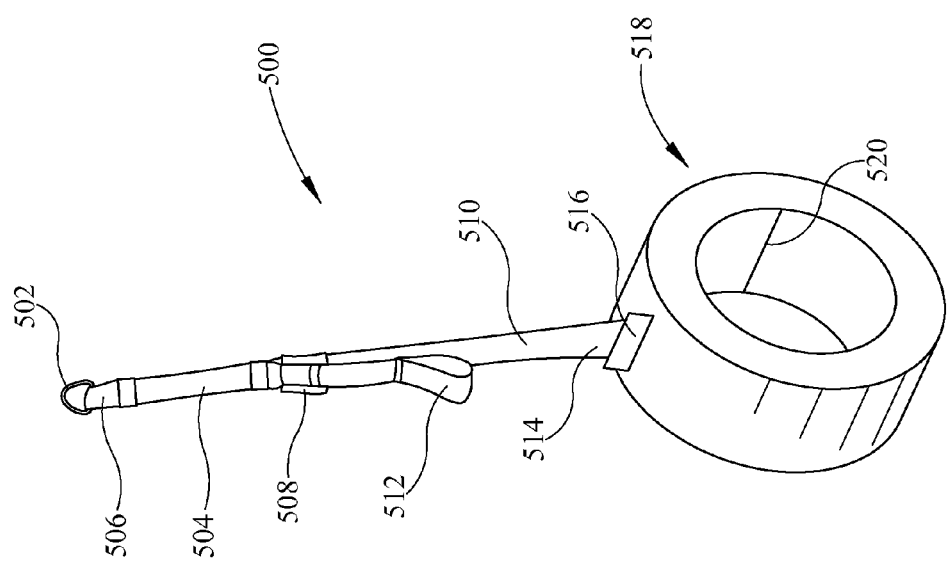
FIG. 18 is a perspective view of a lateral distractor strap for use with the distraction apparatus of FIG. 14.
Figure 19:
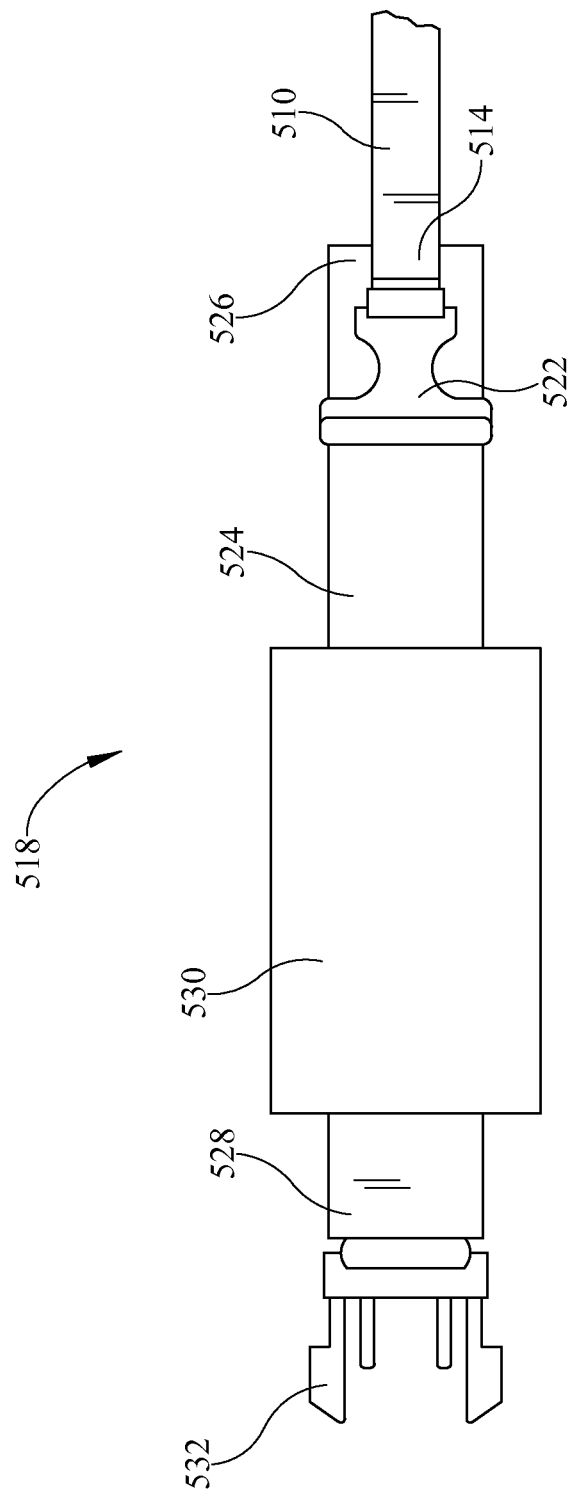
FIG. 19 is a top plan view of a sleeve member of a lateral distractor strap.

The shoulder distraction apparatus 400 provides for several methods of adjustability and several directions of adjustability. Referring to FIG. 14, the extension bar 400 can extend and retract in the direction of arrow 401 and can rotate about axis 403. Braking mechanisms between the extension bar 400 and the upper rod 14 may be included with the system 8 to control the ease of extension, retraction, and rotation of extension bar 400. Additionally, the operator can adjust sterile strap 500, which is shown in FIGS. 18 and 19, to adjust the lateral traction force provided by sterile strap 500 to the patient's arm without touching nonsterile components. Intraoperative control of the adjustments described herein provides quicker, more accurate positioning compared to systems and methods known in the art.

Easy adjustment of extension and retraction of the extension bar 400, along with the extension bar 400 providing sufficient length, allows for lateral traction to be pulled superior to the patient's shoulder without a member of the sterile staff pushing on the patient's arm to achieve superior displacement of the humeral head. Rotation of the extension bar 400 about axis 403 allows for adjusting anterior and posterior traction vectors without a member of the sterile staff pressing on the patient's shoulder. Such adjustments may be desirable in lateral shoulder arthroscopy.

Figure 15:
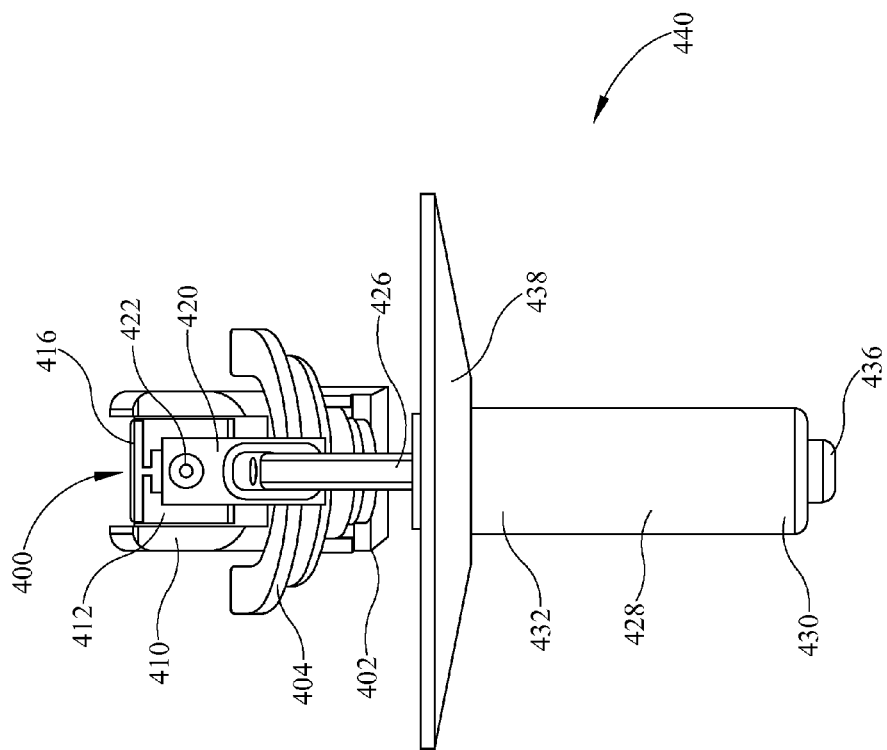
FIG. 15 is an end elevation view of the distraction apparatus of FIG. 14.

The shoulder distraction apparatus 400 includes a mast 402 connectable to a surgical arm positioning system 8 as shown in FIGS. 14 and 15. Illustratively, the mast 402 is connectable to the upper rod 14. The mast 402 is attached to a platform 404.

Figure 16:
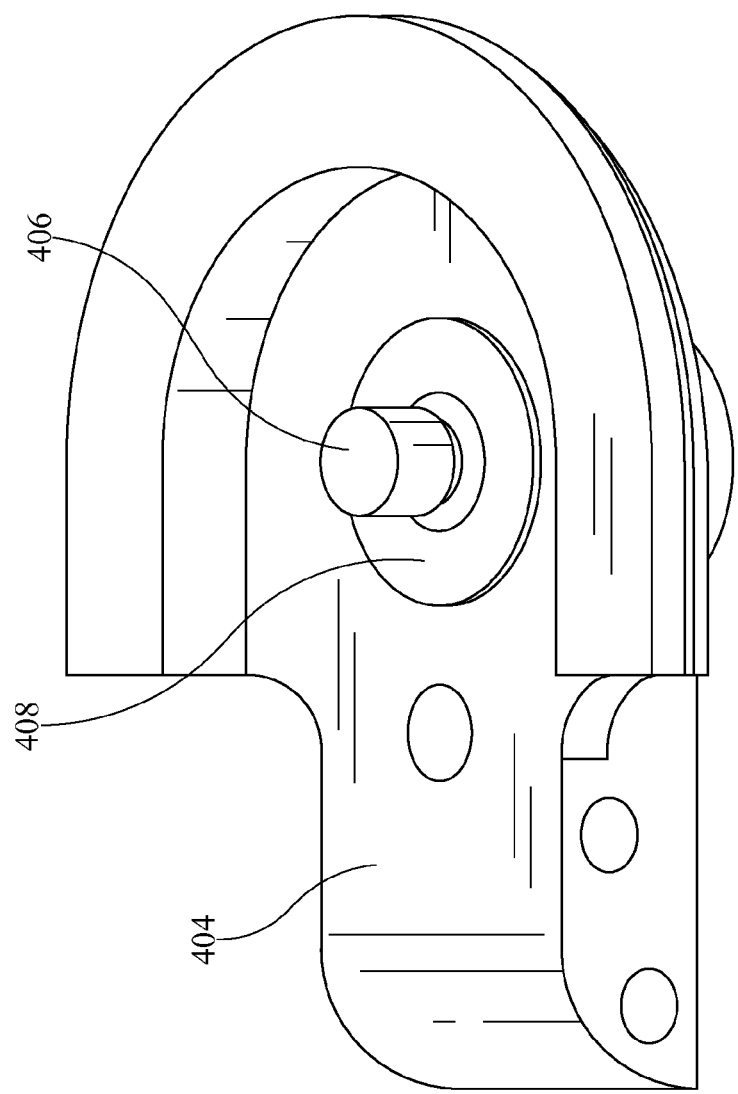
FIG. 16 is a perspective view of a platform of the distraction apparatus of FIG. 14.
Figure 17:
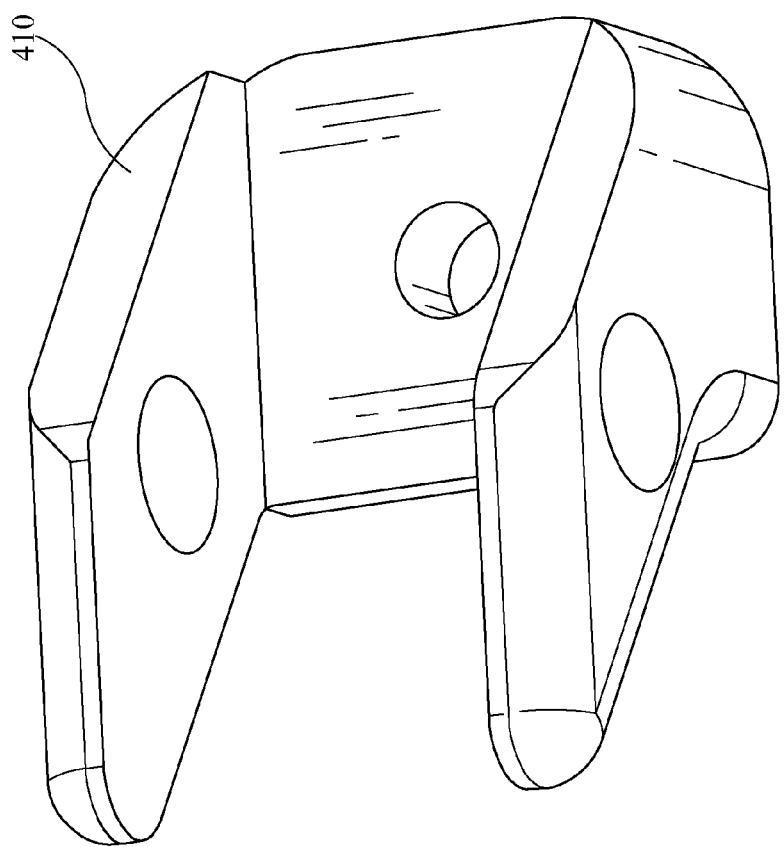
FIG. 17 is a perspective view of an angled bracket of the distraction apparatus of FIG. 14.

The platform 404 is configured to engage a rotation stud 406, as shown in FIG. 16. The rotation stud 406 is surrounded by a washer 408 and is attached to an angled bracket 410, shown in FIG. 17. The angled bracket 410 may rotate relative to the platform 404, resulting in movement of components attached to the angled bracket 410, discussed hereinbelow.

The angled bracket 410 is attached to a pair of wheels 412. The wheels 412 are engaged by rails 414 of a lateral beam 416 such that the lateral beam 416 may be moved relative to the angled bracket 410, the platform 404, and the mast 402.

The lateral beam 416 is attached to a pivot connector 418 that is pivotably attached to a pivot member 420. The pivot member 420 is pivotably attached to the pivot connector 418 by a pivot pin 422. The pivot member 420 has a hook pin 424 capable of detachably receiving a hook 426. In some embodiments, the hook 426 is pivotably attachable to the hook pin 424 of the pivot member 420. Illustratively, the pivot member 420 may pivot relative to the pivot connector 418 in a direction perpendicular to the pivoting of the hook 426 relative to the pivot connector 418. Pivoting of the pivot member 420 and the hook 426 allow the shoulder distraction apparatus 400 to respond to adjustment of the patient's arm without itself needing additional adjustment.

The hook 426 is attached to a tension meter 428 having a first end 430 and a second end 432. The hook 426 is attached to the second end 432 of the tension meter 428. A hook lock 434 for locking the hook 426 to the hook pin 424 of the pivot member 420 is also attached to the second end 432 of the tension meter 428. The first end 430 of the tension meter 428 has a hanger 436 capable of receiving a lateral distractor strap 500. When the lateral distractor strap 500 is attached to the hanger 436 and tension is applied to a patient's arm by the lateral distractor strap 500, the tension meter 428 provides a physician information indicating the amount of traction applied to the patient's arm.

In some embodiments, the tension meter 428 is surrounded by a hanger flange 438 for separating sterilized components from non-sterilized components. One skilled in the art will appreciate that the hanger flange 438 may be attached to the shoulder distraction apparatus 400 in any manner that separates sterilized components from non-sterilized components and alternative configurations are within the scope of this disclosure.

When the shoulder distraction apparatus 400 is not in use for surgery, components of the shoulder distraction apparatus 400 may be sterilized. The hanger 436, the tension meter 428, the hanger flange 438, the hook 426, and the hook lock 434 form a detachable assembly 440 and may be detached from other components and sterilized. The use of the detachable assembly 440 provides the benefit of allowing individual components to be sterilized. Also, the detachable assembly 440 may be easily attached to the rest of the shoulder distraction apparatus 400 by a sterile physician while maintaining sterility without the assistance of non-sterile personnel.

The lateral beam 416 is adjusted relative to the angled bracket 410 to adjust the position of the hanger 436 to account for factors such as the length of the patient's arm, the position of the patient's arm, or the patient's position on the surgical table. The position of the hanger 436 may also be adjusted by rotation of the angled bracket 410 relative to the platform 404. The position of the hanger 436 may further be adjusted by one or both of pivoting of the hook 426 about the hook pin 424 and pivoting the pivot member 420 about the pivot pin 422. The shoulder distraction apparatus 400 provides the benefit of allowing for several methods of adjustability, thereby allowing the physician to control the position of the hanger 436.

Figure 38:
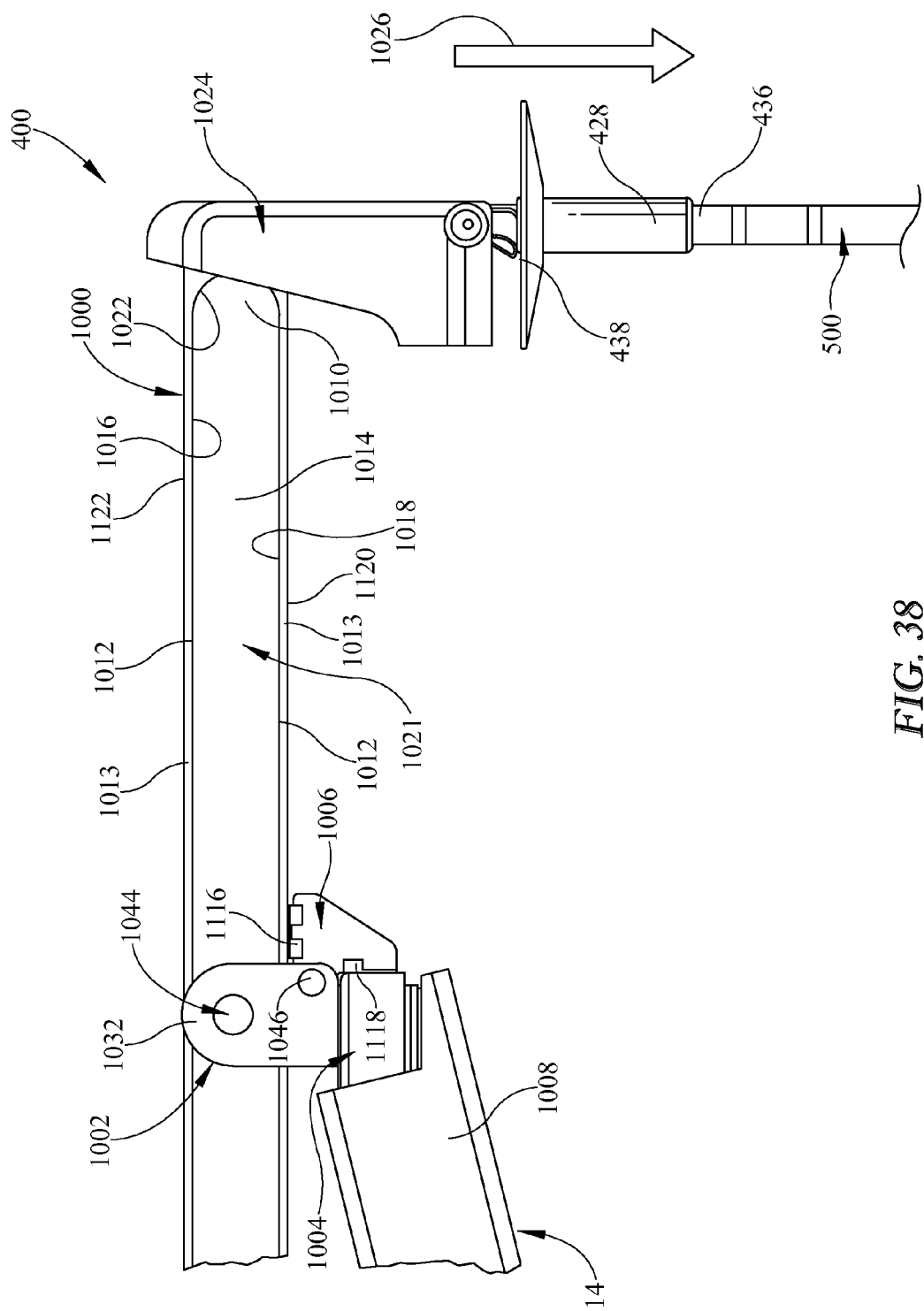
FIG. 38 is a side elevation view of a portion of a shoulder distraction apparatus with a lateral distractor strap hanging downwardly therefrom.
Figures 42A, 42B:
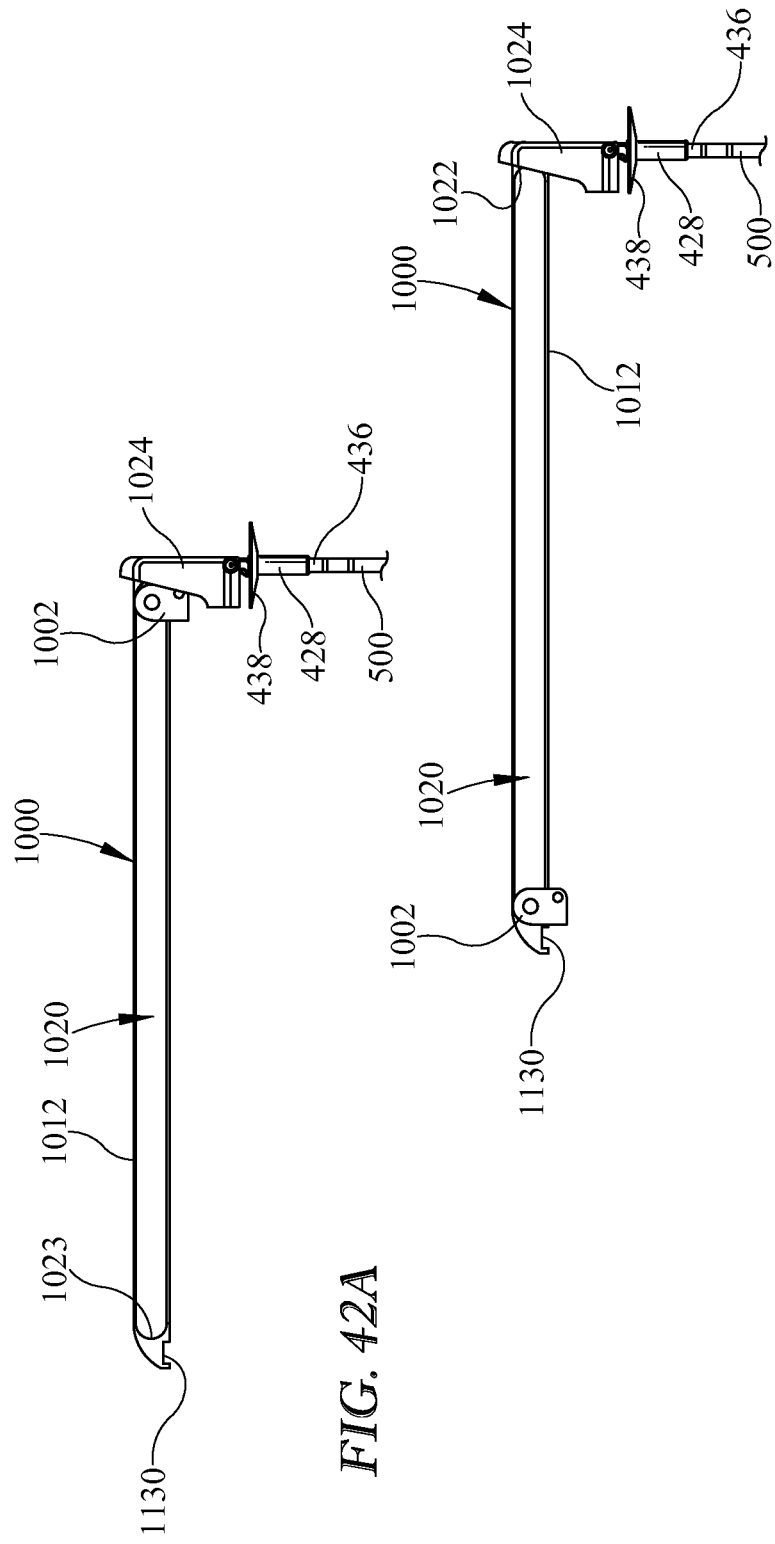
FIG. 42A is a partial side elevation view of the shoulder distraction apparatus of FIG. 38 with the extension bar in a released, retracted position.
FIG. 42B is a partial side elevation view of the shoulder distraction apparatus of FIG. 38 with the extension bar in a released, extended position.

Referring now to FIG. 38, in the second embodiment, the shoulder distraction apparatus 400 is substituted by a shoulder distraction apparatus 1400 that includes an extension bar 1000, a wheel bracket 1002, a platform 1004, a brake foot 1006, a link 1024, and a lateral distractor strap 500. The platform 1004 supports the wheel bracket 1002 and is attached to a first end region 1008 of the upper rod 14. It should be appreciated that the platform 1004 may be attached to other components of the surgical arm positioning system 8 or may be supported by an assembly other than the surgical arm positioning system 8. For example, the platform 1004 may be attached to a post that is attached to the surgical table in some embodiments. The wheel bracket 1002 is coupled to the extension bar 1000 such that the extension bar 1000 extends and retracts relative to the upper rod 14 as shown in FIGS. 42A and 42B.

The link 1024 is attached to a first end 1010 of the extension bar 1000, and the lateral distractor strap 500 hangs downwardly from the link 1024. The link 1024 is configured to pivot about the first end 1010 of the extension bar 1000 toward and away from the wheel bracket 1002. The lateral distractor strap 500 is adapted to receive a patient's arm such that a lateral distraction force is applied to the patient's arm and a corresponding downward force is applied to the first end 1010 of the extension bar 1000 in the direction indicated by arrow 1026 in FIG. 38. The extension bar 1000, the wheel bracket 1002, the platform 1004, and the brake foot 1006 illustratively comprise stainless steel, but in some embodiments may alternatively or additionally comprise other materials. Suitable materials include, but are not limited to, other metals such as aluminum, iron, or metal alloys; or plastics such as polypropylene.

Figure 39:
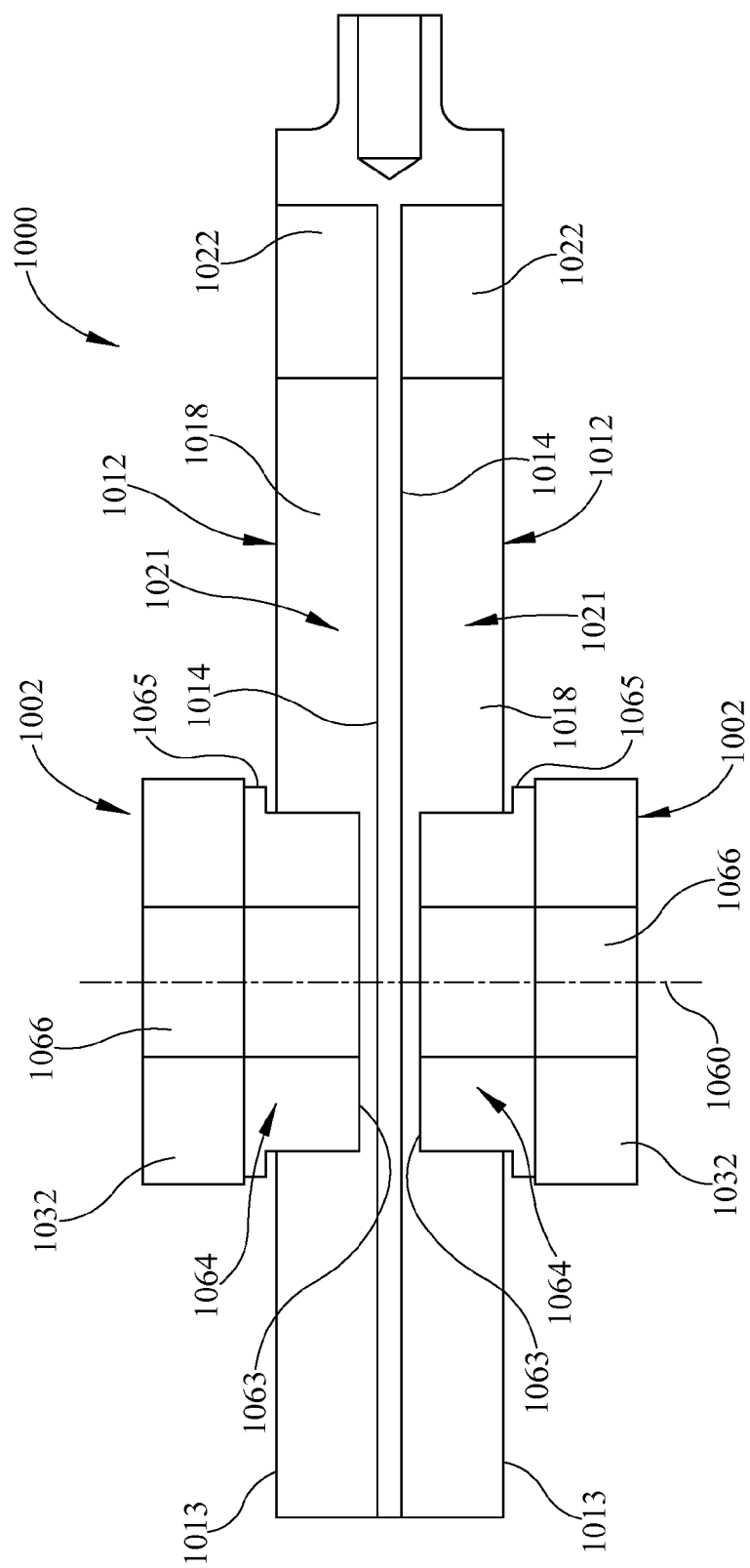
FIG. 39 is a partial cross-sectional view of the shoulder distraction apparatus of FIG. 38.

The extension bar 1000 has an outer lower surface 1120, an outer upper surface 1122 opposite the outer lower surface 1120, and an I-shaped cross section to provide tracks 1012 on opposite sides of the extension bar 1000 as shown in FIGS. 38 and 39. Each track 1012 has a substantially vertical inner surface 1014, a top surface 1016, and a bottom surface 1018. The top and bottom surfaces 1016, 1018 are substantially parallel to each other along the length of the extension bar 1000 and are substantially perpendicular to inner surface 1014. The inner, top, and bottom surfaces 1014, 1016, 1018 of each track 1012 define a wheel-receiving gap 1021. The extension bar 1000 has first stop surfaces 1022 and second stop surfaces 1023 (see FIGS. 42A, 42B, and 43) at opposite ends of the extension bar 1000.

Figure 40:
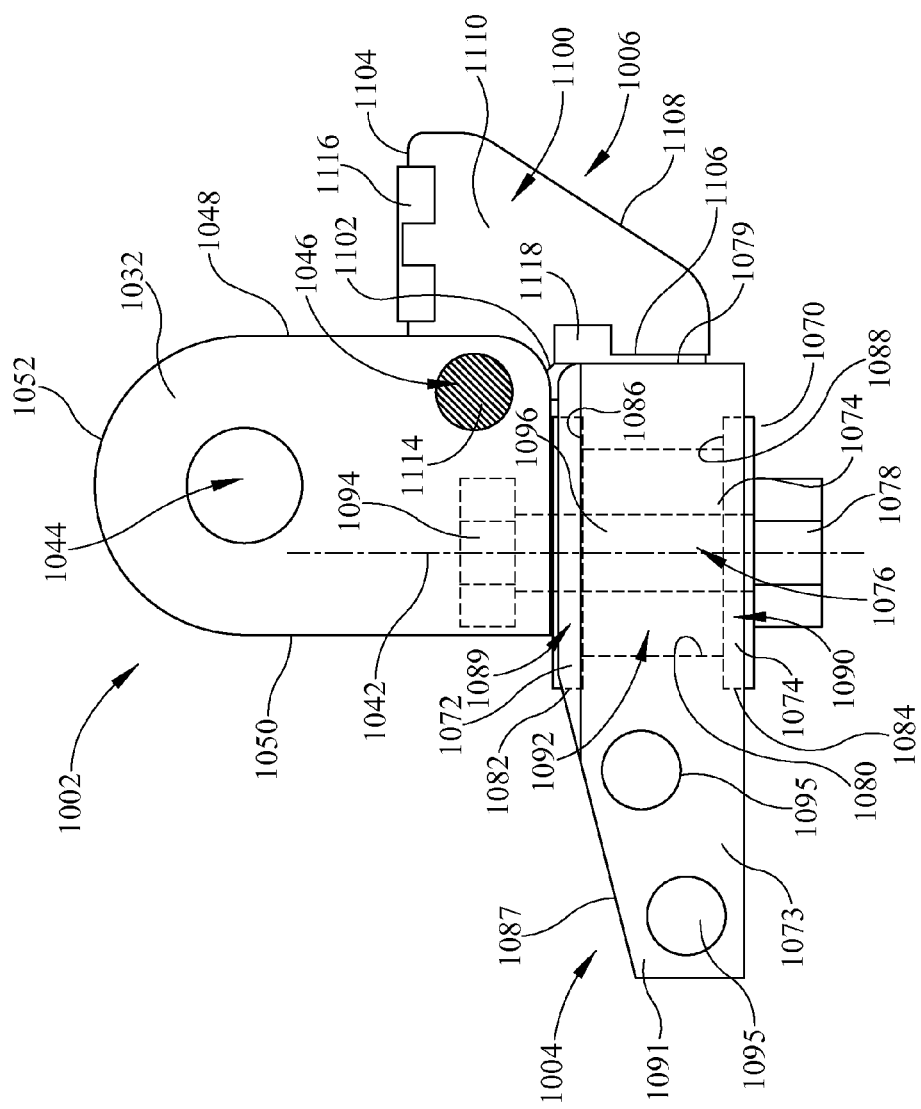
FIG. 40 is a side elevation view showing components of the shoulder distraction apparatus of FIG. 38 including a wheel bracket, a platform beneath the wheel bracket, and a brake foot to the right of both the wheel bracket and the platform.
Figure 41:
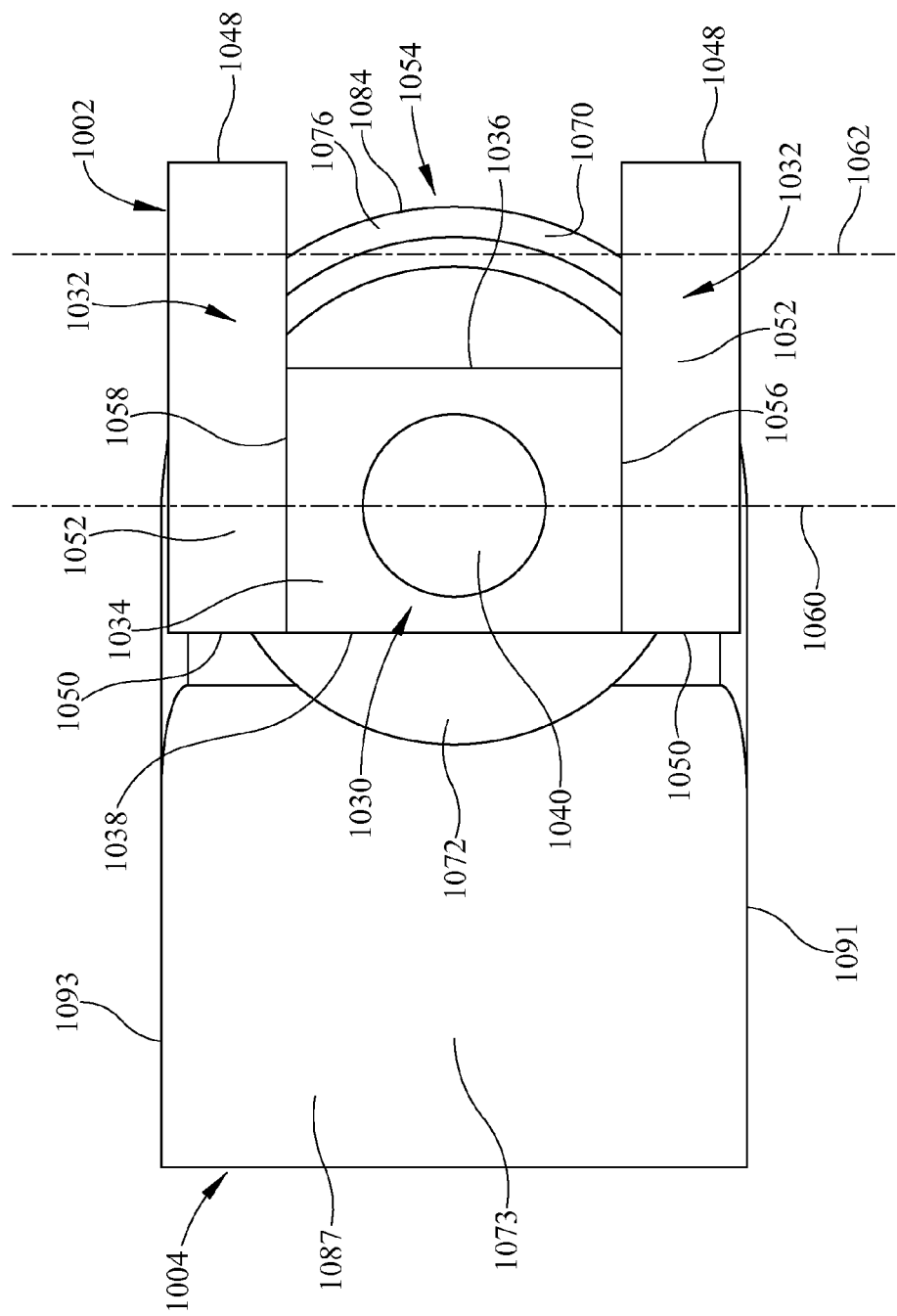
FIG. 41 is a top plan view of the wheel bracket and platform of the shoulder distraction apparatus of FIG. 38.

The wheel bracket 1002 has a body 1030 and two arms 1032 as shown in FIGS. 40 and 41. The body 1030 has a top face 1034, a bottom face (not shown) opposite the top face 1034, a front side 1036, a back side 1038 opposite the front side 1036, a left side 1056, and a right side 1058 opposite the left side 1056 as shown in FIG. 40. The left and right sides 1056, 1058 connect the front and back sides 1036, 1038. A hole 1040 extends through the body 1030 from the top face 1034 to the bottom face. The center of the hole defines a first rotational axis, indicated by broken line 1042 as shown in FIG. 40. The left side 1056 and the right side 1058 of the body 1030 each has one of the arms 1032 extending therefrom. The arms 1032 extend substantially parallel to each other from the top face 1034 and the front side 1036 of the body 1030.

Each of the arms 1032 of the wheel bracket 1002 has an upper hole 1044, a lower hole 1046, a front side 1048, a back side 1050, and a top surface 1052. The front and back sides 1048, 1050 extend away from the body 1030 of the wheel bracket 1002 to the top surface 1052. The top surface 1052 has substantially semicircular curvature in the illustrative example. The arms 1032 mirror each other in structure, forming two parallel planes defining a gap 1054 therebetween as shown in FIG. 41. The gap 1054 is sized to receive the extension bar 1000.

The centers of the upper holes 1044 of the arms 1032 define a second rotational axis, indicated by broken line 1060 in FIG. 41. The second rotational axis 1060 is perpendicular to the first rotational axis 1042. The upper holes 1044 are located in the arms 1032 such that the second axis 1060 is closer to the front side 1036 than the back side 1038 of the body 1030 and the second axis 1060 does not intersect the first axis 1042. The centers of the lower holes 1046 define a third rotational axis, indicated by broken line 1062. The third rotational axis 1062 is perpendicular to the first rotational axis 1042 and parallel to the second rotational axis 1060. The lower holes 1046 are located in the arms 1032 such that the distance between the third axis 1062 and the front side 1048 of each arm 1032 is shorter than the distance between the second axis 1060 and the front side 1048 of each arm 1032. Additionally, the distance between the third axis 1062 and the top face 1034 of the body 1030 is shorter than the distance between the second axis 1060 and the top face 1034 of the body 1030.

The wheel bracket 1002 has two wheels 1064 mounted thereto as shown in FIG. 39. An axel 1066 is coupled to each wheel 1064. Each of the upper holes 1044 of the arms 1032 of the wheel bracket 1002 receives a respective one of the axels 1066 such that the wheels 1064 are coupled to opposite sides of the wheel bracket 1002 and coaxially rotate about the second axis 1060. The wheels 1064 extend into the gap 1054 of the wheel bracket 1002 and inner annular surfaces 1063 of the wheels 1064 face each other. The wheels 1064 are engaged by opposite tracks 1012 and reside within the wheel-receiving gaps 1020 of the extension bar 1000.

The distance between the inner annular surfaces 1063 of the wheels 1064 is slightly larger than the distance between the inner surfaces 1014 of opposite tracks 1012 of the extension bar 1000 so that the wheels 1064 can rotate without interference from surfaces 1014. The spacing between the wheels 1064 is sufficiently small such that the wheels 1064 prevent more than a slight amount of lateral shifting of the extension bar 1000 relative to the wheel bracket 1002 in a direction perpendicular to the inner surfaces 1014 of the tracks 1012. In the illustrative embodiment, each wheel has an annular flange 1065 which serves as a thrust bearing between edges 1013 of tracks 1012 and the respective arm 1032 as shown in FIG. 39. It should be appreciated that, in some embodiments, one wheel 1064 and one track 1012 may couple the wheel bracket 1002 to the extension bar 1000. In further embodiments, the wheel 1064 may be replaced by a sled, glide pad, or other mechanism capable of permitting translation of the extension bar 1000 relative to the bracket 1002.

The platform 1004 has a body 1070, upper and lower thrust washers 1072, 1074, a bolt 1076, and a nut 1078 as shown in FIGS. 40 and 41. The body 1070 has a curved outer surface 1079 that extends about 180° circumferentially around the platform 1004 and is centered at the first rotation axis 1042. The body 1070 also has an internal passageway therein having a substantially cylindrical upper recess 1089 having a first diameter, a substantially cylindrical lower recess 1090 having a second diameter, and a substantially cylindrical cavity 1092 connecting the recesses 1089, 1090 and having a third diameter as shown in FIG. 40. The upper recess 1089 is defined by an upper inner annular wall 1082 having the first diameter and the lower recess 1090 is defined by a lower annular wall 1084 having the second diameter. The cylindrical cavity 1092 is defined by a center inner annular wall 1080 having the third diameter.

The inner annular walls 1080, 1082, 1084 are substantially cylindrical and are substantially parallel to each other. An upper shoulder surface 1086 substantially perpendicular to the inner annular walls 1080, 1082, 1084 connects the upper inner annular wall 1082 to the center inner annular wall 1080. A lower shoulder surface 1088 connects the lower annular wall 1084 to the center inner annular wall 1080. In the illustrative embodiment, the first diameter is substantially the same as the second diameter. In some embodiments, the platform 1004 comprises a substantially cylindrical bronze bushing having a diameter slightly smaller than the third diameter that resides within the cylindrical cavity 1092.

The upper and lower thrust washers 1072, 1074 each have an outer wall having an outer diameter and an inner wall having an inner diameter and defining a hole therein. The outer diameter of the upper thrust washer 1072 is slightly smaller than the first diameter of the upper recess 1089 and larger than the third diameter of the cylindrical cavity 1092. The outer diameter of the lower thrust washer 1074 is slightly smaller than the second diameter of the lower recess 1090 and larger than the third diameter of the cylindrical cavity 1092. The upper and lower thrust washers 1072, 1074 reside within the upper and lower recesses 1089, 1090, respectively, and extend slightly above and below the body 1070 of the platform 1004, respectively, as shown in FIG. 40. The bottom face of the body 1030 of the bracket 1002 rests against the upper thrust washer 1072. The washers 1072, 1074 illustratively comprise bronze and are impregnated with oil.

The bolt 1076 has a head portion 1094 and a threaded portion 1096 having a substantially cylindrical shape as shown in FIG. 40. The diameter of the threaded portion 1096 is slightly smaller than the inner diameter of the thrust washers 1072, 1074, and the head portion 1094 has a larger diameter than the inner diameter of the upper thrust washer 1072. The threaded portion 1096 of the bolt 1076 extends through the hole 1040 of the wheel bracket 1002, the hole of the upper thrust washer 1072, and beyond the hole of the lower thrust washer 1074 such that the head portion 1094 rests against the top face 1034 of the body 1030 of the bracket 1002 and the center of the threaded portion 1096 of the bolt 1076 is substantially aligned with the first rotational axis 1042. The resulting configuration allows the bracket 1002 and components coupled thereto, including the extension bar 1000, to rotate relative to the platform 1004 about the first axis 1042. The nut 1078 is threaded onto the threaded portion 1096 of the bolt 1076 to hold the bracket 1002 to the platform 1002. In the illustrative embodiment, the nut 1078 may be tightened or loosened along the threaded portion 1096 of the bolt 1076 to adjust the ease at which the bracket 1002 rotates relative to the platform 1004.

It is to be appreciated that other mechanisms to permit rotation of the bracket 1002 relative to the platform 1004 are contemplated by this disclosure. For example, the platform 1004 may comprise a bearing (e.g., ball bearing or roller bearing) having portions that that can rotate within the body 1070 about the first axis 1042. The bracket 1002 may be fixed to the bearing such that when the bearing rotates about the first rotational axis 1042 within the body 1070, the wheel bracket 1002 also rotates about the first rotation axis 1042. To adjust the ease at which the bracket 1002 rotates, a mechanism such as a clutch may be coupled to the bracket 1002.

The body 1070 of the platform 1004 has a foot portion 1073 that extends away from the first axis 1042 and attaches to the first end region 1008 of the upper rod 14 to mount the shoulder distraction apparatus 400 to the rest of the surgical arm positioning system 8 as shown in FIGS. 38, 40, and 41. The foot portion 1073 of the platform 1004 has a top wall 1087, a left wall 1091, and a right wall 1093. The left wall 1088 extends substantially parallel to the right wall 1093. The left wall 1088 has two mounting holes 1095 therein as shown in FIG. 40. The foot portion 1073 is coupled to the upper rod 14, which in some embodiments is formed as an extrusion such that the foot portion 1073 fits therein. In the illustrative embodiment, the platform 1004 is bolted to the upper rod 14 by bolts that extend through holes in the first end region 1008 of the upper rod 14 and into the mounting holes 1095 of the foot portion 1073. It should be appreciated that the foot portion 1073 may have one, three, four, or more mounting holes 1095 in other embodiments.

The brake foot 1006 includes a body portion 1100 and a connecting portion 1102 as shown in FIG. 40. The brake foot 1006 also has a top surface 1104, a back surface 1106, a front surface 1108, a left surface 1110, and a right surface (not shown) opposite the left surface 1110. The top surface 1104 is oriented substantially perpendicular to the back surface 1106, and the top and back surfaces 1104, 1106 are joined by the connecting portion 1102. The connecting portion 1102 extends away from the back surface 1106, and a hole extends through the connecting portion 1102 from the left surface 1110 to the right surface. The connecting portion 1102 resides in the gap 1054 of the wheel bracket 1002, and the hole of the brake foot 1006 is substantially aligned with the lower holes 1046 of the wheel bracket 1002. A brake pin 1114 extends through the lower holes 1046 of the wheel bracket 1002 and through the hole of the brake foot 1006 to attach the brake foot 1006 to the wheel bracket 1002 such that the brake foot 1006 can pivot relative to the wheel bracket 1002 about the third axis 1062.

The brake foot 1006 includes a horizontal brake 1116 and a vertical brake 1118. The horizontal brake 1116 is positioned on the top surface 1104 of the brake foot 1006, and the vertical brake 1118 is positioned on the back surface 1106 of the brake foot 1006 such that the vertical brake 1118 is oriented substantially perpendicular to the horizontal brake 1116. The horizontal brake 1116 is positioned under the outer lower surface 1120 of the extension bar 1000 and the vertical brake 1118 is positioned over the curved outer surface 1079 of the platform 1004. In some embodiments, the brakes 1116, 1118 comprise a polymeric material such as rubber. In other embodiments, one or both of the brakes 1116, 1118 comprise metal.

Figure 43:
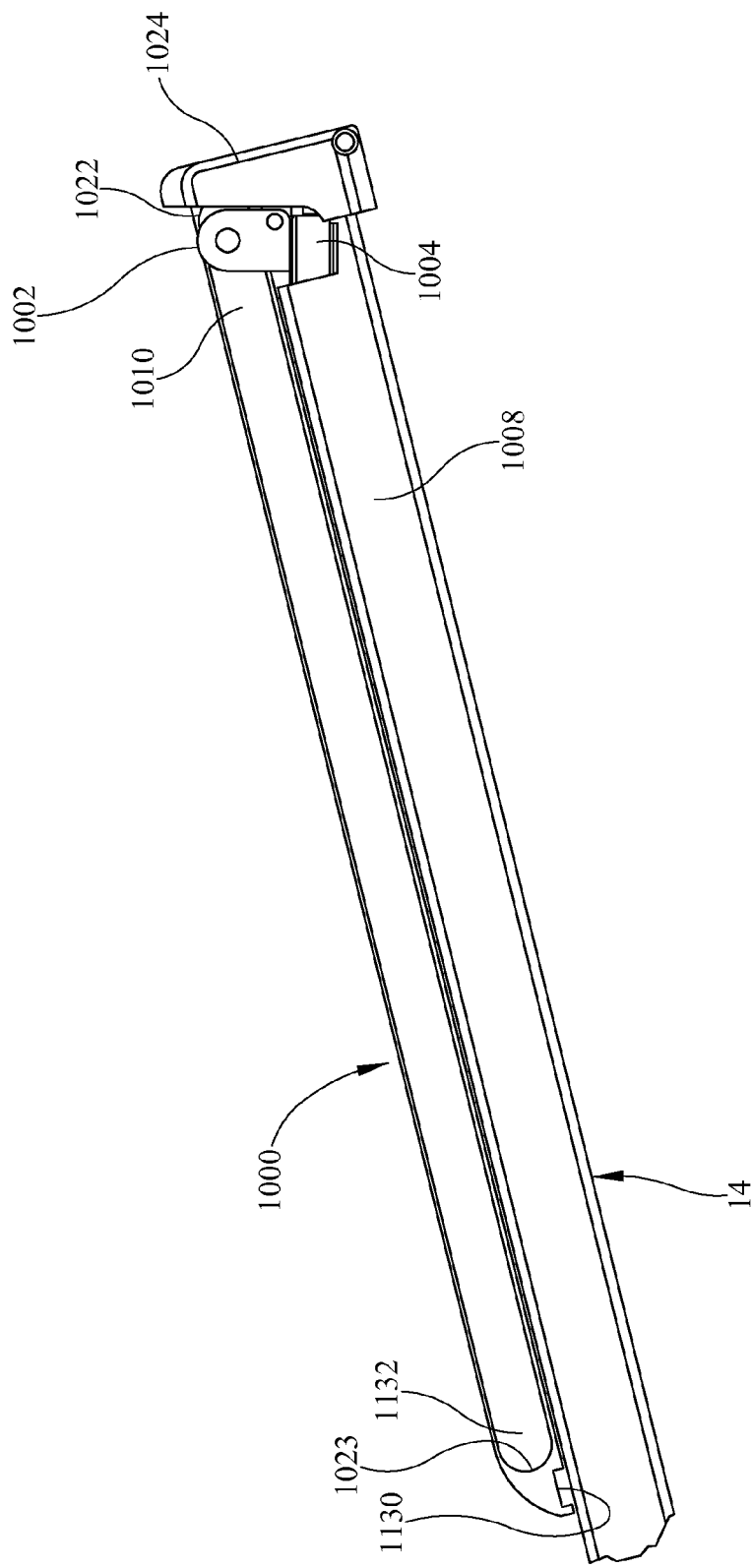
FIG. 43 is a partial side elevation view of the shoulder distraction apparatus of FIG. 38 with the extension bar in a storage position.

The extension bar 1000 includes a magnetic catch 1130 as shown in FIG. 43. The magnetic catch 1130 is positioned at a second end 1132 of the extension bar 1000 opposite the first end 1010 of the extension bar 1000. The magnetic catch 1130 faces the upper rod 14 such that when the second end 1132 of the extension bar 1000 is in contact with the upper rod 14, the magnetic catch 1130 holds the extension bar 1000 against the upper rod 14.

The extension bar 1000 extends and retracts relative to the upper rod 14 between an extended positioned and a retracted position. When the extension bar 1000 is in the retracted position, the wheels 1064 and the first stop surfaces 1022 are in contact such that the first stop surfaces 1022 limit the range of retraction of the extension bar 1000 relative to the upper rod 14 by preventing the extension bar 1000 from further retracting as shown in FIG. 42A. In the retracted position, the center of mass of the extension bar 1000 is positioned behind the wheel bracket 1002 and over the upper rod 14 such that the second end 1132 of the extension bar 1000 falls toward the upper rod 14 when the weight of the second end 1132 is not supported. When the extension bar 1000 is in the extended position, the wheels 1064 and the second stop surfaces 1023 are in contact such that the second stop surfaces 1023 limit the range of extension of the extension bar 1000 relative to the upper rod 14 by preventing the extension bar 1000 from further extending as shown in FIG. 42B.

The extension bar 1000 is movable relative to the wheel bracket along the direction of the inner surfaces 1014 of the tracks 1012. As the extension bar 1000 moves from the retracted position to the extended position, the wheels 1064 and the tracks 1012 guide movement of the extension bar 1000 relative to the upper rod 14 with the wheels 1064 rotating about the second axis 1060 within the wheel-receiving gaps 1020 of the tracks 1012 such that the first end 1010 of the extension bar 1000 moves away from the wheel bracket 1002. As the extension bar 1000 moves from the extended position to the retracted position, the wheels 1064 and the tracks 1012 guide movement of the extension bar 1000 relative to the upper rod 14 with the wheels 1064 rotating about the second axis within the wheel-receiving gaps 1020 of the tracks 1012 such that the first end 1010 of the extension bar 1000 moves toward the wheel bracket 1002. It should be appreciated that, in some embodiments, one wheel 1064 and one track 1012 may be used to guide movement of the extension bar 1000.

The extension bar 1000 is also moveable to a storage position as shown in FIG. 43. When the extension bar is in the storage position, the wheels 1064 and the first stop surfaces 1022 are in contact such that the first stop surfaces 1022 limit the range of retraction of the extension bar 1000 relative to the upper rod 14 by preventing the extension bar 1000 from further retracting, and the second end 1132 of the extension bar 1000 is sufficiently close to the upper rod 14 for the magnetic catch 1130 to interact with the material of the upper rod 14 and hold the extension bar 1000 against the upper rod 14. The link 1024 is shaped such that the wheel bracket 1002, the platform 1004, and the brake foot 1006 can reside or partially reside therein. As the extension bar 1000 moves from the retracted position to the storage position, the wheels 1064 remain substantially in place relative to the tracks 1012 of the extension bar 1000, such that the extension bar 1000 and wheels 1064 rotate about the second axis 1060 causing the first end 1010 of the extension bar 1000 to move upwardly and the second end 1132 of the extension bar 1000 to move downwardly toward the upper rod 14.

As the extension bar 1000 moves from the storage position to the retracted position, the wheels 1064 remain substantially in place relative to the tracks 1012 of the extension bar 1000, such that that the extension bar 1000 and wheels 1064 rotate about the second axis 1060 causing the first end 1010 of the extension bar 1000 to move downwardly and the second end 1132 of the extension bar 1000 to move upwardly away from the upper rod 14. It should be appreciated that the upper rod 14 may lack materials to which the magnetic catch 1130 is attracted, and a receiving piece comprising a material to which the magnetic catch 1130 is attracted may be attached to the upper rod 14 for receiving the magnetic catch 1130. The magnetic catch 1130 allows the shoulder distraction apparatus 400 to be easily stored and does not require any locking mechanism to be manipulated prior to deploying the extension bar 1000.

The extension bar 1000 is rotatable relative to the upper rod 14 between a braked position and a released position. The designation of a braked position or a released position is independent of the designation of a retracted position or an extended position. For example, the extension bar 1000 may be in a braked position or a released position when it is in an extended position, in a retracted position, or between the extended and retraction positions. When a patient's arm is supported by the lateral distractor strap 500, the patient's arm causes the extension bar 1000 to move into the braked position by applying a downward force in the direction indicated by arrow 1026 in FIG. 38 to the first end 1010 of the extension bar 1000. In the braked position, the brake foot 1006 is positioned such that the horizontal brake 1116 is in contact with the outer lower surface 1120 of the extension bar 1000 and the vertical brake 1118 is in contact with the curved outer surface 1079 of the platform 1004. In the braked position, friction between the horizontal brake 1116 and the outer lower surface 1120 of the extension bar 1000 prevents the extension bar 1000 from extending and retracting relative to the wheel bracket 1002, the platform 1004, and the upper rod 14. Also, friction between the vertical brake 1118 and the curved outer surface 1079 prevents the wheel bracket 1002 and the extension bar 1000 from rotating relative to the platform 1004 and the upper rod 14 about axis 1042.

When the lateral distractor strap 500 is not supporting the full weight of the patient's arm, the extension bar 1000 may be in a released position. In the released position, as shown in FIGS. 42A and 42B, the brake foot 1006 is positioned such that friction between the horizontal brake 1116 and the outer lower surface 1120 of the extension bar 1000 is sufficiently limited to allow the extension bar 1000 to extend and retract relative to the wheel bracket 1002. The brake foot 1006 is also positioned such that friction between the vertical brake 1118 and the curved outer surface 1079 is sufficiently small to allow the wheel bracket 1002 and extension bar 1000 to rotate relative to the platform 1004 and the upper rod 14 about axis 1042. The second end 1132 of the extension bar 1000 is closer to the upper rod 14 in the released position than in the braked position, but only by a slight amount as dictated by the amount of compression and expansion experienced by brakes 1116, 1118 when moving between braked and released positions and depending upon the extent of extension and retraction of bar 1000 relative to rod 14. In other words, the first end 1010 of the extension bar 1000 is positioned further upwardly in the released position than in the braked position.

As the extension bar 1000 rotates from the released position to the braked position, the wheels 1064 remain substantially in place relative to the tracks 1012 of the extension bar 1000, such that the extension bar 1000 and wheels 1064 can rotate about the second axis 1060 thereby moving the first end 1010 of the extension bar 1000 downwardly and the second end 1132 of the extension bar 1000 upwardly and away from the upper rod 14. As the first end 1010 of the extension bar 1000 moves downwardly, the outer lower surface 1120 of the extension bar 1000 pushes against the horizontal brake 1116, causing the brake foot 1006 to rotate about the third axis 1062 such that the vertical brake 1118 pushes against the curved outer surface 1079 of the platform 1004. As the extension bar 1000 rotates from the braked position to the released position, the wheels 1064 remain substantially in place relative to the tracks 1012 of the extension bar 1000, such that the extension bar 1000 and wheels 1064 rotate about the second axis 1060 causing the first end 1010 of the extension bar 1000 to move upwardly and the second end 1132 of the extension bar 1000 to move downwardly and toward the upper rod 14. As the first end 1010 of the extension bar 1000 moves upwardly, the outer lower surface 1120 of the extension bar 1000 stops pushing against the horizontal brake 1116 (or, at least the force with which surface 1120 of bar 1000 contacts brake 1116 is lessened sufficiently to permit movement of bar 1000 relative to brake 1116) and releases the brake foot 1006 to rotate about the third axis 1062 such that the vertical brake 1118 stops pushing against the curved outer surface 1079 of the platform 1004 (or, at least the force with which brake 1118 contacts surface 1079 is lessened sufficiently to permit rotation of bar 1000 about axis 1062).

Figure 44:
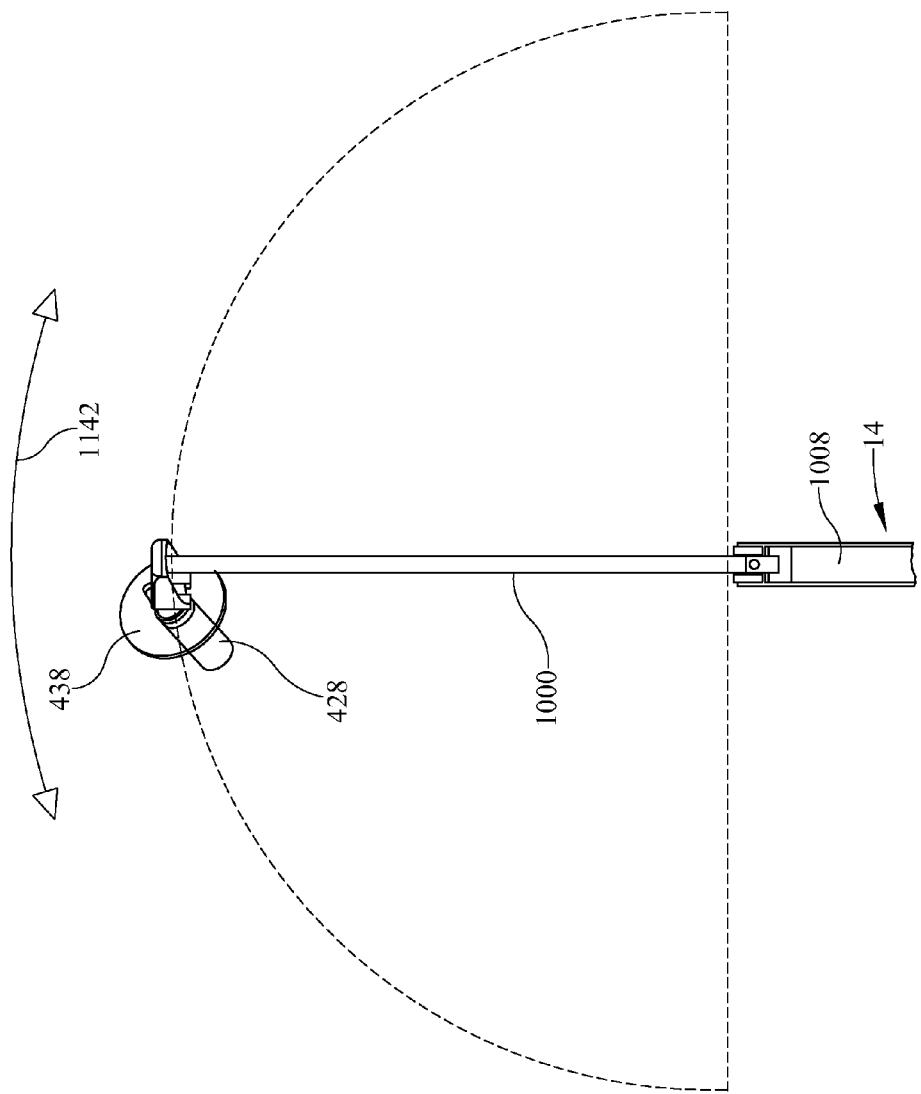
FIG. 44 is a top perspective view of a portion of the shoulder distraction apparatus of FIG. 38.

The extension bar 1000 is also rotatable relative to the upper rod 14 about the first axis 1042 as shown in FIGS. 40 and 44. The direction of rotation of the extension bar is indicated by arrow 1142. As the extension bar 1000 rotates, upper and lower thrust washers 1072, 1074, the bolt 1076, the wheel bracket 1002, and the platform 1004 cooperate such that the wheel bracket 1002 rotates relative to the platform 1004. When torque is applied to the first end 1010 of the extension bar 1000 along the direction of rotation as indicated by arrow 1142, the torque is transmitted from one of the inner surfaces 1014 of the extension bar 1000 to one of the arms 1032 of the wheel bracket 1002 such that the wheel bracket 1002 responds by rotating about axis 1042. It should be appreciated that other mechanisms for rotating the bar 1000 relative to the upper rod 14 are contemplated within the present disclosure. For example, the wheel bracket 1002 may be fixed to the platform 1004, and the platform 1004 may have a rotatable part therein, such as a bearing.

When a patient's arm is supported by the lateral distractor strap 500, the weight of the patient's arm applies a downward force to the first end 1010 of the extension bar 1000 in the direction indicated by arrow 1026, and the lateral distractor strap 500 applies a corresponding lateral distraction force to the patient's arm. The downward force applied by the weight of the patient's arm keeps the extension bar 1000 in the braked position. When a physician supports or partially supports the weight of the patient's arm to release downward force from the first end 1010 of the extension bar 1000, the extension bar 1000 moves toward the released position. When the extension bar 1000 is in the released position, the physician is able to reposition the patient's arm and thereby extend or retract the extension bar 1000 toward the extended or retracted position. When the extension bar 1000 is in the released position, the physician may reposition the patient's arm and thereby rotate the extension bar 1000 relative to the upper rod 14 about the first axis 1042. When the physician has finished repositioning the patient's arm, the physician releases the patient's arm, thereby reapplying downward force to the first end 1010 of the extension bar 1000 and moving the extension bar 1000 from the released position into the braked position. It is to be appreciated that the physician may reposition the patient's arm by adjusting the shoulder distraction apparatus 400 directly. For example, a sterile handle may be attached to the extension bar 1000. When the weight of the patient's arm is supported or partially supported such that the extension bar 1000 is in the released position, the sterile handle may be grasped by a physician or other sterile personnel to rotate, extend, or retract the extension bar 1000 relative to the upper rod 14.

Figure 92:
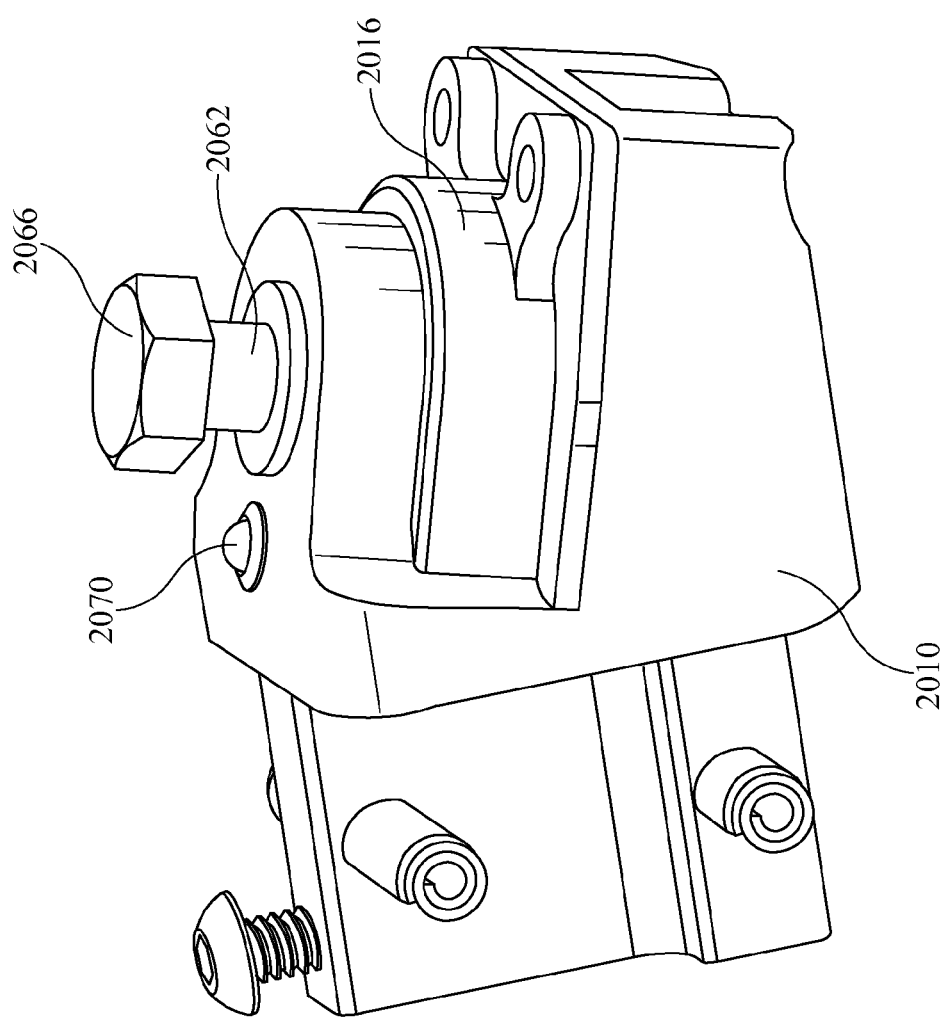
FIG. 92 is a perspective view showing components of the shoulder distraction apparatus of FIG. 88 with the wheel bracket omitted.
Figure 93:
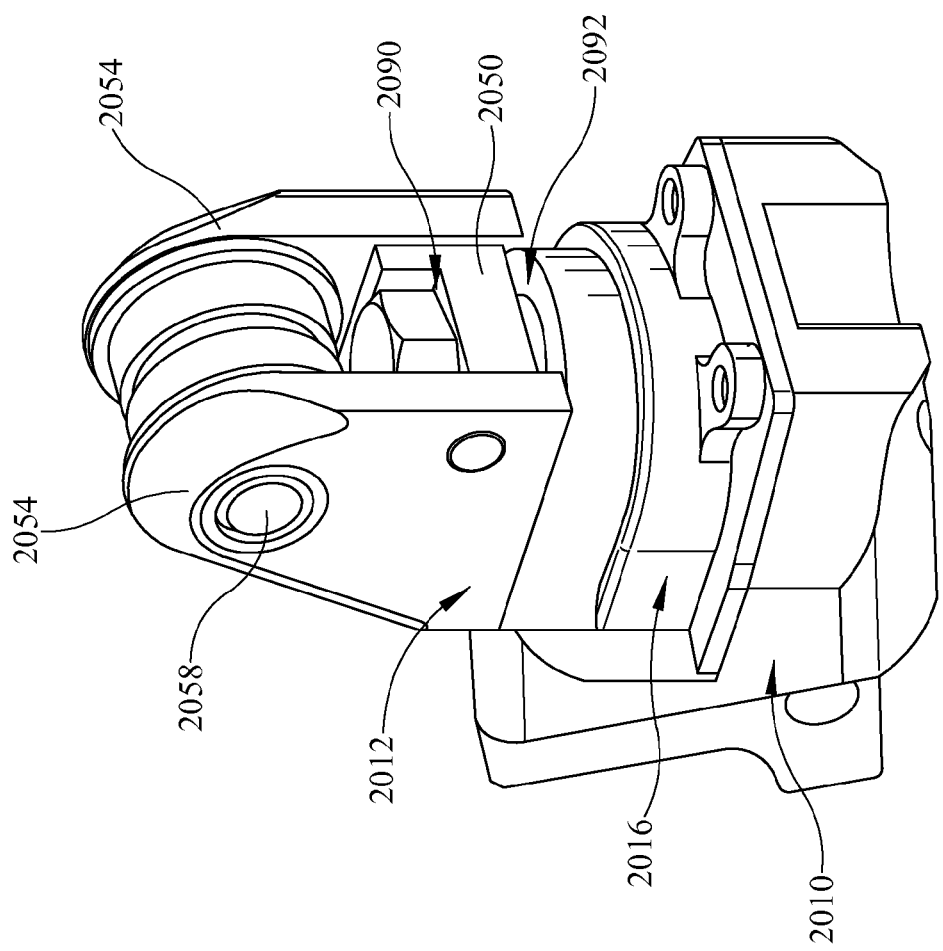
FIG. 93 is a perspective view showing components of the shoulder distraction apparatus of FIG. 88 showing the base of the wheel bracket with the brake foot omitted.
Figure 94:
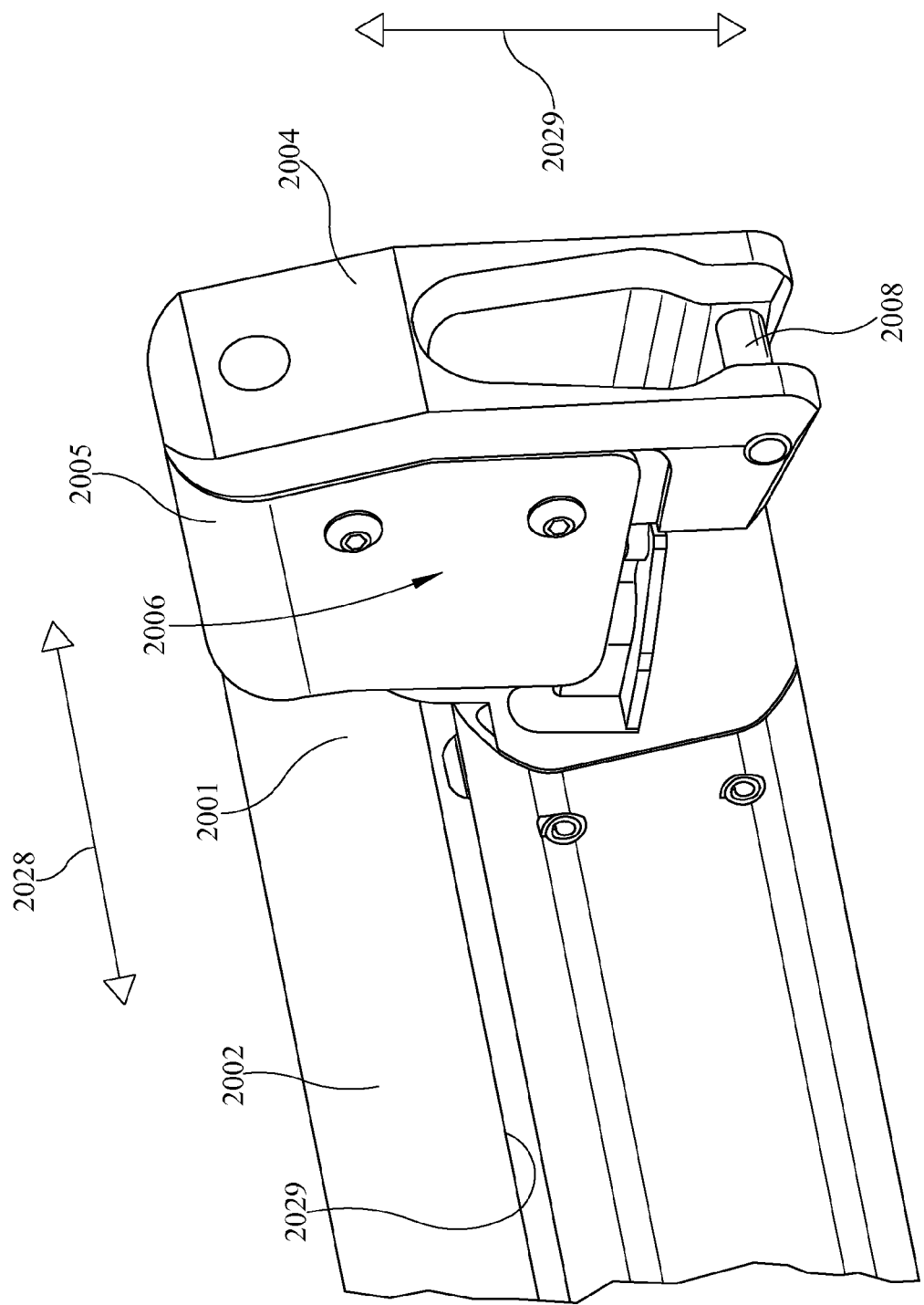
FIG. 94 is a perspective view of the shoulder distraction apparatus of FIG. 88 attached to an end of an upper rod of the surgical arm positioning system of FIG. 61.

In the third embodiment, the shoulder distraction apparatus 400 is substituted by a shoulder distraction apparatus 2000 that includes an extension bar 2002, a hanger 2004 attached to the extension bar 2002, and an adjustment assembly 2006, as shown in FIGS. 88-94. Referring to FIG. 94, lateral traction force is applied to the patient's arm by attaching the patient's arm to the lateral distractor strap 500, which hangs from a pin 2008 of the hanger 2004. The extension bar 2002 and the hanger 2004 are guided and positioned by the adjustment assembly 2006, which is configured to respond to movement of the surgical arm positioning system 8 and the patient's arm.

Figure 89:
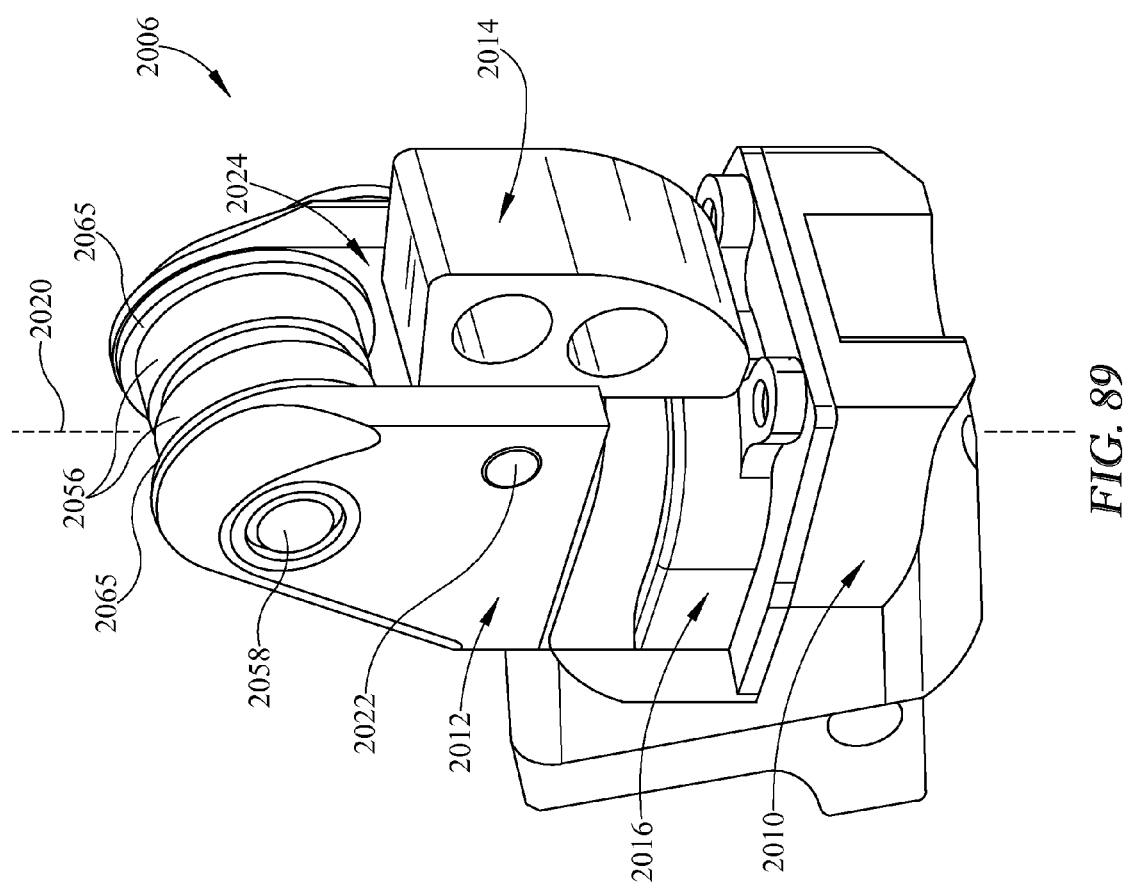
FIG. 89 is a perspective view showing components of the shoulder distraction apparatus of FIG. 88.

Referring now to FIGS. 88 and 89, the adjustment assembly 2006 includes a mounting bracket 2010, a wheel bracket 2012, a brake foot 2014, and a platform 2016. The mounting bracket 2010 is mounted to the upper rod 14 to mount the adjustment assembly 2006 to the frame 10. The wheel bracket 2012 is coupled to the mounting bracket 2010 and can pivot about an axis 2020, as will be described in the further detail below. The brake foot 2014 is coupled to the wheel bracket 2012 by a pin 2022 that extends across a gap 2024 of the wheel bracket 2012 (best seen in FIG. 90) and through an aperture (not shown) of the brake foot 2014. The brake foot 2014 can pivot about the pin 2022 to contact the platform 2016, which encircles the mounting bracket 2010. In some embodiments, the brake foot 2014 and the platform 2016 are both made of metal. As shown in FIG. 94, a cover 2005 surrounds and protects the adjustment assembly 2006.

Figure 90:
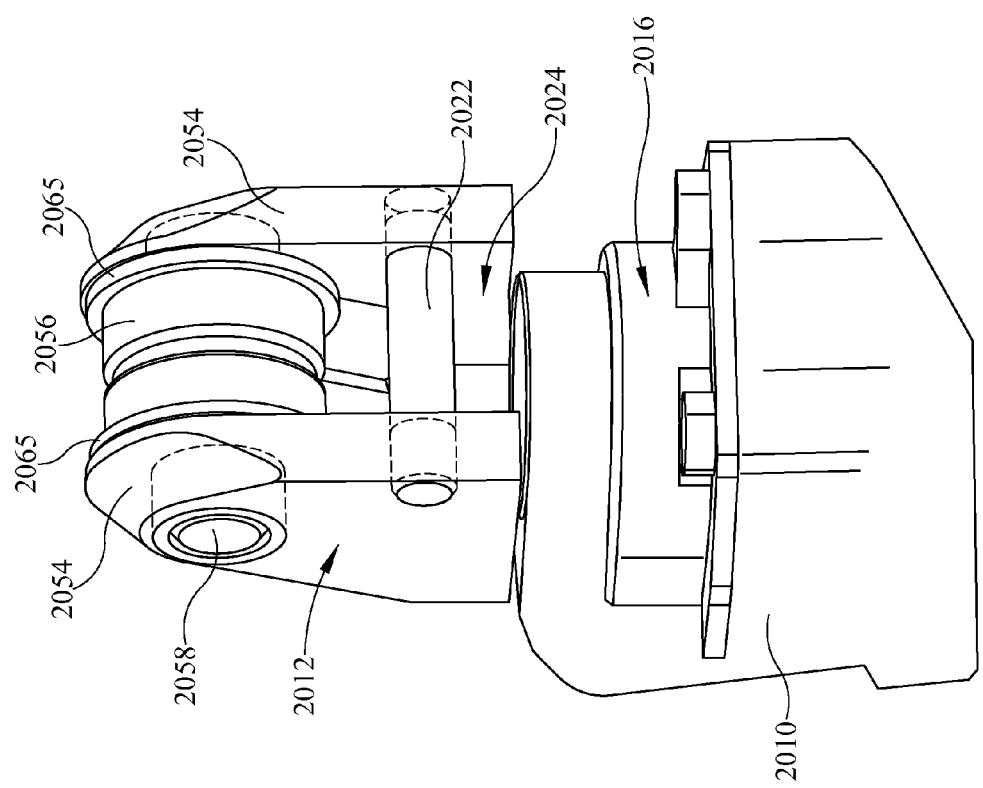
FIG. 90 is a perspective view showing components of the shoulder distraction apparatus of FIG. 88 with the brake foot and a base of the wheel bracket omitted.
Figure 91:
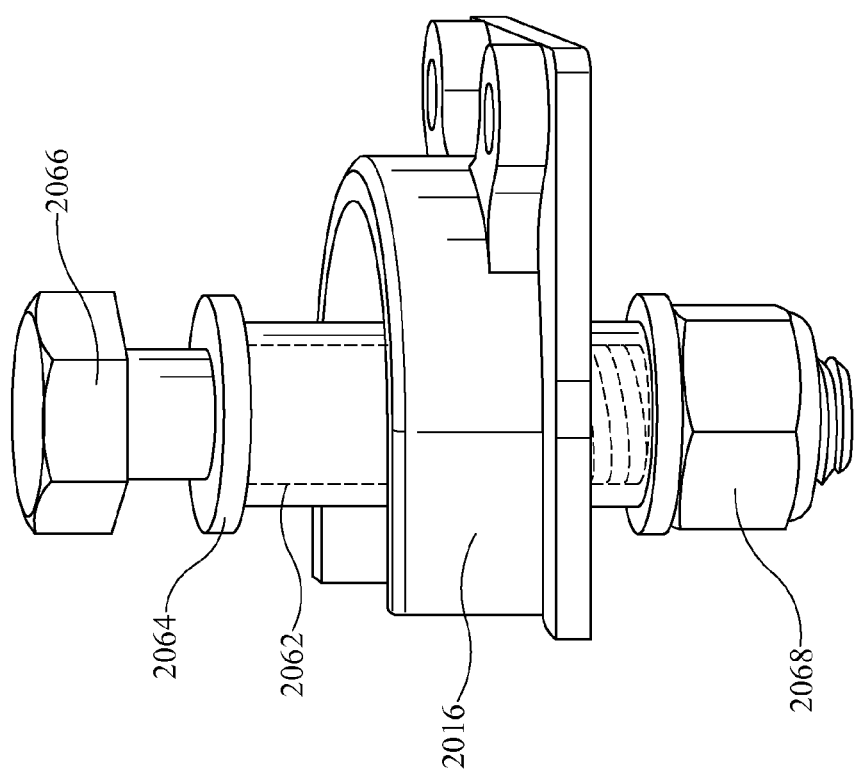
FIG. 91 is a perspective view showing components of the shoulder distraction apparatus of FIG. 88 with the brake foot, mounting bracket, and wheel bracket omitted.

Referring to FIGS. 90, 93 and 94, the wheel bracket 2012 is configured to guide the extension bar 2002 to extend and retract in the direction of arrow 2028. The wheel bracket 2012 has two arms 2054 and a base 2050. Two wheels 2056 are attached to the arms 2054 by axels 2058 such that the wheels 2056 face into the gap 2024 of the wheel bracket 2012, as shown in FIG. 90. In the illustrative embodiment, each wheel has an annular flange 2065 which serves as a thrust bearing. The extension bar 2002, shown in FIG. 94, has an I-shaped cross section to provide tracks (not shown) that engage the wheels 2056. The brake foot 2014 can pivot about the pin 2022 to contact a lower surface 2029 of the extension bar 2002. Interaction between the wheels 2056 and the tracks guide the extension bar 2002 as it extends and retracts relative to the adjustment assembly 2006. Friction between the lower surface 2029 of the extension bar 2002 and the brake foot 2014 causes resistance to extension and retraction of extension bar 2002. In some embodiments, this resistance is sufficient to maintain the position of the extension bar 2002 but can be overcome by the operator to extend or retract extension bar 2002. Extension and retraction of the extension bar can be locked when a notch in an end of the extension bar 2002 opposite the mounting bracket is held by a pin (not shown) located in on the upper rod 14.

Referring now to FIGS. 89 and 93, the mounting bracket 2010 is also configured to guide the extension bar 2002 to rotate about axis 2020. A first hole 2090 extends through the base 2050 of the wheel bracket 2012 and a second hole 2092 extends through the mounting bracket 2010 and is aligned with the first hole 2090. A bolt 2062 and a flange bearing 2064 surrounding the bolt 2062 (shown in FIG. 91) extend through the first and second holes 2090 and 2092 with a head 2066 of the bolt 2062 resting against the base 2050 of the wheel bracket 2012. Opposite the head 2066 of the bolt 2062, a nut 2068 is threaded onto the bolt 2062 and disposed against the mounting bracket 2010. The bolt 2062 is aligned with axis 2020. As shown in FIG. 89, when the wheel bracket rotates about axis 2020, the brake foot 2014 can pivot about the pin 2022 to contact the platform 2016. Friction between the brake foot 2014 and the platform 2016 causes resistance to rotation of the extension bar 2002. In some embodiments, this resistance is sufficient to maintain the position of the extension bar 2002 but can be overcome by the operator to rotate extension bar 2002. Referring to FIG. 92, rotation of the extension bar can be further resisted by a pin 2070 that extends from the mounting bracket 2010 and can be received by an opening (not shown) in the wheel bracket 2012. Rotation of the extension bar 2002 can be locked when an end of the extension bar opposite the mounting bracket is held in a gap 2080 of a block 2082 that is attached to the upper rod 14, as best seen in FIG. 70.

The hanger 2004 is attached to a first end 2001 of the extension bar 2002, and the lateral distractor strap 500 hangs from the pin 2008 of the hanger 2004, as shown in FIG. 94. The lateral distractor strap 500 is adapted to receive a patient's arm such that a lateral distraction force is applied to the patient's arm and a corresponding downward force is applied to the first end 2001 of the extension bar 2000 in the direction indicated by arrow 2029.

Figure 95:
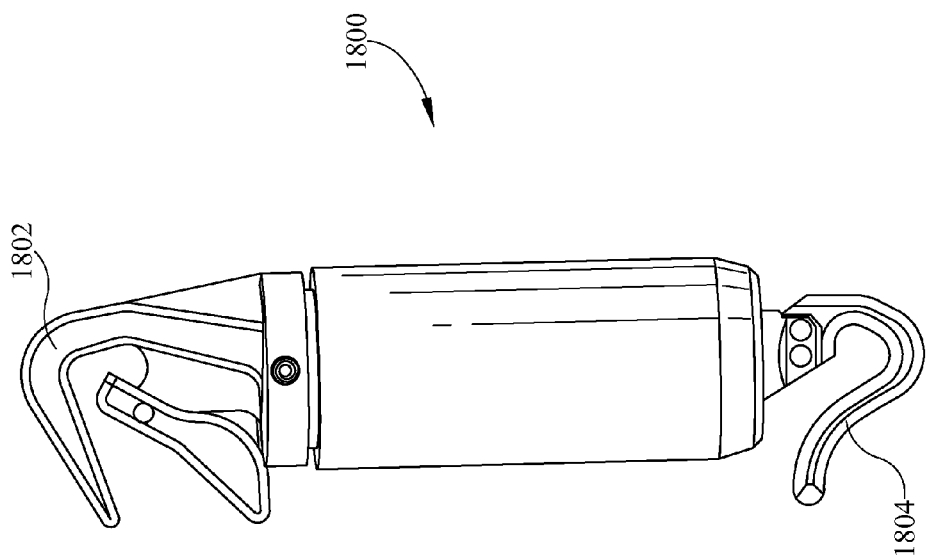
FIG. 95 is a tensiometer that attaches to a hanger of the shoulder distraction apparatus of FIG. 88.

Referring now to FIG. 95, in some embodiments, a tensiometer 1800 hangs from the pin 2008 and the lateral distractor strap hangs from the tensiometer 1800. The tensiometer 1800 has a clip 1802 for attaching to the pin 2008 of the hanger 2004. Opposite the pin, a hook 1804 receives the lateral distractor strap 500.

The lateral distractor strap 500 described herein creates a sterile interaction point, adjustable in length, for the physician to apply or remove traction force to the patient's arm. The lateral distractor strap 500 has a connector 502 for attaching to the hanger 436 of the shoulder distraction apparatus 400, as shown in FIG. 18. In some embodiments, the connector 502 is a metal loop. The connector 502 is attached to a connection tether 504 that forms a loop 506 around the connector. In some embodiments, the connection tether 504 is a webbing strap.

The connection tether 504 is attached to a buckle 508. A cinch strap 510 having a first end 512 and second end 514 is routed through the buckle 508 such that the length of the cinch strap 510 is adjustable. Illustratively, the cinch strap 510 comprises a webbing strap. In some embodiments, the first end 512 of the cinch strap 510 is pulled through the buckle 508 to shorten the length between the connection tether 504 and the second end 514 of the cinch strap 510. In some embodiments, the buckle 508 is a ladderlock type of buckle. In further embodiments, the buckle 508 is a cam buckle or a strap adjuster. The buckle 508 may be any device capable of adjusting the distance between the buckle 508 and the second end 514 of the cinch strap 510 and is not limited to the embodiments described herein. The buckle 508 interacts with the cinch strap 510 such that when the second end 514 of the cinch strap 510 is pulled away from the connection tether 504, the buckle 508 resists lengthening the distance between connection tether 504 and the second end 514 of the cinch strap 510.

In some embodiments, the second end 514 of the cinch strap 510 is attached to a sleeve connector 516 that is attached to a sleeve member 518 as shown in FIG. 18. Illustratively, the sleeve connector 516 is a plastic loop. The sleeve member 518 may be constructed of any material capable of supporting the patient's arm during surgery. In some embodiments, the sleeve member 518 comprises aluminum. The sleeve member 518 may include a fastener 520 for opening and closing the sleeve member 518 to assist in placing the sleeve member 518 around the patient's arm or removing the patient's arm from the sleeve member 518.

In some embodiments, as shown in FIG. 19, the second end 514 of the cinch strap 510 is attached to a receiving end 522 of fastener 520. A sleeve strap 524 having a first end 526 and a second end 528 is attached at the first end 526 of the sleeve strap 524 to the second end 514 of the cinch strap 510. Illustratively, the sleeve strap 524 is wider than the cinch strap 510. A foam pad 530 for interfacing with the skin of the patient's upper arm is attached to the sleeve strap 524. The second end 528 of the sleeve strap 524 is attached to a prong end 532 of the fastener 520. The prong end 532 is capable of connecting to the receiving end 522 of the fastener 520.

The patient's arm may be placed on the foam pad 530 of the sleeve member 518. The second end 528 of the sleeve strap 524 is moved around the patient's arm to the first end 526 of the sleeve strap 524, and the prong end 532 is inserted into the receiving end 522 such that the sleeve member 518 forms a closed loop around the patient's arm.

The sleeve member 518 forms a closed loop around the patient's arm, and the connector 502 is attached to the hanger 436 such that the sleeve member 518 applies traction to the patient's arm and supports the load of the patient's arm. The physician or other caregiver shortens the distance between the connection tether 504 and the second end 514 of the cinch strap 510 to apply additional lateral traction to the patient's arm. The physician or other caregiver lengthens the distance between the connection tether 504 and the second end 514 of the cinch strap 510 to release lateral traction from the patient's arm.

Illustratively, the lateral distractor strap 500 is sterilized prior to use. In some embodiments, sterilization is performed using ultraviolet (UV) irradiation. The lateral distractor strap 500 may be sterilized and packaged as such. In further examples, the lateral distractor strap 500 is disposable. The sterility of the lateral distractor strap 500 allows a sterile physician to adjust lateral traction applied to the patient's arm during surgery without assistance from non-sterile personnel. It is also within the scope of this disclosure for the lateral distraction strap 500 to be sterilized in a chamber using ethylene oxide gas. Thus, the materials from which strap 500 is made are each capable of withstanding exposure to ethylene oxide gas.

Figure 21:
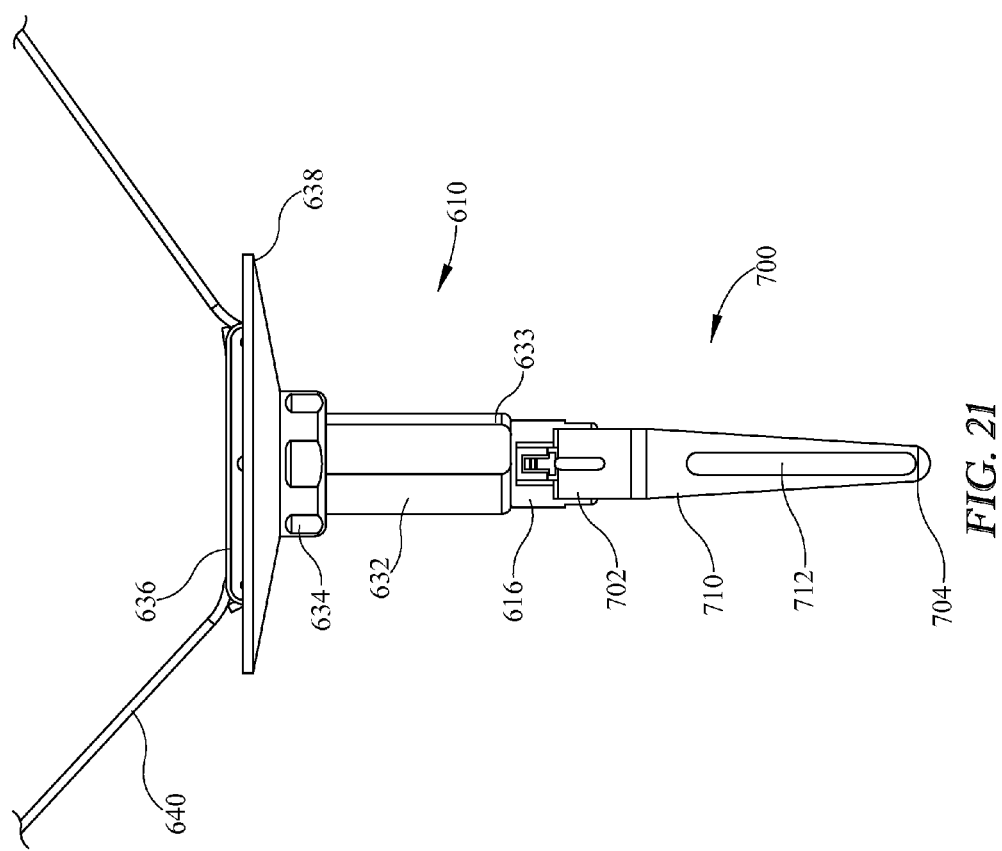
FIG. 21 is a side elevation view of the sterile connection and clip of FIG. 20.

The connection member 48 includes a sterile connection 600 as shown in FIG. 20. The sterile connection 600 includes a receiving assembly 610 adapted to receive a clip 700 as shown in FIGS. 20-21. The receiving assembly 610 is operable to attach to the surgical arm positioning system 8. The clip 700 is operable to attach to a sterile wrap 800 as shown in FIGS. 28-34. The sterile connection 600 described herein controls the patient's arm rotation by connecting the patient's hand and/or forearm to the surgical arm positioning system 8. The sterile connection 600 is designed to work with the surgical arm positioning system 8 to transmit a distal traction force and torque to the patient's arm.

Figure 22:
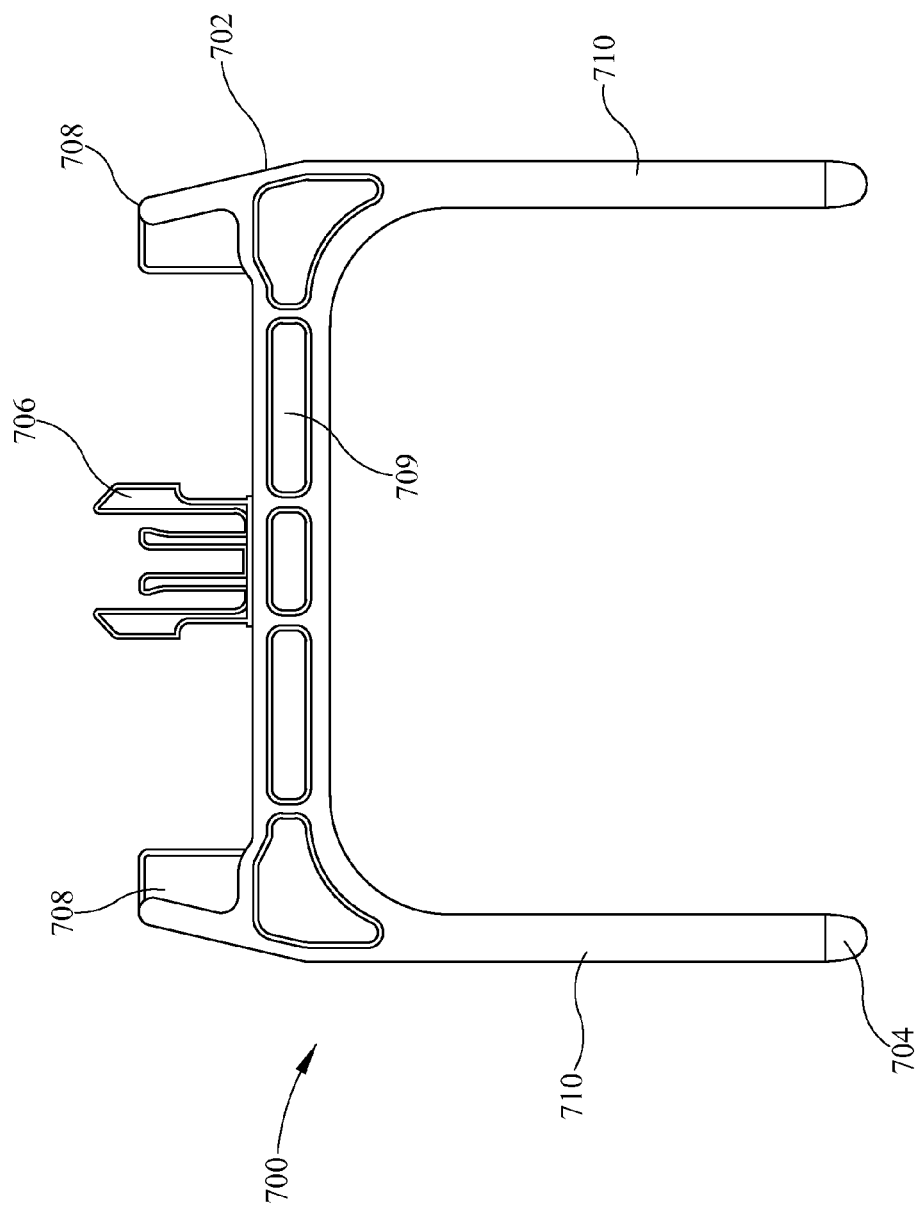
FIG. 22 is a front elevation view of the clip of FIG. 20.

The clip 700 has a distal end 702 and a proximal end 704 as shown in FIG. 22. The clip 700 includes a snap feature 706 and two wide features 708 near the distal end 702 attached to a distal cross portion 709. The snap feature 706 is made of a material having limited flexibility. In some embodiments, the snap feature 706 is made of plastic. Two clip arms 710 extend from the distal cross portion 709 to the proximal end 704. The clip arms 710 each have an opening or slot 712 formed therein as shown in FIG. 21.

Illustratively, dimensions for one embodiment of the clip 700 are shown in Table 1 below in reference to the markings A-K shown in FIG. 23. The dimensions shown in Table 1 relate to one embodiment of the present disclosure and are not to limit possible dimensions and measurements of other embodiments of the clip 700.

TABLE 1

Figure 23:
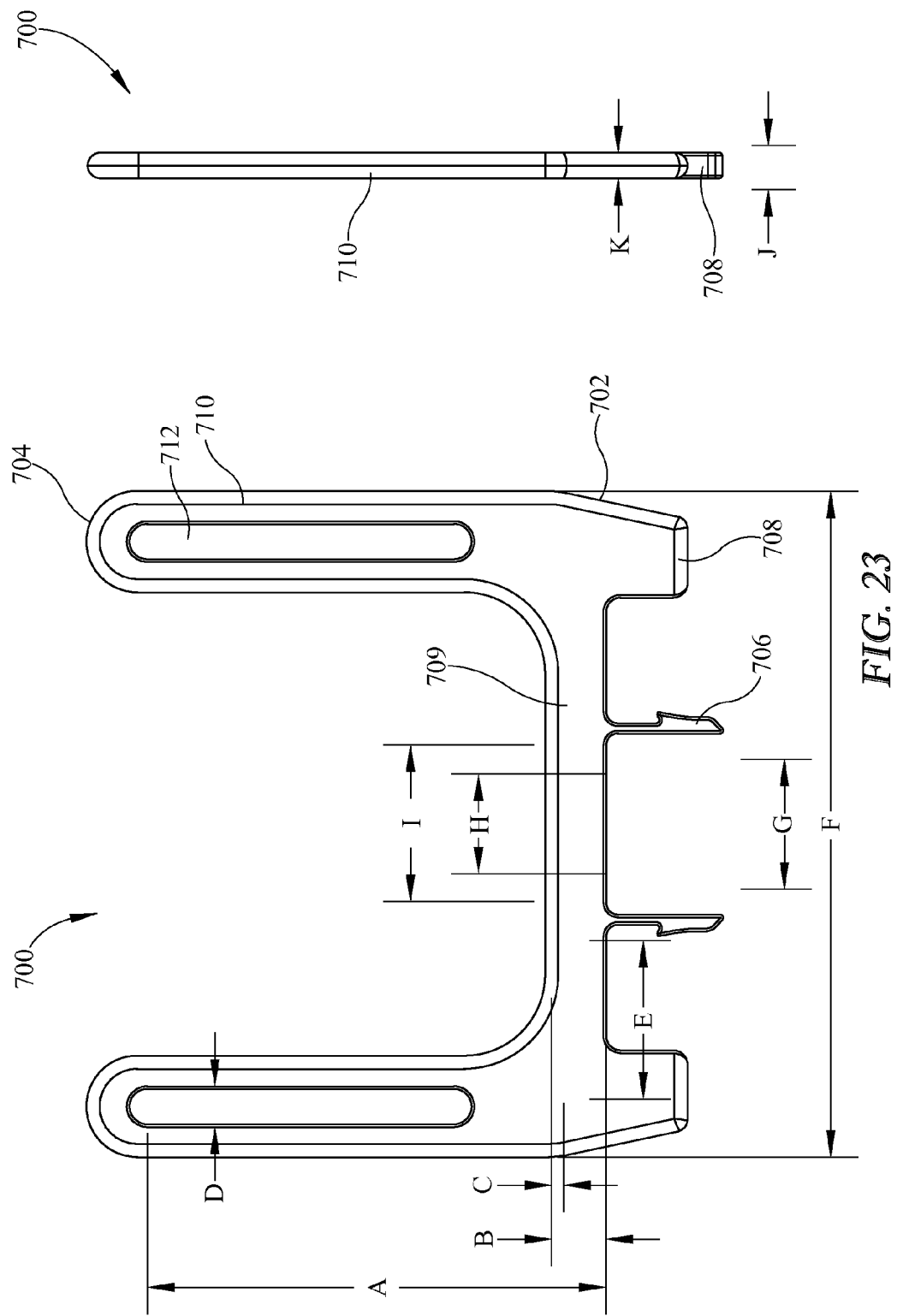
FIG. 23 is a front elevation view of the clip of FIG. 20 showing labels for measurements of the clip.

Dimensions of the Clip 700 as shown in FIG. 23.

| Label | Distance (inches) |
|---|---|
| A | 4.00 |
| B | 0.55 |
| C | 0.15 |
| D | 0.35 |
| E | 1.50 |
| F | 6.50 |
| G | 1.27 |
| H | 0.83 |
| I | 1.50 |
| J | 0.36 |
| K | 0.24 |

Figure 24:
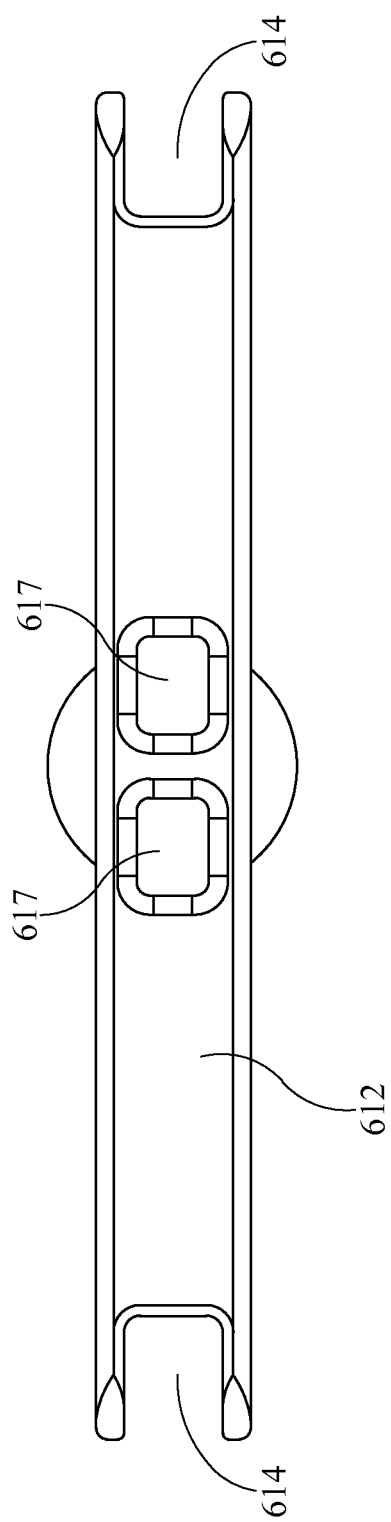
FIG. 24 is a bottom plan view of a buckle of the sterile connection of FIG. 20.

The receiving assembly 610 includes a buckle 612 as shown in FIGS. 20 and 24. The buckle 612 has wide feature receiving gaps 614 and snap feature receiving holes 617 as shown in FIG. 24. The buckle 612 is configured to receive the clip 700 when snap feature 706 is aligned with snap feature receiving holes 617 and the wide features 708 are aligned with the wide feature receiving gaps 614. The snap feature 706 comprises one or more flexible fingers and is made of plastic in some embodiments. The buckle 612 may be plastic, metal, or other materials. When the features 706, 708 are aligned with snap feature receiving holes 617 and the wide feature receiving gaps 614 and the clip 700 and buckle 612 are pushed together, the snap feature 706 flexes to fit through snap feature receiving holes 617 and the wide features 708 fit into the wide feature receiving gaps 614 to attach buckle 612 and clip 700 together.

The wide features 708 do not necessarily lock to the wide feature receiving gaps 614. The interaction between the snap feature 706 and the snap feature receiving holes 617 prevents the clip 700 from disconnecting from the receiving assembly 610 due to axial force. The interaction between the wide features 708 and the wide feature receiving gaps 614 provides the benefit of transmitting torque between buckle 612 and clip 700 while limiting deformation of the clip 700 when the clip 700 is made of a flexible material such as plastic. The clip 700 may be removed from buckle 612 by squeezing, pressing, or pinching the fingers of snap feature 706 together and pulling the clip 700 away from the buckle 612.

Figure 25:
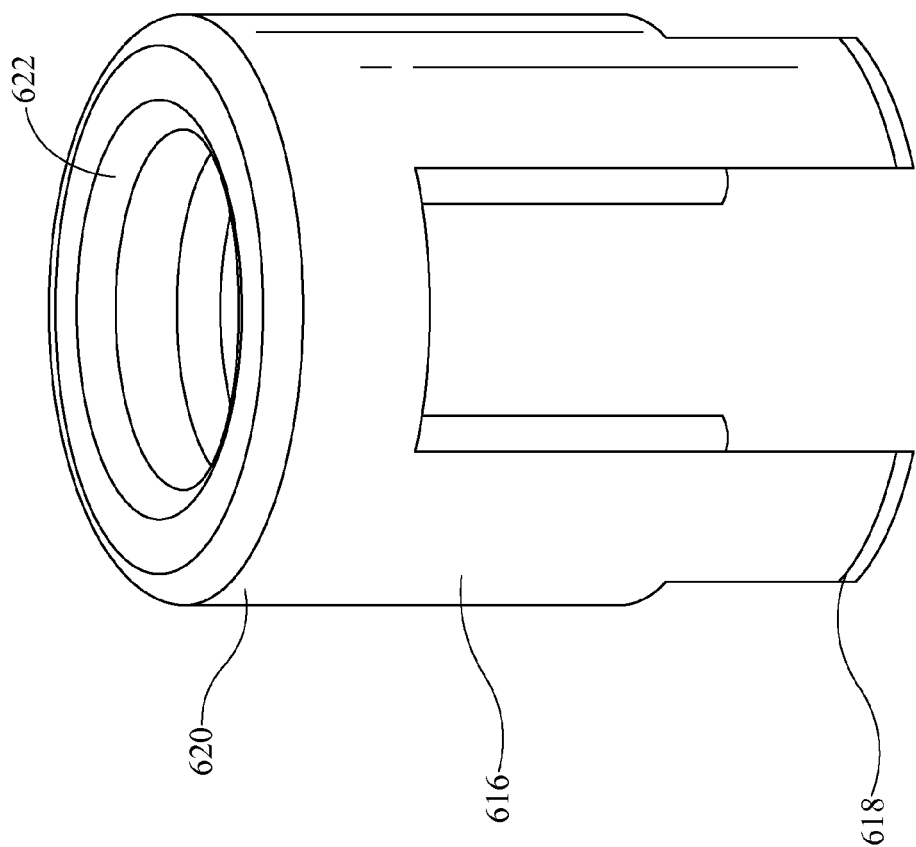
FIG. 25 is a perspective view of a clip adaptor of the sterile connection of FIG. 20.

The buckle 612 is connected to a clip adaptor 616 as shown in FIG. 25. The clip adaptor 616 has a proximal end 618 that is operable to receive and transmit torque to the buckle 612 and a distal end 620 having a rim 622.

Figure 26:
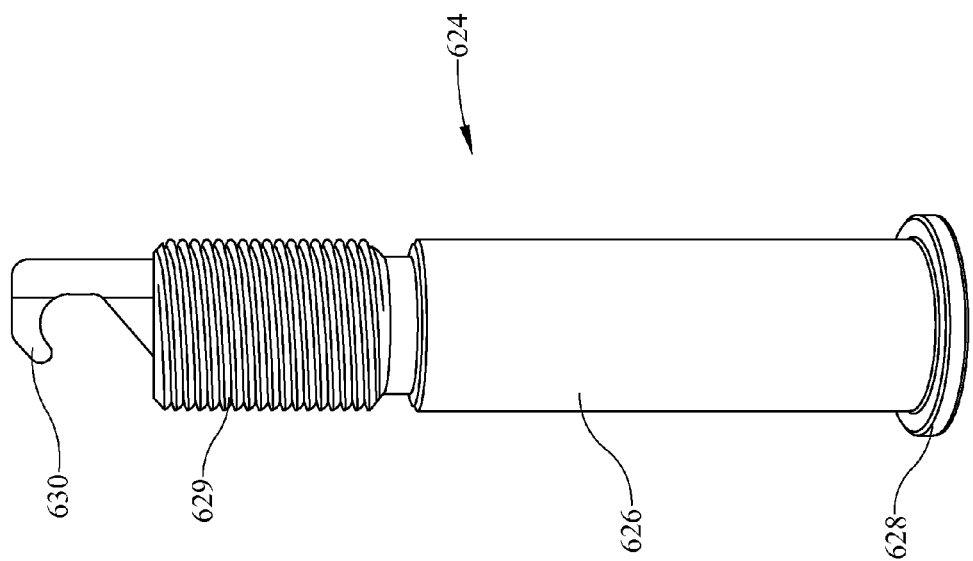
FIG. 26 is a perspective view of a connector of the sterile connection of FIG. 20.
Figure 27:
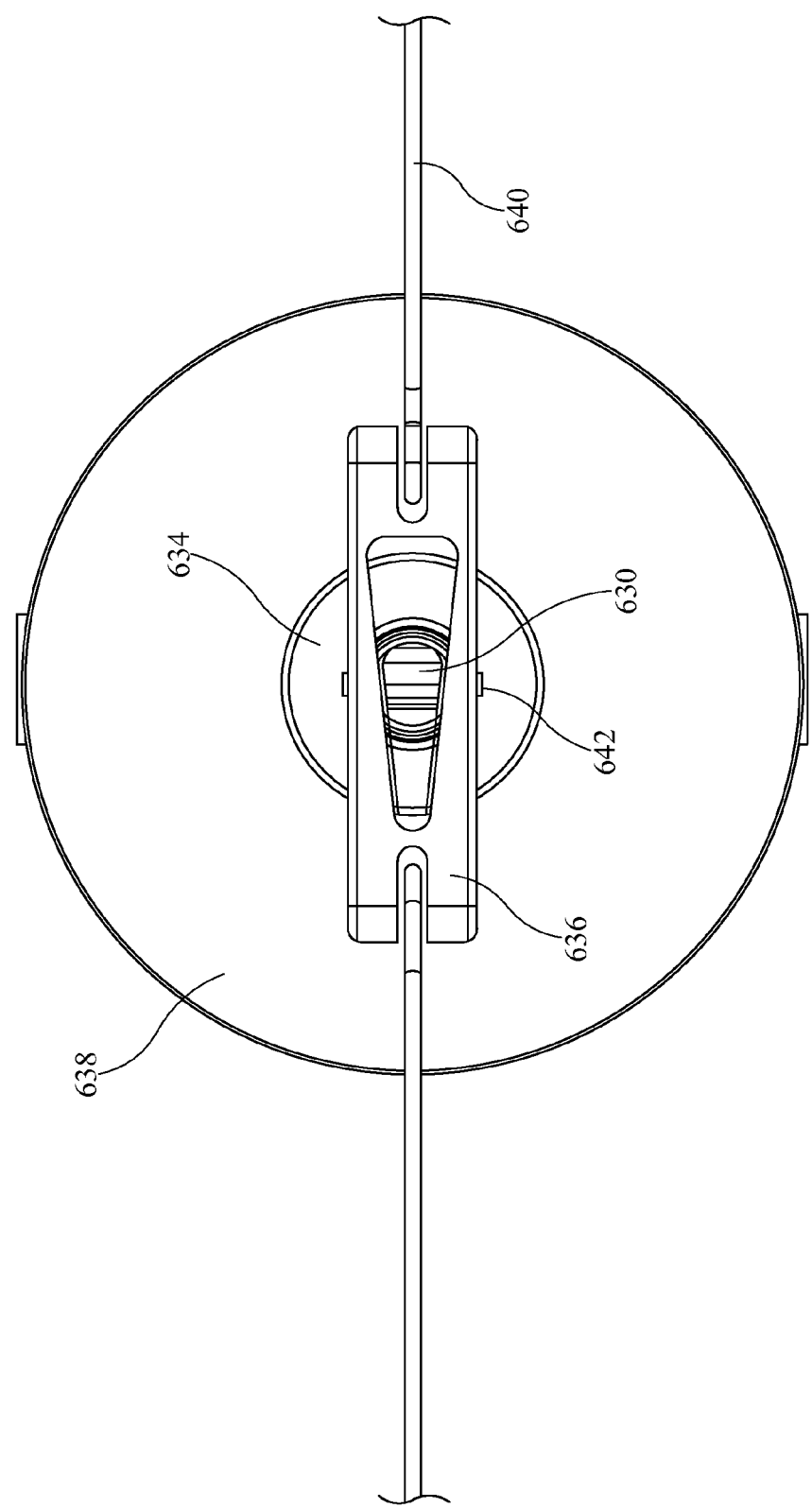
FIG. 27 is a top plan view of the sterile connection of FIG. 20.

The clip adaptor 616 engages a connector 624 having a body portion 626 attached to a cap 628 as shown in FIGS. 26 and 27. The body portion 626 extends into a threaded portion 629 that is externally threaded. The threaded portion 629 is attached to a connector hook 630. The body portion 626, the cap 628, the threaded portion 629, and connector hook 630 are illustratively formed from a monolithic piece of material. The body portion 626 resides within the rim 622 of the clip adaptor 616 such that the body portion 626 is movable within the clip adaptor 616. The diameter of the cap 628 is greater than the diameter of the opening defined by the rim 622 such that contact between the cap 628 and the rim 622 prevents the clip adaptor 616 from sliding off of the connector 624. The force of the contact between the cap 628 and the rim 622 creates sufficient friction between the cap 628 and the rim 622 to prevent rotation and allow torque to be transferred therebetween.

The threaded portion 629 of the connector 624 is threaded within a nut 632 shown in FIGS. 20 and 21. The nut 632 has a proximal end 633 in contact with the distal end 620 of the clip adaptor 616. As the nut 632 rotates and moves closer to the clip adaptor 616, the proximal end 633 of the nut 632 applies pressure to the distal end 620 of the clip adaptor 616, thereby applying pressure between the rim 622 of the clip adaptor 616 and the cap 528 of the connector 624. The pressure applied to the clip adaptor 616 by the connector 624 may be sufficient to prevent rotation of the clip adaptor 616 relative to the connector 624 and thereby preventing rotation of the buckle 612 and, if attached, the clip 700 relative to the connector 624.

Illustratively, the clip adaptor 616, the buckle 612, and the clip 700 may be adjusted by rotation relative to the connector 624. First, the nut 632 is rotated in a first direction such that the proximal end 633 of the nut 632 is moved away from the distal end 620 of the clip adaptor 616. Second, the clip adaptor 616 and attached components are rotated. Third, the nut 632 is rotated in a second direction opposite to the first direction such that the proximal end 633 of the nut 632 is moved toward the distal end 620 of the clip adaptor 616. One skilled in the art will appreciate that adjustment of the clip adaptor 616, the buckle 612, and the clip 700 relative to the connector 724 that includes rotation of the nut 632 is within the scope of this disclosure.

The threaded portion 629 of the connector 624 is also threaded within a knob 634 as shown in FIGS. 20, 21 and 27. The knob 634 is in contact with a cable adaptor 636 and surrounded by a flange 638 such that part of the flange 638 is located between the knob 634 and the cable adaptor 636. The cable adaptor 636 is sometimes referred to herein as a connection member. Thus, cable adaptor 636 is an example of the connection member 48 shown diagrammatically in FIGS. 1, 11 and 12. Thus, the cable adaptor 636 connects to two cable ends 640 of cable 46. The cable adaptor 636 receives the connector hook 630 such that the connector hook 630 hooks around a pin 642 of the cable adaptor 636 and prevents the connector 624 from being pulled off of the cable adaptor 636. Rotation of the knob 634 distally pushes the knob 634 against the cable adaptor 636, thereby pulling the connector hook 630 into the pin 642 of the cable adaptor 636 and locking the connector hook 630 to the cable adaptor 636.

Figure 78:
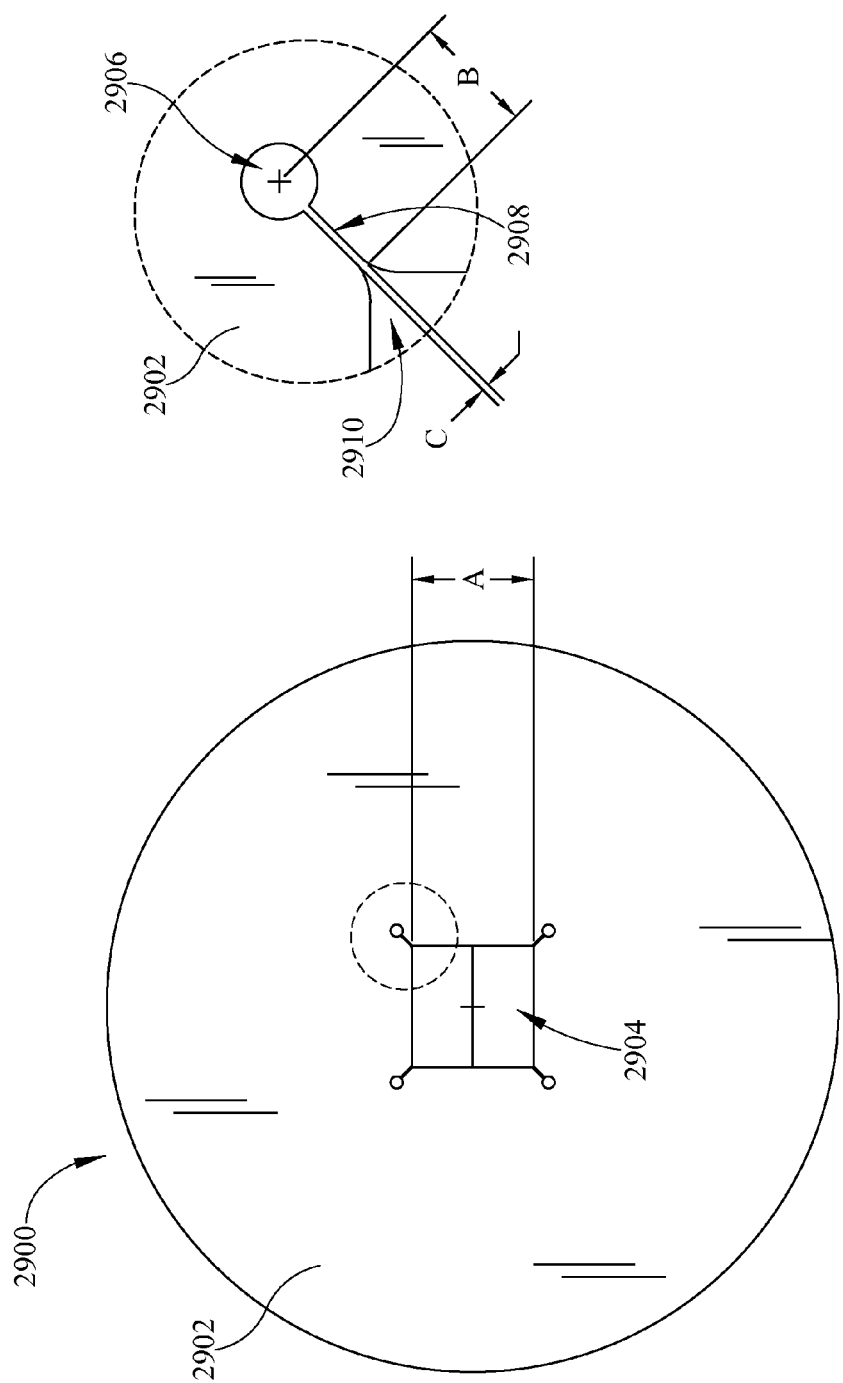
FIG. 78A is a front elevation view of a shield for use with the sterile connection of FIG. 75.
FIG. 78B is a sectional view of the shield of FIG. 78A.

Referring now to FIG. 78A, in some embodiments, the flange 638 is a disposable shield 2900. The shield may be made of translucent white polyethylene or any other suitable plastic or material. The shield 2900 is formed from a circular disc 2902 having a diameter of 7 inches and having a square hole 2904 therein. The square may have sides having a length A of 1.15 inches. Referring to FIG. 78B, the corners 2910 of the square hole 2904 lead to a narrow passageway 2908 having a length B of 0.20 inches and width C of 0.01 inches. The narrow passageway 2908 leads to a circular opening 2906 having a diameter of 0.13 inches.

In some embodiments, the receiving assembly 610 may be further secured to the cable adaptor 636 to prevent inadvertent decoupling by sliding a piece that interacts with a catch. Parts for further securing the receiving assembly 610 to the cable adaptor 636 are located on the sterile end of the flange 638 to maintain sterility.

Illustratively, the cable ends 640 are cables of a non-sterile support device such as the surgical arm positioning system 8. The cable ends 640 and cable adaptor 636 form a non-sterile attachment point for the receiving assembly 610 to attach to the non-sterile surgical arm positioning system 8. The interaction between connector hook 630 and the pin 642 of the cable adaptor 636 may be substituted by other assemblies capable of connecting the receiving assembly 610 to the cable ends 640, such as other assemblies having a hook, a loop, or a key. One skilled in the art will appreciate the mechanical attachment may be any structure capable of attaching the receiving assembly 610 to a surgical arm positioning system 8 and is not limited to the structures shown and described herein.

Figure 55:
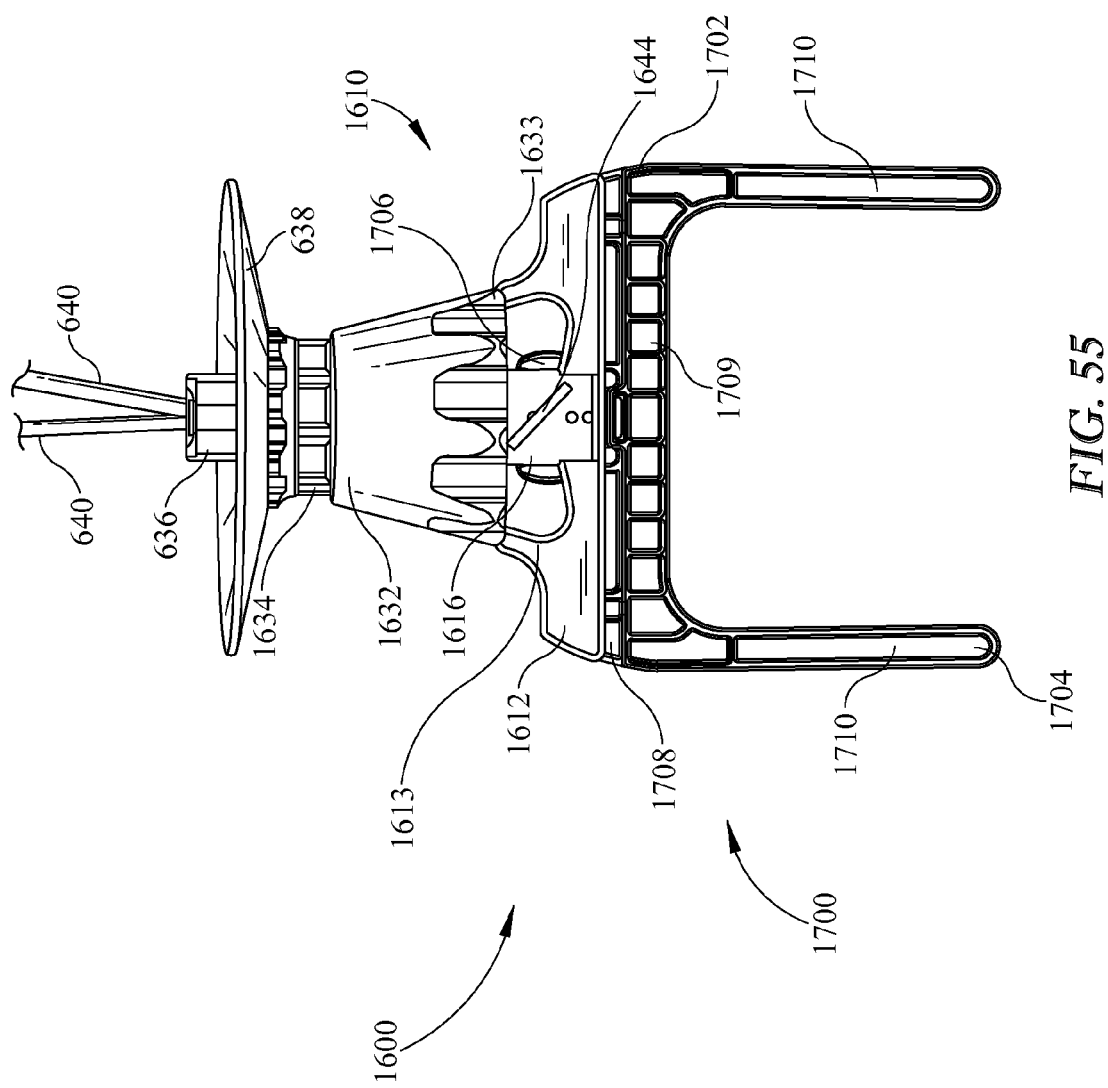
FIG. 55 is a perspective view of a second embodiment of a sterile connection attached to a clip.
Figure 56:
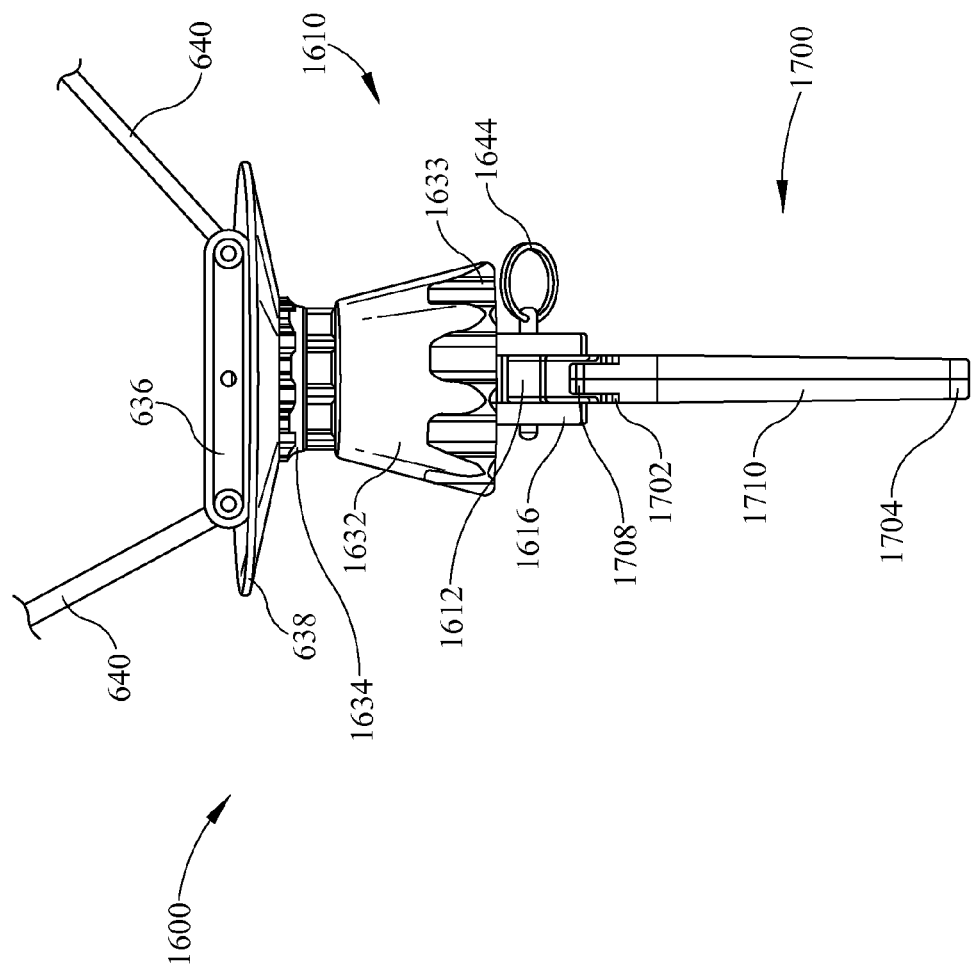
FIG. 56 is a side elevation view of the sterile connection and clip of FIG. 55.

In a second embodiment, the connection member 48 alternatively includes a sterile connection 1600. The sterile connection 1600 includes a receiving assembly 1610 adapted to receive a clip 1700 as shown in FIGS. 55 and 56. The receiving assembly 1610 is attachable to the surgical arm positioning system 8, and the clip 1700 is attachable to a sterile wrap 800 shown in FIGS. 28-34. The sterile connection 1600 described herein controls the patient's arm rotation by connecting the patient's hand and/or forearm to the surgical arm positioning system 8. The sterile connection 1600 is designed to work with the surgical arm positioning system 8 to transmit a distal traction force and torque to the patient's arm.

Figure 57:
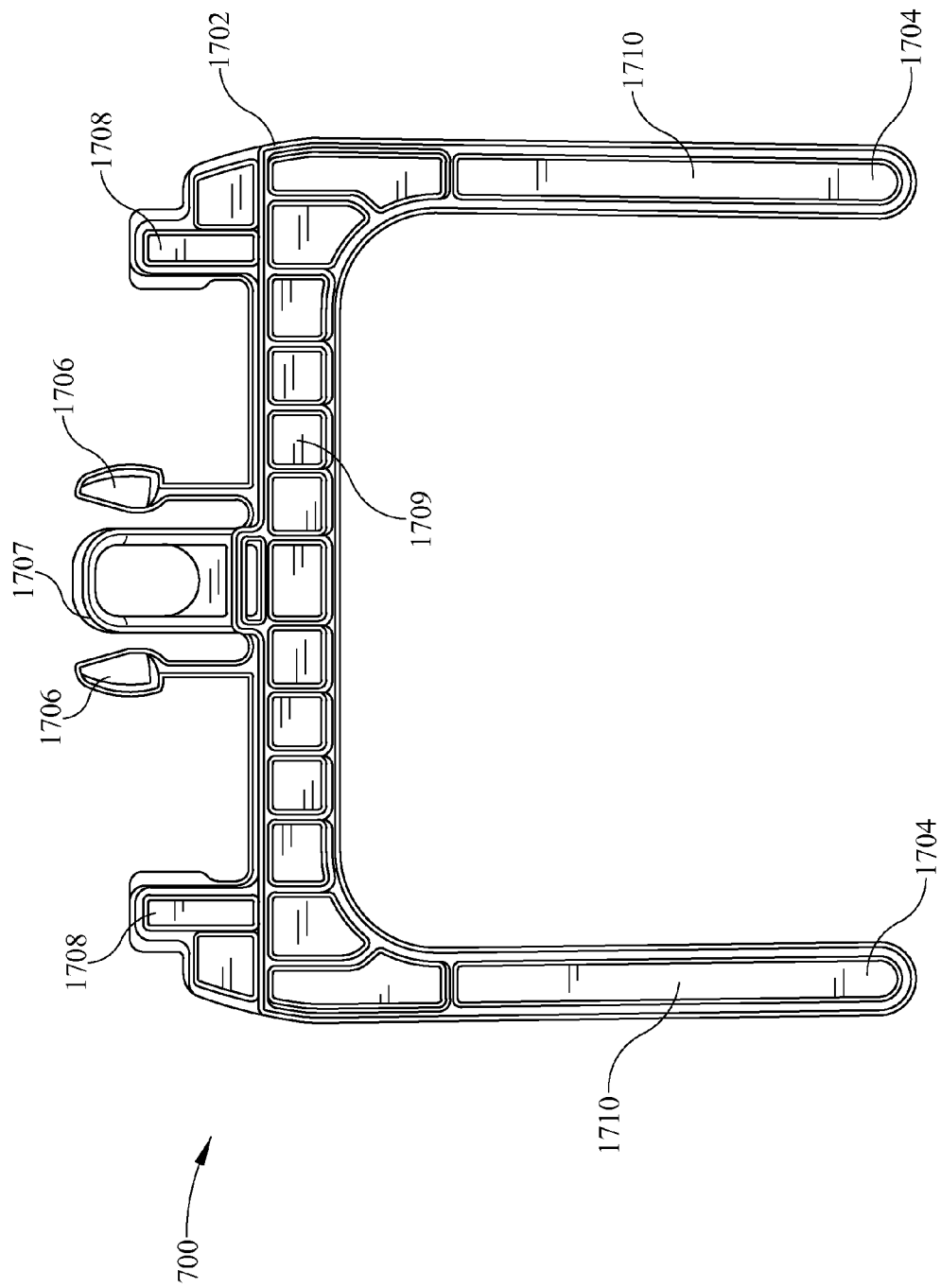
FIG. 57 is a front elevation view of the clip of FIGS. 55 and 56.

The clip 1700 has a distal end 1702 and a proximal end 1704 as shown in FIG. 57. The clip 1700 includes a snap feature 1706, a loop feature 1707, and two wide features 1708 near the distal end 1702 attached to a distal cross portion 1709. The snap feature 1706 is made of a material having limited flexibility. In some embodiments, the snap feature 1706 is made of plastic. Two clip arms 1710 extend from the distal cross portion 1709 to the proximal end 1704.

Figure 58:
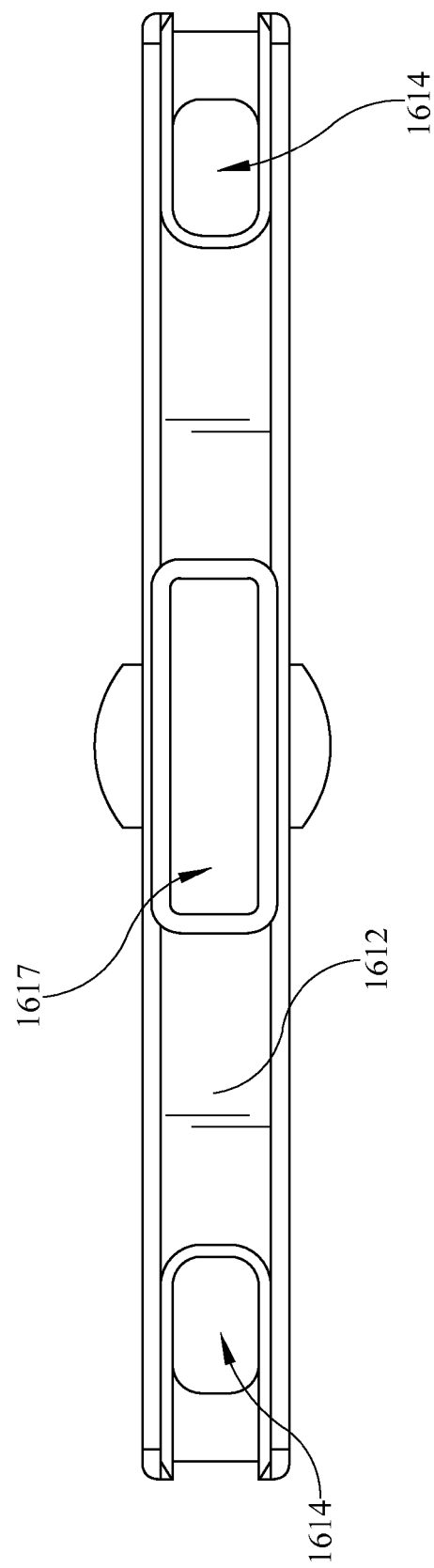
FIG. 58 is a bottom plan view of a buckle of the sterile connection of FIGS. 55 and 56.

The receiving assembly 1610 includes a buckle 1612 as shown in FIGS. 55 and 58. The buckle 1612 has wide feature receiving cavities 1614 and a snap feature receiving hole 1617 as shown in FIG. 58. The buckle 1612 is configured to receive the clip 1700 when snap feature 1706 and loop feature 1707 are aligned with the snap feature receiving hole 1617 and the wide features 708 are aligned with the wide feature receiving cavities 1614. The snap feature 1706 comprises one or more flexible fingers and is made of plastic in some embodiments. The buckle 1612 may be plastic, metal, or other materials. When the features 1706, 1707, 1708 are aligned with the snap feature receiving hole 1617 and the wide feature receiving cavities 1614 and the clip 1700 and buckle 1612 are pushed together, the snap feature 1706 flexes to fit through snap feature receiving hole 1617 and the wide features 1708 fit into the wide feature receiving cavities 1614 to attach buckle 1612 and clip 1700 together.

The wide features 1708 do not necessarily lock to the wide feature receiving cavities 1614. The interaction between the snap feature 1706 and the snap feature receiving hole 1617 prevents the clip 1700 from disconnecting from the receiving assembly 1610 due to axial force. The interaction between the wide features 1708 and the wide feature receiving cavities 1614 provides the benefit of transmitting torque between buckle 1612 and clip 1700 while limiting deformation of the clip 1700 when the clip 1700 is made of a flexible material such as plastic. The clip 1700 may be removed from buckle 1612 by squeezing, pressing, or pinching the fingers of snap feature 1706 together and pulling the clip 1700 away from the buckle 1612.

Figure 59:
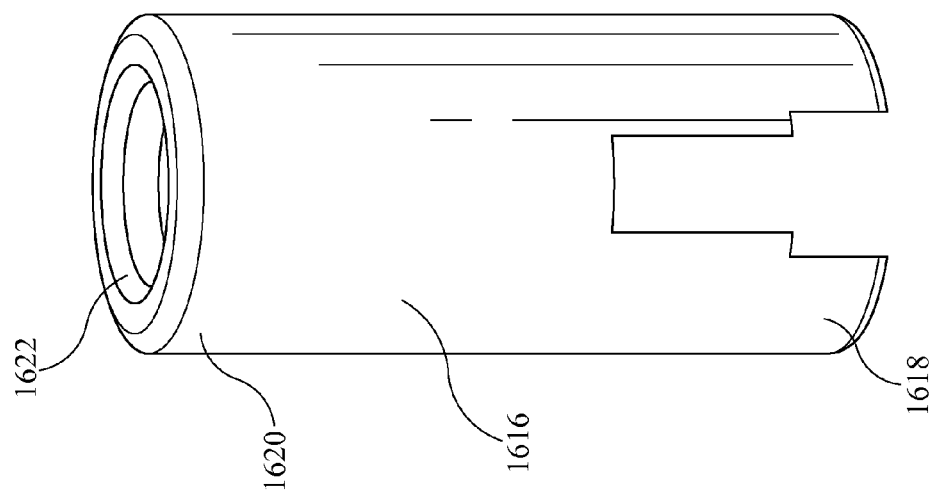
FIG. 59 is a perspective view of a clip adaptor of the sterile connection of FIGS. 55 and 56.

The buckle 1612 is connected to a clip adaptor 1616. The clip adaptor 1616 has a proximal end 1618 that is operable to receive and transmit torque to the buckle 1612 and a distal end 1620 having a rim 1622 as shown in FIG. 59. Compared to buckle 612, buckle 1612 is about twice as long when measured from its proximal end 1618 to its distal end 1620. In some embodiments, the clip adaptor 1616 has a hole therein positioned such that when the clip 1700 is connected to the receiving assembly 1610, the hole in the clip adaptor 1616 is aligned with the loop feature 1707. A clip pin 1644 may be inserted through the hole in the clip adaptor 1616 and through the loop feature 1707 to further prevent the clip 1700 from detaching from the receiving assembly 1610, as shown in FIGS. 55 and 56.

Figure 60:
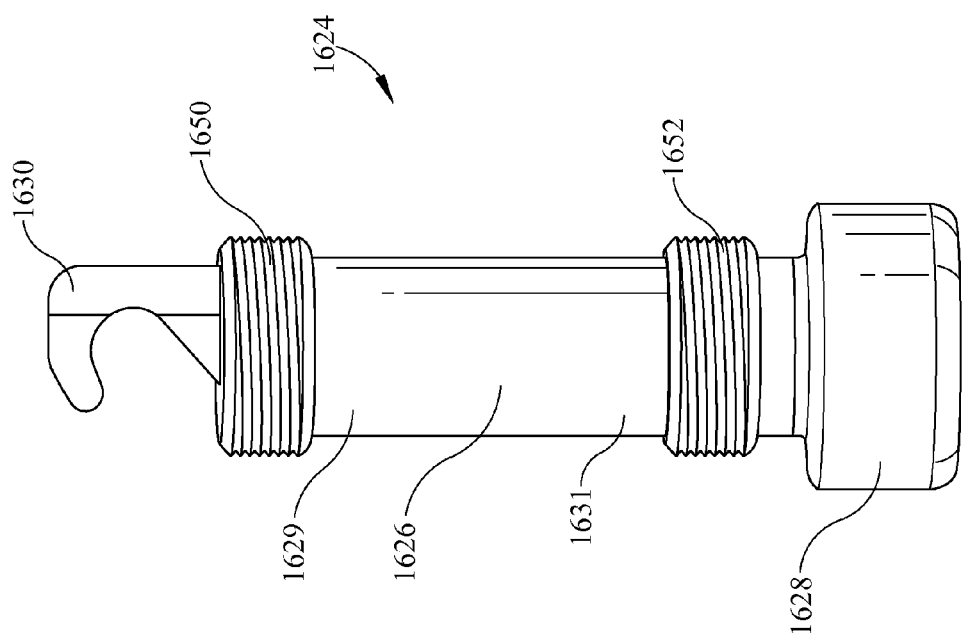
FIG. 60 is a perspective view of a connector of the sterile connection of FIGS. 55 and 56.

The receiving assembly 1610 also comprises a connector 1624 including a distal body portion 1629, a middle body portion 1626, a proximal body portion 1631, a distal knob receiving threaded portion 1650, a proximal knob receiving threaded portion 1652, a cap 1628, and a connector hook 1630 as shown in FIG. 60. The connector 1624 is illustratively formed from a monolithic piece of material. The hook 1630 and the cap 1628 are located on opposite ends of the connector 1624.

A distal knob receiving nut threadedly engages the distal knob receiving threaded portion 1650, and a proximal knob receiving nut threadedly engages the proximal knob receiving threaded portion 1652. The cap 1628 of the connector 1624 resides within the clip adaptor 1616 such that the hook 1630 extends outside of the clip adaptor 1616 and away from the distal end 1620 of the clip adaptor 1616 and such that the cap 1628 can slide within the clip adaptor 1616. The diameter of the opening defined by the rim 1622 of the clip adaptor 1616 is smaller than the diameter of the cap 1628 such that contact between the cap 1628 and the rim 1622 prevents the clip adaptor 1616 from sliding off of the connector 1624.

The proximal knob receiving threaded portion 1652 has a proximal knob 1632 threaded thereto as shown in FIGS. 55 and 56. The proximal knob 1632 has a proximal end 1633 in contact with the distal end 1620 of the clip adaptor 1616. As the proximal knob 1632 rotates and moves closer to the clip adaptor 1616, the proximal end 1633 of the proximal knob 1632 applies pressure to the distal end 1620 of the clip adaptor 1616, thereby applying pressure between the rim 1622 of the clip adaptor 1616 and the cap 1628 of the connector 1624. When the proximal knob 1632 is tightened, the pressure applied to the clip adaptor 1616 by the connector 1624 is sufficient to prevent rotation of the clip adaptor 1616 relative to the connector 1624 and thereby preventing rotation of the buckle 1612 and, if attached, the clip 1700 relative to the connector 1624.

Illustratively, the clip adaptor 1616, the buckle 1612, and the clip 1700 may be rotated relative to the connector 1624 when the proximal knob 1632 is loosened. First, the proximal knob 1632 is rotated in a first direction such that the proximal end 1633 of the proximal knob 1632 is moved away from the distal end 1620 of the clip adaptor 1616. Second, the clip adaptor 1616, the buckle 1612, and the clip 1700 are rotated. Third, the proximal knob 1632 is rotated in a second direction opposite the first direction such that the proximal end 1633 of the proximal knob 1632 is moved toward the distal end 1620 of the clip adaptor 1616.

The distal knob receiving threaded portion 1650 of the connector 1624 is fixed to a distal knob 1634 shown in FIGS. 55 and 56. The distal knob 1634 pushes a flange 638 against a cable adaptor 636 as shown in FIGS. 55 and 56. The cable adaptor 636 is sometimes referred to herein as a connection member. Thus, cable adaptor 636 is an example of the connection member 48 shown diagrammatically in FIGS. 1, 11 and 12. Thus, the cable adaptor 636 connects to two cable ends 640 of cable 46. The cable adaptor 636 receives connector hook 1630 such that the connector hook 1630 hooks around a pin 642 of the cable adaptor 636 and prevents the connector 1624 from being pulled off of the cable adaptor 636. Rotation of the distal knob 1634 distally pushes the distal knob 1634 against the cable adaptor 636, thereby pulling the connector hook 1630 against the pin 642 of the cable adaptor 636 and securing the connector hook 1630 to the cable adaptor 636.

When compared to nut 632, the proximal knob 1632 is wider to further prevent inadvertently decoupling of the clip 1700 from the buckle 1612. When compared to buckle 612, buckle 1612 has snap feature shields 1613 extending distally therefrom to further prevent inadvertently decoupling the clip 1700 from the buckle 1612.

In some embodiments, the receiving assembly 1610 may be further secured to the cable adaptor 636 to prevent inadvertent decoupling by sliding a piece that interacts with a catch. Parts for further securing the receiving assembly 1610 to the cable adaptor 636 are located on the sterile end of the flange 638 to maintain sterility.

When the sterile connection is attached to the patient's arm, the cable ends 640 are pulled in opposing directions. Tension in the cable ends 640 prevents, to a degree proportional to the amount of tension, the receiving assembly 610, or alternatively receiving assembly 1610, and by extension the clip 700, or alternatively the clip 1700, and the patient's arm, from rotating when the patient's arm is attached. The tension of the cable ends 640 resists torque created by any attempt to rotate of the patient's arm and allows the sterile connection 600, or alternatively sterile connection 1600, to maintain a rotated position of the patient's arm.

Illustratively, the cable adaptor 636 and cable ends 640 are non-sterile, while the clip 700, the buckle 612, the clip adaptor 616, the nut 632, the knob 634, and the connector 624, or alternatively the clip 1700, the buckle 1612, the clip adaptor 1616, the proximal knob 1632, the distal knob 1634, and the connector 1624, are sterile. The flange 638, itself sterile, separates the sterile components from the non-sterile components. During adjustment of nut 632 and knob 634, or alternatively of the proximal knob 1632 and the distal knob 1634, the flange 638 prevents sterile personnel from coming into contact with non-sterile components. One skilled in the art will appreciate that the flange 638 may be replaced by other barriers capable of separating the cable adaptor 636 from sterile components that prevent the sterile operator from inadvertently touching non-sterile components. In some embodiments, the sterile connection 600, or alternatively the sterile connection 1600, is designed such that the sterile operator may grab components between the clip 700, or alternatively the clip 1700, and the flange 638 without coming into contact with non-sterile components.

The receiving assembly 610 may be disassembled, allowing the clip 700, the buckle 612, the clip adaptor 616, the nut 632, the knob 634, and the connector 624 to be sterilized between uses. By rotating the knob 634 to thereby move it proximally, the connector hook 630 may be detached from the pin 642 of the cable adaptor 636. Next, the knob 634 may be rotated to be removed from the assembly. In some embodiments, the nut 632, the connector 624, the clip adaptor 616, and the buckle 612 are removed from the rest of the sterile connection 600, as well.

Similarly, the receiving assembly 1610 may be disassembled, allowing the clip 1700, the buckle 1612, the clip adaptor 1616, the proximal knob 1632, the distal knob 1634, and the connector 1624 to be sterilized between uses. By rotating the distal knob 1634 to thereby move it proximally, the connector hook 1630 may be detached from the pin 642 of the cable adaptor 636. Next, the distal knob 1634 may be rotated to be removed from the assembly. In some embodiments, the proximal knob 1632, the connector 1624, the clip adaptor 1616, and the buckle 1612 are removed from the rest of the sterile connection 1600, as well.

Disassembling the receiving assembly 610, or alternatively the receiving assembly 1610, allows smaller individual components to be sterilized rather than larger components. Disassembling the receiving assembly 610, or alternatively the receiving assembly 1610, into smaller components provides the advantage of allowing for smaller sterilization devices. In some embodiments, the components may be sterilized using an autoclave. In further embodiments, the clip 700 may be made of a sterilized disposable material. In still further embodiments, the clip 700 may be reusable and sterilized between uses.

In the third embodiment, the connection member 48 alternatively includes a sterile connection 2600. The sterile connection 2600 includes a receiving assembly 2610 adapted to receive a clip 2700 as shown in FIGS. 75 and 86. The receiving assembly 2610 is attachable to the surgical arm positioning system 8, and the clip 2700 is attachable to a sterile wrap 800 shown in FIGS. 76-87. The sterile connection 2600 described herein controls the patient's arm rotation by connecting the patient's hand and/or forearm to the surgical arm positioning system 8. The sterile connection 2600 is designed to work with the surgical arm positioning system 8 to transmit a distal traction force and torque to the patient's arm.

Figure 72:
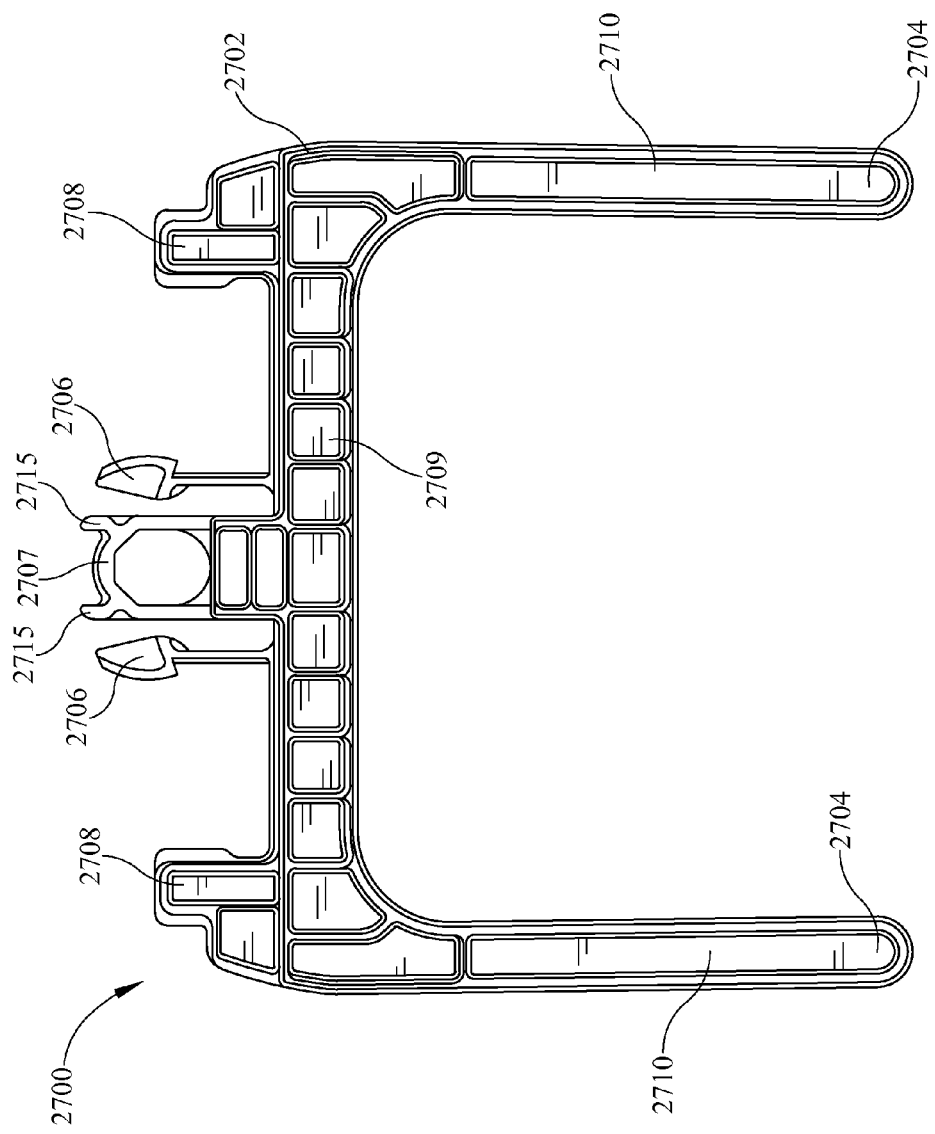
FIG. 72 is a front elevation view of another embodiment of the clip of FIG. 20.

Referring now to FIG. 72, the clip 2700 has a distal end 2702 and a proximal end 2704. The clip 2700 includes a snap feature 2706, a loop feature 2707, and two wide features 2708 near the distal end 2702 attached to a distal cross portion 2709. Two prongs 2715 extend from the loop feature 2707 on opposite sides of the loop feature 2707. The snap features 2706 are made of a material having limited flexibility such that the operator can squeeze the snap features 2706 toward each other. After the operator releases the snap features 2706, the snap features 2706 spring back away from each other to their equilibrium positions. In some embodiments, the snap features 2706 are made of plastic. Two clip arms 2710 extend from the distal cross portion 2709 to the proximal end 2704.

In the third embodiment, the dimensions of the clip 2700 are the same as those of clip 700 except for those shown in Table 2 below in reference to the markings A-J shown in FIG. 81A-81C. The dimensions shown in Table 2 and relate to the third embodiment of the present disclosure and are not to limit possible dimensions and measurements of other embodiments of the clip 2700.

TABLE 2

Dimensions of the Clip 2700 as shown in FIG. 81A-81C.

| Label | Distance (inches) |
|---|---|
| A | 0.260 |
| B | 0.360 |
| C | 6.52 |
| D | 0.560 |
| E | 4.340 |
| F | 1.440 ± 0.003 |
| G | 0.560 |

TABLE 2-continued

Dimensions of the Clip 2700 as shown in FIG. 81A-81C.

| Label | Distance (inches) |
|---|---|
| H | 0.100 |
| I | 0.760 |
| J | 0.140 |

Referring now to FIG. 75, in the third embodiment, the sterile connection 2600 is the same as the sterile connection 1600 of the second embodiment, unless described otherwise herein. Additionally, components of the sterile connection 2600 and sterile connection 1600 that have reference numbers ending in the same last two digits after "16" and "26" are understood to be identical unless described otherwise herein. For example, hypothetical parts 1699 and 2699 would be identical unless described otherwise herein.

Figure 73:
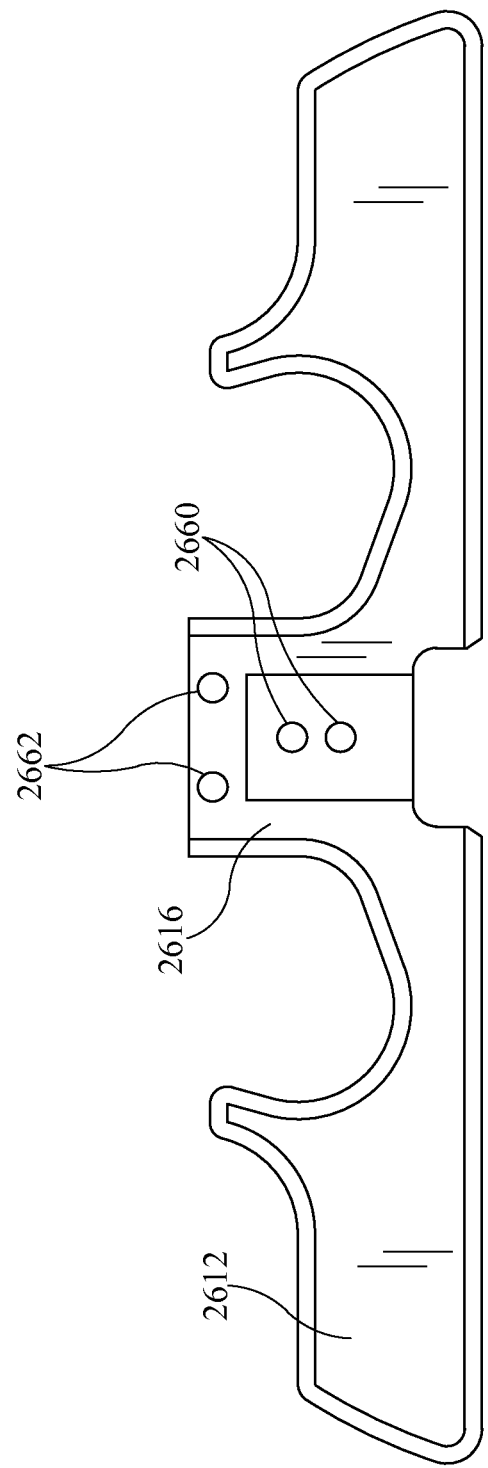
FIG. 73 is a front elevation view of another embodiment of the buckle of FIG. 24.

As shown in FIGS. 73 and 75, the receiving assembly 2610 of the sterile connection 2600 includes a buckle 2612 that has a modified shape compared to the buckle 1612. The buckle 2612 has two first pin holes 2660 for receiving a clip pin 1644. Additionally, the buckle 2612 has two second pin holes 2662. When the clip 2700 is inserted into the buckle 2612, the pin holes 2662 are positioned between the two prongs 2715 of the clip 2700, as shown in FIG. 73. Pins 2663 may be inserted into the pin holes 2662 to further prevent the clip 2700 from disengaging from the buckle 2612 and detaching from the receiving assembly 2610 when the surgical arm positioning system 8 is in use with a patient.

Figure 74:
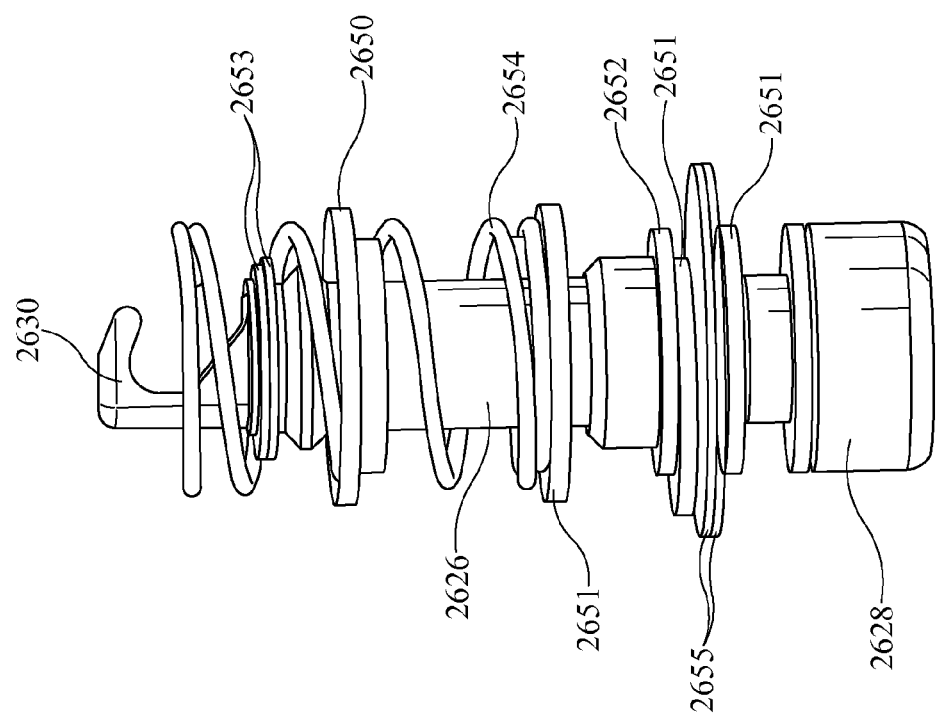
FIG. 74 is a perspective view of another embodiment of the connector of FIG. 26.

Referring now to FIG. 74, the receiving assembly 2610 of the sterile connection 2600 also includes a connector 2624 that is modified compared to the connector 1624. The connector 2624 includes a middle body portion 2626, a proximal knob receiving portion 2652, a cap 2628, and a connector hook 2630 as shown in FIG. 74. The connector 2624 is surrounded by wide washers 2655, narrow washers 2651, and a flange washer 2650. The hook 2630 and the cap 2628 are located on opposite ends of the connector 2624.

Referring now to FIGS. 74 and 75, a distal knob 2634 receiving nut engages the flange washer 2650, and a proximal knob receiving nut engages one of the wide washers 2655. The cap 2628 of the connector 2624 resides within the clip adaptor 1616 (shown in FIG. 59) in contact with the rim 1622 of the clip adapter 1616 such that the hook 2630 extends outside of the clip adaptor 1616 and away from the distal end 1620 of the clip adaptor 1616. The diameter of the opening defined by the rim 1622 of the clip adaptor 1616 is smaller than the diameter of the cap 2628 such that contact between the cap 2628 and the rim 1622 prevents the clip adaptor 1616 from sliding off of the connector 2624.

Referring now to FIGS. 74 and 75, the proximal knob 2632 has a proximal facing inner surface (not shown) in contact with the wide washer 2655 such that the proximal end 2633 of the proximal knob faces toward the clip 2700. The distal knob 2634 has a distal facing inner surface (not shown) in contact with the flange washer 2650. A spring 2654 is disposed about the connector 2624 distal to the wide washers 2655. When the hook 2630 of the connector 2624 is received by the cable adaptor 636, the spring compresses as the distal knob 2634 moves closer to the cable adaptor 636. As a result of the spring 2654 compressing, the proximal knob 2632 is pushed toward the clip adaptor 1616 such that the proximal end 2633 of the proximal knob 2632 applies pressure to the distal end 1620 of the clip adaptor 1616, thereby applying pressure between the rim 1622 of the clip adaptor 1616 and the cap 2628 of the connector 2624.

Additionally, when the spring 2654 is compressed and the hook 2630 engages the pin 642 (shown in FIG. 27) of the connector 636, a proximal surface of the distal knob 2634 applies pressure to a distal surface of the flange washer 2650, thereby pulling the hook 2630 toward the pin 642 and securing the hook 2630 to the connector 636. When the hook 2630 is attached to the cable adaptor 636, the pressure applied to the clip adaptor 1616 by the connector 2624 is sufficient to prevent rotation of the clip adaptor 1616 relative to the connector 2624 and thereby preventing undesired rotation of the buckle 2612 and, if attached, the clip 2700 relative to the connector 2624 during surgery. As such, the operator can connect sterile connection 2600 to the surgical arm positioning system 8 by first placing the narrow washers 2651, wide washers 2655, spring 2654, clip adaptor 2612 and connector 1616, proximal knob 1632, and distal knob 1634 around the connector 2624; second, pushing the connector hook 2630 into the cable adaptor 636 to compress the spring 2654 while engaging the pin 642 of the cable adaptor 636 with the connector hook; and third, releasing the sterile connection 2600.

A sterile wrap 800, as shown in FIG. 28-31 is used for wrapping around the patient's arm, hand, and wrist and connecting the patient's arm to the clip 700 which, in turn, connects the patient's arm to the sterile connection 600. Illustratively, the sterile wrap 800 includes a sheet 802 having an interior side 804 having an interior surface and an exterior side 806 having exterior surface. The interior surface is made of foam, such as a low density sheet of foam, and the exterior surface is made of loop material having loops. The loop material is any material capable of interacting with a hook material having hooks such that the hooks become attached to the loops, thereby fastening the materials together. In other embodiments, fastening may be accomplished by clasps, hooks, snaps, or the like.

The disposable wrap is shaped to wrap onto itself around specific parts of the patient's hand and forearm to support the patient's arm. Supporting the patient's arm by wrapping aids in torque transmission by reducing the amount that the foam can stretch. The sterile wrap 800 is attached to the clip 700 in a way that the patient's skin will not be in direct contact with rigid materials when wrapped by the sterile wrap 800.

The sheet includes a wrist portion 808, a first clip cover portion 810, a second clip cover portion 812, and a forearm portion 814. The wrist portion 808 is situated at a first edge 816 of the sheet 802. The forearm portion 814 is situated at a second edge 818 of the sheet 802.

The first clip cover portion 810 extends from the wrist portion 808. The second clip cover portion 812 extends from the forearm portion 814. The first clip cover portion 810 is coupled to the second clip cover portion 812 by a hinge portion 820 situated between the first clip cover portion 810 and the second clip cover portion 812. The hinge portion 820 includes a perforation 822 and two indentations or notches 824 arranged in a linear pattern.

The wrist portion 808 includes a first strap 826 and a second strap 828. The first strap 826 is attached to a tab 830 having the hook material. The hook material has hooks facing the interior side 804 of the sheet. The exterior side 806 of the second strap 828, having the loop material, is sized to receive the tab 830 of the first strap 826 such that the two straps 826, 828 adhere due to interaction between the hooks of the tab 830 of the first strap 826 and the loops of the exterior side 806 of the second strap 828.

The first clip cover portion 810 includes two flaps 832 attached to two tabs 834, each tab having the hook material.

The hook material has hooks facing the interior side 804 of the sheet 802. The exterior side 806 of the second clip cover portion 812, having the loop material, receives the flaps 832 of the first clip cover portion 810 when the sheet 802 is folded such that the interior surfaces 804 of the first and second clip cover portions 810, 812 face each other.

The forearm portion 814 includes three straps 836a, 836b, 836c each attached to one of three tabs 838a, 838b, 838c each having the hook material. The hook material has hooks facing the interior side 804 of the sheet 802. A first and a second of the straps 836a, 836c of the forearm portion 814 extend in a direction opposite a third of the straps 836b of the forearm portion. The exterior side 806 of forearm portion 814, having the loop material, is operable to receive the tabs 838a, 838b, 838c of the forearm portion.

Figure 29:
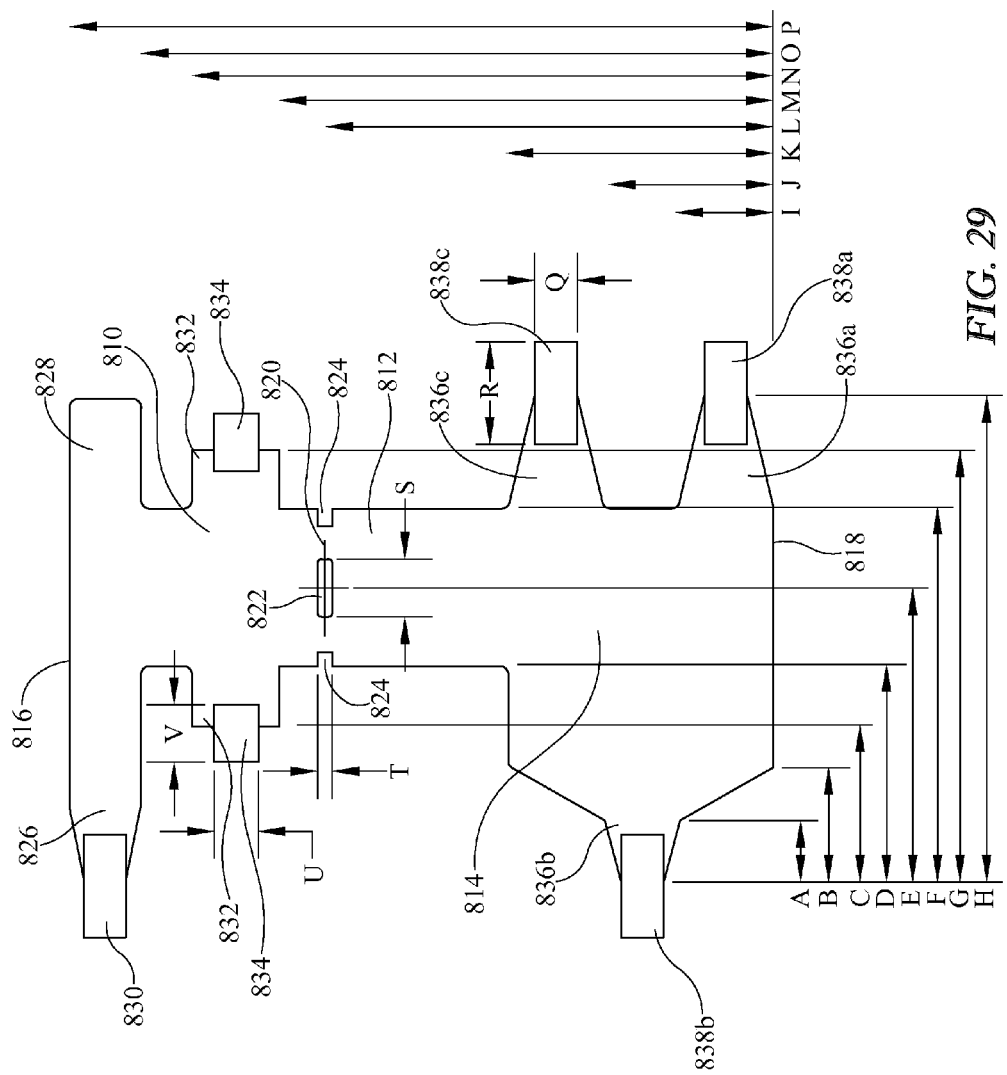
FIG. 29 is a front elevation view of the sterile wrap of FIG. 28 showing labels for measurements of the sterile wrap.

Illustratively, dimensions for a sterile wrap 800 are shown in Table 4 in reference to the markings A-V as shown in FIG. 29. The dimensions shown in Table 3 relate to one embodiment of the present disclosure and are not to limit possible dimensions and measurements of the sterile wrap 800.

TABLE 3

Dimensions of the Sterile Wrap 800 as shown in FIG. 29.

| Label | Distance (inches) |
| --- | --- |
| A | 2 |
| B | 3⅛ |
| C | 5¼ |
| D | 7¼ |
| E | 10 |
| F | 12¾ |
| G | 14¾ |
| H | 16½ |
| I | 3¼ |
| J | 5¾ |
| K | 9 |
| L | 15¼ |
| M | 16¾ |
| N | 19¾ |
| O | 21½ |
| P | 24 |
| Q | 1½ |
| R | 3½ |
| S | 2 |
| T | ½ |
| U | 1½ |
| V | 2 |

The sterile wrap 800 may be attached to the clip 700 by placing the snap feature 706 of the clip 700 through the perforation 822 and the wide features 708 of the clip 700 through the indentations 824. Alternatively, the sterile wrap 800 may be attached to the clip 1700 by placing the snap feature 1706 and the loop feature 1707 of the clip 1700 through the perforation 822 and the wide features 1708 of the clip 1700 through the indentations 824. After the clip 700 is placed in the sheet 802, each of the flaps 832 of the first clip cover portion 810 are placed through one of the openings 712 in the clip arms 710 of the clip 700, thus forming a loop. Alternatively, after the clip 1700 is placed in the sheet 802, each of the flaps 832 of the first clip cover portion 810 are wrapped around one of the clip arms 1710 of the clip 1700, thus forming a loop. The loop is closed by attaching the flaps 832 to themselves such that two parts of the exterior side 806 of each flap 832 are in contact. In some embodiments, the flaps 832 are sewn to themselves around the openings 712.

When the sterile wrap 800 is not attached to the clip 700, the sheet 802 is substantially flat. Thus, the sterile wrap 800 is easily stored or stacked in the flat position along with other wraps 800, if desired.

Figure 28:
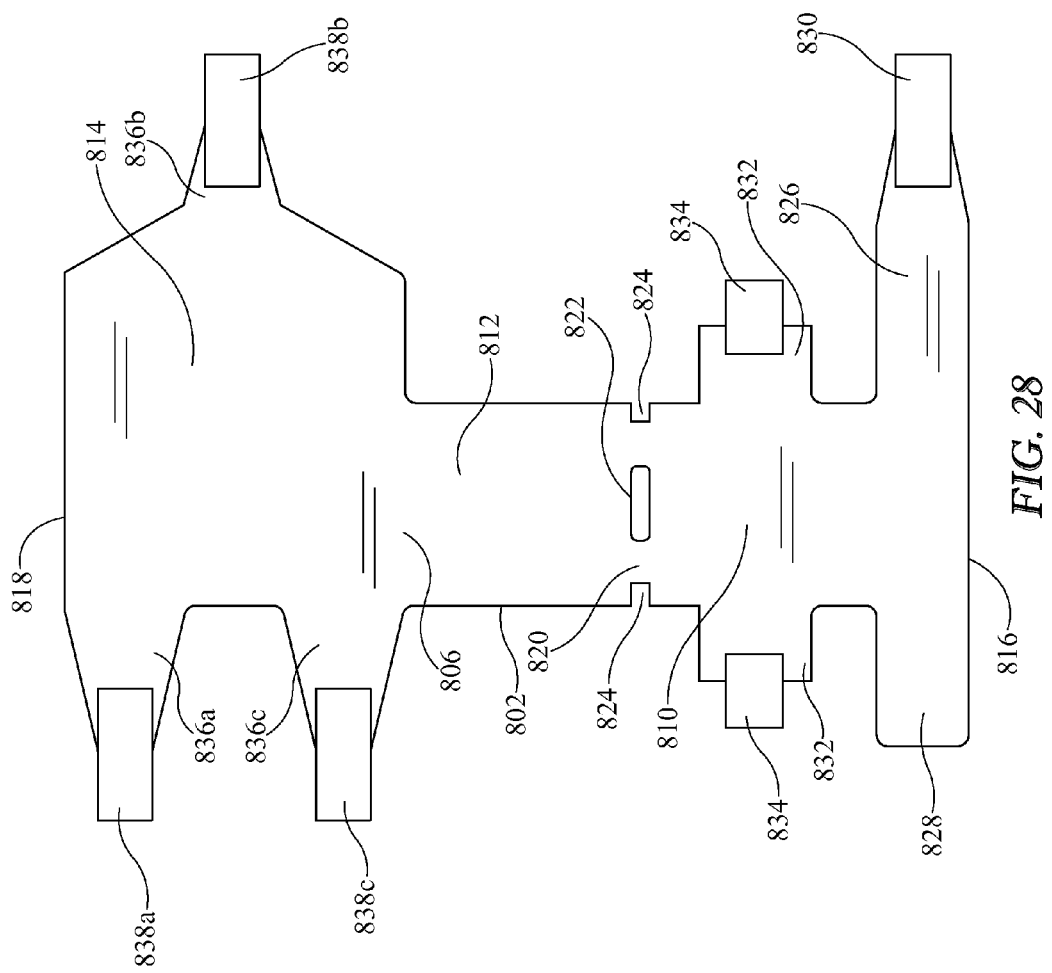
FIG. 28 is a front elevation view of a sterile wrap.
Figure 30:
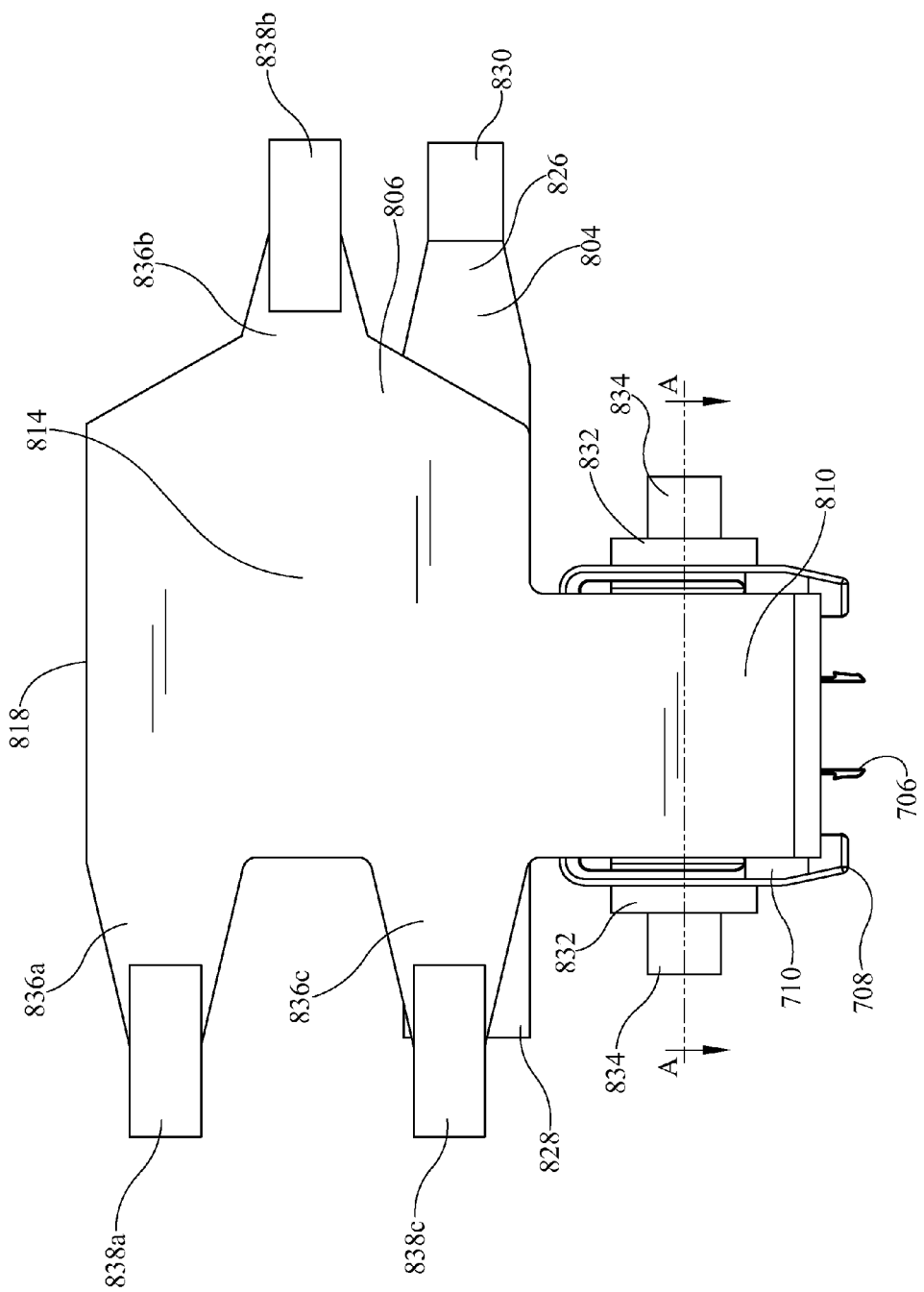
FIG. 30 is a front elevation view of the sterile wrap of FIG. 28 attached to the clip of FIG. 20, the sterile wrap in a partially folded position.
Figure 31:
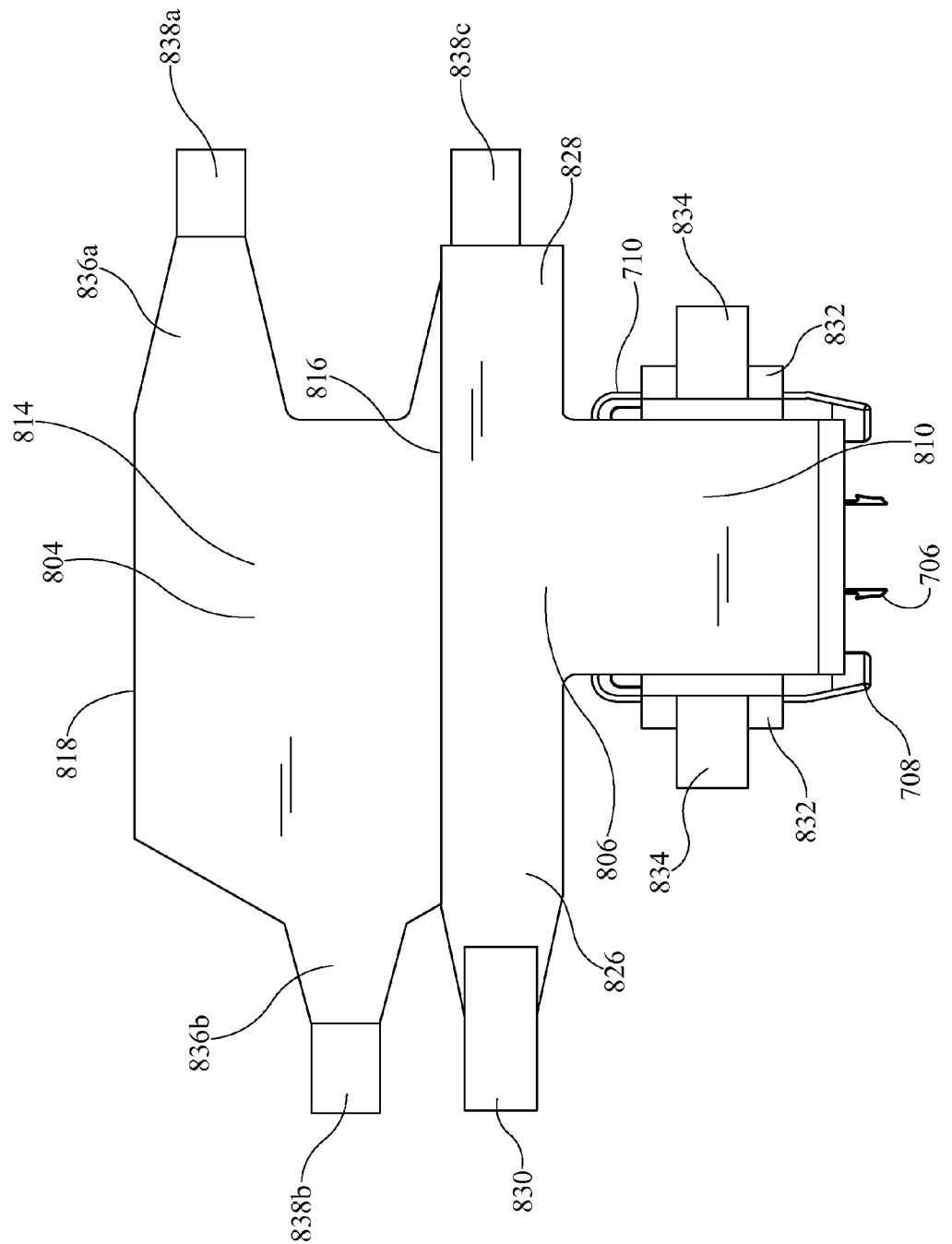
FIG. 31 is a rear elevation view of the sterile wrap of FIG. 28 attached to the clip of FIG. 20, the sterile wrap in the partially folded position.
Figure 32:
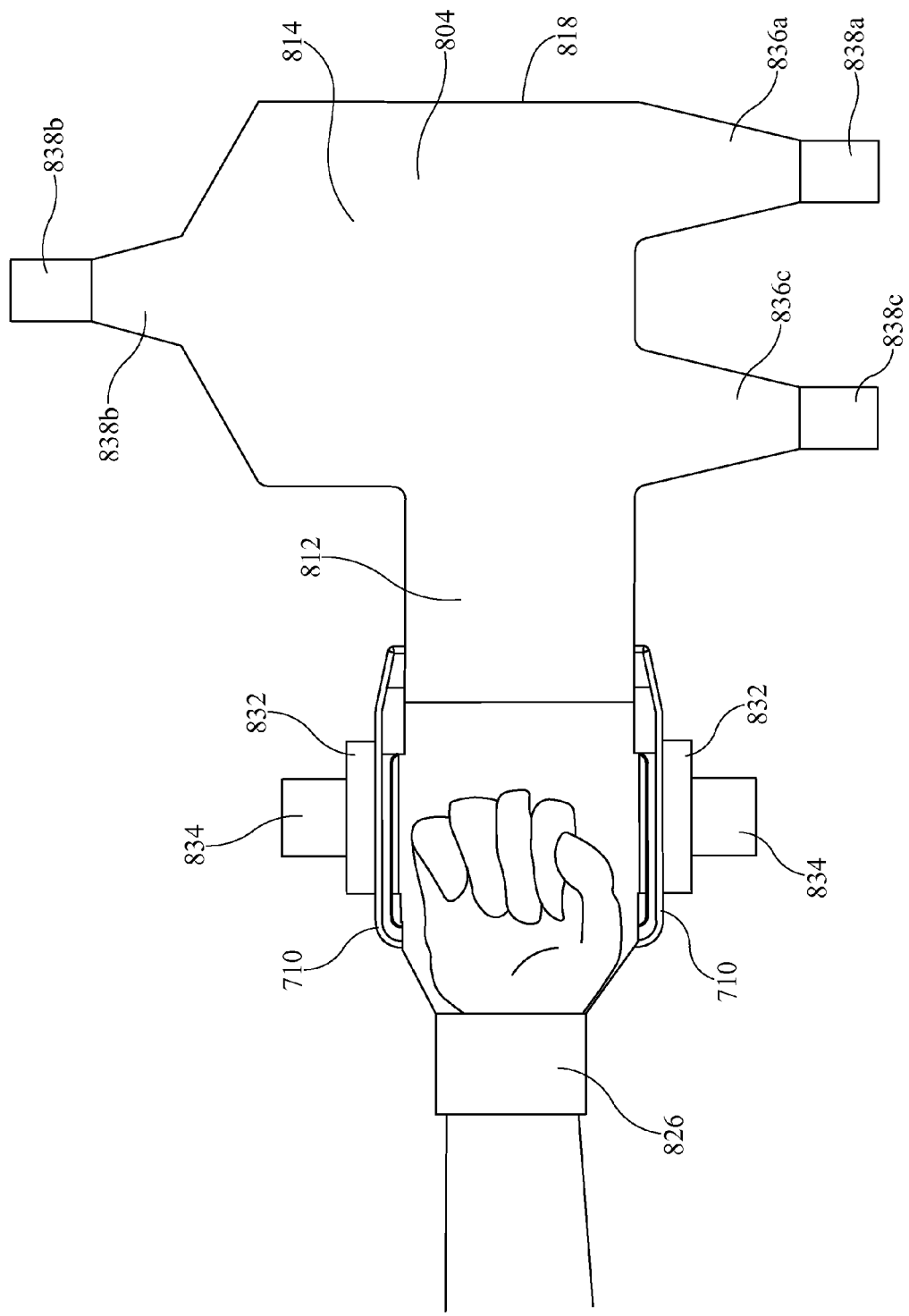
FIG. 32 is a front elevation view of the sterile wrap of FIG. 28 attached to the clip of FIG. 20 and wrapped around a patient's wrist in a wrist wrapped position.
Figure 33:
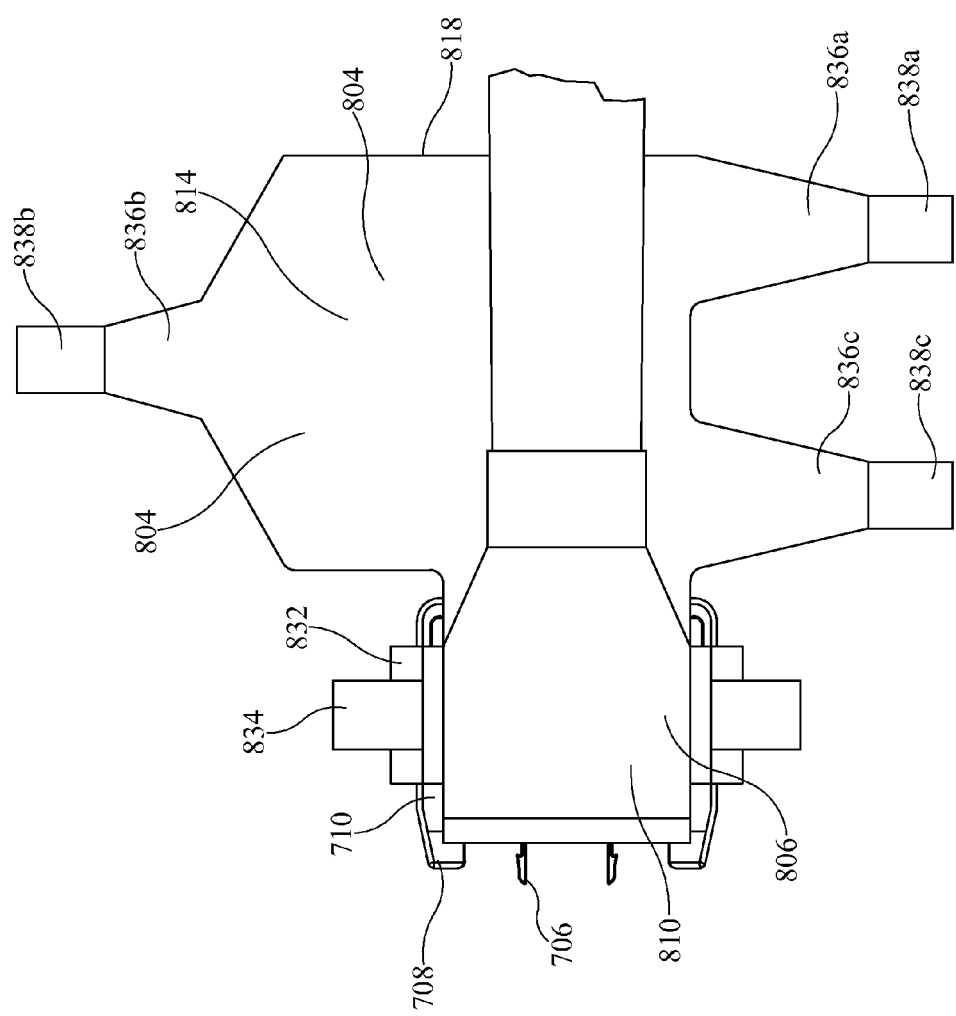
FIG. 33 is a rear elevation view of the sterile wrap of FIG. 28 attached to the clip of FIG. 20 and wrapped around a patient's wrist in a wrist wrapped folded position.
Figure 34:
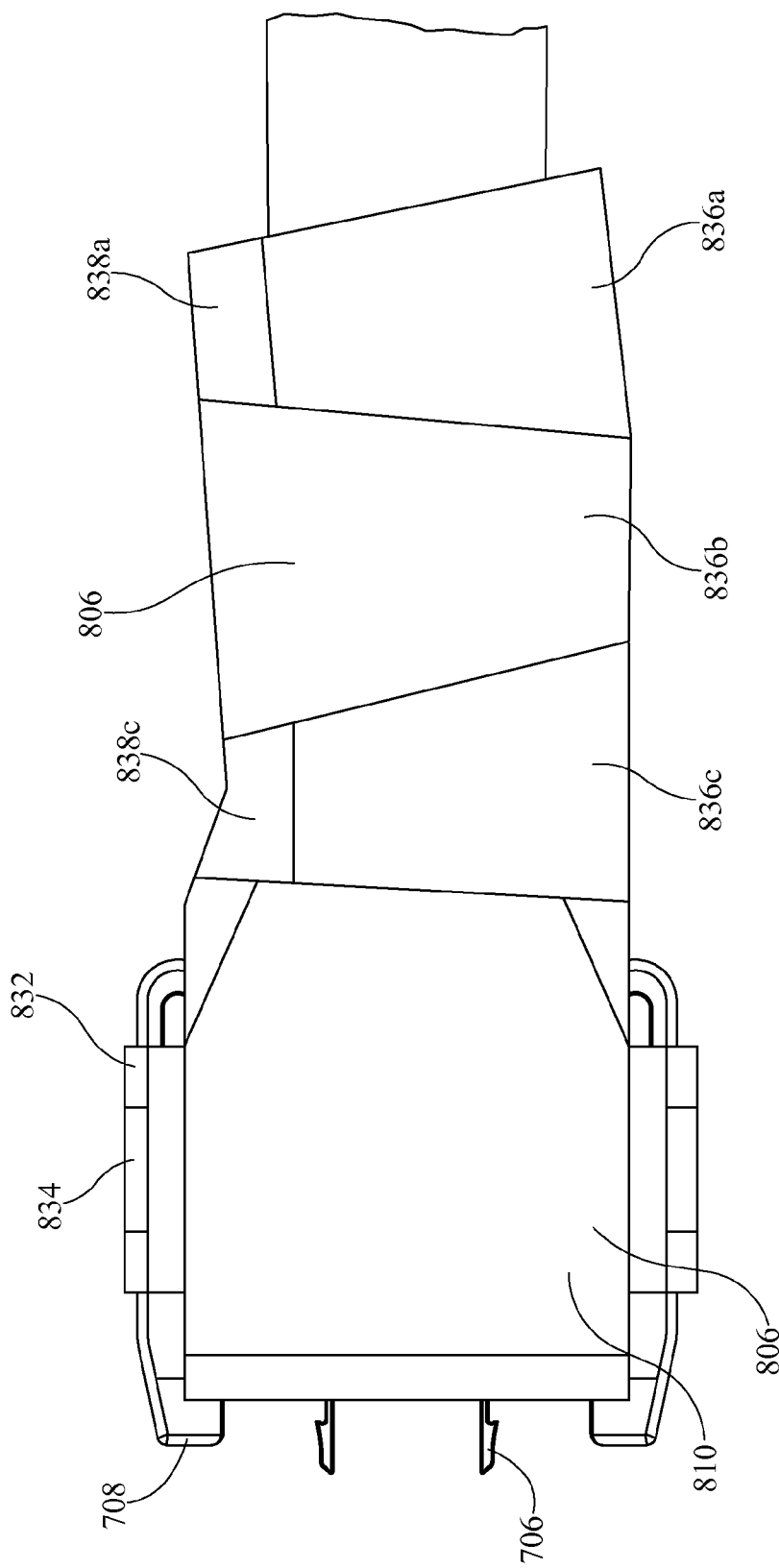
FIG. 34 is a rear elevation view of the sterile wrap of FIG. 28 attached to the clip of FIG. 20 and wrapped around a patient's wrist in a wrist forearm wrapped folded position.

The disposable wrap is foldable between a flat position, shown in FIGS. 28-29, a folded position, shown in FIGS. 30-31, a wrist wrapped position, shown in FIG. 32, a wrist wrapped folded position, shown in FIG. 33 and a wrist forearm wrapped position, shown in FIG. 34.

To move the sterile wrap 800 from the flat position to the folded position, the hinge portion 820 is bent such that the wrist portion 808 extends over and is substantially parallel to the second clip cover portion 812 and/or the forearm portion 814. In some embodiments, the sterile wrap 800 may be attached to the clip 700, or alternatively the clip 1700, and packaged in the folded position. Packaging the sterile wrap 800 and the clip 700, or alternatively the clip 1700, together in the folded position provides the benefit of a conveniently sized package. To further attach the sterile wrap 800 to the clip 700, or alternatively the clip 1700, the sterile wrap 800 may be moved into the folded position and sewn or stitched to itself parallel to and near the distal cross portion 709 of the clip 700, or alternatively the distal cross portion 1709 of the clip 1700, as shown in FIG. 30.

After attaching the sterile wrap 800 to the clip 700, or alternatively the clip 1700, the wrist portion 808 is wrapped around the patient's wrist. The back of the patient's hand is placed against the interior side 804 of the wrist portion 808 and/or first clip cover portion 810 of the sterile wrap 800 with the straps 826, 828 of the wrist portion 808 near the patient's wrist and the patient's fingers near the hinge portion 820. The second strap 828 is placed around the patient's wrist such that the interior side 804 of the sheet 802 is in contact with the patient's wrist. The first strap 826 is then placed around the second strap 828 and the tab 830 is attached to the exterior side 806 of the second strap 828. The resulting position of the sterile wrap 800 is a wrist wrapped position as shown in FIG. 32.

When the sterile wrap 800 is in the wrist wrapped position, the sheet 802 is folded at the hinge portion 820 such that the interior side 804 of the forearm portion 814 is in contact with the patient's forearm. The resulting position of the sterile wrap 800 is a wrist wrapped folded position as shown in FIG. 33.

When the sterile wrap is in the wrist wrapped folded position, the third strap 836b of the forearm portion is moved across the patient's forearm and secured to the exterior side 806 of the forearm portion 814 between the first strap 836a and the second strap 836c of the forearm portion 814. The first strap 836a and the second strap 836c of the forearm portion 814 are moved across the patient's forearm and secured to the exterior side 806 of the forearm portion 814. The flaps 832 of the first clip cover portion 810 are moved around the clip 700, or alternatively the clip 1700, and attached to the exterior side 806 of the second clip cover portion 812. The resulting position of the sterile wrap 800 is a wrist forearm wrapped position as shown in FIG. 34.

When the sterile wrap 800 is in the wrist forearm wrapped position, the patient's arm is ready to be connected to the surgical arm positioning system 8. Particularly, the clip 700 is attached to the buckle 612 of the receiving assembly 610 that, in turn, is attached to the surgical arm positioning system 8. Alternatively, the clip 1700 is attached to the buckle 1612 of the receiving assembly 1610 that, in turn, is attached to the surgical arm positioning system 8.

Figure 77:
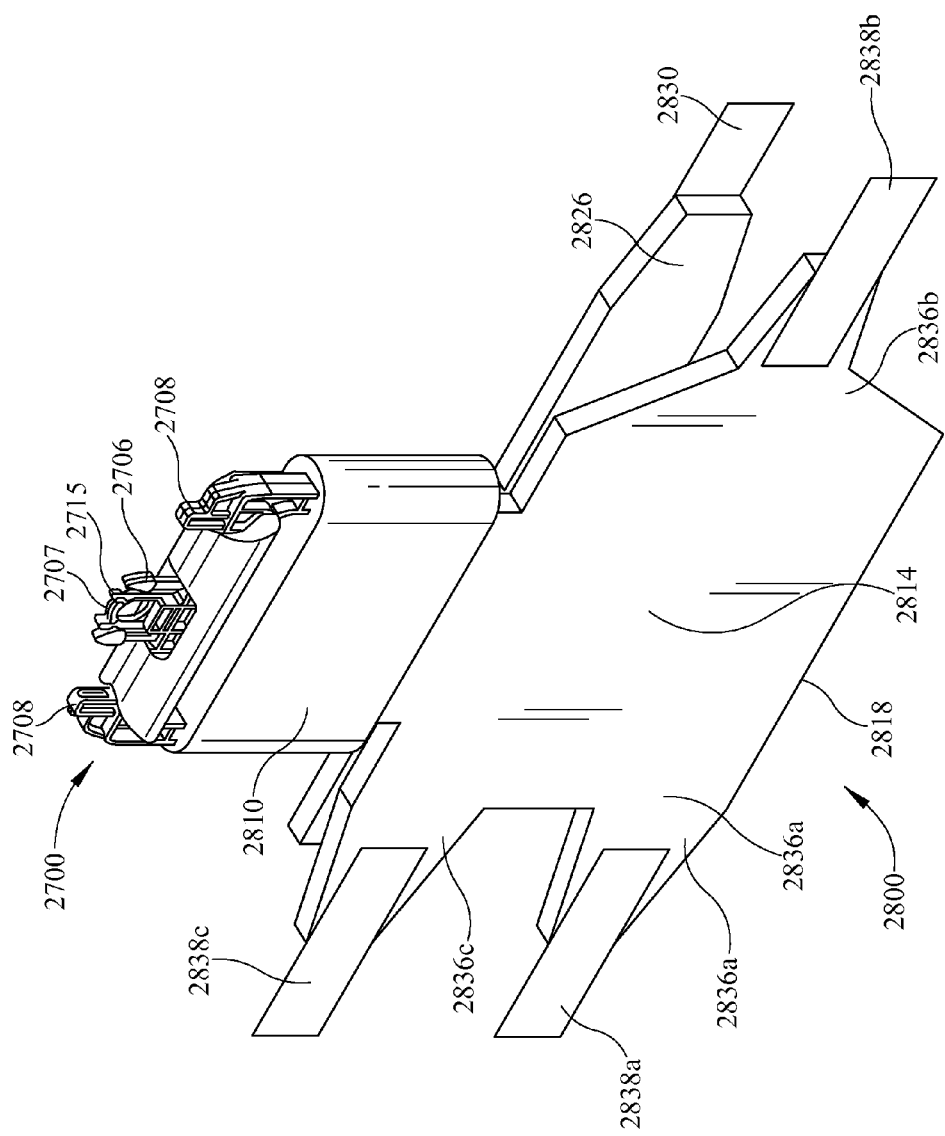
FIG. 77 is a perspective view of the sterile wrap of FIGS. 76A-76C attached to the clip of FIG. 72.

Referring now to FIGS. 76A-87, the sterile wrap 2800, is substituted by sterile wrap 2800 in the third embodiment. As best seen in FIG. 77, the sterile wrap 2800 includes a sheet 2802 having an interior side 2804 having an interior surface and an exterior side 2806 having exterior surface. The interior surface is made of foam, such as a low density sheet of foam, and the exterior surface is made of loop material having loops. The loop material is any material capable of interacting with a hook material having hooks such that the hooks become attached to the loops, thereby fastening the materials together. In other embodiments, fastening may be accomplished by clasps, hooks, snaps, or the like.

Figure 79:
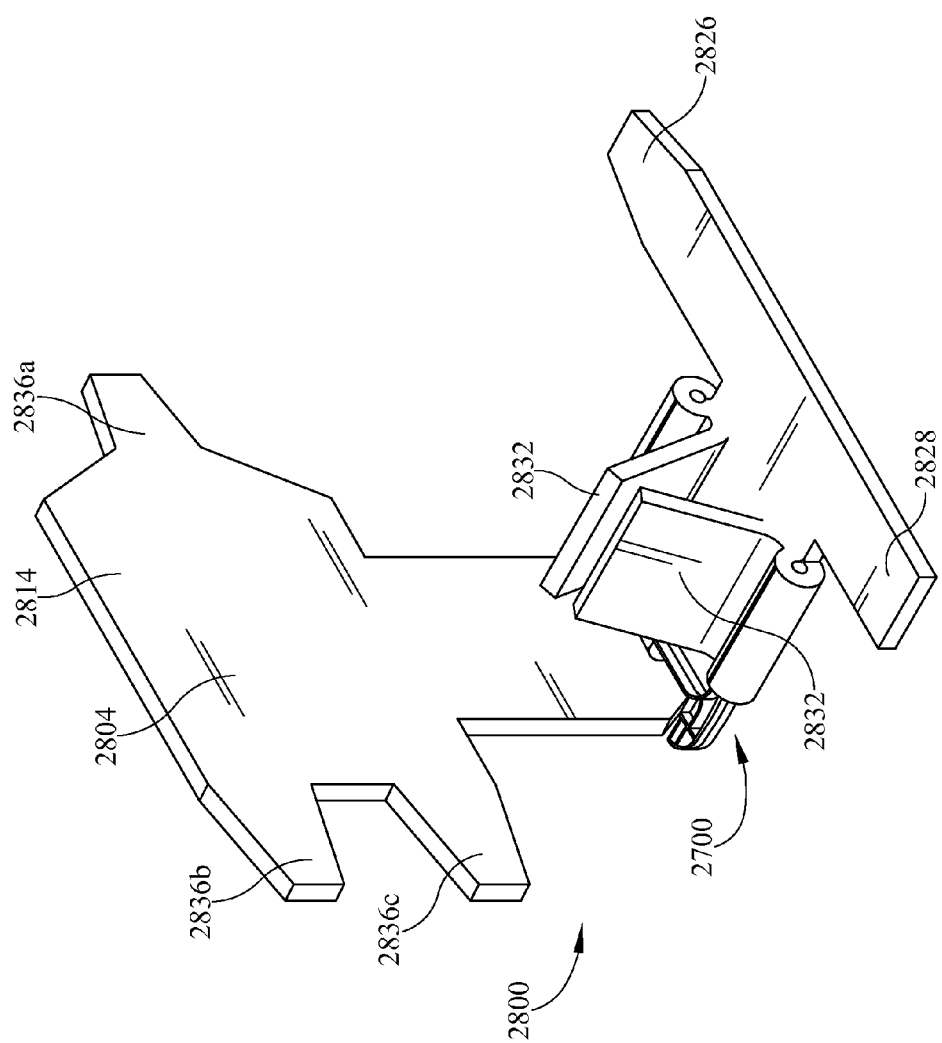
FIG. 79 is a perspective view of the sterile wrap and clip of FIG. 77.

The disposable wrap is shaped to wrap onto itself around specific parts of the patient's hand and forearm to support the patient's arm. Supporting the patient's arm by wrapping aids in torque transmission by reducing the amount that the foam can stretch. As shown in FIGS. 77 and 79, the sterile wrap 2800 is attached to the clip 2700 in a way that the patient's skin will not be in direct contact with rigid materials when wrapped by the sterile wrap 2800.

Referring now to FIGS. 76A and 79, the sheet includes a wrist portion 2808, a first clip cover portion 2810, a second clip cover portion 2812, and a forearm portion 2814. The wrist portion 2808 is situated at a first edge 2816 of the sheet 2802. The forearm portion 2814 is situated at a second edge 2818 of the sheet 2802.

The first clip cover portion 2810 extends from the wrist portion 2808. The second clip cover portion 2812 extends from the forearm portion 2814. The first clip cover portion 2810 is coupled to the second clip cover portion 2812 by a hinge portion 2820 situated between the first clip cover portion 2810 and the second clip cover portion 2812. The hinge portion 2820 includes a perforation 2822 and two indentations or notches 2824 arranged in a linear pattern.

The wrist portion 2808 includes a first strap 2826 and a second strap 2828. The first strap 2826 is attached to a tab 2830 having the hook material. The hook material has hooks facing the interior side 2804 of the sheet. The exterior side 2806 of the second strap 2828, having the loop material, is sized to receive the tab 2830 of the first strap 2826 such that the two straps 2826 and 2828 adhere due to interaction between the hooks of the tab 2830 of the first strap 2826 and the loops of the exterior side 2806 of the second strap 2828.

The first clip cover portion 2810 includes two flaps 2832 attached to two tabs 2834, each tab having the hook material. The hook material has hooks facing the interior side 2804 of the sheet 2802. The exterior side 2806 of the second clip cover portion 2812, having the loop material, receives the flaps 2832 of the first clip cover portion 2810 when the sheet 2802 is folded such that the interior surfaces 2804 of the first and second clip cover portions 2810 and 2812 face each other.

The forearm portion 2814 includes three straps 2836*a*, 2836*b*, 2836*c* each attached to one of three tabs 2838*a*, 2838*b*, and 2838*c* each having the hook material. The hook material has hooks facing the interior side 2804 of the sheet 2802. A first and a second of the straps 2836*a*, 2836*c* of the forearm portion 2814 extend in a direction opposite a third of the straps 2836*b* of the forearm portion. The exterior side 2806 of forearm portion 2814, having the loop material, is operable to receive the tabs 2838*a*, 2838*b*, and 2838*c* of the forearm portion.

Illustratively, dimensions for a sterile wrap 2800 are shown in Table 4 in reference to the markings A-V as shown in FIGS. 76A and 76B. Angle W has a value of 100°. The dimensions shown in Table 4 relate to one embodiment of the present disclosure and are not to limit possible dimensions and measurements of the sterile wrap 2800.

TABLE 4

Dimensions of the Sterile Wrap 2800 as shown in FIG. 76A-76C.

| Label | Distance (inches) |
|---|---|
| A | 19½ |
| B | 18½ |
| C | 16½ |
| D | 15 |
| E | 12¾ |
| F | 10 |
| G | 7¼ |
| H | 1 |
| I | 3 |
| J | 5½ |
| K | 8½ |
| L | 15¾ |
| M | 17¾ |
| N | 21¾ |
| O | 22½ |
| P | 25 |
| Q | 1½ |
| R | ½ |
| S | 0.16 ± 0.05 |
| T | 4.25 |
| U | 1.60 ± 0.05 |
| V | 1.00 ± 0.05 |

Figure 80:
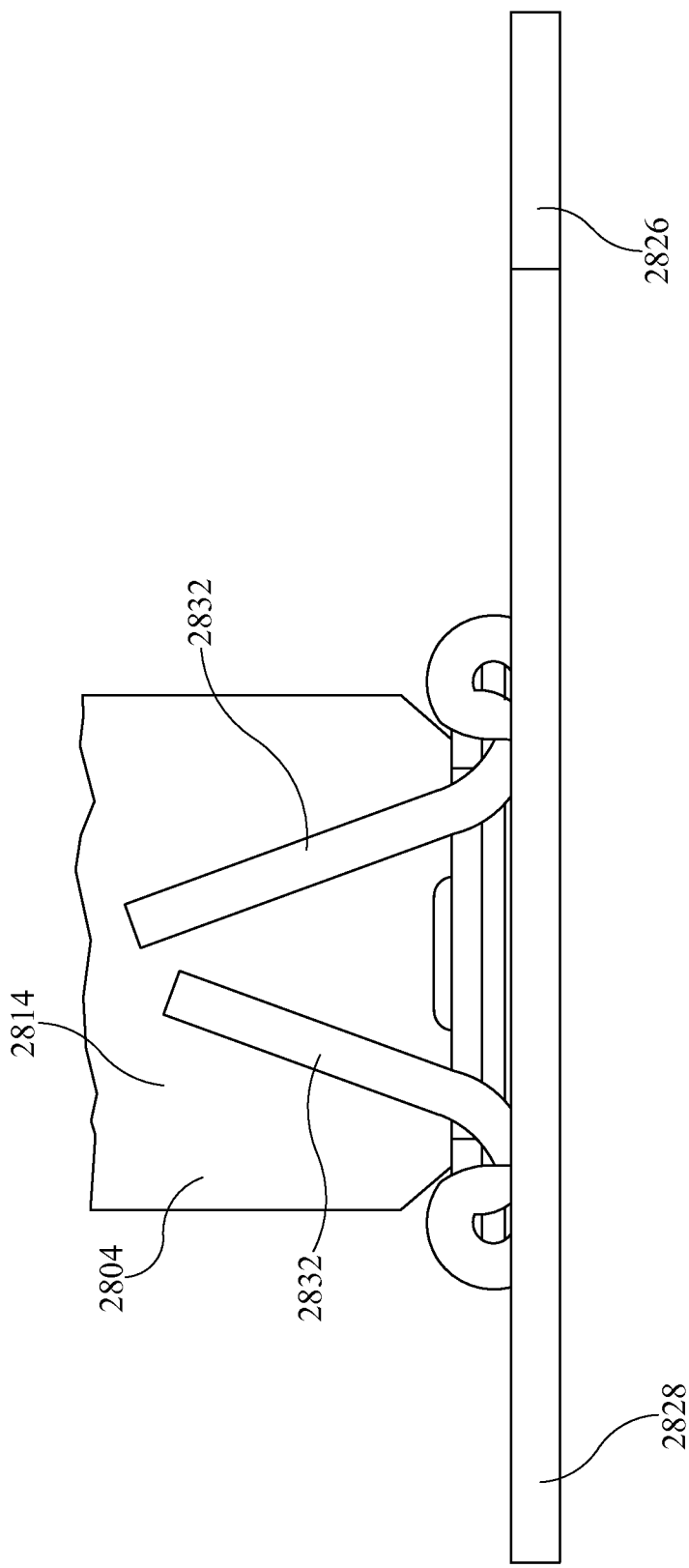
FIG. 80 is a side elevation view of the sterile wrap and clip of FIG. 77.

Referring now to FIG. 77, the sterile wrap 2800 may be attached to the clip 2700 by placing the snap feature 2706 and loop feature 2707 of the clip 2700 through the perforation 2822 and the wide features 2708 of the clip 2700 through the indentations 2824. As shown in FIGS. 79 and 80, after the clip 2700 is placed in the sheet 2802, each of the flaps 2832 of the first clip cover portion 2810 are wrapped around one of the clip arms 2710 of the clip 2700, thus forming a loop. The loop is closed by attaching the flaps 2832 to themselves such that two parts of the exterior side 2806 of each flap 2832 are in contact. In some embodiments, the flaps 2832 are sewn to themselves around the openings 2712.

When the sterile wrap 2800 is not attached to the clip 700, the sheet 2802 is substantially flat. Thus, the sterile wrap 2800 is easily stored or stacked in the flat position along with other wraps 2800, if desired.

Figure 82:
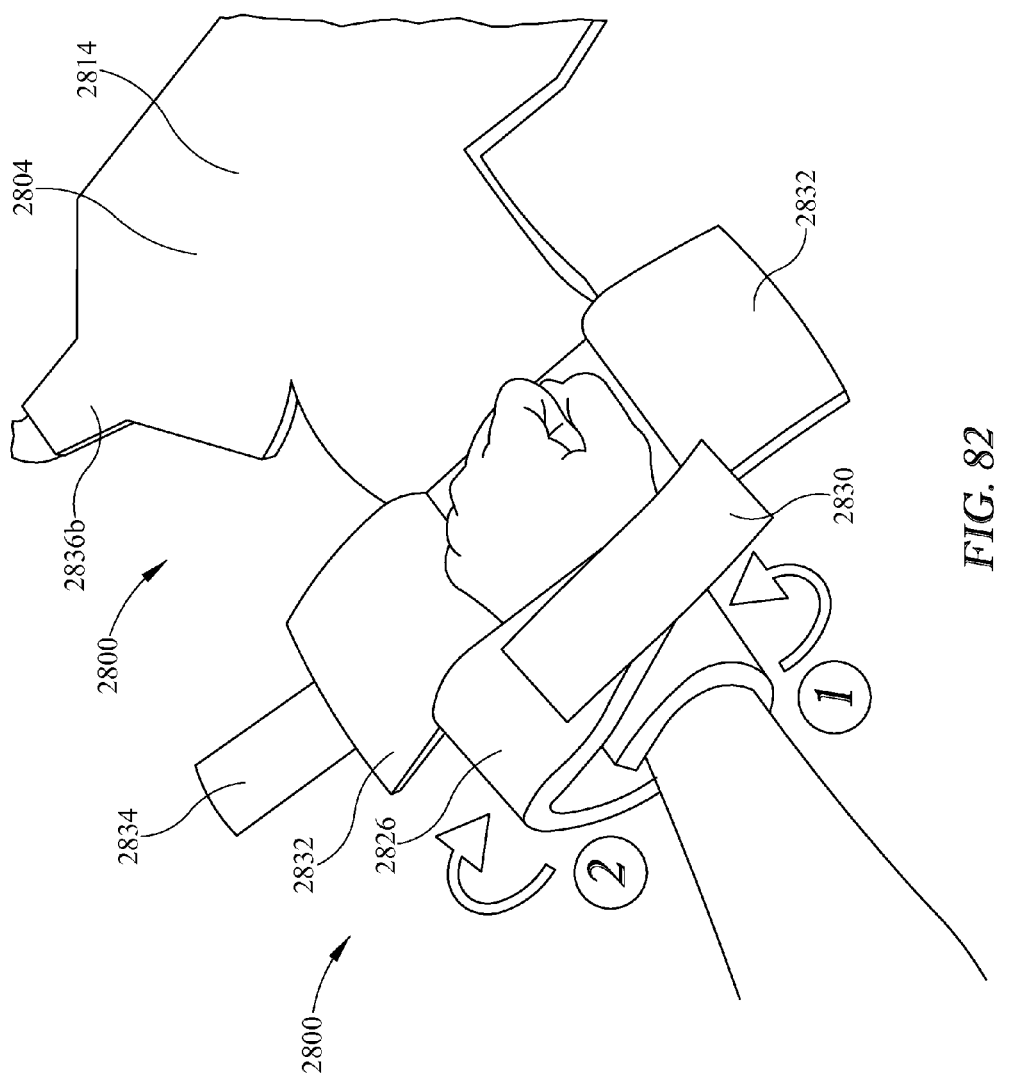
FIG. 82 is a perspective view of the sterile wrap and clip of FIG. 77 showing steps 1 and 2 of attaching the sterile wrap to a patient's arm.
Figure 83:
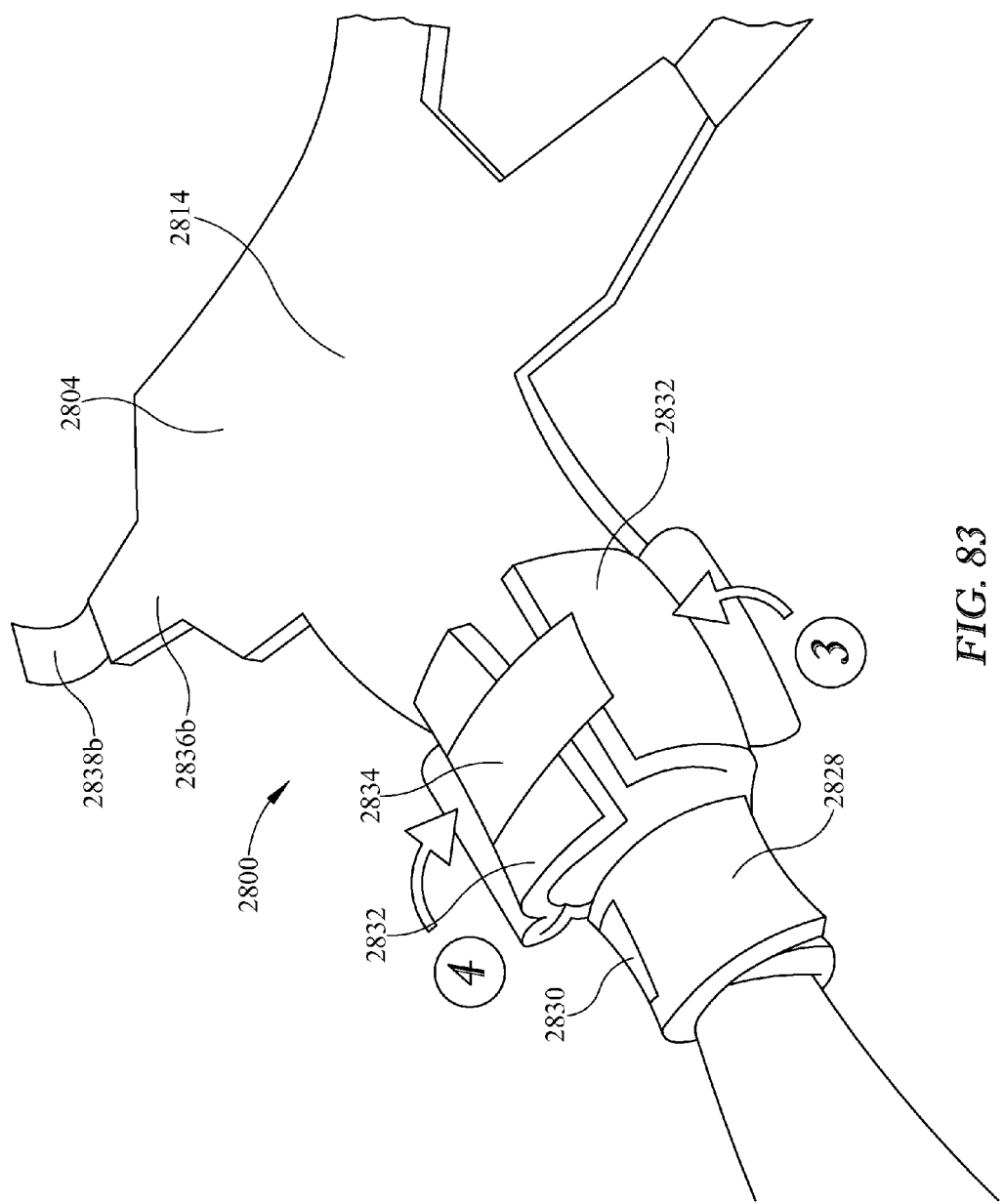
FIG. 83 is a perspective view of the sterile wrap and clip of FIG. 77 showing steps 3 and 4 of attaching the sterile wrap to the patient's arm.
Figure 84:
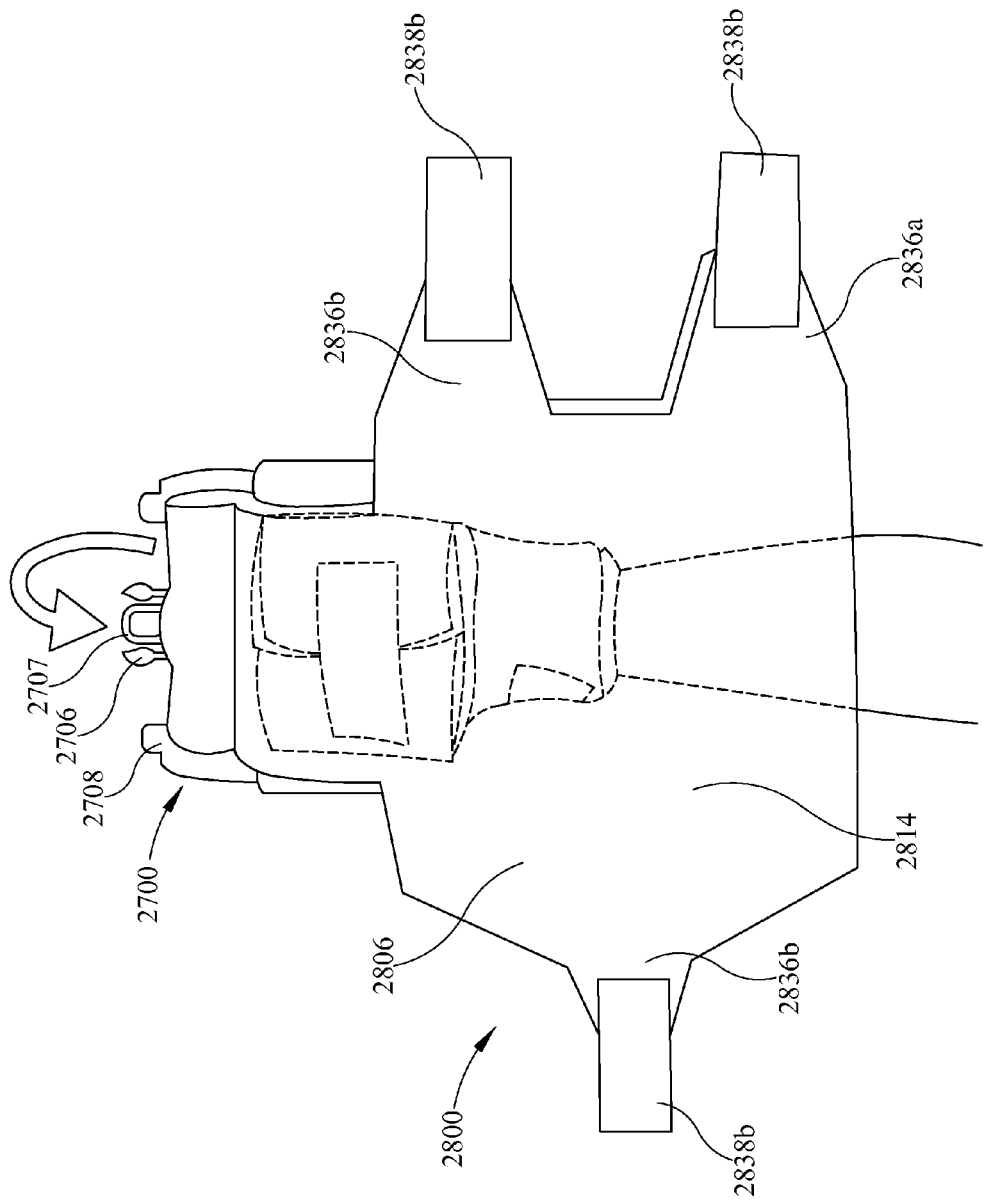
FIG. 84 is a perspective view of the sterile wrap and clip of FIG. 77 partially folded around the patient's arm.
Figure 85:
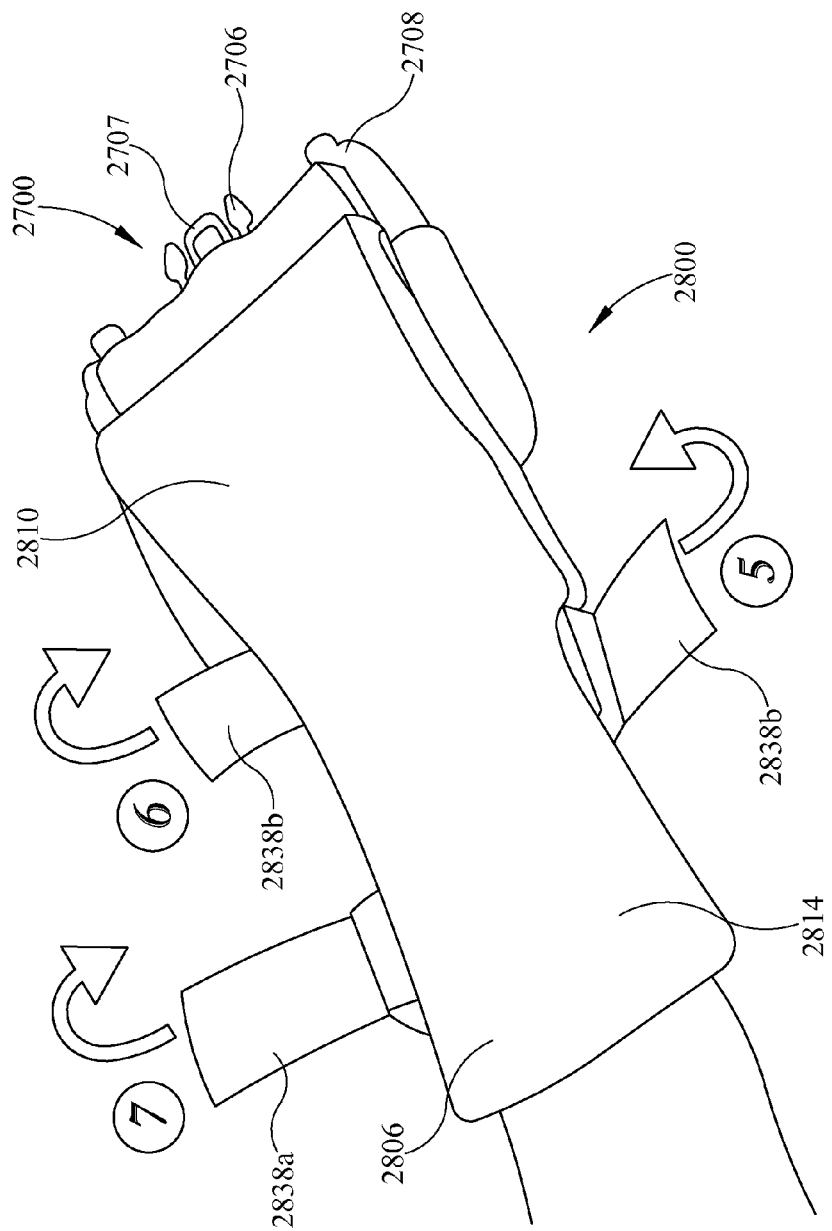
FIG. 85 is a perspective view of the sterile wrap and clip of FIG. 77 showing steps 5, 6, and 7 of attaching the sterile wrap to the patient's arm.
Figure 86:
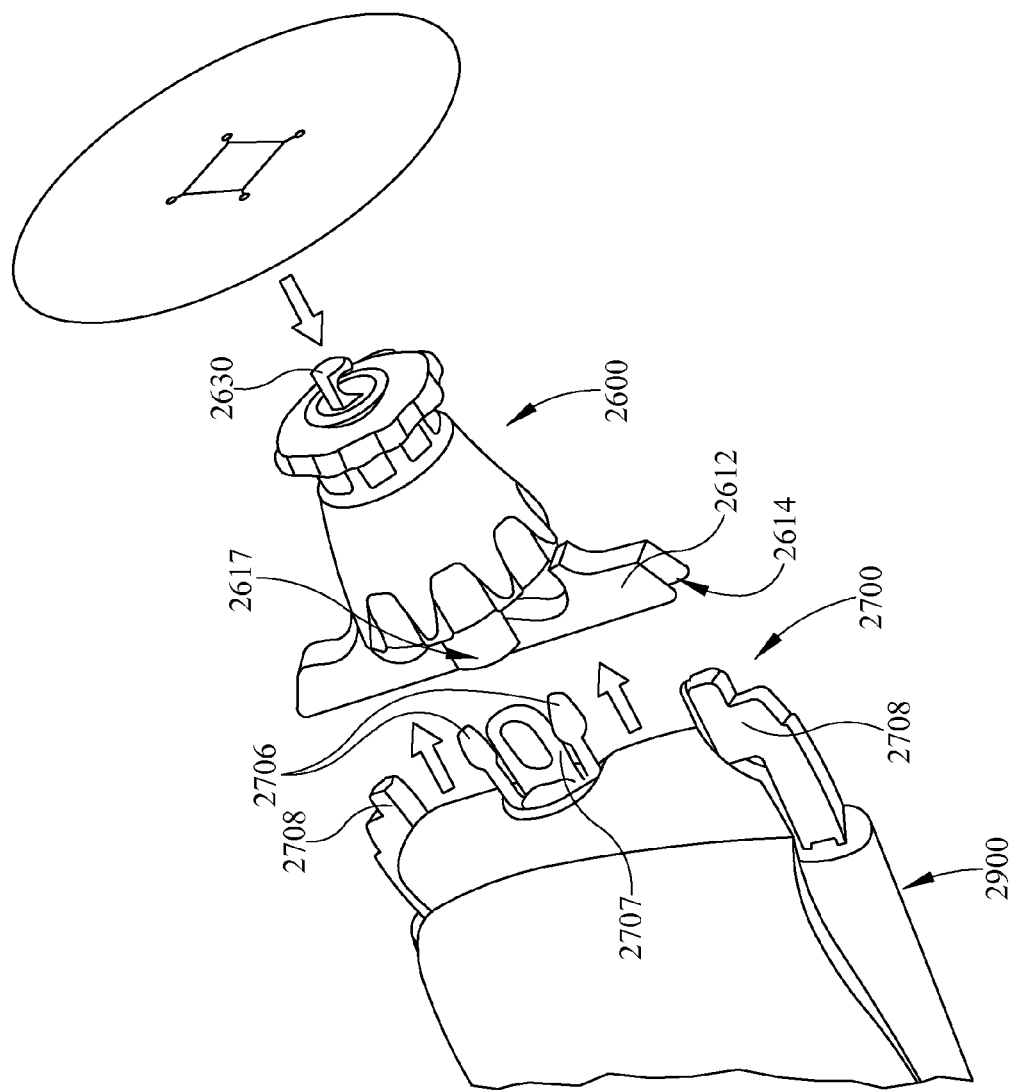
FIG. 86 is an exploded view of the sterile wrap and clip of FIG. 77 and the shield of FIG. 78.

The disposable wrap is folded around the patients arm to attach the patient to the clip 2700 and the rest of the surgical arm positioning system 8 over several steps, as shown in FIGS. 82-86. Referring to FIG. 82, in a first step, with the patient's arm resting against the interior surfaces 2804 of the disposable wrap 2800, the second strap is wrapped around the patient's arm toward the first strap 2826. Next, in a second step, the first strap 2826 is wrapped around the patient's arm over the first strap 2826. As shown in FIG. 83, in a third step, one of the flaps 2832 is folded over the patient's hand, followed by a fourth step of folding the other one of the flaps 2832 over the patient's hand. Referring now to FIG. 84, after the fourth step, the forearm portion 2814 is folded over the flaps 2832. As shown in FIG. 85, in a fifth step, strap 2838*b* is folded over the patient's forearm. In a sixth step, strap 2838*c* is folded over the patient's forearm. Strap 2838*a* is folded over the patient's forearm in a seventh step to finish securing the patient's arm to the clip 2700 by the sterile wrap 2800. Referring now to FIG. 86, after the patient's arm is secured to the clip 2700, the clip 2700 is inserted into the receiving assembly 2610.

Figure 87A:
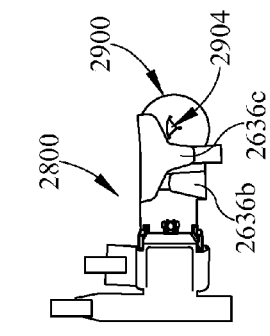
FIGS. 87A-87I are perspective views of the sterile wrap and clip of FIG. 77 showing different steps of folding and packaging the sterile wrap and clip.
Figure 87B:
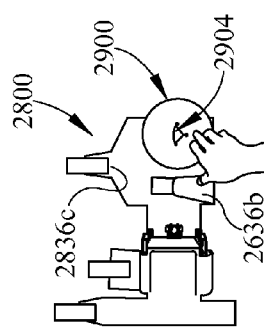
Figure 87C:
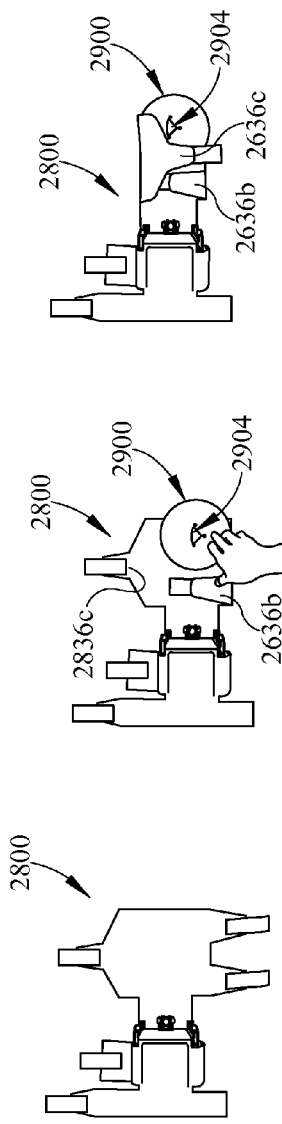
Figure 87D:
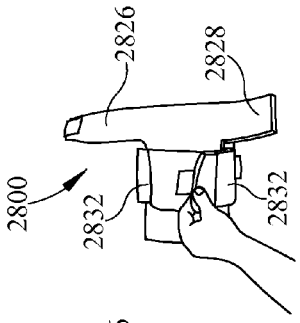
Figure 87E:
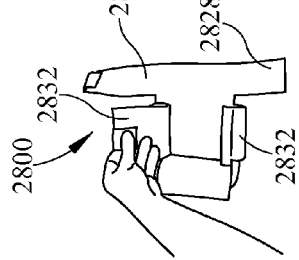
Figure 87F:
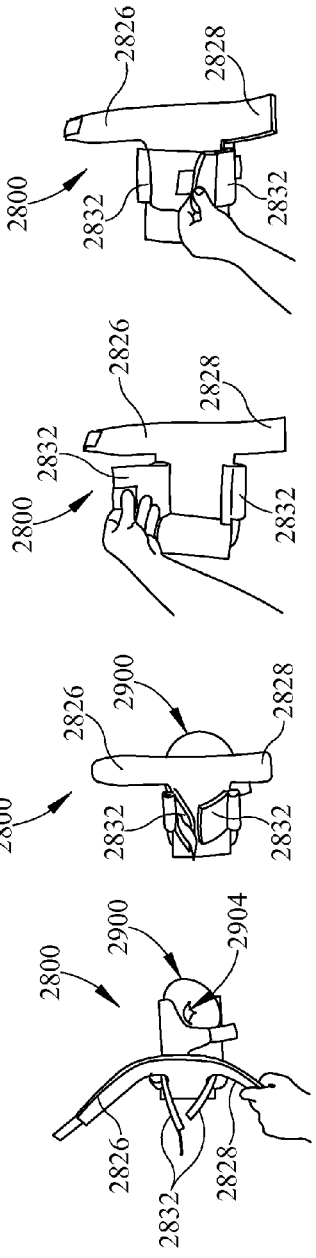
Figure 87G:
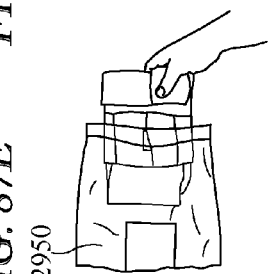
Figure 87H:
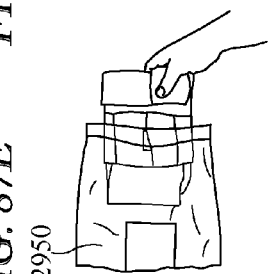
Figure 87I:
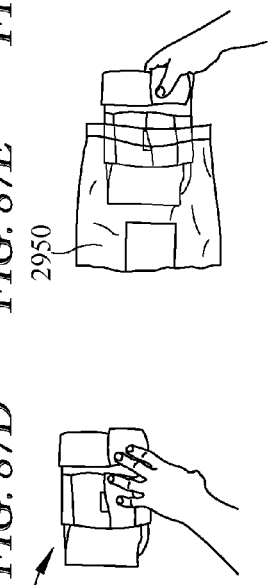

Referring now to FIGS. 87A-87I, the sterile wrap 2800 may be folded along with the shield 2900 (shown in FIGS. 78A and 78B) and packaged in a plastic bag 2950. Starting with sterile wrap 2800 in a flat, unfolded position, as shown in FIG. 87A, the shield 2900 may be placed onto the wrap 2800 with strap 2836a placed through the hole 2904 of the shield 2900, as shown in FIG. 87B. Next, strap 2836c is folded over the shield 2900, as shown in FIG. 87C, followed by moving first and second straps 2826 and 2828 toward the shield 2900, as shown in FIG. 87D. As shown in FIGS. 87E-87G, the flaps 2832 are next folded around the rest of the sterile wrap 2800. Finally, moving from FIG. 87G to FIG. 87H, first and second straps 2826 and 2828 around folded around each other such that the sterile wrap 2800 is substantially square. As shown in FIG. 87I, the folded sterile wrap 2800 is inserted into the plastic bag 2950.

Figure 35:
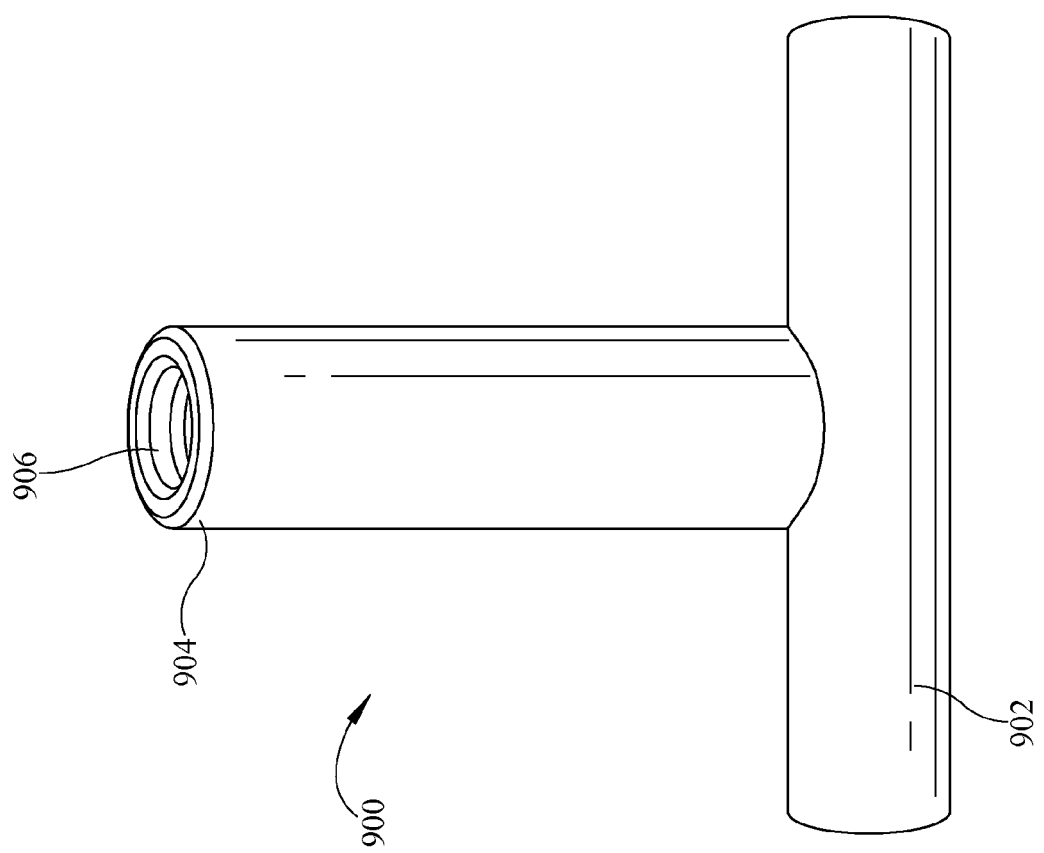
FIG. 35 is a perspective view of a T-shaped handle of a sterile connection.
Figure 36:
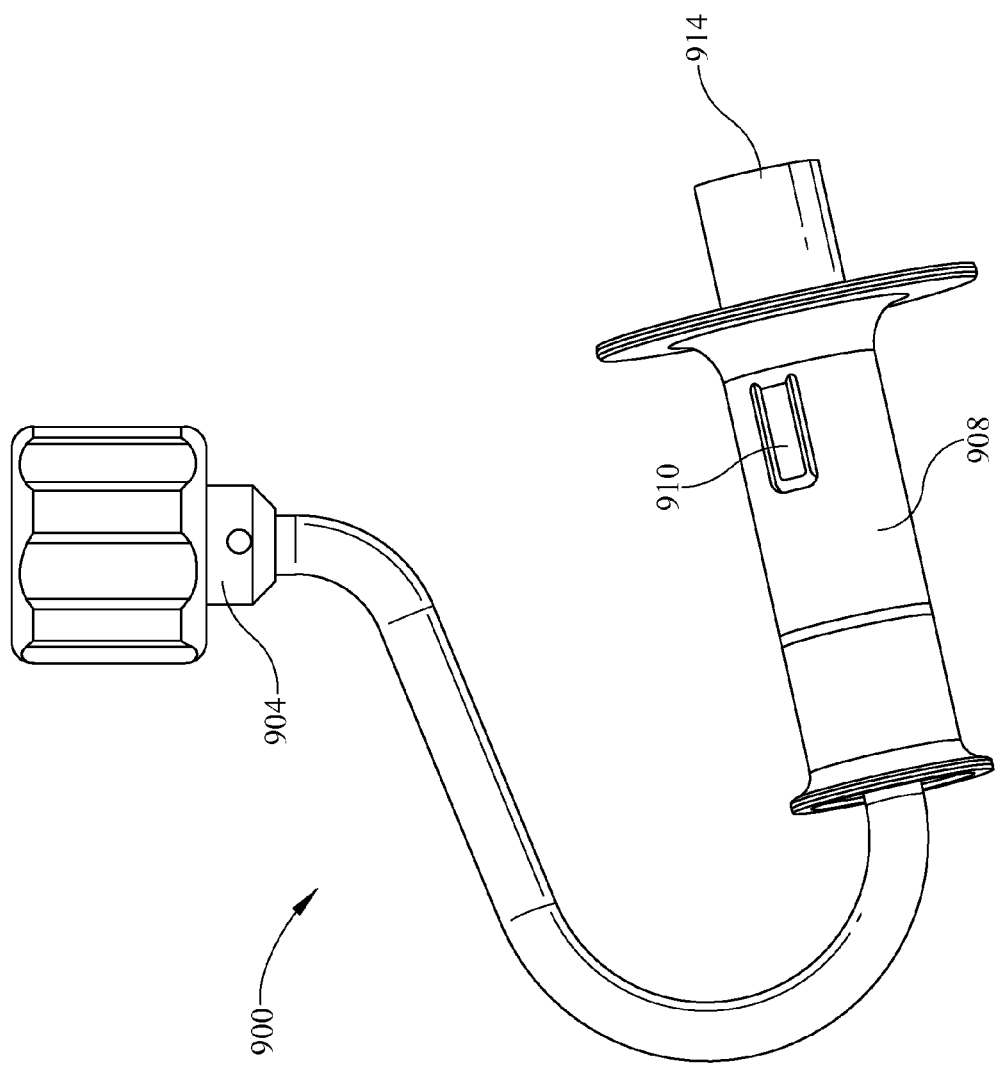
FIG. 36 is a perspective view of a J-shaped handle of a sterile connection attached to a sterile handle cover.
Figure 37:
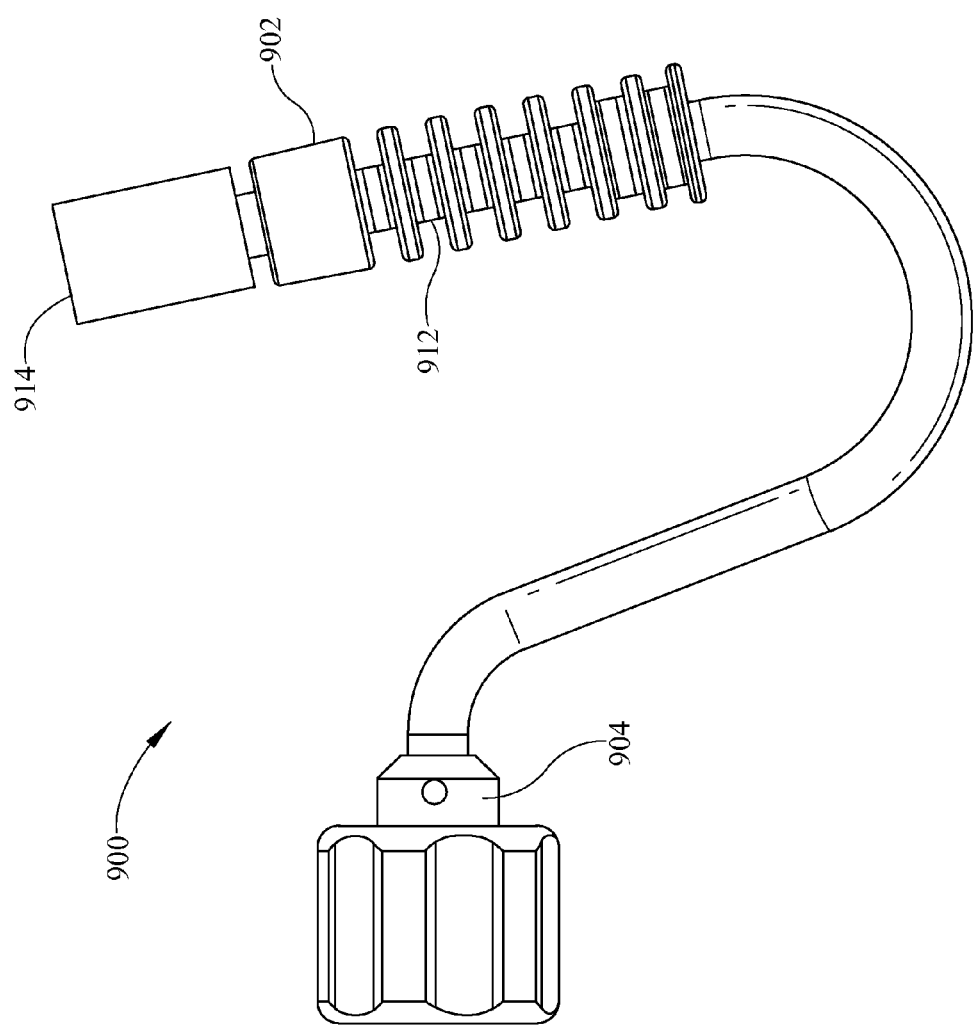
FIG. 37 is side elevation view of the J-shaped handle of FIG. 38 with the sterile handle cover omitted.

In some embodiments, the clip adaptor 616 is substituted by a handle 900 as shown in FIGS. 35-37. The handle forms a T-shape (shown in FIG. 35) in some embodiments and forms a J-shape (shown in FIGS. 36 and 37) in other embodiments and has a proximal end 902 that is operable to be gripped by the patient's hand and a distal end 904 having a rim 906. The handle 900 may be any shape that allows it to be gripped by the patient. The proximal end 902 of the handle may be at an angle of about 78° from the distal end 904 in the J-shaped embodiment, for example. However, the angle between the proximal end 902 and the distal end 904 may be any angle that substantially matches the grip angle of the patient's hand.

A sterile handle cover 908 is fitted to the proximal end 902 of the handle 900 such that the patient may grip the sterile handle cover 908 without making contact with the handle 900. The sterile handle cover 908 is stiff but flexible and, in some embodiments, is made of plastic. The patient's hand is wrapped around the sterile handle cover 908 and a material such as foam is wrapped around the patient's hand to hold the patient's hand closed around the sterile handle cover 908. The sterile handle cover 908 may be wrapped or coated in a cushioning material such as foam. The sterile handle cover 908 slides onto the proximal end 902 of the handle and snaps into place with a radial snap feature 910. The proximal end 902 of the handle 900 has a series of grooves 912 therein to accept the radial snap feature 910. When the sterile handle cover 908 is over the handle 900 and the radial snap feature 910 is in one of the grooves 912, a release mechanism 914 may be operated to disengage the radial snap feature 910, allowing the handle 900 and the sterile handle cover 908 to be decoupled. In some examples, the release mechanism 914 includes a button, a lever, or a knob.

The handle 900 engages the connector 624. The body 626 of the connector 624 resides within the rim 906 of the handle 900 such that the body 626 is movable within the handle 900. The diameter of the cap 628 is greater than the diameter of the opening defined by the rim 906 such that contact between the cap 628 and the rim 906 prevents the handle 900 from sliding off of the connector 624. The force of the contact between the cap 628 and the rim 906 may create sufficient friction between the cap 628 and the rim 906 to prevent rotation and allow torque to be transferred therebetween. As the handle 900 is rotated about the axis of its distal end 904, torque is transmitted to the patient's hand by the handle cover 908 that is gripped by the patient's hand.

The sterile connection 600, clip 700, and sterile wrap 800, or alternatively the sterile connection 1600, the clip 1700, and the sterile wrap 800, securely attach the patient's limbs to non-sterile support devices, such as a surgical arm positioning system 8. By attaching the patient's limbs to the sterile connection 600, or alternatively the sterile connection 1600, and attaching the sterile connection 600, or alternatively the sterile connection 1600, to non-sterile support devices, a single sterile staff member can attach the patient's sterilely prepared limb to the non-sterile support device without assistance from non-sterile personnel. The sterile operator can hold the sterile part of the receiving assembly 610 and place the connector hook 630 around the pin 642 of the cable adaptor 636 to attach the receiving assembly 610 to the cable adaptor 636 without touching non-sterile components. Alternatively, the sterile operator can hold the sterile part of the receiving assembly 1610 and place the connector hook 1630 around the pin 642 of the cable adaptor 636 to attach the receiving assembly 1610 to the cable adaptor 636 without touching non-sterile components. The sterile connection 600 and its use can save manpower by allowing a single person to connect the patient's arm to the non-sterile support device and reducing the chance of breaking sterility. The sterile connection 600 and its use can also save cost by limiting the amount of disposable material required to attach the patient's arm to the non-sterile support device.

The sterile connection 600, clip 700, and sterile wrap 800, or alternatively the sterile connection 1600, the clip 1700, and the sterile wrap 800, provide several additional benefits. Attaching a sterile connection 600 to a support system having two cable ends 640 provides the advantage of allowing for arm angle adjustability. The sterile connection 600 is easy to attach and detach to a support device. Also, the sterile connection 600 can be detached by an operator while maintaining sterility. The sterile connection 600 resists accidental decoupling. The sterile connection 600 does not require the patient's limb to be secured against rigid components, thereby addressing concerns of pressure points.

Although certain illustrative embodiments have been described in detail above, variations and modifications exist within the scope and spirit of this disclosure as described and defined in the following claims.

The invention claimed is:

1. A surgical arm positioning system comprising:
   a frame having a first frame member and a second frame member;
   when mounted to a surgical table that is lying horizontally, the second frame member being supported with respect to the first frame member to form an obtuse angle between the first frame member and the second frame member,
   the first frame member having a first longitudinal axis, the second frame member having a second longitudinal axis, wherein the first longitudinal axis intersects the second longitudinal axis when mounted to the surgical table such that the first longitudinal axis and second longitudinal axis lie in the same vertically oriented plane;
   a cable having two end portions coupled to a connection member of a hand grip such that the cable and connection member form a continuous loop,
   a plurality of pulleys including a first pulley movable along the first frame member and a second pulley movable along the second frame member, wherein the first and second pulleys are linked to that the first and second pulleys move in unison along the respective first and second frame members, wherein the continuous loop is trained around the plurality of pulleys, and
   a tensile resistance member engaged with the cable for providing tensile force to the cable thereby to resist movement of the continuous loop.

2. The surgical arm positioning system of claim 1, wherein the tensile resistance member is a clutch providing a resistive torque to one of the pulleys.

3. The surgical arm positioning system of claim 1, further comprising a weight engaged with the cable.

4. The surgical arm positioning system of claim 1, wherein the two end portions form an angle from about 120 to about 180 degrees at the connection member.

5. The surgical arm positioning system of claim 1, wherein when a patient's arm is attached to the connection member, the cable resists movement along the pulleys to keep the patient's arm stationary after the patient's arm is placed at any position having between about 0 degrees and about 30 degrees of arm abduction.

6. The surgical arm positioning system of claim 1, wherein a third pulley of the plurality of pulleys is mounted at a fixed location relative to the frame.

7. The surgical arm positioning system of claim 6, wherein at least one of the first and second pulleys is coupled to a bracket that resists movement along the frame.

8. The surgical arm positioning system of claim 1, further comprising a semi-locked clamp configured to permit pivoting a frame.

9. The surgical arm positioning system of claim 8, wherein the semi-locked clamp provides resistance to rotation of the frame.

10. The surgical arm positioning system of claim 1, further comprising a lower pulley bracket to which the first pulley is coupled and an upper pulley bracket to which the second pulley is coupled, wherein when a patient's arm is attached to the connection member, the lower and upper pulley brackets resist movement relative to the frame to keep the arm stationary and the lower and upper pulley brackets move relative to the frame in response to moving a patient's arm.

11. The surgical arm positioning system of claim 10, wherein movement of one of the lower and upper pulley brackets influences movement of the other of the lower and upper pulley brackets.

12. The surgical arm positioning system of claim 11, wherein a distance between the lower and upper pulley brackets is fixed.

13. The surgical arm positioning system of claim 12, further comprising a connecting rod fixing the distance between the lower and upper pulley brackets and linking the first and second pulleys.

14. The surgical arm positioning system of claim 10, wherein the lower pulley bracket and the upper pulley bracket each extend from a respective channel formed in the corresponding first and second frame member.

15. The surgical arm positioning system of claim 14, wherein the tensile resistance member comprises a clutch providing a resistive torque to one of the pulleys.

16. The surgical arm positioning system of claim 14, wherein the tensile resistance member comprises a weight.

17. The surgical arm positioning system of claim 14, wherein the cable resists movement along said pulleys and the lower and upper pulley brackets resist movement along the frame to keep the patient's arm stationary after the patient's arm is placed at any position having between about 0 degrees and about 70 degrees of arm abduction.

18. The surgical arm positioning system of claim 10, further comprising a semi-locked clamp configured to permit pivoting of the frame.

19. The surgical arm positioning system of claim 18, wherein the semi-locked clamp provides resistance to rotation of the frame.

20. The surgical arm positioning system of claim 1, further comprising a lower assembly and an upper assembly each carrying a respective one of the first and second pulleys, the lower and upper assemblies being adjustable along the frame, and a connecting rod coupled to the lower and upper assemblies to maintain a substantially fixed distance between the lower and upper assemblies.

21. The surgical arm positioning system of claim 20, wherein the tensile resistance member comprises a clutch providing a resistive torque to at least one of the pulleys.

22. The surgical arm positioning system of claim 20, wherein the tensile resistance member comprises a weight.

23. The surgical arm positioning system of claim 20, wherein the two end portions form an angle from about 120 to about 180 degrees at the connection member.

24. The surgical arm positioning system of claim 20, wherein the connecting rod that maintains the substantially fixed distance between the lower and upper assemblies pivots relative to the upper and lower assemblies as the lower and upper assemblies move along the frame.

25. The surgical arm positioning system of claim 20, wherein when a patient's arm is attached to the connection member, the cable resists movement along said pulleys and the lower and upper assemblies resist movement along the frame to keep the patient's arm stationary after the patient's arm is placed at any position having between about 0 degrees and about 70 degrees of arm abduction.

26. The surgical arm positioning system of claim 20, further comprising a semi-locked clamp configured to permit pivoting of the frame.

27. The surgical arm positioning system of claim 26, wherein the semi-locked clamp provides resistance to rotation of the frame.

\* \* \* \* \*